US010576087B2

(12) United States Patent
Zhou et al.

(10) Patent No.: US 10,576,087 B2
(45) Date of Patent: *Mar. 3, 2020

(54) FUSED TRICYCLIC COMPOUNDS AS RAF KINASE INHIBITORS

(71) Applicant: BEIGENE, LTD., Camana Bay, Grand Cayman (KY)

(72) Inventors: Changyou Zhou, Princeton, NJ (US); Shaohui Wang, Beijing (CN); Guoliang Zhang, Beijing (CN)

(73) Assignee: BEIGENE, LTD., Grand Cayman (KY)

( * ) Notice: Subject to any disclaimer, the term of this patent is extended or adjusted under 35 U.S.C. 154(b) by 0 days.

This patent is subject to a terminal disclaimer.

(21) Appl. No.: 15/882,064

(22) Filed: Jan. 29, 2018

(65) Prior Publication Data
US 2019/0000857 A1    Jan. 3, 2019

Related U.S. Application Data

(60) Continuation of application No. 15/004,311, filed on Jan. 22, 2016, now Pat. No. 9,895,376, which is a division of application No. 14/369,379, filed as application No. PCT/CN2011/085146 on Dec. 31, 2011, now Pat. No. 9,273,046.

(51) Int. Cl.
| | | |
|---|---|---|
| *A61K 31/5365* | (2006.01) |
| *C07D 471/04* | (2006.01) |
| *C07D 405/14* | (2006.01) |
| *C07D 473/30* | (2006.01) |
| *C07D 498/04* | (2006.01) |
| *C07D 519/00* | (2006.01) |
| *A61K 31/437* | (2006.01) |
| *A61K 31/4375* | (2006.01) |
| *A61K 31/4439* | (2006.01) |
| *A61K 31/506* | (2006.01) |
| *A61K 31/52* | (2006.01) |

(52) U.S. Cl.
CPC ........ *A61K 31/5365* (2013.01); *A61K 31/437* (2013.01); *A61K 31/4375* (2013.01); *A61K 31/4439* (2013.01); *A61K 31/506* (2013.01); *A61K 31/52* (2013.01); *C07D 405/14* (2013.01); *C07D 471/04* (2013.01); *C07D 473/30* (2013.01); *C07D 498/04* (2013.01); *C07D 519/00* (2013.01)

(58) Field of Classification Search
CPC ................................................ A61K 31/5365
See application file for complete search history.

(56) References Cited

U.S. PATENT DOCUMENTS

| 8,110,687 | B2 | 2/2012 | Calderwood et al. |
| 9,273,046 | B2 | 3/2016 | Zhou et al. |
| 9,895,376 | B2 | 2/2018 | Zhou et al. |
| 2010/0184791 | A1 | 7/2010 | Li et al. |
| 2010/0197924 | A1 | 8/2010 | Gould et al. |
| 2010/0292205 | A1 | 11/2010 | Lefker |
| 2016/0206621 | A1 | 7/2016 | Zhou et al. |
| 2018/0127412 | A1 | 5/2018 | Zhang et al. |

FOREIGN PATENT DOCUMENTS

| WO | WO 2006/065703 | 6/2006 |
| WO | WO 2006/084015 | 8/2006 |
| WO | WO 2007/067444 | 6/2007 |
| WO | WO 2007/136572 | 11/2007 |
| WO | WO 2007/136573 | 11/2007 |
| WO | WO 2008/030448 | 3/2008 |
| WO | WO 2013/097224 | 7/2013 |
| WO | WO 2016/165626 | 10/2016 |

OTHER PUBLICATIONS

International Preliminary Report on Patentability for International Application No. PCT/CN2011/085146, dated Jul. 1, 2014, 6 pages.
International Search Report and Written Opinion for International Application No. PCT/CN2011/085146, dated Sep. 27, 2012, 10 pages.
Supplementary European Search Report for European Application No. 11879096.3, dated Jul. 30, 2015, 4 pages.
European Search Report for European Application No. 16167542.6, dated Nov. 14, 2016, 5 pages.
International Search Report and Written Opinion for International Application No. PCT/CN2016/079251, dated Jul. 21, 2016, 8 pages.
Banales, "Cholangiocarcinoma: current knowledge and future perspectives consensus statement from the European Network for the Study of Cholangiocarcinoma (ENS-CCA)," Nature Reviews Gastroenterology and Hepatology, 2016, 13:261-280.
Blackburn, C. et al., "Discovery and optimization of N-acyl and N-aroylpyrazolines as B-Raf kinase inhibitors," Bioorganic & Medicinal Chemistry Letters 20 (2010) 4795-4799.
Boniface, M. M. et al., "Multidisciplinary management for esophageal and gastric cancer," Cancer Management and Research, 2016:8 39-44.
Cantwell-Dorris, E. R. et al., "BRAF$^{V600E}$: Implications for Carcinogenesis and Molecular Therapy," Mol Cancer Ther., 10(3):385-394 (Mar. 2011).
Damia, G. et al., "Contemporary pre-clinical development of anticancer agents—What are the optimal preclinical models?" European Journal of Cancer, 45 (2009) 2768-2781.
Garson, K. et al., "Models of ovarian cancer—Are we there yet?," Molecular and Cellular Endocrinology 239 (2005) 15-26.
Gerratana, L. et al., "Do platinum salts fit all triple negative breast cancers?" Cancer Treatment Reviews 48 (2016) 34-41.
Gyawali, B. et al., "Chemotherapy in locally advanced head and neck squamous cell carcinoma," Cancer Treatment Reviews, 44 (2016) 10-16.
Howington, J. A. et al., "Treatment of Stage I and II Non-small Cell Lung Cancer," Diagnosis and Management of Lung Cancer, 3rd ed: American College of Chest Physicians Evidence-Based Clinical Practice Guidelines, Chest 2013; 143(5)(Suppl):e278S-e313S.

(Continued)

*Primary Examiner* — David K O'Dell
(74) *Attorney, Agent, or Firm* — Cooley LLP

(57) ABSTRACT

Provided are certain fused tricyclic compounds and salts thereof, compositions thereof, and methods of use therefor.

16 Claims, No Drawings

(56) References Cited

OTHER PUBLICATIONS

Jett, J. R. et al., "Treatment of Small Cell Lung Cancer," Diagnosis and Management of Lung Cancer, 3rd ed: American College of Chest Physicians Evidence-Based Clinical Practice Guidelines, Chest 2013; 143(5)(Suppl):e400S-e419S.

Johnson, J. et al., "Relationships between drug activity in NCI preclinical in vitro and in vivo models and early clinical trials," British Journal of Cancer (2001) 84(10):1424-1431.

Kebebew, E. et al., "The Prevalence and Prognostic Value of BRAF Mutation in Thyroid Cancer," Ann. Surg., 2007; 246:466-471.

Khire, U. R. et al., "Omega-carboxypyridyl substituted ureas as Raf kinase inhibitors: SAR of the amide substituent," Bioorganic & Medicinal Chemistry Letters 14 (2004) 783-786.

Labenz, J. et al., "The epidemiology, diagnosis and treatment of Barrett's carcinoma," Dtsch Arztebl Int, 2015; 112:224-234.

Ledford, H., "US cancer institute overhauls cell lines," Nature, Feb. 25, 2016, vol. 530, p. 391.

Lowinger, T. B. et al., "Design and Discovery of Small Molecules Targeting Raf-1 Kinase," Current Pharmaceutical Design, (2002), 8:2269-2278.

Martin-Liberal, J. et al., "New RAF kinase inhibitors in cancer therapy," Expert Opinion on Pharmacotherapy, (2014) 15(9):1235-1245.

Ocana, A. et al., "Preclinical development of molecular targeted agents for cancer," Nat. Rev. Clin. Oncol., (2011) 8:200-209.

Raphael, B. J. et al., "Identifying driver mutations in sequenced cancer genomes: computational approaches to enable precision medicine," Genome Medicine, 2014; 6(5):1-17.

Sale, S. et al., "Models of ovarian cancer metastasis: Murine models," Drug Discovery Today, Disease Models, 2006; 3:149-154.

Sanz-Garcia, E. et al., "Current and advancing treatments for metastatic colorectal cancer," Expert Opinion on Biological Therapy, 16(1):93-110 (2016).

Schober, M. et al., "New Advances in the Treatment of Metastatic Pancreatic Cancer," Digestion, 2015; 92:175-184.

Sharma, S. V. et al., "Cell line-based platforms to evaluate the therapeutic efficacy of candidate anticancer agents," Nature Reviews Cancer (Apr. 2010), 10:241-253.

Simone, J. V., Part XIV Oncology, 154 Introduction, In: Cecil Textbook of Medicine, 20th Edition, vol. 1, Bennett, J. C. (ed.) (1996) pp. 1004-1010.

Socinski, M. A. et al., "Treatment of Stage IV Non-small Cell Lung Cancer," Diagnosis and Management of Lung Cancer, 3rd ed: American College of Chest Physicians Evidence-Based Clinical Practice Guideline, Chest 2013; 143(5)(Suppl):e341S-e368S.

Yoo, S. et al., "New drugs in prostate cancer," Prostate International, 4 (2016) 37-42.

Zambon, A. et al., "Small molecule inhibitors of BRAF in clinical trials," Bioorganic & Medicinal Chemistry Letters, 22 (2012) 789-792.

Zheng, G. et al., "Clinical detection and categorization of uncommon and concomitant mutations involving BRAF," BMC Cancer, 2015; 15:779, 10 pages.

Extended European Search Report for European Application No. 16779601.0, dated Jul. 24, 2018, 6 pages.

Bowker, M. J. et al., "A Procedure for Salt Selection and Optimization," Chapter 7 In: Handbook of Pharmaceutical Salts: Properties, Selection, and Use, Helvetica Chimca ACTA, pp. 162-173 (Jan. 2002).

Caira, M. R. et al., "Crystalline polymorphism of organic compounds," Topics in Current Chemistry, vol. 198, 1998, pp. 163-208.

FUSED TRICYCLIC COMPOUNDS AS RAF KINASE INHIBITORS

CROSS-REFERENCE TO RELATED APPLICATION

This application is a continuation of U.S. patent application Ser. No. 15/004,311 filed on Jan. 22, 2016, which is a division of U.S. patent application Ser. No. 14/369,379 filed on Oct. 23, 2014, which is a U.S. National Stage Application under 35 U.S.C. § 371 of International Application No. PCT/CN2011/085146, which was filed on Dec. 31, 2011 with the title "FUSED TRICYCLIC COMPOUNDS AS RAF KINASE INHIBITORS", the disclosures of each of which are hereby incorporated by reference in their entireties for all purposes.

Disclosed herein are fused tricyclic compounds, pharmaceutical compositions comprising at least one such fused tricyclic compound*processes for the preparation thereof, and the use thereof in therapy. Disclosed herein are certain tricyclic compounds that can be useful for inhibiting Raf kinase and for treating disorders mediated thereby.

The Raf/MEK/ERK pathway is of interest for cell survival, growth, proliferation and tumorigenesis (Zebisch et al., Curr Med Chem. 14(5): 601-623, 2007; Roberts and Der, Oncogene 26 (22): 3291-3310, 2007; Montagut and Seltleman, Cancer Lett. 283(2): 125-134, 2009). Stimulation of the Raf/MEK/ERK signal transduction pathway may occur after binding of a ligand to the membrane-bound receptor tyrosine kinase. GTP-bound RAS can be activated, which can subsequently promote the activation of the Raf family proteins (A-Raf, B-Raf and Raf1, formerly known as C-Raf) (Wellbrock et al., Nat. Rev. Mol. Cell Biol. 5: 875-885, 2004). Mutations in various RAS GTPases and B-Raf kinase in the Raf/MEK/ERK signal pathway have been reported to constitutively activate the MAPK pathway, resulting in increased cell division and survival (Bos, Cancer Res. 49: 4682-4689, 1989; Hoshino et al., Oncogene. 18(3): 813-822, 1999). For example, B-Raf mutations are reportedly found in a large percentage of human melanomas and thyroid cancers (Davies et al., Nature417: 949-954, 2002) (Cohen et al., J. Nat. Cancer Inst. 95(8): 625-627,2003; Kimura et al., Cancer Res. 63(7): 1454-1457, 2003; Pollock and Meltzer, Cancer Cell2: 5-7, 2002). In addition, lower, but still significant frequency of B-Raf mutations have been reported in Barrel's adenocarcinoma (Garnett et al., Cancer Cell6:313-319,2004; Sommerer et al., Oncogene 23(2): 554-558, 2004), breast cancer (Davies et al., Nature417: 949-954, 2002), cervical cancer (Moreno-Bueno et al., Clin. Cancer Res. 12(12): 365-3866, 2006), cholangiocarcinoma (Tannapfel et al., Gut. 52(5): 706-712, 2003), glioblastoma (Knobbe et al., Acta Neuropathol. (Berl.). 108(6): 467-470, 2004), colorectal cancer (Yuen et al., Cancer Res. 62(22): 6451-6455, 2002; Davies et al., Nature417: 949-954, 2002), gastric cancer (Lee et al., Oncogene22(44): 6942-6945), lung cancer (Brose et al., Cancer Res. 62(23): 6997-7000, 2002), ovarian cancer (Russell and McCluggage, J. Pathol. 203(2): 617-619,2004; Davies et al., Nature417: 949-954, 2002), pancreatic cancer (Ishimura et al., Cancer Lett. 199(2): 169-173, 2003), prostate cancer (Cho et al., Int. J. Cancer. 119(8): 1858-1862, 2006), and hematologic cancers (Garnett and Marais, Cancer Cell6: 313-319, 2004). These reports suggest that B-Raf is one of the most frequently mutated genes in human cancers. B-Raf kinase can represent an excellent target for anticancer therapy based on preclinical target validation, epidemiology and drugability.

Inhibitors of Raf kinases have been discussed for use in disruption of tumor cell growth and hence in the treatment of cancers, e.g. melanoma, colorectal cancer including large intestinal colon carcinoma, histiocytic lymphoma, lung adenocarcinoma, small cell lung cancer, and pancreatic and breast carcinoma (Crump, Current Pharmaceutical Design 8: 2243-2248, 2002; Sebastien et al., Current Pharmaceutical Design 8: 2249-2253, 2002), and/or in the treatment or prophylaxis of disorders associated with neuronal degeneration resulting from ischemic events, including cerebral ischemia after cardiac arrest, stroke and multi-infarct dementia. Inhibitors of Raf kinases have also been discussed for use after cerebral ischemic events such as those resulting from head injury, surgery and/or during childbirth (York et al., Mol. and Cell. Biol, 20(21): 8069-8083,2000; Chin et al., Neurochem. 90: 595-608, 2004), as well as in polycystic kidney disease (Nagao et al., Kidney Int. 63(2): 427-437, 2003).

In addition, certain hyperproliferative disorders may be characterized by the over activation of Raf kinase functions, for example, by mutations or over expression of the protein. Accordingly, inhibitors of Raf kinases can be useful in the treatment of hyperproliferative disorders, such as cancer.

Small molecule inhibitors of B-Raf kinases are being developed for anticancer therapy. Nexavar® (sorafenib tosylate) is a multikinase inhibitor, which includes inhibition of B-Raf kinases, and is approved for the treatment of patients with advanced renal cell carcinoma and unresectable hepatocellular carcinoma. Other Raf inhibitors have also been disclosed or have entered clinical trials, for example SB-590885, RAF-265, PLX-4032, GSK2118436 and XL-281.

Other B-Raf inhibitors are also known. See, for example, U.S. Patent Application Publication 2006/0189627, U.S. Patent Application Publication 2006/0281751, U.S. Patent Application Publication 2007/0049603, International Patent Application Publication WO 2007/002325, International Patent Application Publication WO 2007/002433, International Patent Application Publication WO 03/068773 and International Patent Application Publication WO 2007/013896.

Certain nitrogen-containing heteroaryl-substituted aryl bicyclic compounds have been identified as Raf inhibitors. See, for example, International Patent Application Publication WO 2007/067444 and U.S. Patent Application Publication 2010/0197924.

Certain Raf kinase inhibitors have also been identified. See, for example, International Patent Application Publication WO 2005/062795, International Patent Application Publication WO 2008/079906, International Patent Application Publication WO 2008/079909, International Patent Application Publication WO 2006/066913, International Patent Application WO 2008/028617 and International Patent Application Publication WO 2009/012283.

Disclosed herein are compounds that can inhibit Raf kinases, such as B-Raf kinases. Provided is at least one compound selected from compounds of Formula I:

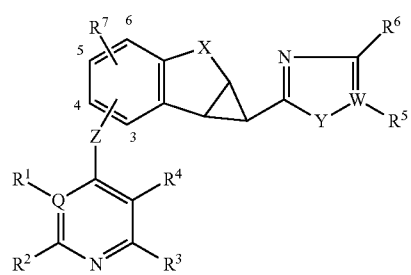

stereoisomers thereof, and pharmaceutically acceptable salts thereof, wherein:
  Q is selected from C and N;
  W is selected from C and N;
  X is selected from $CH_2$ and O;
  Y is selected from $NR^{12}$, O, and S;
  Z is selected from O, S, $NR^{13}$, CO, SO, $SO_2$, and $CR_{13}R_{14}$;
  $R^1$, $R^2$, $R^3$, $R^4$, $R^5$, and $R^6$, which may be the same or different, are each selected from hydrogen, halogen, haloalkyl, alkyl, alkenyl, cycloalkyl, aryl, heterocyclyl, heteroaryl, alkynyl, —CN, —$NR^{13}R^{14}$, —$OR^{13}$, —$COR^{13}$, —$CO_2R^{13}$, —$CONR^{13}R^{14}$, —$C(=NR^{13})NR^{14}R^{15}$, —$NR^{13}COR^{14}$, —$NR^{13}CONR^{14}R^{15}$, —$NR^{13}CO_2R^{14}$, —$SO_2R^{13}$, —$NR^{13}SO_2NR^{14}R^{15}$, and —$NR^{13}SO_2R^{14}$, wherein the alkyl, alkenyl, alkynyl, cycloalkyl, heteroaryl, aryl, and heterocyclyl are optionally substituted with at least one substituent $R^{16}$, or ($R^1$ and $R^2$), and/or ($R^3$ and $R^4$), and/or ($R^5$ and $R^6$), together with the ring to which they are attached, form a fused ring selected from heterocyclyl, and heteroaryl rings optionally substituted with at least one substituent $R^{16}$; provided that $R^1$ is absent when Q is N, and $R^5$ is absent when W is N;
  $R^7$ is selected from hydrogen, halogen, alkyl, —O-alkyl, and —S-alkyl;
  $R^{12}$ is selected from hydrogen and alkyl;
  $R^{13}$, $R^{14}$ and $R^{15}$, which may be the same or different, are each selected from H, haloalkyl, alkyl, alkenyl, alkynyl, cycloalkyl, heterocyclyl, aryl, and heteroaryl; or ($R^{13}$ and $R^{14}$), and/or ($R^{14}$ and $R^{15}$) together with the atom(s) to which they are attached, each form a ring selected from heterocyclyl, and heteroaryl rings optionally substituted with at least one substituent $R^{16}$;
  $R^{16}$ is selected from halogen, haloalkyl, alkyl, alkenyl, cycloalkyl, aryl, heteroaryl, heterocyclyl, alkynyl, oxo, —CN, —OR', —NR'R'', —COR', —$CO_2R'$, —CONR'R'', —C(=NR')NR''R''', —NR'COR'', —NR'CONR'R''', —$NR'CO_2R''$, —$SO_2R'$, —$SO_2aryl$, —$NR'SO_2NR''R'''$, and $NR'SO_2R''$, wherein R', R'', and R''' are independently selected from H, haloalkyl, alkyl, alkenyl, alkynyl, cycloalkyl, heterocyclyl, aryl, and heteroaryl, or (R' and R''), and/or (R'' and R''') together with the atoms to which they are attached, form a ring selected from heterocyclyl, arid heteroaryl rings.

Also provided is a pharmaceutical composition comprising at least one pharmaceutically acceptable carrier and at least one compound selected from compounds of Formula (I), stereoisomers thereof, and pharmaceutically accept salts thereof described herein.

Also provided is a method of treating cancer responsive to inhibition of Raf kinase comprising administering to a subject in need of treating for such cancer an amount of at least one compound selected from compounds of Formula (I), stereoisomers thereof, and pharmaceutically accept sails thereof described herein effective to treat the cancer.

Also provided is a use of at least one compound selected from compounds of Formula (I), stereoisomers thereof, and pharmaceutically accept salts thereof described herein in manufacture of a medicament for inhibiting Raf kinases.

Also provided is a use of at least one compound selected from compounds of Formula (I), stereoisomers thereof, and pharmaceutically accept salts thereof described herein in the manufacture of a medicament for treating cancer.

As used herein, the following words, phrases and symbols are generally intended to have the meanings as set forth below, except to the extent that the context in which they are used indicates otherwise. The following abbreviations and terms have the indicated meanings throughout:

The term "alkyl" herein refers to a hydrocarbon group selected from linear and branched saturated hydrocarbon groups comprising from 1 to 18, such as from 1 to 12, further such as from 1 to 6, carbon atoms. Examples of the alkyl group can be selected from methyl, ethyl, 1-propyl or n-propyl ("n-Pr"), 2-propyl or isopropyl ("i-Pr"), 1-butyl or n-butyl ("n-Bu"), 2-methyl-1-propyl or isobutyl ("i-Bu"), 1-methylpropyl or s-butyl ("s-Bu"), and 1,1-dimethylethyl or t-butyl ("t-Bu"). Other examples of the alkyl group can be selected from 1-pentyl (n-pentyl, —$CH_2CH_2CH_2CH_2CH_3$), 2-pentyl (—$CH(CH_3)CH_2CH_2CH_3$), 3-pentyl (—$CH(CH_2CH_3)_2$), 2-methyl-2-butyl (—$C(CH_3)_2CH_2CH_3$), 3-methyl-2-butyl (—$CH(CH_3)CH(CH_3)_2$), 3-methyl-1-butyl (—$CH_2CH_2CH(CH_3)_2$), 2-methyl-1-butyl (—$CH_2CH(CH_3)CH_2CH_3$), 1-hexyl (—$CH_2CH_2CH_2CH_2CH_2CH_3$), 2-hexyl (—$CH(CH_3)CH_2CH_2CH_2CH_3$), 3-hexyl (—$CH(CH_2CH_3)(CH_2CH_2CH_3)_2$), 2-methyl-2-pentyl (—$C(CH_3)_2CH_2CH_2CH_3$), 3-methyl-2-pentyl (—$CH(CH_3)CH(CH_3)CH_2CH_3$), 4-methyl-2-pentyl (—$CH(CH_3)CH_2CH(CH_3)_2$), 3-methyl-3-pentyl (—$C(CH_3)(CH_2CH_3)_2$), 2-methyl-3-pentyl (—$CH(CH_2CH_3)CH(CH_3)_2$), 2,3-dimethyl-2-butyl (—$C(CH_3)_2CH(CH_3)_2$) and 3,3-dimethyl-2-butyl (—$CH(CH_3)C(CH_3)_3$) groups.

The term "alkenyl" herein refers to a hydrocarbon group selected from linear and branched hydrocarbon groups comprising at least one C=C double bond and from 2 to 18, such as from 2 to 6, carbon atoms. Examples of the alkenyl group may be selected from ethenyl or vinyl (—$CH=CH_2$), prop-1-enyl (—$CH=CHCH_3$), prop-2-enyl (—$CH_2CH=CH_2$), 2-methylprop-1-enyl, but-1-enyl, but-2-enyl, but-3-enyl, buta-1,3-dienyl, 2-methylbuta-1,3-diene, hex-1-enyl, hex-2-enyl, hex-3-enyl, hex-4-enyl, and hexa-1,3-dienyl groups.

The term "alkynyl" herein refers to a hydrocarbon group selected from linear and branched hydrocarbon group, comprising at least one C≡C triple bond and from 2 to 18, such as from 2 to 6, carbon atoms. Examples of the alkynyl group include, ethynyl (—C≡CH), 1-propynyl (—C≡$CCH_3$), 2-propynyl (propargyl, —$CH_2$C≡CH), 1-butynyl, 2-butynyl, and 3-butynyl groups.

The term "cycloalkyl" herein refers to a hydrocarbon group selected from saturated and partially unsaturated cyclic hydrocarbon groups, comprising monocyclic and polycyclic (e.g., bicyclic and tricyclic) groups. For example, the cycloalkyl group may comprise from 3 to 12, such as 3 to 8, further such as 3 to 6, 3 to 5, or 3 to 4 carbon atoms. Even further for example, the cycloalkyl group may be selected from monocyclic group comprising from 3 to 12, such as 3 to 8, 3 to 6 carbon atoms. Examples of the monocyclic cycloalkyl group include cyclopropyl, cyclobutyl, cyclopentyl, 1-cyclopent-1-enyl, 1-cyclopent-2-enyl, 1-cyclopent-3-enyl, cyclohexyl, 1-cyclohex-1-enyl, 1-cyclohex-2-enyl, 1-cyclohex-3-enyl, cyclohexadienyl, cycloheptyl, cyclooctyl, cyclononyl, cyclodecyl, cycloundecyl, and cyclododecyl groups. Examples of the bicyclic cycloalkyl groups include those having from 7 to 12 ring atoms arranged as a bicyclic ring selected from [4,4], [4,5], [5,5], [5,6] and [6,6] ring systems, or as a bridged bicyclic ring selected from bicyclo[2.2.1]heptane, bicyclo[2.2.2]octane, and bicyclo[3.2.2]nonane. The ring may be saturated or have at least one double bond (i.e. partially unsaturated), but is not fully conjugated, and is not aromatic, as aromatic is defined herein.

The term "Aryl" herein refers to a group selected from:
  5- and 6-membered carbocyclic aromatic rings, for example, phenyl;
  bicyclic ring systems such as 7 to 12 membered bicyclic ring systems wherein at least one ring is carbocyclic and aromatic, selected, for example, from naphthalene, indane, and 1,2,3,4-tetrahydroquinoline; and tricyclic, ring systems such as 10 to 15 membered tricyclic ring systems wherein at least one ring is carbocyclic and aromatic, for example, fluorene.

For example, the aryl group is selected from 5 and 6-membered carbocyclic aromatic rings fused to a 5- to 7-membered cycloalkyl or heterocyclic ring optionally comprising at least one heteroatom selected from N, O, and S, provided that the point of attachment is at the carbocyclic aromatic ring when the carbocyclic aromatic ring is fused with a heterocyclic ring, and the point of attachment can be at the carbocyclic aromatic ring or at the cycloalkyl group when the carbocyclic aromatic ring is fused with a cycloalkyl group. Bivalent radicals formed from substituted benzene derivatives and having the free valences at ring atoms are named as substituted phenylene radicals. Bivalent radicals derived from univalent polycyclic hydrocarbon radicals whose names end in "-yl" by removal of one hydrogen atom from the carbon atom with the free valence are named by adding "-idene" to the name of the corresponding univalent radical, e.g., anaphthyl group with two points of attachment is termed naphthyl idene. Aryl, however, does not encompass or overlap in any way with heteroaryl, separately defined below. Hence, if one or more carbocyclic aromatic rings are fused with a heterocyclic aromatic ring, the resulting ring system is heteroaryl, not aryl, as defined herein.

The term "halogen" or "halo" herein refers to F, Cl, Br or I.

The term "heteroaryl" herein refers to a group selected from:

5- to 7-membered aromatic, monocyclic rings comprising at least one heteroatom, for example, from 1 to 4, or, in some embodiments, from 1 to 3, heteroatoms, selected from N, O, and S, with the remaining ring atoms being carbon;

8- to 12-membered bicyclic rings comprising at least one heteroatom, for example, from 1 to 4, or, in some embodiments, from 1 to 3, or, in other embodiments, 1 or 2, heteroatoms, selected from N, O, and S, with the remaining ring atoms being carbon and wherein at least one ring is aromatic and at least one heteroatom is present in the aromatic ring; and 11- to 14-membered tricyclic rings comprising at least one heteroatom, for example, from 1 to 4, or in some embodiments, from 1 to 3, or, in other embodiments, 1 or 2, heteroatoms, selected from N, O, and S, with the remaining ring atoms being carbon and wherein at least one ring is aromatic and at least one heteroatom is present in an aromatic ring.

For example, the heteroaryl group includes a 5- to 7-membered heterocyclic aromatic ring fused to a 5- to 7-membered cycloalkyl ring. For such fused, bicyclic heteroaryl ring systems wherein only one of the rings comprises at least one heteroatom, the point of attachment maybe at the heteroaromatic ring or at the cycloalkyl ring.

When the total number of S and O atoms in the heteroaryl group exceeds 1, those heteroatoms are not adjacent to one another. In some embodiments, the total number of S and O atoms in the heteroaryl group is not more than 2. In some embodiments, the total number of S and O atoms in the aromatic heterocycle is not more than 1.

Examples of the heteroaryl group include, but are not limited to, (as numbered from the linkage position assigned priority 1) pyridyl (such as 2-pyridyl, 3-pyridyl, or 4-pyridyl), cinnolinyl, pyrazinyl, 2,4-pyrimidinyl, 3,5-pyrimidinyl, 2,4-imidazolyl, imidazopyridinyl, isoxazolyl, oxazolyl, thiazolyl, isothiazolyl, thiadiazolyl, tetrazolyl, thienyl, triazinyl, benzothienyl, furyl, benzofuryl, benzoimidazolyl, indolyl, isoindolyl, indolinyl, phthalazinyl, pyrazinyl, pyridazinyl, pyrrolyl, triazolyl, quinolinyl, isoquinolinyl, pyrazolyl, pyrrolopyridinyl (such as 1H-pyrrolo[2,3-b]pyridin-5-yl), pyrazolopyridinyl (such as 1H-pyrazolo[3,4-b]pyridin-5-yl), benzoxazolyl (such as benzo[d]oxazol-6-yl), pteridinyl, purinyl, 1-oxa-2,3-diazolyl, 1-oxa-2,4-diazolyl, 1-oxa-2,5-diazolyl, 1-oxa-3,4-diazolyl, 1-thia-2,3-diazolyl, 1-thia-2,4-diazolyl, 1-thia-2,5-diazolyl, 1-thia-3,4-diazolyl, furazanyl, benzofurazanyl, benzothiophenyl, benzothiazolyl, benzoxazolyl, quinazolinyl, quinoxalinyl, naphthyridinyl, furopyridinyl, benzothiazolyl (such as benzo[d]thiazol-6-yl), indazolyl (such as 1H-indazol-5-yl) and 5,6,7,8-tetrahydroisoquinoline.

The term "heterocyclic" or "heterocycle" or "heterocyclyl" herein refers to a ring selected from 4- to 12-membered monocyclic, bicyclic and tricyclic, saturated and partially unsaturated rings comprising at least one carbon atoms in addition to at least one heteroatom, such as from 1-4 heteroatoms, further such as from 1-3, or further such as 1 or 2 heteroatoms, selected from oxygen, sulfur, and nitrogen. "Heterocycle" herein also refers to a 5- to 7-membered heterocyclic ring comprising at least one heteroatom selected from N, O, and S fused with 5-, 6-, and/or 7-membered cycloalkyl, carbocyclic aromatic or heteroaromatic ring, provided that the point of attachment is at the heterocyclic ring when the heterocyclic ring is fused with a carbocyclic aromatic or a heteroaromatic ring, and that the point of attachment can be at the cycloalkyl or heterocyclic ring when the heterocyclic ring is fused with cycloalkyl. "Heterocycle" herein also refers to an aliphatic spirocyclic ring comprising at least one heteroatom selected from N, O, and S, provided that the point of attachment is at the heterocyclic ring. The rings may be saturated or have at least one double bond (i.e. partially unsaturated). The heterocycle may be substituted with oxo. The point of the attachment may be carbon or heteroatom in the heterocyclic ring. A heterocycle is not a heteroaryl as defined herein.

Examples of the heterocycle include, but not limited to, (as numbered from the linkage position assigned priority 1) 1-pyrrolidinyl, 2-pyrrolidinyl, 2,4-imidazolidinyl, 2,3-pyrazolidinyl, 1-piperidinyl, 2-piperidinyl, 3-piperidinyl, 4-piperidinyl, 2,5-piperazinyl, pyranyl, 2-morpholinyl, 3-morpholinyl, oxiranyl, aziridinyl, thiiranyl, azetidinyl, oxetanyl, thietanyl, 1,2-dithiolanyl, 1,3-dithietanyl, dihydropyridinyl, tetrahydropyridinyl, thiomorpholinyl, thioxanyl, piperazinyl, homopiperazinyl, homopiperidinyl, azepanyl, oxepanyl, thiepanyl, 1,4-oxathianyl, 1,4-dioxepanyl, 1,4-oxathiepanyl, 1,4-oxaazepanyl, 1,4-dithiepanyl, 1,4-thiazepanyl and 1,4-diazepane 1,4-dithianyl, 1,4-azathianyl, oxazepinyl, diazepinyl, thiazepinyl, dihydrothienyl, dihydropyranyl, dihydrofuranyl, tetrahydrofuranyl, tetrahydrothienyl, tetrahydropyranyl, tetrahydrothiopyranyl, 1-pyrrolinyl, 2-pyrrolinyl, 3-pyrrolinyl, indolinyl, 2H-pyranyl, 4H-pyranyl, 1,4-dioxanyl, 1,3-dioxolanyl, pyrazolinyl, pyrazolidinyl, dithianyl, dithiolanyl, pyrazolidinyl, imidazolinyl, pyrimidinonyl, 1,1-dioxo-thiomorpholinyl, 3-azabicyco[3.1.0]hexanyl, 3-azabicyclo[4.1.0]heptanyl and azabicyclo[2.2.2]hexanyl. A substituted heterocycle also includes a ring system substituted with one or more oxo moieties, such as piperidinyl N-oxide, morpholinyl-N-oxide, 1-oxo-1-thiomorpholinyl and 1,1-dioxol-1-thiomorpholinyl.

The term "fused ring" herein refers to a polycyclic ring system, e.g., a bicyclic or tricyclic ring system, in which two rings share only two ring atoms and one bond in common.

Examples of fused rings may comprise a fused bicyclic cycloalkyl ring such as those having from 7 to 12 ring atoms arranged, as a bicyclic ring selected from [4,4], [4,5], [5,5], [5,6] and [6,6] ring systems as mentioned above; a fused bicyclic aryl ring such as 7 to 12 membered bicyclic aryl ring systems as mentioned above, a fused tricyclic aryl ring such as 10 to 15 membered tricyclic aryl ring systems mentioned above; a fused bicyclic heteroaryl ring such as 8- to 12-membered bicyclic heteroaryl rings as mentioned above, a fused tricyclic heteroaryl ring such as 11- to 14-membered tricyclic heteroaryl rings as mentioned above; and a fused bicyclic or tricyclic heterocyclyl ring as mentioned above.

Compounds described herein may contain an asymmetric center and may thus exist as enantiomers. Where the compounds described herein possess two or more asymmetric centers, they may additionally exist as diastereomers. Enantiomers and diastereomers fall within the broader class of stereoisomers. All such possible stereoisomers as substantially pure resolved enantiomers, racemic mixtures thereof, as well as mixtures of diastereomers are intended to be included. All stereoisomers of the compounds disclosed herein and/or pharmaceutically acceptable salts thereof are intended to be included. Unless specifically mentioned otherwise, reference to one isomer applies to any of the possible isomers. Whenever the isomeric composition is unspecified, all possible isomers are included.

The term "substantially pure" as used herein means that the target stereoisomer contains no more than 35%, such as no more than 30%, further such as no more than 25%, even further such as no more than 20%, by weight of any other stereoisomer(s). In some embodiments, the term "substantially pure" means that the target stereoisomer contains no more than 10%, for example, no more than 5%, such as no more than 1%, by weight of any other stereoisomer(s).

When compounds described herein contain olefinic double bonds, unless specified otherwise, such double bonds are meant to include both E and Z geometric isomers.

Some of the compounds described herein may exist with different points of attachment of hydrogen, referred to as tautomers. For example, compounds including carbonyl —$CH_2C(O)$— groups (keto forms) may undergo tautomerism to form hydroxyl —$CH$=$C(OH)$— groups (enol forms). Both keto and enol forms, individually as well as mixtures thereof, are also intended to be included where applicable.

It may be advantageous to separate reaction products from one another and/or from starting materials. The desired products of each step or series of steps is separated and/or purified (hereinafter separated) to the desired degree of homogeneity by the techniques common in the art. Typically such separations involve multiphase extraction, crystallization from a solvent or solvent mixture, distillation, sublimation, or chromatography. Chromatography can involve any number of methods including, for example: reverse-phase and normal phase; size exclusion; ion exchange; high, medium and low pressure liquid chromatography methods and apparatus; small scale analytical; simulated moving bed ("SMB") and preparative thin or thick layer chromatography, as well as techniques of small scale thin layer and flash chromatography. One skilled in the art will apply techniques most likely to achieve the desired separation.

Diastereomeric mixtures can be separated into their individual diastereomers on the basis of their physical chemical differences by methods well known to those skilled in the art, such as by chromatography and/or fractional crystallization. Enantiomers can be separated by converting the enantiomeric mixture into a diastereomeric mixture by reaction with an appropriate optically active compound (e.g., chiral auxiliary such as a chiral alcohol or Mosher's acid chloride), separating the diastereomers and converting (e.g., hydrolyzing) the individual diastereoisomers to the corresponding pure enantiomers. Enantiomers can also be separated by use of a chiral HPLC column.

A single stereoisomer, e.g., a substantially pure enantiomer, may be obtained by resolution of the racemic mixture using a method such as formation of diastereomers using optically active resolving agents (Eliel, E. and Wilen, S. Stereochemistry of Organic Compounds. New York: John Wiley & Sons, Inc., 1994; Lochmuller, C. H., et al. "Chromatographic resolution of enantiomers: Selective review." J. Chromatogr., 113(3) (1975): pp. 283-302). Racemic mixtures of chiral compounds of the invention can be separated and isolated by any suitable method, including: (1) formation of ionic, diastereomeric salts with chiral compounds and separation by fractional crystallization or other methods, (2) formation of diastereomeric compounds with chiral derivatizing reagents, separation of the diastereomers, and conversion to the pure stereoisomers, and (3) separation of the substantially pure or enriched stereoisomers directly under chiral conditions. See: Wainer, Irving W., Ed. Drug Stereochemistry: Analytical Methods and Pharmacology. New York: Marcel Dekker, Inc., 1993.

"Pharmaceutically acceptable salts" include, but are not limited to salts with inorganic acids, selected, for example, from hydrochlorates, phosphates, diphosphates, hydrobromates, sulfates, sulfinates, and nitrates; as well as salts with organic acids, selected, for example, from malates, maleates, fumarates, tartrates, succinates, citrates, lactates, methanesulfonates, p-toluenesulfonates, 2-hydroxyethylsulfonates, benzoates, salicylates, stearates, alkanoates such as acetate, and salts with HOOC—$(CH_2)_n$—COOH, wherein n is selected from 0 to 4. Similarly, examples of pharmaceutically acceptable cations include, but are not limited to, sodium, potassium, calcium, aluminum, lithium, and ammonium.

In addition, if a compound disclosed herein is obtained as an acid addition salt, the free base can be obtained by basifying a solution of the acid salt. Conversely, if the product is a free base, an addition salt, such as a pharmaceutically acceptable addition salt, may be produced by dissolving the free base in a suitable organic solvent and treating the solution with an acid, in accordance with conventional procedures for preparing acid addition salts from base compounds. Those skilled in the art will recognize various synthetic methodologies that may be used without undue experimentation to prepare non-toxic pharmaceutically acceptable addition salts.

As defined herein, "pharmaceutically acceptable salts thereof" include salts of at least one compound of Formulae I, II, III, IV, and/or V, and salts of the stereoisomers of at least one compound of Formulae I, II, III, IV, and/or V, such as salts of enantiomers, and/or salts of diastereomers.

"Treating," "treat," or "treatment" or "alleviation" refers to administering at least one compound and/or at least one stereoisomer thereof, and/or at least one pharmaceutically acceptable salt thereof disclosed herein to a subject in recognized need thereof that has, for example, cancer.

The term "effective amount" refers to an amount of at least one compound and/or at least one stereoisomer thereof, and/or at least one pharmaceutically acceptable salt thereof disclosed herein effective to "treat," as defined above, a disease or disorder in a subject.

The term "at least one substituent" disclosed herein includes, for example, from 1 to 4, such as from 1 to 3, further as 1 or 2, substituents. For example, "at least one substituent $R^{16}$" disclosed herein includes from 1 to 4, such as from 1 to 3, further as 1 or 2, substituents selected from the list of $R^{16}$ as described herein.

Provided is at least one compound selected from compounds of Formula I:

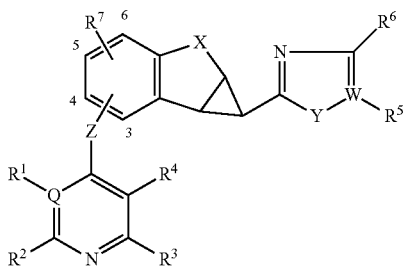

I stereoisomers thereof, and pharmaceutically acceptable salts thereof,
wherein:
Q is selected from C and N;
W is selected from C and N;
X is selected from $CH_2$ and O;
Y is selected from $NR^{12}$, O, and S;
Z is selected from O, S, $NR^{13}$, CO, SO, $SO_2$, and $CR^{13}R^{14}$;
$R^1$, $R^2$, $R^3$, $R^4$, $R^5$, and $R^6$, which may be the same or different, are each selected from hydrogen, halogen, haloalkyl, alkyl, alkenyl, cycloalkyl, aryl, heterocyclyl, heteroaryl, alkynyl, —CN, —$NR^{13}R^{14}$, —$OR^{13}$, —$COR^{13}$, —$CO_2R^{13}$, —$CONR^{13}R^{14}$, —$C(=NR^{13})NR^{14}R^{15}$, —$NR^{13}COR^{14}$, —$NR^{13}CONR^{14}R^{15}$, —$NR^{13}CO_2R^{14}$, —$SO_2R^{13}$, —$NR^{13}SO_2NR^{14}R^{15}$, —$NR^{13}SO_2R^{14}$, and —$NR^{13}SO_2$aryl, wherein the alkyl, alkenyl, alkynyl, cycloalkyl, heteroaryl, aryl, and heterocyclyl are optionally substituted with at least one substituent $R^{16}$, or ($R^1$ and $R^2$), and/or ($R^3$ and $R^4$), and/or ($R^5$ and $R^6$), together with the ring to which they are attached, form a fused ring selected from heterocyclyl, and heteroaryl rings optionally substituted with at least one substituent $R^{16}$; provided that $R^1$ is absent when Q is N, and $R^5$ is absent when W is N;
$R^7$ is selected from hydrogen, halogen, alkyl, —O-alkyl, and —S-alkyl;
$R^{12}$ is selected from hydrogen and alkyl;
$R^{13}$, $R^{14}$ and $R^{15}$, which may be the same or different, are each selected from H, haloalkyl, alkyl, alkenyl, alkynyl, cycloalkyl, heterocyclyl, aryl, and heteroaryl; or ($R^{13}$ and $R^{14}$), and/or ($R^{14}$ and $R^{15}$) together with the atom(s) to which they are attached, each form a ring selected from heterocyclyl, and heteroaryl rings optionally substituted with at least one substituent $R^{16}$;
$R^{16}$ is selected from halogen, haloalkyl, alkyl, alkenyl, cycloalkyl, aryl, heteroaryl, heterocyclyl, alkynyl, oxo, —CN, —OR', —NR'R'', —COR', —$CO_2R'$, —CONR'R'', —C(=NR')NR''R''', —NR'COR'', —NR'CONR'R'', —NR'$CO_2R''$, —$SO_2R'$, —$SO_2$aryl, —NR'$SO_2$NR''R''', NR'$SO_2R''$, and —NR'$SO_2$aryl, wherein R', R'', and R''' are independently selected from H, haloalkyl, alkyl, alkenyl, alkynyl, cycloalkyl, heterocyclyl, aryl, and heteroaryl, or (R' and R''), and/or (R'' and R''') together with the atoms to which they are attached, form a ring selected from heterocyclyl, and heteroaryl rings.

In some embodiments, X is $CH_2$.
In some embodiments, X is O.
In some embodiments, Y is NH and W is C.
In some embodiments, Y is S and W is C.
In some embodiments, Q is C.
In some embodiments, Q is N and $R^1$ is absent.
In some embodiments, Z is O.
In some embodiments, each of $R^1$ and $R^2$ is hydrogen.
In some embodiments, $R^3$ and $R^4$ together with the ring to which they are attached, form a fused ring selected from a heterocycle or heteroaryl ring, such as naphthyridinyl (e.g., dihydronaphthyridinyl), pyrrolopyridinyl (e.g., pyrrolo[2,3-b]pyridin-4-yl), and purinyl, said ring being optionally substituted with at least one substituent $R^{16}$, such as oxo.
In some embodiments, $R^3$ and $R^4$, which may be the same or different, are each selected from hydrogen, —$CONR^{13}R^{14}$, such as —$CONHCH_3$, and heteroaryl (e.g., imdazole) optionally substituted with at least one substituent $R^{16}$, such as at least one haloalkyl, wherein the haloalkyl is, for example, —$CF_3$.
In some embodiments, $R^5$ and $R^6$ together with the ring to which they are attached, form a fused ring which is a heteroaryl ring, such as benzoimidazolyl (e.g., 1H-benzo[d]imidazol-2-yl), and imidazopyridinyl (e.g., 3H-imidazo[4,5-c]pyridin-2-yl), said heteroaryl ring being optionally substituted with at least one substituent $R^{16}$, such as haloalkyl (e.g., —$CF_3$), alkyl (e.g., methyl, tert-butyl), halogen, CN, haloalkyloxy (e.g., $OCF_3$), alkyloxy (e.g., methoxy), hydroxyl, and phenyl.
In some embodiments, $R^5$ and $R^6$, which may be the same or different, are each selected from hydrogen, aryl, such as phenyl, and heteroaryl (e.g., pyridyl) optionally substituted with at least one substituent $R^{16}$, such as such as haloalkyl (e.g., —$CF_3$), alkyl (e.g., methyl, tert-butyl), halogen, CN, haloalkyloxy (e.g., $OCF_3$, etc.), alkyloxy (e.g., methoxy), hydroxyl, and phenyl.
In some embodiments, the at least one compound selected from compounds of Formula (I), stereoisomers thereof, and pharmaceutically acceptable salts thereof, is selected from compounds of Formula (II) below:

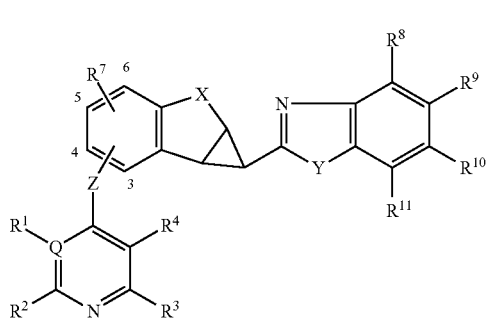

II stereoisomers thereof, and pharmaceutically acceptable salts thereof,
wherein:
Q is selected from C and N;
X is selected from $CH_2$ and O;
Y is selected from $NR^{12}$, O, and S;
Z is selected from O, S, $NR^{13}$, CO, SO, $SO_2$, and $CR^{13}R^{14}$;
$R^1$, $R^2$, $R^3$, $R^4$, $R^8$, $R^9$, $R^{10}$ and $R^{11}$, which may be the same or different, are each selected from hydrogen, halogen, haloalkyl, alkyl, alkenyl, cycloalkyl, aryl, heterocyclyl, heteroaryl, alkynyl, —CN, —NR$^{13}$R$^{14}$, —OR$^{13}$, —COR$^{13}$, —CO$_2$R$^{13}$, —CONR$^{13}$R$^{14}$, —C(=NR$^{13}$)NR$^{14}$R$^{15}$, —NR$^{13}$COR$^{14}$, —NR$^{13}$CONR$^{14}$R$^{15}$, —NR$^{13}$CO$_2$R$^{14}$, —SO$_2$R$^{13}$, —NR$^{13}$SO$_2$NR$^{14}$R$^{15}$, and —NR$^{13}$SO$_2$R$^{14}$, wherein the alkyl, alkenyl, alkynyl, cycloalkyl, heteroaryl, aryl, and heterocyclyl are each optionally substituted with at least one substituents R$^{16}$, or (R$^1$ and R$^2$), and/or (R$^3$ and R$^4$), and/or (R$^8$ and R$^9$), and/or (R$^9$ and R$^{10}$), and/or (R$^{10}$ and R$^{11}$) together with the ring to which they are attached, form a fused ring selected from heterocyclyl, and heteroaryl rings optionally substituted with at least one substituent R$^{16}$; provided that R$^1$ is absent when Q is N;

R$^7$ is selected from hydrogen, halogen, alkyl, —O-alkyl, and —S-alkyl;

R$^{12}$ is selected from hydrogen and alkyl;

R$^{13}$, R$^{14}$ and R$^{15}$, which may be the same or different, are each selected from H, haloalkyl, alkyl, alkenyl, alkynyl, cycloalkyl, heterocyclyl, aryl, and heteroaryl; or (R$^{13}$ and R$^{14}$), and/or (R$^{14}$ and R$^{15}$) together with the atom(s) to which they are attached, each form a ring selected from heterocyclyl, and heteroaryl rings optionally substituted with at least one substituent R$^{16}$;

R$^{16}$ is selected from halogen, haloalkyl, alkyl, alkenyl, cycloalkyl, aryl, heteroaryl, heterocyclyl, alkynyl, oxo, —CN, —OR', —NR'R", —COR', —CO$_2$R', —CONR'R", —C(=NR')NR"R'", —NR'COR", —NR'CONR'R", —NR'CO$_2$R", —SO$_2$R', —SO$_2$aryl, —NR'SO$_2$NR"R'", NR'SO$_2$R", and —NR'SO$_2$aryl, wherein R', R", and R'" are independently selected from H, haloalkyl, alkyl, alkenyl, alkynyl, cycloalkyl, heterocyclyl, aryl, and heteroaryl, or (R' and R"), and/or (R"and R'") together with the atoms to which they are attached, form a ring selected from heterocyclyl, and heteroaryl rings.

In some embodiment, X in Formula (II) is O.

In some embodiments, X in Formula (II) is CH$_2$.

In some embodiments, Y in Formula (II) is S.

In some embodiments, Z in Formula (II) is O.

In some embodiments, Q in Formula (II) is C.

In some embodiments, Q in Formula (II) is N and R$^1$ in Formula (II) is absent.

In some embodiment, R$^3$ and R$^4$ together with the ring to which they are attached, form a fused ring selected from a heterocycle or heteroaryl ring, such as naphthyridinyl (e.g., dihydronaphthyridinyl), pyrrolopyridinyl (e.g., pyrrolo[2,3-b]pyridin-4-yl), and purinyl, said ring being optionally substituted with at least one substituent R$^{16}$, such as oxo.

In some embodiments, each of R$^1$ and R$^2$ is hydrogen.

In some embodiments, R$^3$ and R$^4$, which may be the same or different, are each selected from hydrogen, —CONR$^{13}$R$^{14}$, such as —CONHCH$_3$, and heteroaryl (e.g., imdazole) optionally substituted with at least one substituent R$^{16}$, such as at least one haloalkyl, wherein the haloalkyl is, for example, —CF$_3$.

In some embodiments, R$^8$, R$^9$, R$^{10}$, and R$^{11}$ in Formula (II), which may be the same or different, are each selected from alkyl(e.g., methyl, tert-butyl), hydrogen, haloalkyl (e.g., —CF$_3$), halogen, hydroxy, —CN, —Oalkyl (e.g., methoxy), and —Ohaloalkyl (e.g., OCF$_3$), and aryl (e.g., phenyl).

In some embodiments, the at least one compound selected from compounds of Formula (I), stereoisomers thereof, and pharmaceutically acceptable salts thereof, is selected from compounds of Formula (III)

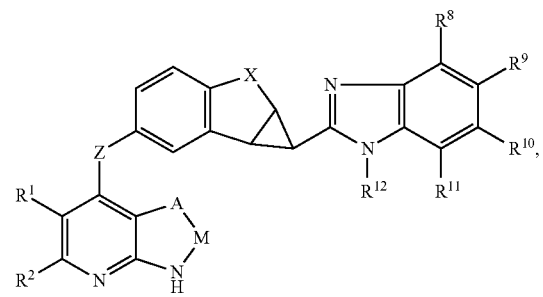

stereoisomers thereof, and pharmaceutically acceptable salts thereof, wherein:

X is selected from CH$_2$ and O;

Z is selected from O, S, NR$^{13}$, CO, SO, SO$_2$, and CR$^{13}$R$^{14}$;

A is selected from —CH$_2$—, —CH$_2$CH$_2$—, —CH=CH—, =CH—, —NR$^{13}$—, —CH$_2$—O—, —O—, and —S—;

M is selected from =CH— and —C(O)—; or M is absent;

R$^1$, R$^2$, R$^8$, R$^9$, R$^{10}$ and R$^{11}$, which may be the same or different, are each selected from hydrogen, halogen, haloalkyl, alkyl, alkenyl, cycloalkyl, aryl, heterocyclyl, heteroaryl, alkynyl, —CN, —NR$^{13}$R$^{14}$, —OR$^{13}$, —COR$^{13}$, —CO$_2$R$^{13}$, —CONR$^{13}$R$^{14}$, —C(=NR$^{13}$)NR$^{14}$R$^{15}$, —NR$^{13}$COR$^{14}$, —NR$^{13}$CONR$^{14}$R$^{15}$, —NR$^{13}$CO$_2$R$^{14}$, —SO$_2$R$^{13}$, —SO$_2$aryl, —NR$^{13}$SO$_2$NR$^{14}$R$^{15}$, and —NR$^{13}$SO$_2$R$^{14}$, wherein the alkyl, alkenyl, alkynyl, cycloalkyl, heteroaryl, aryl, and heterocyclyl are each optionally substituted with at least one substituent R$^{16}$, or (R$^1$ and R$^2$), and/or (R$^8$ and R$^9$), and/or (R$^9$ and R$^{10}$), and/or (R$^{10}$ and R$^{11}$) together with the ring to which they are attached, form a fused ring selected from heterocyclyl, and heteroaryl rings optionally substituted with at least one substituent R$^{16}$;

R$^{12}$ is selected from hydrogen and alkyl;

R$^{13}$, R$^{14}$ and R$^{15}$, which may be the same or different, are each selected from H, haloalkyl, alkyl, alkenyl, alkynyl, cycloalkyl, heterocyclyl, aryl, and heteroaryl; or (R$^{13}$ and R$^{14}$), and/or (R$^{14}$ and R$^{15}$) together with the atom(s) to which they are attached, each form a ring selected from heterocyclyl, and heteroaryl rings optionally substituted with at least one substituent R$^{16}$;

R$^{16}$ is selected from halogen, haloalkyl, alkyl, alkenyl, cycloalkyl, aryl, heteroaryl, heterocyclyl, alkynyl, oxo, —CN, —OR', —NR'R", —COR', —CO$_2$R', —CONR'R", —C(=NR')NR"R'", —NR'COR", —NR'CONR'R", —NR'CO$_2$R", —SO$_2$R', —SO$_2$aryl, —NR'SO$_2$NR"R'", NR'SO$_2$R", and —NR'SO$_2$aryl, wherein R', R", and R'" are independently selected from H, haloalkyl, alkyl, alkenyl, alkynyl, cycloalkyl, heterocyclyl, aryl, and heteroaryl, or (R' and R"), and/or (R" and R'") together with the atoms to which they are attached, form a ring selected from heterocyclyl, and heteroaryl rings.

In some embodiments, A-M in Formula (III) is —CH$_2$—CH$_2$—C(O)—.

In some embodiments, A-M in Formula (III) is —CH=CH—.

In some embodiments, A-M in Formula (III) is —CH$_2$—O—C(O)—.

In some embodiments, $R^{12}$ in Formula (III) is H.
In some embodiments, X in Formula (III) is O.
In some embodiments, X in Formula (III) is $CH_2$.
In some embodiments, Z in Formula (III) is O.
In some embodiments, $R^8$, $R^9$, $R^{10}$, and $R^{11}$ in Formula (III), which may be the same or different, are each selected from alkyl (e.g., methyl, tert-butyl), hydrogen, haloalkyl (e.g., —$CF_3$), halogen, hydroxy, —CN, —Oalkyl (e.g., methoxy), —Ohaloalkyl (e.g., $OCF_3$), and aryl (e.g., phenyl).

In some embodiments, the at least one compound selected from compounds of Formula (I), stereoisomers thereof, and pharmaceutically acceptable salts thereof, is selected from compounds of Formula (IV):

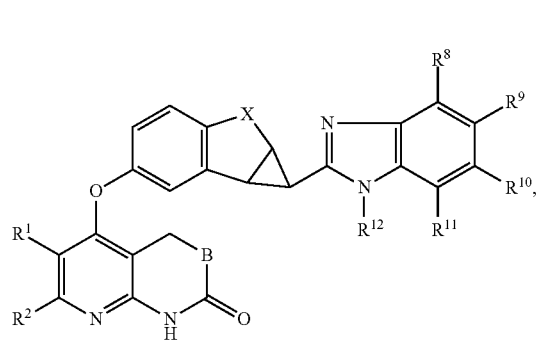

IV stereoisomers thereof, and pharmaceutically acceptable salts thereof,
wherein:
B is selected from $CH_2$, O, and $NR^{13}$;
X is selected from $CH_2$ and O;
$R^1$, $R^2$, $R^8$, $R^9$, $R^{10}$ and $R^{11}$, which may be the same or different, are each selected from hydrogen, halogen, haloalkyl, alkyl, alkenyl, cycloalkyl, aryl, heterocyclyl, heteroaryl, alkynyl, —CN, —$NR^{13}R^{14}$, —$OR^{13}$, —$COR^{13}$, —$CO_2R^{13}$, —$CONR^{13}R^{14}$, —$C(=NR^{13})NR^{14}R^{15}$, —$NR^{13}COR^{14}$, —$NR^{13}CONR^{14}R^{15}$, —$NR^{13}CO_2R^{14}$, —$SO_2R^{13}$, —$SO_2$aryl, —$NR^{13}SO_2NR^{14}R^{15}$, and —$NR^{13}SO_2R^{14}$, wherein the alkyl, alkenyl, alkynyl, cycloalkyl, heteroaryl, aryl, and heterocyclyl are each optionally substituted with at least one substituent $R^{16}$, or ($R^1$ and $R^2$), and/or ($R^8$ and $R^9$), and/or ($R^9$ and $R^{10}$), and/or ($R^{10}$ and $R^{11}$) together with the ring to which they are attached, form a fused ring selected from heterocyclyl, and heteroaryl rings optionally substituted with at least one substituent $R^{16}$;
$R^{12}$ is selected from hydrogen and alkyl;
$R^{13}$, $R^{14}$ and $R^{15}$, which may be the same or different, are each selected from H, haloalkyl, alkyl, alkenyl, alkynyl, cycloalkyl, heterocyclyl, aryl, and heteroaryl; or ($R^{13}$ and $R^{14}$), and/or ($R^{14}$ and $R^{15}$) together with the atom(s) to which they are attached, each form a ring selected from heterocyclyl, and heteroaryl rings optionally substituted with at least one substituent $R^{16}$;
$R^{16}$ is selected from halogen, haloalkyl, alkyl, alkenyl, cycloalkyl, aryl, heteroaryl, heterocyclyl, alkynyl, oxo, —CN, —OR', —NR'R", —COR', —$CO_2$R', —CONR'R", —C(=NR')NR"R"', —NR'COR", —NR'CONR'R"', —$NR'CO_2R"$, —$SO_2$R', —$SO_2$aryl, —$NR'SO_2NR"R"'$, $NR'SO_2R"$, and —$NR'SO_2$aryl, wherein R', R", and R"' are independently selected from H, haloalkyl, alkyl, alkenyl, alkynyl, cycloalkyl, heterocyclyl, aryl, and heteroaryl, or (R' and R"), and/or (R" and R"') together with the atoms to which they are attached, form a ring selected from heterocyclyl, and heteroaryl rings.

In some embodiments, $R^1$ and $R^2$, which may be the same or different, are each selected from hydrogen, alkyl, and halo.

In some embodiments, $R^{12}$ in Formula (IV) is H.
In some embodiments, X in Formula (IV) is O.
In some embodiments, X in Formula (IV) is $CH_2$.
In some embodiments, $R^8$, $R^9$, $R^{10}$, and $R^{11}$ in Formula (IV), which may be the same or different, are each selected from alkyl (e.g., methyl, tert-butyl), hydrogen, haloalkyl (e.g., —$CF_3$), halogen, hydroxy, —CN, —Oalkyl(e.g., methoxy), —Ohaloalkyl(e.g., $OCF_3$), and aryl (e.g., phenyl).

In some embodiments, the at least one compound selected from compounds of Formula (I), stereoisomers thereof, and pharmaceutically acceptable salts thereof, is selected from compounds of Formula (V):

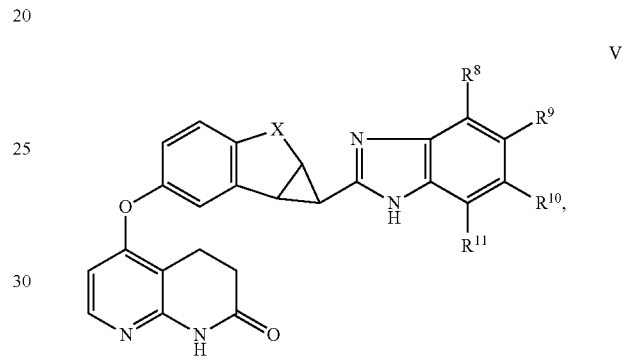

V stereoisomers thereof, and pharmaceutically acceptable salts thereof,
wherein:
X is selected from $CH_2$ and O;
$R^8$, $R^9$, $R^{10}$ and $R^{11}$, which may be the same or different, are each selected from hydrogen, halogen, alkyl, alkenyl, cycloalkyl, aryl, heterocyclyl, heteroaryl, alkynyl, —$NR^{13}R^{14}$, —$OR^{13}$, —$COR^{13}$, —$CO_2R^{13}$, —$CONR^{13}R^{14}$, —$C(=NR^{13})NR^{14}R^{15}$, —$NR^{13}COR^{14}$, —$NR^{13}CONR^{14}R^{15}$, —$NR^{13}CO_2R^{14}$, —$SO_2R^{13}$, —$SO_2$aryl, —$NR^{13}SO_2NR^{14}R^{15}$, and —$NR^{13}SO_2R^{14}$, wherein the alkyl, alkenyl, alkynyl, cycloalkyl, heteroaryl, aryl, and heterocyclyl are each optionally substituted with at least one substituent $R^{16}$, or ($R^8$ and $R^9$), and/or ($R^9$ and $R^{10}$), and/or ($R^{10}$ and $R^{11}$) together with the ring to which they are attached, form a fused ring selected from heterocyclyl, and heteroaryl rings optionally substituted with at least one substituent $R^{16}$;
$R^{13}$, $R^{14}$ and $R^{15}$, which may be the same or different, are each selected from H, haloalkyl, alkyl, alkenyl, alkynyl, cycloalkyl, heterocyclyl, aryl, and heteroaryl; or ($R^{13}$ and $R^{14}$), and/or ($R^{14}$ and $R^{15}$) together with the atom(s) to which they are attached, each form a ring selected from heterocyclyl, and heteroaryl rings optionally substituted with at least one substituent $R^{16}$;
$R^{16}$ is selected from halogen, haloalkyl, alkyl, alkenyl, cycloalkyl, aryl, heteroaryl, heterocyclyl, alkynyl, oxo, —CN, —OR', —NR'R", —COR', —$CO_2$R', —CONR'R", —C(=NR')NR"R"'H, —NR'COR", —NR'CONR'R"', —$NR'CO_2R"$, —$SO_2$R', —$SO_2$aryl, —$NR'SO_2NR"R"'$, $NR'SO_2R"$, and —$NR'SO_2$aryl, wherein R', R", and R"' are independently selected from H, haloalkyl, alkyl, alkenyl, alkynyl, cycloalkyl, heterocyclyl, aryl, and heteroaryl, or (R' and R''), and/or (R'' and R''') together with the atoms to which they are attached, form a ring selected from heterocyclyl, and heteroaryl rings.

In some embodiments, the at least one compound of Formula (V) is optically pure.

In some embodiments, X in Formula (V) is O.

In some embodiments, X in Formula (V) is CH$_2$.

In some embodiments, $R^8$, $R^9$, $R^{10}$, and $R^{11}$ in Formula (III), which may be the same or different, are each selected from alkyl (e.g., methyl, tert-butyl), hydrogen, haloalkyl (e.g., —CF$_3$), halogen, hydroxy, —CN, —Oalkyl (e.g., methoxy), —Ohaloalkyl (e.g., OCF$_3$), and aryl (e.g., phenyl).

Also provided herein is at least one compound selected from the following compounds, stereoisomers thereof, and pharmaceutically acceptable salts thereof:

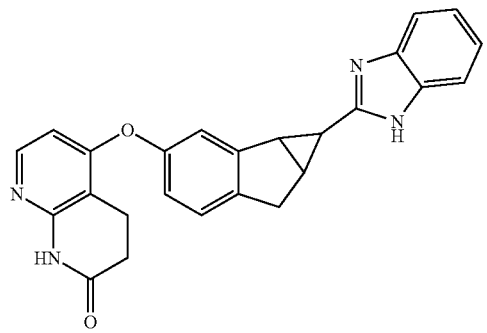

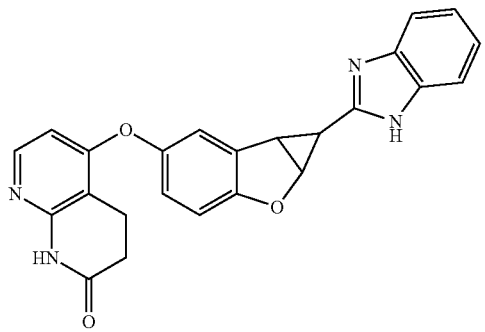

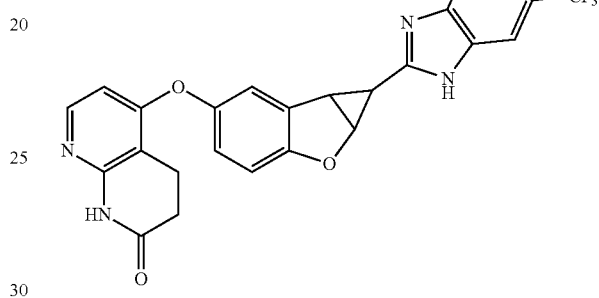

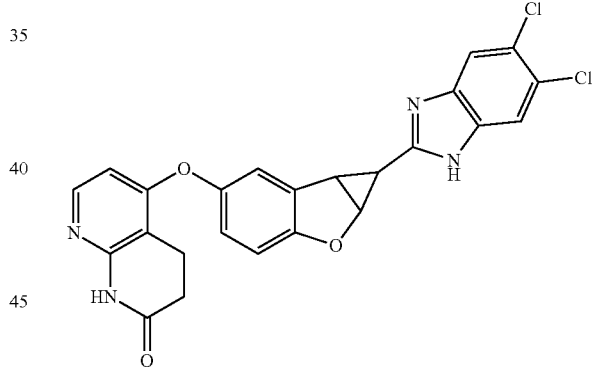

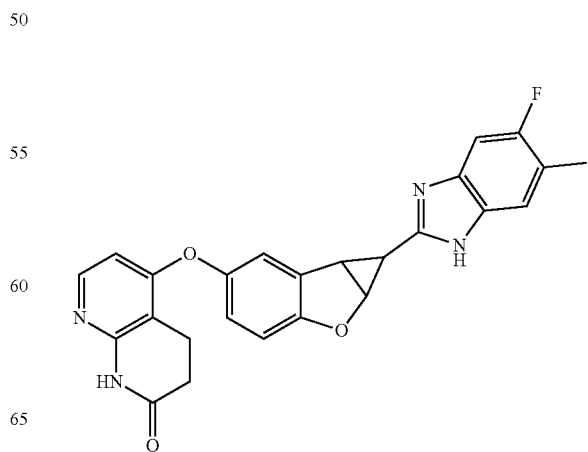

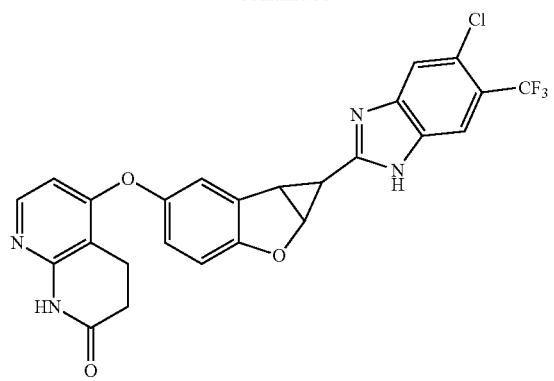
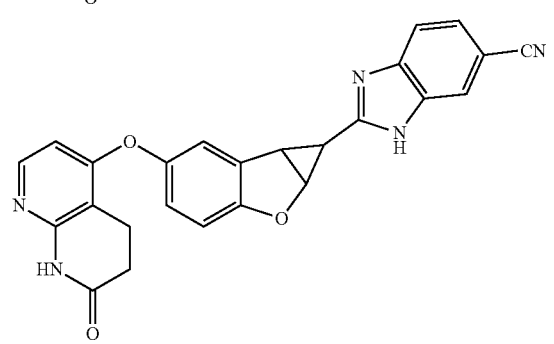
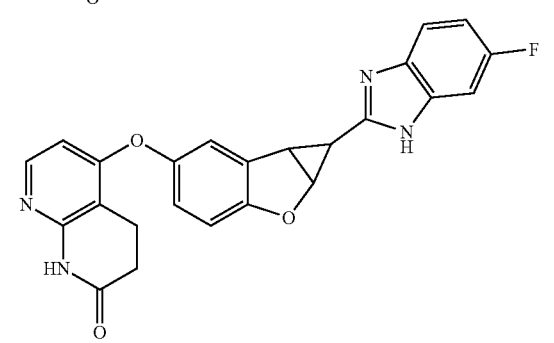
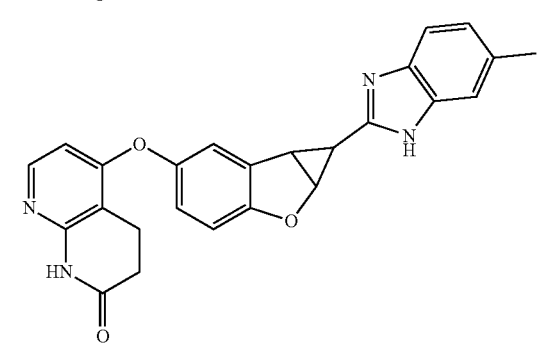
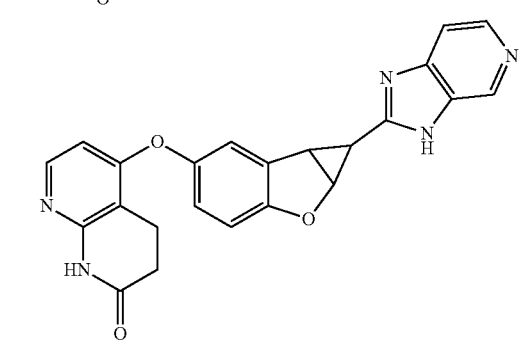
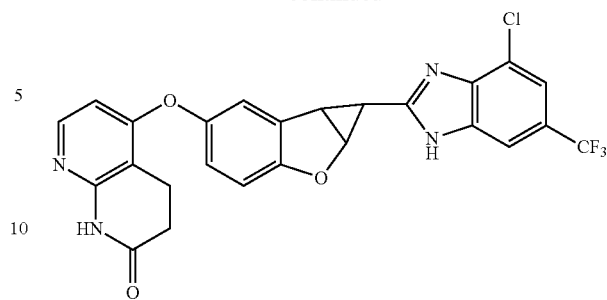
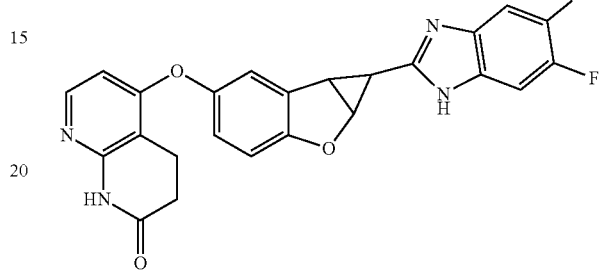
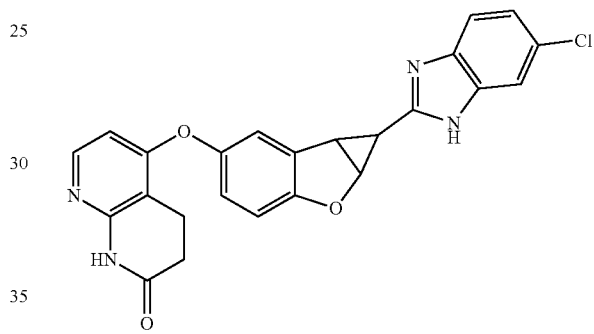
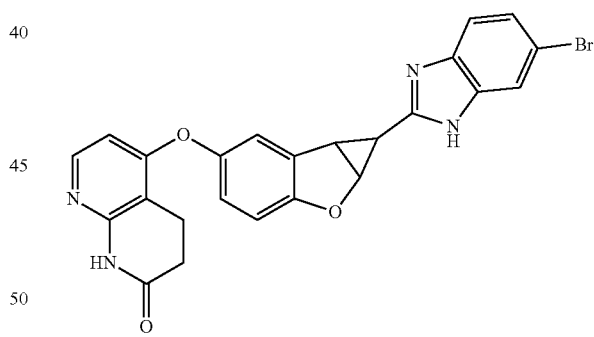
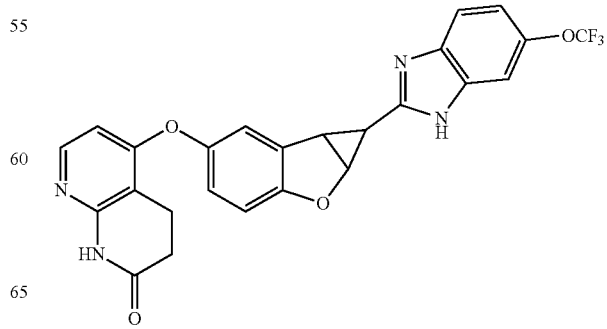

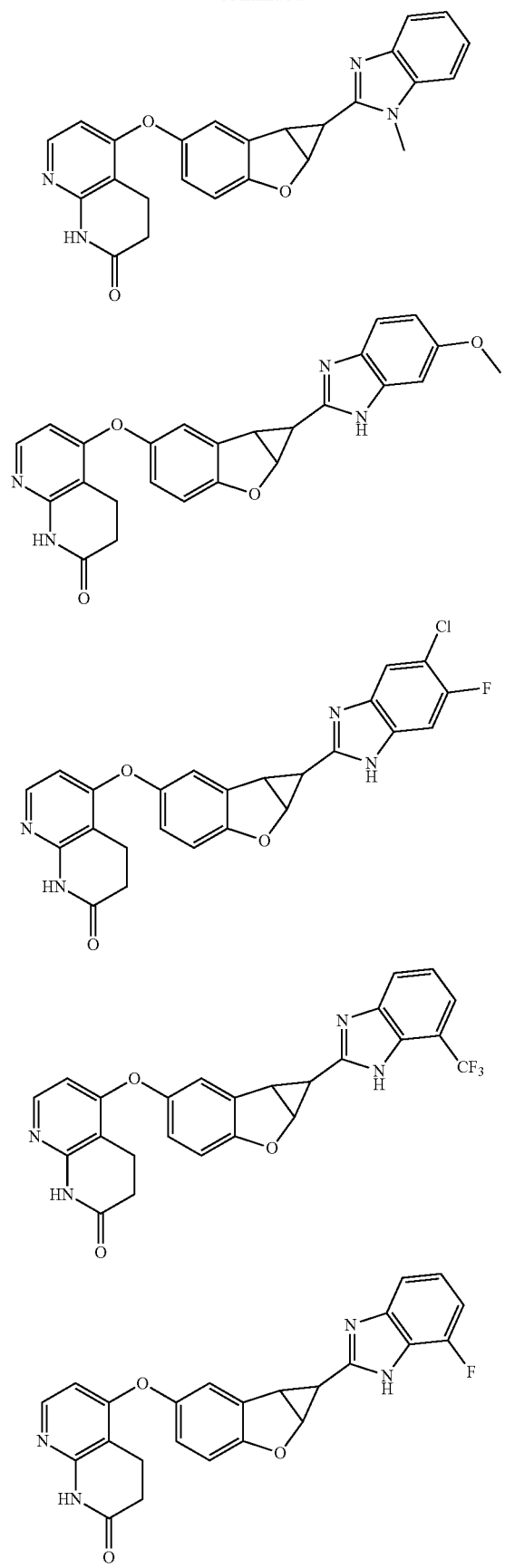
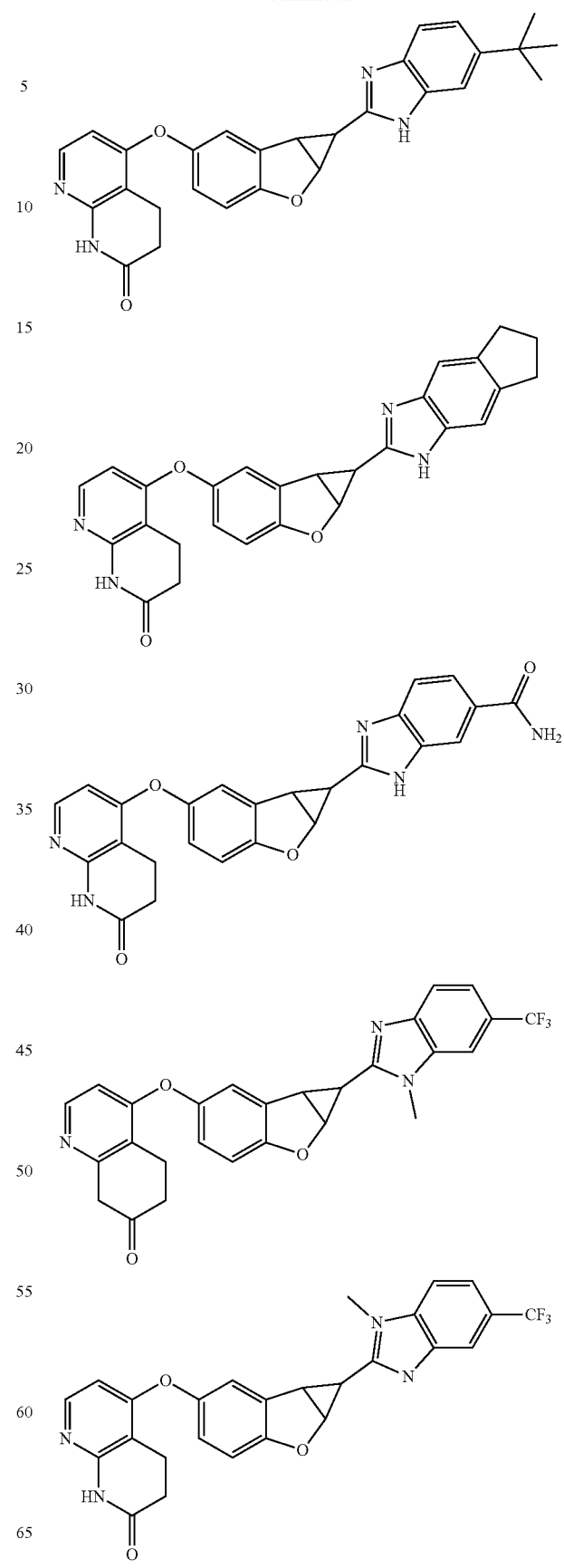

21
-continued
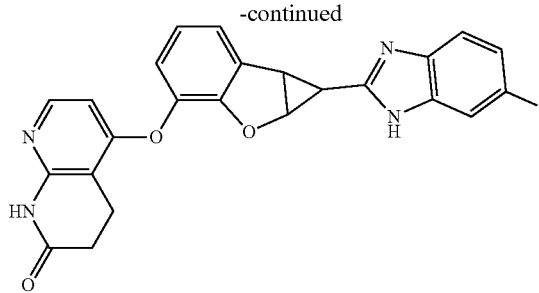
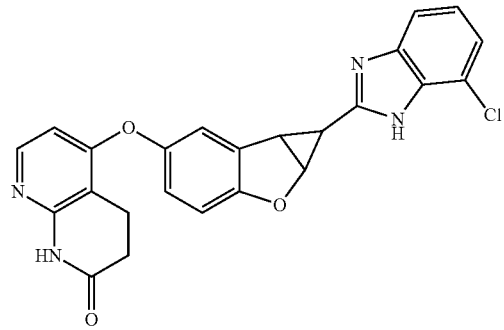
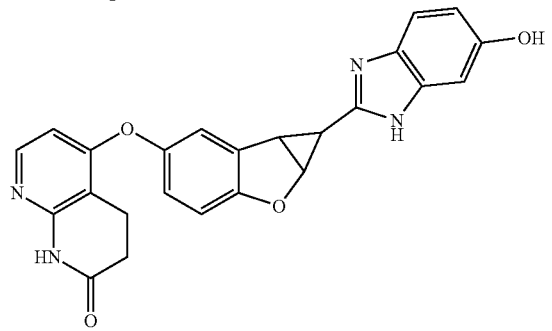
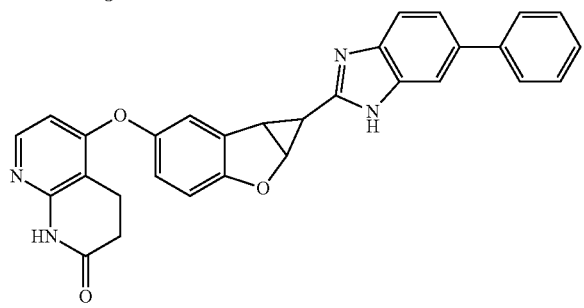
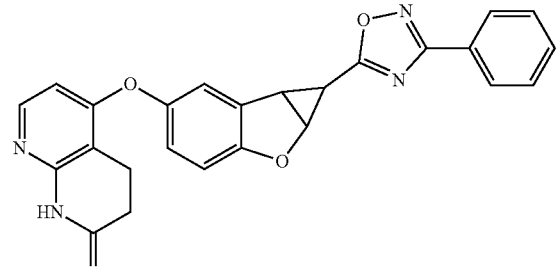
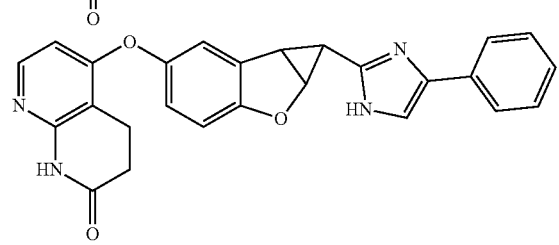
22
-continued
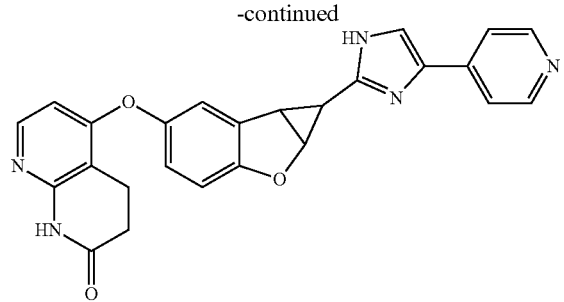
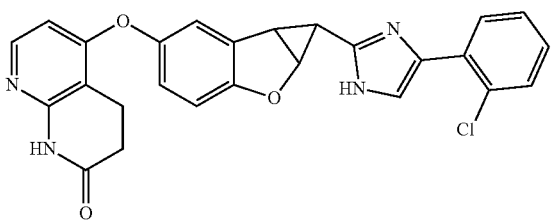
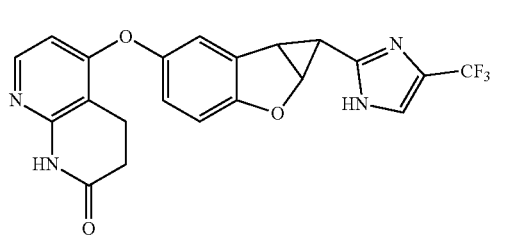
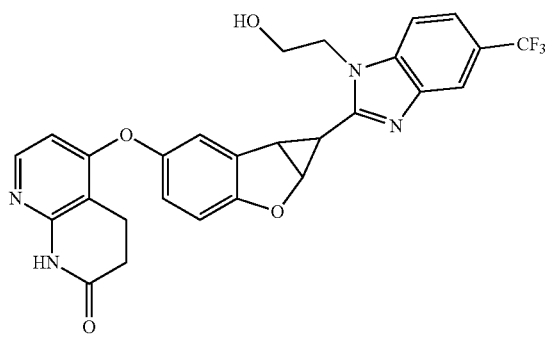
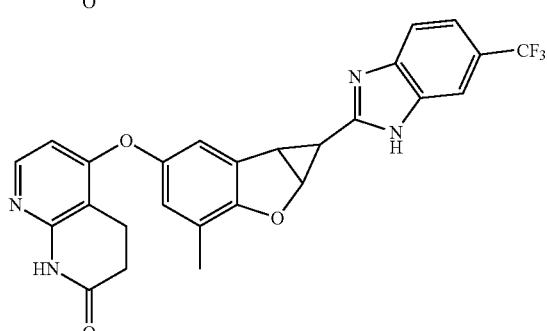
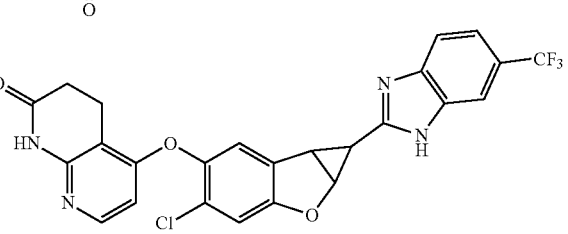

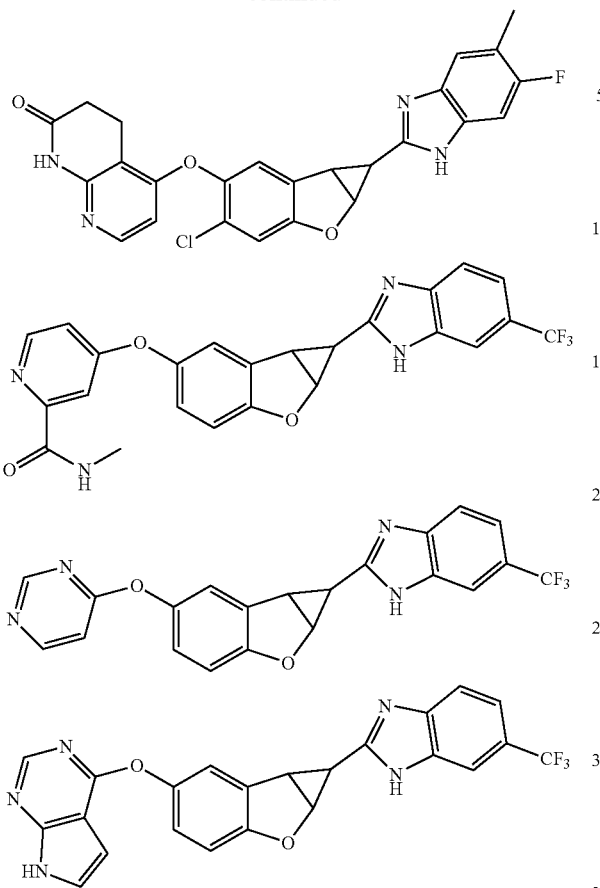
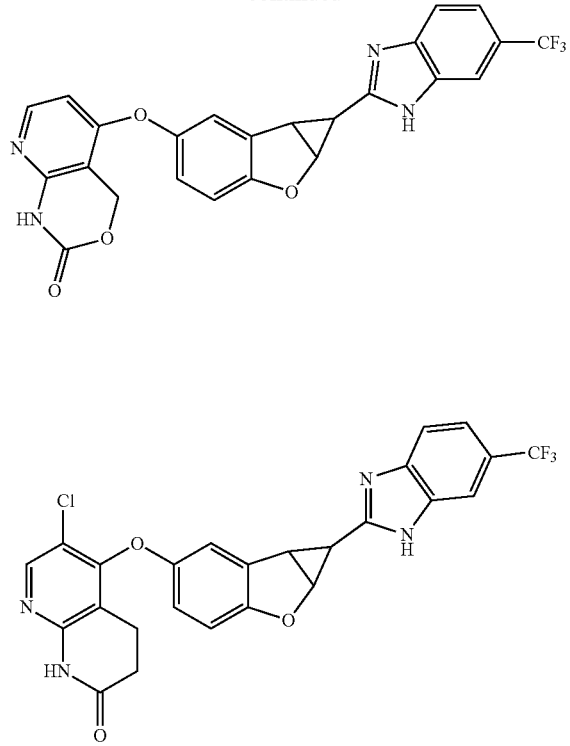
Also provided herein is at least one compound selected from the following compounds showing the following stereochemistry:
Compound 1.2a
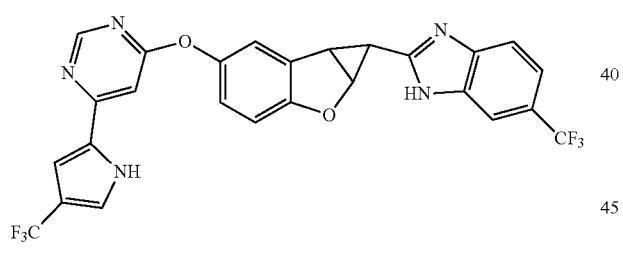
Compound 1.2b
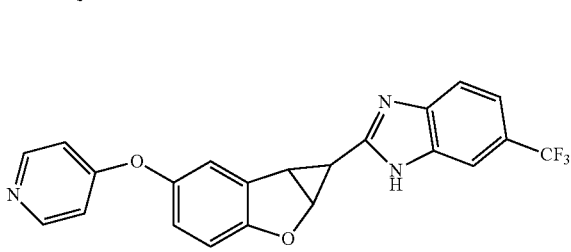

Compound 2.2a
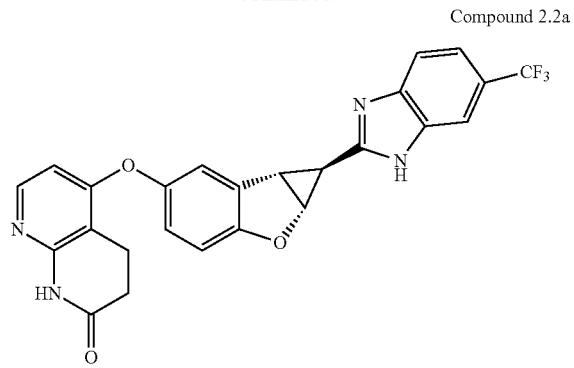
Compound 2.4b
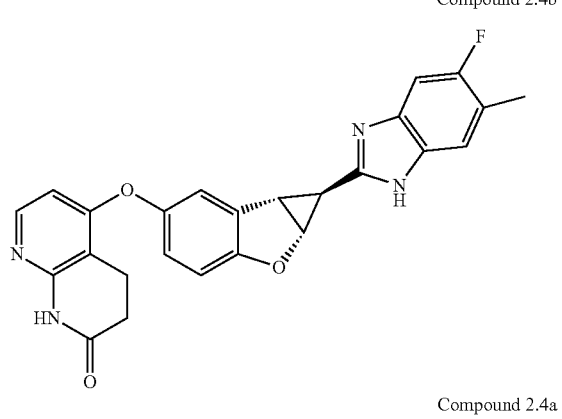
Compound 2.2b
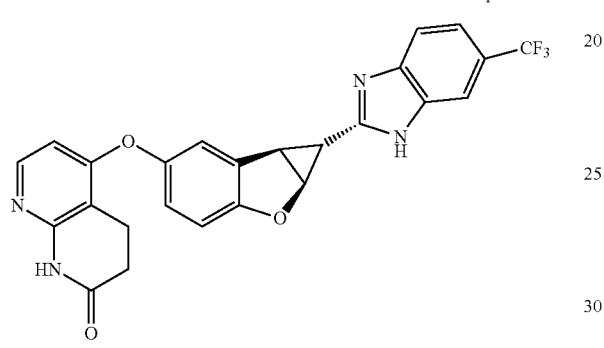
Compound 2.4a
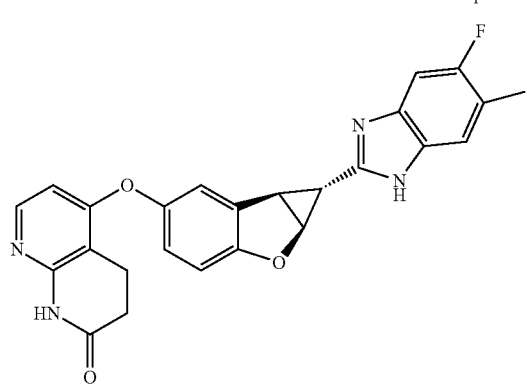
Compound 2.3b
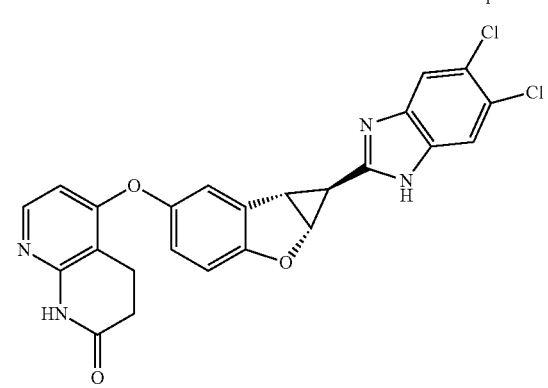
Compound 2.5b
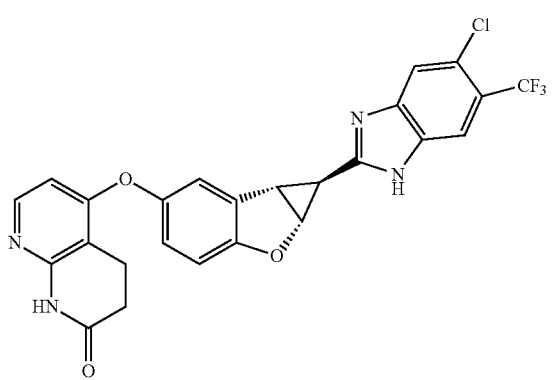
Compound 2.3a
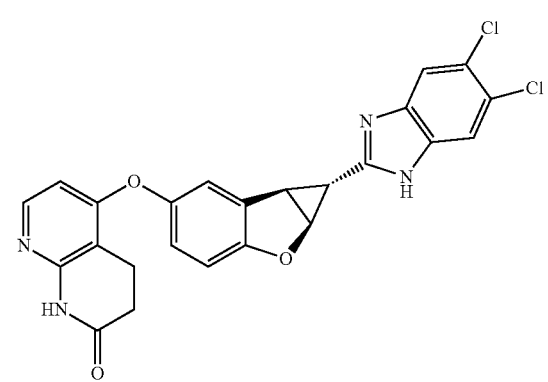
Compound 2.5a
The compounds disclosed herein, and/or the pharmaceutically acceptable salts thereof, can be synthesized from commercially available starting materials taken together with the disclosure herein. The following scheme illustrates methods for preparation of some of the compounds disclosed herein.

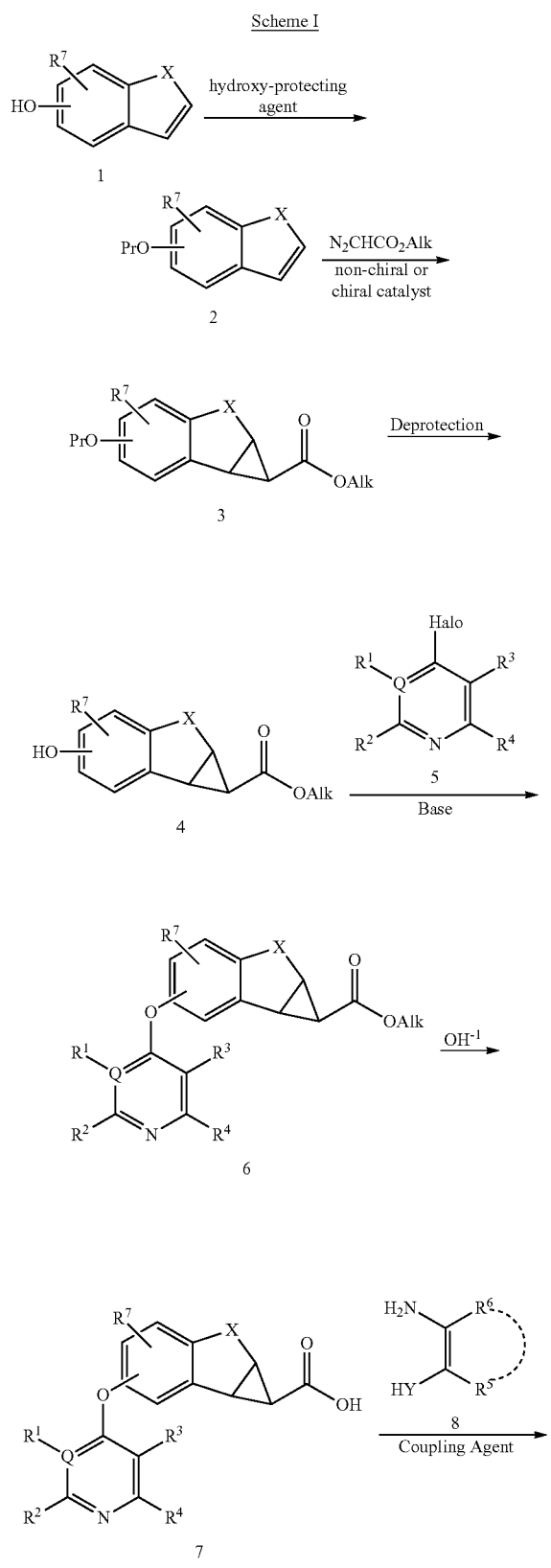
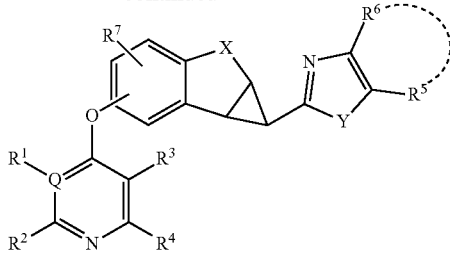

Pr = protecting group;
PrO = protected hydroxy group;
Alk = alkyl group;
Halo = halogen;

In this scheme, the hydroxyl group of a commercially available hydroxyl benzofuran or hydroxyindene of formula I is protected with a hydroxyl protecting group (such as methyl, ethyl, isopropyl, benzyl, p-methoxybenzyl, trityl, methoxymethyl, tetrahydropyranyl acetyl, benzoate, trimethylsilyl, triethylsilyl, tri-isopropylsilyl, tert-butyl dimethylsilyl or tert-butyldiphenylsilyl, further such as benzyl from benzyl bromide, and tert-butyldiphenylsilyl from TBSCl) to provide a protected hydroxybenzofuran or hydroxyindene of formula 2. The compound of formula 2 reacts with alkyl diazo-acetate (such as ethyl diazo-acetate) in the presence of a Rh or Cu catalyst to provide a cyclopropane derivative of formula 3. The chiral derivative of formula 3 may be obtained by using a chiral catalyst formed in situ from $Cu(OOCCF_3)_2$ and a chiral amino alcohol or by using a commercially available chiral Rh catalyst. The compound of formula 3 is deprotected as described above to provide a phenol derivative of formula 4(for example, the TBS protecting group may be removed by treating with pyridine hydrogen fluoride). The resulting phenol derivative of formula 4 reacts with haloheteroaryl derivative of formula 5(such as fluoro-substituted heteroaryl derivative of formula 5) to provide a compound of formula 6, which subsequently is hydrolyzed into the free acid of formula 7 by using a base such as sodium hydroxide. The further coupling and cyclization of the acid 7 is accomplished under standard conditions known in the art to provide a compound of Formula I.

Also provided herein is a method of treating cancer responsive to inhibition of Raf kinase comprising administering to a subject, such as a mammal or human, in need of treating for the cancer an effective amount of at least one compound selected from compounds of Formula (I) (such as Formulae (II), (III), (IV) and (V)), stereoisomers thereof, and pharmaceutically acceptable salts thereof described herein.

The at least one compound selected from compounds of Formula (I) (such as Formulae (II), (III), (IV) and (V)), stereoisomers thereof, and pharmaceutically acceptable salts thereof may be employed alone or in combination with at least one other therapeutic agent for treatment. In some embodiments, the at least one compound selected from compounds of Formula (I) (such as Formulae (II), (III), (IV) and (V)), stereoisomers thereof, and pharmaceutically acceptable salts thereof can be used in combination with at least one additional therapeutic agent. The at least one additional therapeutics agent can be, for example, selected from anti-hyperproliferative, anti-cancer, and chemotherapeutic agents. The at least one compound and/or at least one pharmaceutically acceptable salt disclosed herein may be administered with the at least one other therapeutic agent in a single dosage form or as a separate dosage form. When administered as a separate dosage form, the at least one other therapeutic agent may be administered prior to, at the same time as, or following administration of the at least one compound and/or at least one pharmaceutically acceptable salt disclosed herein A "chemotherapeutic agent" is a chemical compound useful in the treatment of cancer, regardless of mechanism of action. Chemotherapeutic agents include compounds used in "targeted therapy" and conventional chemotherapy. Suitable chemotherapeutic agents can be, for example, selected from: agents that induce apoptosis; polynucleotides (e.g., ribozymes); polypeptides (e.g., enzymes); drugs; biological mimetics; alkaloids; alkylating agents; antitumor antibiotics; antimetabolites; hormones; platinum compounds; monoclonal antibodies conjugated with anti-cancer drugs, toxins, and/or radionuclides; biological response modifiers (e.g., interferons, such as IFN-a and interleukins, such as IL-2); adoptive immunotherapy agents; hematopoietic growth factors; agents that induce tumor cell differentiation (e.g., all-trans-retinoic acid); gene therapy reagents; antisense therapy reagents and nucleotides; tumor vaccines; and inhibitors of angiogenesis.

Examples of chemotherapeutic agents include Erlotinib (TARCEVA®, Genentech/OSI Pharm.); Bortezomib (VELCADE®, Millennium Pharm.); Fulvestrant (FASLODEX®, AstraZeneca); Sunitinib (SUTENT®, Pfizer); Letrozole (FEMARA®, Novartis); Imatinib mesylate (GLEEVEC®, Novartis); PTK787/ZK 222584 (Novartis); Oxaliplatin (Eloxatin®, Sanofi); 5-FU (5-fluorouracil); Leucovorin; Rapamycin (Sirolimus, RAPAMUNE®, Wyeth); Lapatinib (TYKERB®, GSK572016, Glaxo Smith Kline); Lonafarnib (SCH 66336); Sorafenib (NEXAVAR®, Bayer); Irinotecan (CAMPTOSAR®, Pfizer) and Gefitinib (IRESSA®, AstraZeneca); AG 1478, AG 1571 (SU 5271, Sugen); alkylating agents such as thiotepa and CYTOXAN® cyclosphosphamide; alkyl sulfonates such as busulfan, improsulfan and piposulfan; aziridines such as benzodopa, carboquone, meturedopa, and uredopa; ethylenimines and methylamelamines such as altretamine, triethylenemelamine, triethylenephosphoramide, triethylenethiophosphoramide and trimethylomelamine; acetogenins (such as bullatacin and bullatacinone); a camptothecin (such as the synthetic analog topotecan); bryostatin; callystatin; CC-1065 and its adozelesin, carzelesin and bizelesin synthetic analogs; cryptophycins (such as cryptophycin 1 and cryptophycin 8); dolastatin; duocarmycin and the synthetic analogs thereof, such as KW-2189 and CB1-TM1; eleutherobin; pancratistatin; a sarcodictyin; spongistatin; nitrogen mustards such as chlorambucil, chlomaphazine, chlorophosphamide, estramustine, ifosfamide, mechlorethamine, mechlorethamine oxide hydrochloride, melphalan, novembichin, phenesterine, prednimustine, trofosfamide, uracil mustard; nitrosureas such as carmustine, chlorozotocin, fotemustine, lomustine, nimustine, and ranimnustine; antibiotics such as the enediyne antibiotics (e.g., calicheamicin, such as calicheamicin gammaII and calicheamicin omegaII (Angew Chem. Intl. Ed. Engl. (1994) 33:183-186); dynemicin, such,as dynemicin A; bisphosphonates, such as clodronate; an esperamicin; as well as neocarzinostatin chromophore and related chromoprotein enediyne antibiotic chromophores, actacinomysins, actinomycin, authramycin, azaserine, bleomycins, cactinomycin, carabicin, caminomycin, carzinophilin, chromomycinis, dactinomycin, daunorubicin, detorubicin, 6-diazo-5-oxo-L-norleucine, ADRIAMYCIN® (doxorubicin), morpholino-doxorubicin, cyanomorpholino-doxorubicin, 2-pyrrolino-doxorubicin and deoxydoxorubicin), epirubicin, esorubicin, idarubicin, marcellomycin, mitomycins such as mitomycin C, mycophenolic acid, nogalamycin, olivomycins, peplomycin, porfiromycin, puromycin, quelamycin, rodorubicin, streptonigrin, streptozocin, tubercidin, ubenimex, zinostatin, zorubicin; anti-metabolites such as methotrexate and 5-fluorouracil (5-FU); folic acid analogs such as denopterin, methotrexate, pteropterin, trimetrexate; purine analogs such as fludarabine, 6-mercaptopurine, thiamiprine, thioguanine; pyrimidine analogs such as ancitabine, azacitidine, 6-azauridine, carmofur, cytarabine, dideoxyuridine, doxifluridine, enocitabine, floxuridine; and rogens such as calusterone, dromostanolone propionate, epitiostanol, mepitiostane, testolactone; anti-adrenals such as aminoglutethimide, mitotane, trilostane; folic acid replenisher such as frolinic acid; aceglatone; aldophosphamide glycoside; amino levulinic acid; eniluracil; amsacrine; bestrabucil; bisantrene; edatraxate; defofamine; demecolcine; diaziquone; elformithine; elliptinium acetate; an epothilone; etoglucid; gallium nitrate; hydroxyurea; lentinan; lonidainine; maytansinoids such as maytansine and ansamitocins; mitoguazone; mitoxantrone; mopidanmol; nitracrine; pentostatin; phenamet; pirarubicin; losoxantrone; podophyllinic acid; 2-ethylhydrazide; procarbazine; PSK® polysaccharide complex (JHS Natural Products, Eugene, Oreg.); razoxane; rhizoxin; sizofuran; spirogermanium; tenuazonic acid; triaziquone; 2,2',2''-trichlorotriethylamine; trichothecenes (such as T-2 toxin, verracurin A, roridin A and anguidine); urethan; vindesine; dacarbazine; mannomustine; mitobronitol; mitolactol; pipobroman; gacytosine; arabinoside ("Ara-C"); cyclophosphamide; thiotepa; taxoids, e.g., TAXOL® (paclitaxel; Bristol-Myers Squibb Oncology, Princeton, N.J.), ABRAXANE® (Cremophor-free), albumin-engineered nanoparticle formulations of paclitaxel (American Pharmaceutical Partners, Schaumberg, Ill.), and TAXOTERE® (doxetaxel; Rhone-Poulenc Rorer, Antony, France); chloranmbucil; GEMZAR® (gemcitabine); 6-thioguanine; mercaptopurine; methotrexate; platinum analogs such as cisplatin and carboplatin; vinblastine; etoposide (VP-16); ifosfamide; mitoxantrone; vincristine; NAVELBINE® (vinorelbine); novantrone; teniposide; edatrexate; daunomycin; aminopterin; capecitabine (XELODA®); ib and ronate; CPT-11; topoisomerase inhibitor RFS 2000; difluoromethylornithine (DMFO); retinoids such as retinoic acid; and pharmaceutically acceptable salts, acids and derivatives of any of the above.

The "chemotherapeutic agent" can also be selected, for example, from: (i) anti-hormonal agents that act to regulate or inhibit hormone action on tumors such as anti-estrogens and selective estrogen receptor modulators (SERMs), including, for example, tamoxifen (including NOLVADEX®; tamoxifen citrate), raloxifene, droloxifene, 4-hydroxytamoxifen, trioxifene, keoxifene, LY117018, onapristone, and FARESTON® (toremifine citrate); (ii) aromatase inhibitors that inhibit the enzyme aromatase, which regulates estrogen production in the adrenal glands, such as, for example, 4(5)-imidazoles, aminoglutethimide, MEGASE® (megestrol acetate), AROMASIN® (exemestane; Pfizer), formestanie, fadrozole, RIVISOR® (vorozole), FEMARA® (letrozole; Novartis), and ARIMIDEX® (anastrozole; AstraZeneca); (iii) anti- and rogens such as flutamide, nilutamide, bicalutamide, leuprolide, and goscrelin; as well as troxacitabine (a 1,3-dioxolane nucleoside cylosine analog); (iv) protein kinase inhibitors; (v) lipid kinase inhibitors; (vi) antisense oligonucleotides, such as those which inhibit expression of genes in signaling pathways implicated in aberrant cell proliferation, such as, for example, PKC-alpha, Ralf and H-Ras; (vii) ribozymes such as VEGF expression inhibitors (e.g., ANGIOZYME®) and HER$^2$ expression inhibitors; (viii) vaccines such as gene therapy vaccines, for example, ALLOVECTIN®, LEUVECTIN®, and VAXID®; PROLEUKIN® rIL-2; a topoisomerase 1 inhibitor such as LURTOTECAN(®); ABARELIX® rmRH; (ix) anti-angiogenic agents such as bevacizumab (AVASTIN®, Genentech); and (x) pharmaceutically acceptable salts, acids and derivatives of any of the above.

The "chemotherapeutic agent" can also be selected, for example, from therapeutic antibodies such as alemtuzumab (Campath), bevacizumab (AVASTIN®, Genentech); cetuximab (ERBITUX®, Imclone); panitumumab (VECTIBIX®, Amgen), rituximab (RITUXAN®, Genentech/Biogen Idec), pertuzumab (OMNITARG®, 2C4, Genentech), trastuzumab (HERCEPTIN®, Genentech), tositumomab (Bexxar, Corixia), and the antibody drug conjugate, gemtuzumab ozogamicin (MYLOTARG®, Wyeth).

Humanized monoclonal antibodies with therapeutic potential as chemotherapeutic agents in combination with the at least one compound selected from compounds of Formula (I) (such as Formulae (II), (III), (IV) and (V)), stereoisomers thereof, and pharmaceutically acceptable salt thereof may, for example, be selected from: alemtuzumab, apolizumab, aselizumab, atlizumab, bapineuzumab, bevacizumab, bivatuzumab mertansine, cantuzumab mertansine, cedelizumab, certolizumab pegol, cidfusituzumab, cidtuzumab, daclizumab, eculizumab, efalizumab, epratuzumab, erlizumab, felvizumab, fontolizumab, gemtuzumab ozogamicin, inotuzumab ozogamicin, ipilimumab, labetuzumab, lintuzumab, matuzumab, mepolizumab, motavizumab, motovizumab, natalizumab, nimotuzumab, nolovizumab, numavizumab, ocrelizumab, omalizumab, palivizumab, pascolizumab, pecfusituzumab, pectuzumab, pertuzumab, pexelizumab, ralivizumab, ranibizumab, reslivizumab, reslizumab, resyvizumab, rovelizumab, ruplizumab, sibrotuzumab, siplizumab, sontuzumab, tacatuzumab tetraxetan, tadocizumab, talizumab, tefibazumab, tocilizumab, toralizumab, trastuzumab, tucotuzumab celmoleukin, tucusituzumab, umavizumab, urtoxazumab, and visilizumab.

Also provided herein is a composition comprising at least one compound selected from compounds of Formula (I) (such as Formulae (II), (III), (IV) and (V)), stereoisomers thereof, and pharmaceutically acceptable salts thereof, and at least one pharmaceutically acceptable carrier.

The composition comprising at least one compound selected from compounds of Formula (I) (such as Formulae (II), (III), (IV) and (V)), stereoisomers thereof, and pharmaceutically acceptable salts thereof can be administered in various known manners, such as orally, topically, rectally, parenterally, by inhalation spray, or via an implanted reservoir, although the most suitable route in any given case will depend on the particular host, and nature and severity of the conditions for which the active ingredient is being administered. The term "parenteral" as used herein includes subcutaneous, intracutaneous, intravenous, intramuscular, intraarticular, intraarterial, intrasynovial, intrasternal, intrathecal, intralesional and intracranial injection or infusion techniques. The compositions disclosed herein may be conveniently presented in unit dosage form and prepared by any of the methods well known in the art.

The at least one compound selected from Formula (I) (such as Formulae (II), (III), (IV) and (V)), stereoisomers thereof, and pharmaceutically acceptable salts thereof can be administered orally in solid dosage forms, such as capsules, tablets, troches, dragées, granules and powders, or in liquid dosage forms, such as elixirs, syrups, emulsions, dispersions, and suspensions. The at least one compound selected from compounds of Formula (I) (such as Formulae (II), (III), (IV) and (V)), stereoisomers thereof, and pharmaceutically acceptable salts thereof disclosed herein can also be administered parenterally, in sterile liquid dosage forms, such as dispersions, suspensions or solutions. Other dosages forms that can also be used to administer the at least one compound selected from Formula (I) (such as Formulae (II), (III), (IV) and (V)), stereoisomers thereof, and pharmaceutically acceptable salts thereof disclosed herein as an ointment, cream, drops, transdermal patch or powder for topical administration, as an ophthalmic solution or suspension formation, i.e., eye drops, for ocular administration, as an aerosol spray or powder composition for inhalation or intranasal administration, or as a cream, ointment, spray or suppository for rectal or vaginal administration.

Gelatin capsules containing the at least one compound and/or the at least one pharmaceutically acceptable salt thereof disclosed herein and powdered carriers, such as lactose, starch, cellulose derivatives, magnesium stearate, stearic acid, and the like, can also be used. Similar diluents can be used to make compressed tablets. Both tablets and capsules can be manufactured as sustained release products to provide for continuous release of medication over a period of time. Compressed tablets can be sugar coated or film coated to mask any unpleasant taste and protect the tablet from the atmosphere, or enteric coated for selective disintegration in the gastrointestinal tract.

Liquid dosage forms for oral administration can further comprise at least one agent selected from coloring and flavoring agents to increase patient acceptance.

In general, water, a suitable oil, saline, aqueous dextrose (glucose), and related sugar solutions and glycols such as propylene glycol or polyethylene gycols can be examples of suitable carriers for parenteral solutions. Solutions for parenteral administration may comprise a water soluble salt of the at least one compound describe herein, at least one suitable stabilizing agent, and if necessary, at least one buffer substance. Antioxidizing agents such as sodium bisulfite, sodium sulfite, or ascorbic acid, either alone or combined, can be examples of suitable stabilizing agents. Citric acid and its salts and sodium EDTA can also be used as examples of suitable stabilizing agents. In addition, parenteral solutions can further comprise at least one preservative, selected, for example, from benzalkonium chloride, methyl- and propylparaben, and chlorobutanol.

A pharmaceutically acceptable carrier is, for example, selected from carriers that are compatible with active ingredients of the composition (and in some embodiments, capable of stabilizing the active ingredients) and not deleterious to the subject to be treated. For example, solubilizing agents, such as cyclodextrins (which can form specific, more soluble complexes with the at least one compound and/or at least one pharmaceutically acceptable salt disclosed herein), can be utilized as pharmaceutical excipients for delivery of the active ingredients. Examples of other carriers include colloidal silicon dioxide, magnesium stearate, cellulose, sodium lauryl sulfate, and pigments such as D&C Yellow #10. Suitable pharmaceutically acceptable carriers are described in Remington's Pharmaceutical Sciences, A. Osol, a standard reference text in the art.

The at least one compound selected from compounds of Formula (I) (such as Formulae (II), (III), (IV) and (V)), stereoisomers thereof, and pharmaceutically acceptable salts thereof disclosed herein can further be examined for efficacy in treating cancer by in vivo assays. For example, the at least one compound and/or the at least one pharmaceutically acceptable salts thereof disclosed herein can be administered to an animal (e.g., a mouse model) having cancer and its therapeutic effects can be accessed. Positive results in one or more of such tests are sufficient to increase the scientific storehouse of knowledge and hence sufficient to demonstrate practical utility of the compounds and/or salts tested. Based on the results, an appropriate dosage range and administration route for animals, such as humans, can also be determined.

For administration by inhalation, the at least one compound selected from compounds of Formula (I) (such as Formulae (II), (III), (IV) and (V)), stereoisomers thereof, and pharmaceutically acceptable salts thereof disclosed herein may be conveniently delivered in the form of an aerosol spray presentation from pressurized packs or nebulisers. The at least one compound selected from compounds of Formula (I) (such as Formulae (II), (III), (IV) and (V)), stereoisomers thereof, and pharmaceutically acceptable salts thereof disclosed herein may also be delivered as powders, which may be formulated and the powder composition may be inhaled with the aid of an insufflation powder inhaler device. One exemplary delivery system for inhalation can be a metered dose inhalation (MDI) aerosol, which may be formulated as a suspension or solution of at least one compound selected from compounds of Formula (I) (such as Formulae (II), (III), (IV) and (V)), stereoisomers thereof, and pharmaceutically acceptable salts thereof disclosed herein in at least one suitable propellant, selected, for example, from fluorocarbons and hydrocarbons.

For ocular administration, an ophthalmic preparation may be formulated with an appropriate weight percentage of a solution or suspension of the at least one compound selected from compounds of Formula (I) (such as Formulae (II), (III), (IV) and (V)), stereoisomers thereof, and pharmaceutically acceptable salts thereof disclosed herein in an appropriate ophthalmic vehicle, such that the at least one compound selected from compounds of Formula (I) (such as Formulae (II), (III), (IV) and (V)), stereoisomers thereof, and at least one pharmaceutically acceptable salts thereof disclosed herein is maintained in contact with the ocular surface for a sufficient time period to allow the compound to penetrate the corneal and internal regions of the eye.

Useful pharmaceutical dosage-forms for administration of the at least one compound selected from compounds of Formula (I) (such as Formulae (II), (III), (IV) and (V)), stereoisomers thereof, and pharmaceutically acceptable salts thereof disclosed herein include, but are not limited to, hard and soft gelatin capsules, tablets, parenteral injectables, and oral suspensions.

The dosage administered will be dependent on factors, such as the age, health and weight of the recipient, the extent of disease, type of concurrent treatment, if any, frequency of treatment, and the nature of the effect desired. In general, a daily dosage of the active ingredient can vary, for example, from 0.1 to 2000 milligrams per day. For example, 10-500 milligrams once or multiple times per day may be effective to obtain the desired results.

In some embodiments, a large number of unit capsules can be prepared by filling standard two-piece hard gelatin capsules each with, for example, 100 milligrams of the at least one compound selected from compounds of Formula (I) (such as Formulae (II), (III), (IV) and (V)), stereoisomers thereof, and pharmaceutically acceptable salt thereof disclosed herein in powder, 150 milligrams of lactose, 50 milligrams of cellulose, and 6 milligrams magnesium stearate.

In some embodiments, a mixture of the at least one compound selected from compounds of Formula (I) (such as Formulae (II), (III), (IV) and (V)), stereoisomers thereof, and pharmaceutically acceptable salts thereof a digestible oil such as soybean oil, cottonseed oil or olive oil can be prepared and injected by means of a positive displacement pump into gelatin to form soft gelatin capsules containing 100 milligrams of the active ingredient. The capsules are washed and dried.

In some embodiments, a large number of tablets can be prepared by conventional procedures so that the dosage unit comprises, for example, 100 milligrams of the at least one compound selected from compounds of Formula (I) (such as Formulae (II), (III), (IV) and (V)), stereoisomers thereof, and pharmaceutically acceptable salts thereof, 0.2 milligrams of colloidal silicon dioxide, 5 milligrams of magnesium stearate, 275 milligrams of microcrystalline cellulose, 11 milligrams of starch and 98.8 milligrams of lactose. Appropriate coatings may be applied to increase palatability or delay absorption.

In some embodiments, a parenteral composition suitable for administration by injection can be prepared by stirring 1.5% by weight of the at least one compound and/or at least an enantiomer, a diastereomer, or pharmaceutically acceptable salt thereof disclosed herein in 10% by volume propylene glycol. The solution is made to the expected volume with water for injection and sterilized.

In some embodiment, an aqueous suspension can be prepared for oral administration. For example, each 5 milliliters of an aqueous suspension comprising 100 milligrams of finely divided at least one compound selected from compounds of Formula (I) (such as Formulae (II), (III), (IV) and (V)), stereoisomers thereof, and pharmaceutically acceptable salts thereof, 100 milligrams of sodium carboxymethyl cellulose, 5 milligrams of sodium benzoate, 1.0 grams of sorbitol solution, U.S.P., and 0.025 milliliters of vanillin can be used.

The same dosage forms can generally be used when the at least one compound selected from compounds of Formula (I) (such as Formulae (II), (III), (IV) and (V)), stereoisomers, thereof, and pharmaceutically acceptable salts thereof are administered stepwise or in conjunction with at least one other therapeutic agent. When drugs are administered in physical combination, the dosage form and administration route should be selected depending on the compatibility of the combined drugs. Thus the term "coadministration" is understood to include, the administration of at least two agents concomitantly or sequentially, or alternatively as a fixed dose combination of the at least two active components.

The at least one compound selected from compounds of Formula (I) (such as Formulae (II), (III), (IV) and (V)), stereoisomers thereof, and pharmaceutically acceptable salt thereof disclosed herein can be administered as the sole active ingredient or in combination with at least one second active ingredient, selected, for example, from other active ingredients known to be useful for treating cancers in a patient.

The examples below are intended to be purely exemplary and should not be considered to be limiting in any way. Efforts have been made to ensure accuracy with respect to numbers used (for example, amounts, temperature, etc.), but some experimental errors and deviations should be accounted for. Unless indicated otherwise, temperature is in degrees Centigrade. Reagents were purchased from commercial suppliers such as Sigma-Aldrich, Alfa Aesar, or TCI, and were used without further purification unless otherwise indicated.

Unless otherwise indicated, the reactions set forth below were performed under a positive pressure of nitrogen or argon or with a drying tube in anhydrous solvents; the reaction flasks were fitted with rubber septa for the introduction of substrates and reagents via syringe; and glassware was oven dried and/or heat dried.

Unless otherwise indicated, column chromatography purification was conducted on a Biotage system (Manufacturer: Dyax Corporation) having a silica gel column or on a silica SepPak cartridge (Waters), or was conducted on a Teledyne Isco Combiflash purification system using pre-packed silica gel cartridges.

$^1$H NMR spectra were recorded on a Varian instrument operating at 400 MHz. $^1$H-NMR spectra were obtained using CDCl$_3$, CD$_2$Cl$_2$, CD$_3$OD, D$_2$O, d$_6$-DMSO, d$_6$-acetone or (CD$_3$)$_2$CO as solvent and tetramethylsilane (0.00 ppm) or residual solvent (CDCl$_3$: 7.25 ppm; CD$_3$OD: 3.31 ppm; D$_2$O: 4.79 ppm; d$_6$-DMSO: 2.50 ppm; d$_6$-acetone: 2.05; (CD$_3$)$_2$CO: 2.05) as the reference standard. When peak multiplicities are reported, the following abbreviations are used: s (singlet), d (doublet), t (triplet), q (quartet), qn (quintuplet), sx (sextuplet), m (multiplet), br (broadened), dd (doublet of doublets), dt (doublet of triplets). Coupling constants, when given, are reported in Hertz (Hz). All compound names except the reagents were generated by ChemDraw version 12.0.

In the following examples, the abbreviations below are used:

AcOH Acetic acid
Aq Aqueous
Brine Saturated aqueous sodium chloride solution
Bn Benzyl
BnBr Benzyl Bromide
CH$_2$Cl$_2$ Dichloromethane
DMF N,N-Dimethylformamide
Dppf 1,1"-bis(diphenylphosphino)ferrocene
DBU 1,8-diazabicyclo[5.4.0]undec-7-ene
DIEA or DIPEA N,N-diisopropylethylamine
DMAP 4-N,N-dimethylaminopyridine
DMF N,N-dimethylformamide
DMSO Dimethyl sulfoxide
EtOAc Ethyl acetate
EtOH Ethanol
Et$_2$O or ether Diethyl ether
G grams
h or hr hour
HATU 2-(1H-7-Azabenzotriazol-1-yl)-1,1,3,3-tetramethyl uronium hexafluorophosphate Methanaminium
HCl Hydrochloric acid
HPLC High-performance liquid chromatography
IPA 2-propanol
i-PrOH Isopropyl alcohol
Mg milligrams
mL milliliters
Mmol millimole
MeCN Acetonitrile
MeOH Methanol
Min minutes
ms or MS Mass spectrum
Na$_2$SO$_4$ Sodium sulfate
PE petroleum ether
PPA Polyphosphoric acid
Rt Retention time
Rt or rt Room temperature
TBAF Tetra-butyl ammonium fluoride
TBSCl tert-Butyldimethylsilyl chloride
TFA Trifluoroacetic acid
THF tetrahydro furan
TLC thin layer chromatography
μL microliters

EXAMPLE 1

Synthesis of Compounds 1.1-1.3

Compound 1.1

-continued

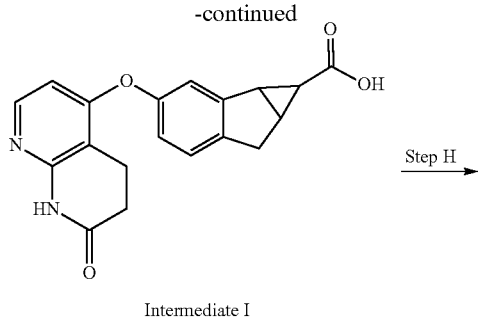

Intermediate I

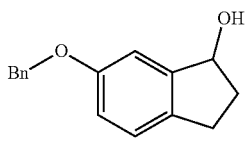 [SMILES: OC1CCc2ccc(OCc3ccccc3)cc21]

Step H

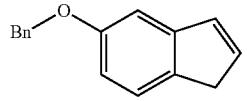 [SMILES: C1=Cc2cc(OCc3ccccc3)ccc2C1]

Step I

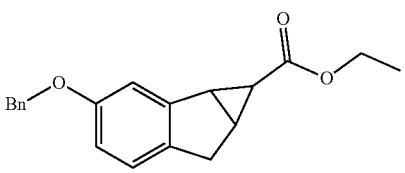 [SMILES: CCOC(=O)C1C2Cc3ccc(OCc4ccccc4)cc3C21]

Compound 1.1

Step A: 6-(Benzyloxy)-2,3-dihydroinden-1-one

To a stirred solution of 6-hydroxy-2,3-dihydroinden-1-one (30 g, 0.203 mol) in 300 mL DMF was added K₂CO₃ (70 g, 0.507 mol), followed by addition of BnBr (38.2 g, 0.225 mol) dropwise at 0° C. The mixture was allowed to warm to ambient temperature and stirred for 20 h. The mixture was diluted with EtOAc (500 mL), then filtered to remove the solid. The filtrate was washed with brine (200 mL×5), dried over anhydrous sodium sulfate, and concentrated in vacuo. The resulted solid was recrystallized in ether to give the title compound (44.5 g, 92%) as a white solid. $^{1}$H-NMR (600 MHz, CDCl$_3$) δ 7.47-7.46 (m, 2H), 7.44-7.39 (m, 3H), 7.38-7.35 (m, 1H), 7.31-7.30 (m, 2H), 5.12 (s, 2H), 3.11-3.09 (m, 2H), 2.76-2.74 (m, 2H) ppm.

Step B: 6-(Benzyloxy)-2,3-dihydro-1H-inden-1-ol

To a stirred solution of the product from Step A (44 g, 0.185 mol) in 500 mL of MeOH was added NaBH4 (7.1 g, 0.186 mol) in portions at 0° C. The mixture was allowed to warm to ambient temperature and stirred for 20 hours. The reaction mixture was concentrated and charged with 200 mL of aqueous NaOH (20%). The resulted mixture was extracted with EtOAc (200 mL×3). The combined organic extracts was washed with brine (200 mL×3), dried, and concentrated to give the title compound (32.0 g, 72%) as a white solid. $^{1}$H-NMR (600 MHz, CDCl$_3$) δ 7.46-7.42 (m, 2H), 7.41-7.36 (m, 2H), 7.34-7.30 (m, 1H), 7.15 (d, J=8.2 Hz, 1H), 7.04 (d, J=2.4 Hz, 1H), 6.90 (dd, J=8.2, 2.5 Hz, 1H), 5.20 (t, J=6.2 Hz, 1H), 5.07 (s, 2H), 3.01-2.95(m, 1H), 2.79-2.72 (m, 1H), 2.55-2.47 (m, 1H), 2.01-1.87 (m, 1H) ppm.

Step C: 5-(Benzyloxy)-1H-indene

To a stirred solution of the product from Step B (15.0 g, 62.5 mmol) in toluene (200 mL) was added p-TsOH (1.0 g, 6.25 mmol) at ambient temperature and the mixture was heated at 80° C. for 1.5 hours. The mixture was concentrated and purified by column chromatography (eluted with PE:EtOAc=30:1) to give the title compound (12.3 g, 89%) as a white solid. $^{1}$H-NMR (600 MHz, CDCl$_3$) δ 7.47-7.46 (m, 2H), 7.41-7.33 (m, 5H), 7.06-7.05 (m, 1H), 6.85-6.84 (m, 1H), 6.60-6.58 (m, 1H), 5.11 (s, 2H), 3.35 (m, 2H) ppm.

Step D: (±)-exo-Ethyl 3-(benzyloxy)-1,1a,6,6a-tetrahydrocyclopropa[a]indene-1-carboxylate To a solution of the product from Step C (10 g, 45 mmol) and Copper (I) triflate (2:1 complex with toluene, 0.23 g, 4.5 mmol) in dichloromethane (200 mL) was added ethyl diazoacetate (47 mL, 450 mol) in dichloromethane (50 mL) through a syringe pump over a period of 10 hours at room temperature. The mixture was stirred at room temperature for another 2 hours. The reaction was filtered and the filtrate was concentrated under reduced pressure. The residue was purified by silica gel chromatography (eluted with PE=100%) to obtain the title compound as yellow oil (5.5 g, 40%). ¹H-NMR (600 MHz, DMSO-d₆) δ 7.39-7.36 (m, 2H), 7.33-7.29 (m, 2H), 7.27-7.23 (m, 1H), 6.99 (d, J=8.3 Hz, 1H), 6.95 (d, J=2.4 Hz, 1H), 6.72 (dd, J=8.3, 2.3 Hz, 1H), 4.98 (s, 2H), 4.09 (q, J=7.0 Hz, 2H), 3.11 (dd, J=17.2, 6.3 Hz, 1H), 2.90 (d, J=17.2 Hz, 1H), 2.82 (d, J=6.5 Hz, 1H), 2.35 (td, J=6.4, 3.3 Hz, 1H), 1.24-1.17 (m, 3H), 1.13-1.05 (m, 1H) ppm.

Step E: (±)-exo-Ethyl 3-hydroxy-1,1a,6,6a-tetrahydrocyclopropa[a]indene-1-carboxylate

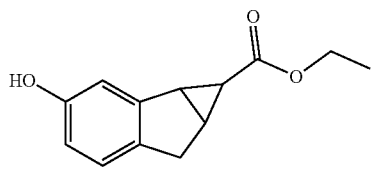 [SMILES: CCOC(=O)C1C2Cc3ccc(O)cc3C21]

To a mixture of Pd/C (0.4 g) in MeOH (20 mL) was added a solution of the product from Step D (4 g, 0.013 mol) in MeOH (20 mL) at room temperature. The mixture was stirred at room temperature under H₂ atmosphere for 2 hours. The mixture was filtered and the filtrate was concentrated. The residue was purified by silica gel chromatography (eluted with EtOAc:PE=1:10) to yield the title compound (2.3 g, 82%) as colorless oil. ¹H-NMR (600 MHz, CD₃OD) δ 6.91 (d, J=8.1 Hz, 1H), 6.75 (d, J=2.3 Hz, 1H), 6.54 (dd, J=8.2, 2.2 Hz, 1H), 4.08 (q, J=7.0 Hz, 2H), 3.09 (dd, J=17.0, 6.3 Hz, 1H), 2.87 (d, J=17.0 Hz, 1H), 2.78 (d J=6.4 Hz, 1H), 2.33 (td, J=6.4, 3.2 Hz, 1H), 1.21 (t, J=6.9 Hz, 3H), 1.09-1.06 (m, 1H) ppm.

Step F: (±)-exo-Ethyl 3-((7-oxo-5,6,7,8-tetrahydro-1,8-naphthyridin-4-yl)oxy)-1,1a,6,6a-tetrahydrocyclopropa[a] indene-1-carboxylate

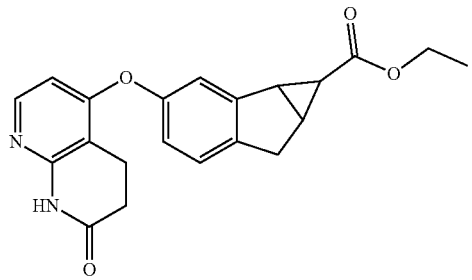 [SMILES: CCOC(=O)C1C2Cc3ccc(Oc4ccnc5c4CCC(=O)N5)cc3C21]

The mixture of the product from step E (2.0 g, 9 mmol), 5-fluoro-3,4-dihydro-1,8-naphthyridin-2(1H)-one (1.5 g, 9 mmol) and cesium carbonate (6 g, 18 mmol) in DMF (30 mL) was stirred at 120° C. for 2 hours. The reaction was diluted with water (30 mL) and extracted with ethyl acetate (2×40 mL). The combined organic phase was washed with brine (50 mL), dried over sodium sulfate anhydrous and concentrated under reduced pressure. The residue was purified by silica gel chromatography (eluted with EtOAc:PE=1:5~1:1) to obtain the title compound (1.4 g, 42%) as a white solid.

Step G: (±)-exo-3-((7-Oxo-5,6,7,8-tetrahydro-1,8-naphthyridin-4-yl)oxy)-1,1a,6,6a-tetrahydrocyclopropa[a]indene-1-carboxylic acid (Intermediate I)

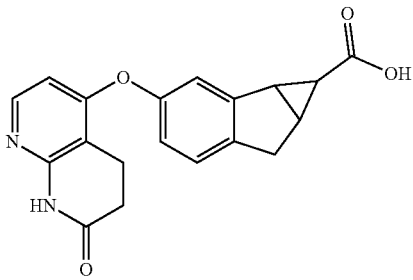 [SMILES: O=C1CCc2c(Oc3ccc4c(c3)C3C(C4)C3C(=O)O)ccnc2N1]

Sodium hydroxide solution (7.7 mL, 2 M, 15 mmol) was added to a stirred solution of the product from Step F(1.4 g, 3.8 mmol) in THF (24 mL) and methanol (24 mL) at room temperature. The mixture was stirred at 60° C. for 2 hours. The solvent was removed under reduced pressure and the residue was dissolved into water (20 mL). The solution was neutralized-with HCl (1 mol/L) to pH=7 and white solid precipitated out of solution. The white solid was collected by filtration and dried in air to give the title compound (0.9 g, 70%). ¹H-NMR (600 MHz, DMSO-d₆) δ 10.47 (s, 1H), 7.97 (d, J=5.7 Hz, 1H), 7.28-7.14 (m, 3H), 6.88 (d, J=8.1 Hz, 1H), 6.29 (d, J=5.8 Hz, 1H), 3.19 (dd, J=17.6, 6.4 Hz, 1H), 3.00 (d, J=17.6 Hz, 1H), 2.92 (t, J=7.7 Hz, 2H), 2.81 (d, J=6.3 Hz, 1H), 2.54 (t, J=7.7 Hz, 2H), 2.37-2.31 (m, 1H), 1.08-1.05 (m, 1H) ppm.

Step H: (±)-exo-N-(2-aminophenyl)-3-((7-oxo-5,6,7,8-tetrahydro-1,8-naphthyridin-4-yl)oxy)-1,1a,6,6a-tetrahydrocyclopropa[a]indene-1-carboxamide

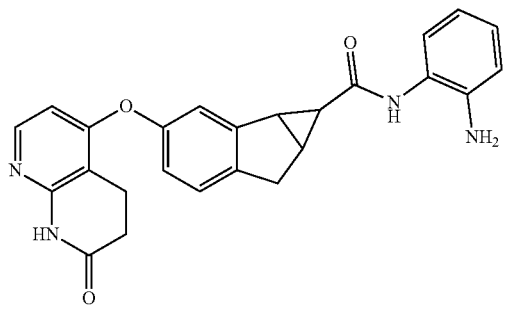 [SMILES: Nc1ccccc1NC(=O)C1C2Cc3ccc(Oc4ccnc5c4CCC(=O)N5)cc3C21]

To a solution of Intermediate I (30 mg, 0.089 mmol), benzene-1,2-diamine (9.6 mg, 0.089 mmol) and HATU (37 mg, 0.101 mmol) in DMF (1 mL) was added DIPEA (0.1 mL) at room temperature. The mixture was stirred at room temperature overnight. The reaction was diluted with water (5 mL) and extracted with ethyl acetate (2×10 mL). The combined organic phase was washed with brine, dried over sodium sulfate anhydrous and concentrated under reduced pressure. The residue was used in next step directly without further purification. MS: M/e 427 (M+1)⁺.

Step I: (±)-exo-5-((1-(1H-benzo[d]imidazol-2-yl)-1,1a,6,6a-tetrahydrocyclopropa[a]inden-3-yl)oxy)-3,4-dihydro-1,8-naphthyridin-2(1H)-one (Compound 1.1)

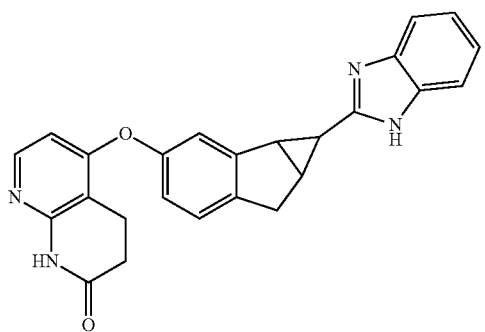 [SMILES: O=C1CCc2c(Oc3ccc4c(c3)C3C(C4)C3c3nc4ccccc4[nH]3)ccnc2N1]

The mixture of the product from Step H (38 mg, 0.089 mmol) in acetic acid (2 mL) was stirred at 80° C. for 3 hours. Solvent was removed and a solution of NaOH (2 mL, 2 mol/L) was added to the residue. The mixture was extracted with EtOAc (2×10 mL). The combined organic phase was washed with brine (20 mL), dried over sodium sulfate anhydrous and concentrated under reduced pressure. The residue was purified by prep-HPLC to give the title compound as a white solid. $^1$H-NMR (600 MHz, DMSO-$d_6$) δ 10.52 (s, 1H), 8.01 (d, J=5.7 Hz, 1H), 7.75 (dd, J=6.1, 3.2 Hz, 2H), 7.51 (dd, J=6.1, 3.1 Hz, 2H), 7.39 (d, J=8.3 Hz, 1H), 7.23 (d, J=2.3 Hz, 1H), 7.02 (dd, J=8.2, 2.3 Hz, 1H), 6.34 (d, J=5.8 Hz, 1H), 3.48-3.41 (m, 2H), 3.25 (d, J=17.9 Hz, 1H), 3.01-2.95 (m, 1H), 2.92 (t, J=7.7 Hz, 2H), 2.55 (t, J=7.7 Hz, 2H), 2.02 (t, J=3.1 Hz, 1H) ppm. MS: M/e 409 (M+1)$^+$.

Compound 1.2: (±)-exo-5-((1-(6-(trifluoromethyl)-1H-benzo[d]imidazol-2-yl)-1,1a,6,6a-tetrahydrocyclopropa[a]inden-3-yl)oxy)-3,4-dihydro-1,8-naphthyridin-2(1H)-one

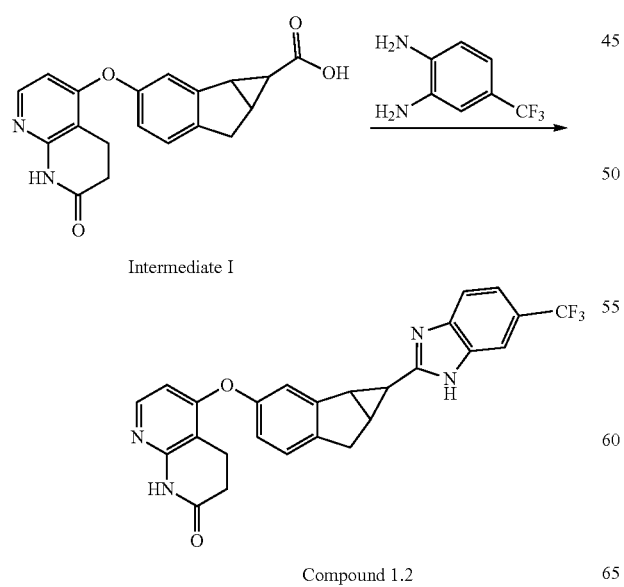

To a solution of Intermediate I (338 mg, 1.0 mmol), 4-(trifluoromethyl)benzene-1,2-diamine (190 mg, 1.1 mmol) and DIPEA(500 mg, 3.9 mmol) in DMF (10 mL) was added HATU (405 mg, 1.1 mmol) at room temperature. The mixture was stirred at room temperature for 20 hrs. The reaction was diluted with ethyl EtOAc (50 mL).The mixture was washed with brine (3×20 mL), dried over sodium sulfate anhydrous and concentrated under reduced pressure.

The residue was dissolved in acetic acid (10 mL) and the mixture was stirred at 90° C. for 5 hrs. Solvent was removed. The residue was diluted with EtOAc (50 mL). The organic phase was washed with a solution of saturated sodium bicarbonate (2×20 mL), brine (2×20 mL), dried over sodium sulfate anhydrous and concentrated under reduced pressure. The residue was purified by silica gel chromatography (eluted with DCM: MeOH=50:1~20:1) to give the title compound (245 mg, 51%) as a white solid. $^1$H-NMR (600 MHz, DMSO-$d_6$) δ 10.50 (s, 1H), 8.00 (d, J=5.7 Hz, 1H), 7.87 (s, 1H), 7.71 (d, J=8.2 Hz, 1H), 7.58-7.48 (m, 1H), 7.35 (d, J=8.2 Hz, 1H), 7.23 (d, J=2.3 Hz, 1H), 6.96 (dd, J=8.2, 2.4 Hz, 1H), 6.33 (d, J=5.8 Hz, 1H), 3.38 (dd, J=17.9, 6.5 Hz, 1H), 3.24-3.15 (m, 2H), 2.98-2.89 (m, 2H), 2.81-2.73 (m, 1H), 2.58-2.52 (m, 2H), 1.87-1.80 (m, 1H) ppm. MS: M/e 477 (M+1)$^+$ Compound 1.2 was separated into two enantiomeric stereoisomers (Compound 1.2a, earlier peak, and Compound 1.2b, later peak) by chiral prep-HPLC. The chiral separation conditions are shown below.

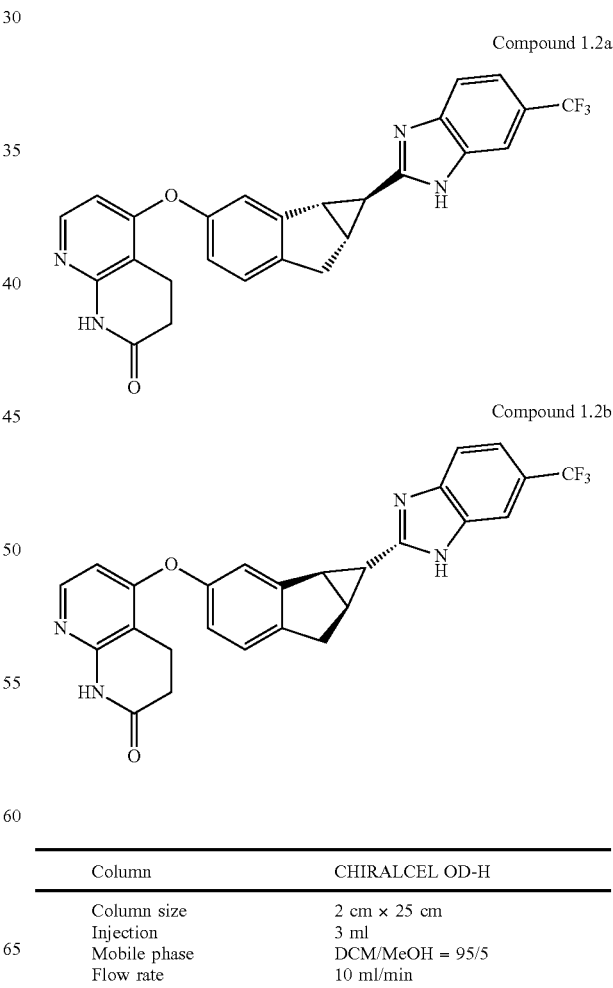

| Column | CHIRALCEL OD-H |
|---|---|
| Column size | 2 cm × 25 cm |
| Injection | 3 ml |
| Mobile phase | DCM/MeOH = 95/5 |
| Flow rate | 10 ml/min |

-continued

| Column | CHIRALCEL OD-H |
|---|---|
| Wave length | UV 254 nm |
| Temperature | 35° C. |
| Sample solution | 4 mg/ml in mobile phase |
| Prep-SFC equipment | YMC-100 |

Compound 1.3

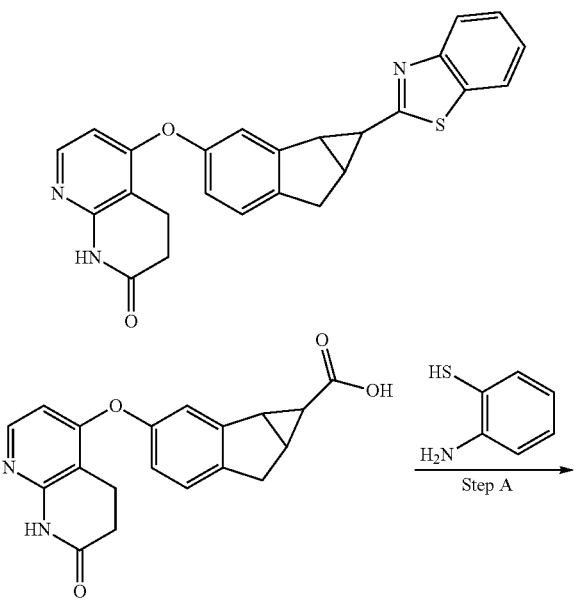

Step A: (±)-exo-N-(2-mercaptophenyl)-3-((7-oxo-5,6,7,8-tetrahydro-1,8-naphthyridin-4-yl)oxy)-1,1a,6,6a-tetrahydrocyclopropa[a]indene-1-carboxamide

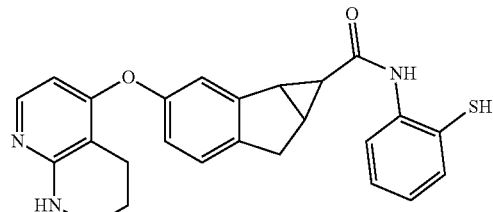

To a solution of Intermediate I (34 mg, 0.1 mmol), in $CH_2Cl_2$ (3.0 mL) was added $(COCl)_2$ (0.03 mL, 0.4 mmol) and DMF (cat.) at room temperature under $N_2$. The mixture was stirred for 1.5 hrs. Then the solvent was removed and the residue was dissolved with $CH_2Cl_2$ (3.0 mL) and then DIPEA (0.07 mL, 0.4 mmol) and 2-aminobenzenethiol (14 mg, 0.11 mmol) was added at 0° C. under $N_2$. The mixture was stirred at room temperature for 2 hrs. The mixture was extracted with $CH_2Cl_2$, washed with brine, dried over $Na_2SO_4$, filtered and concentrated. The residue was purified by prep-TLC ($CH_2Cl_2$:MeOH=10:1) to give the crude product (20 mg) as a yellow solid, which was used directly in the next step.

Step B: (±)-exo-5-((1-(benzo[d]thiazol-2-yl)-1,1a,6,6a-tetrahydrocyclopropa[a]inden-3-yl)oxy)-3,4-dihydro-1,8-naphthyridin-2(1H)-one (Compound 1.3)

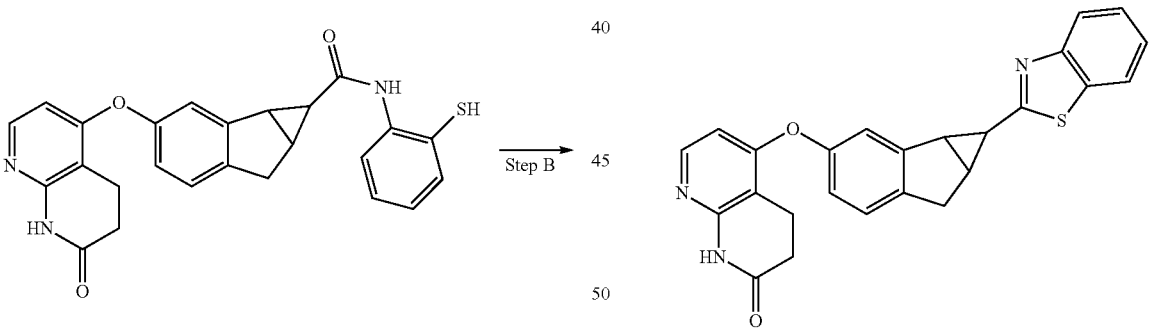

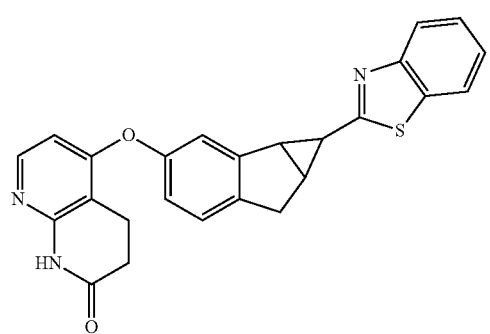

To a solution of the product from Step A (20 mg, crude) in toluene (4.0 mL) was added PPA (200 mg). The mixture was stirred at 140° C. for 3 hours. The reaction was cooled to it and the solvent was removed. The residue was dissolved with $CH_2Cl_2$ (10 mL), washed with saturated $NaHCO_3$ solution and extracted with $CH_2Cl_2$ (2×15 mL). The combined organic phases were washed with brine (10 mL), dried over anhydrous sodium sulfate and concentrated under reduced pressure. The residue was purified by prep-HPLC to afford the title compound (3.8 mg, 9%, two steps) as a light yellow solid. $^1$H-NMR (400 MHz, $CD_3OD$) δ 7.94-7.83 (m, 3H), 7.47-7.43 (m, 1H), 7.35-7.29 (m, 2H), 7.16 (d, J=2.4 Hz, 1H), 6.92 (d, J=2.4 Hz, 1H), 6.34 (d, J=6.0 Hz, 1H), 3.42-3.36 (m, 1H), 3.29-3.26 (m, 1H), 3.22-3.19 (m, 1H), 3.04 (t, J=8.0 Hz, 2H), 2.77-2.72 (m, 1H), 2.66-2.62 (m, 2H), 2:05-2.03 (m, 1H) ppm. MS: M/e 426 (M+1)⁺.

EXAMPLE 2

Synthesis of Compounds 2.1-2.37

Compound 2.1

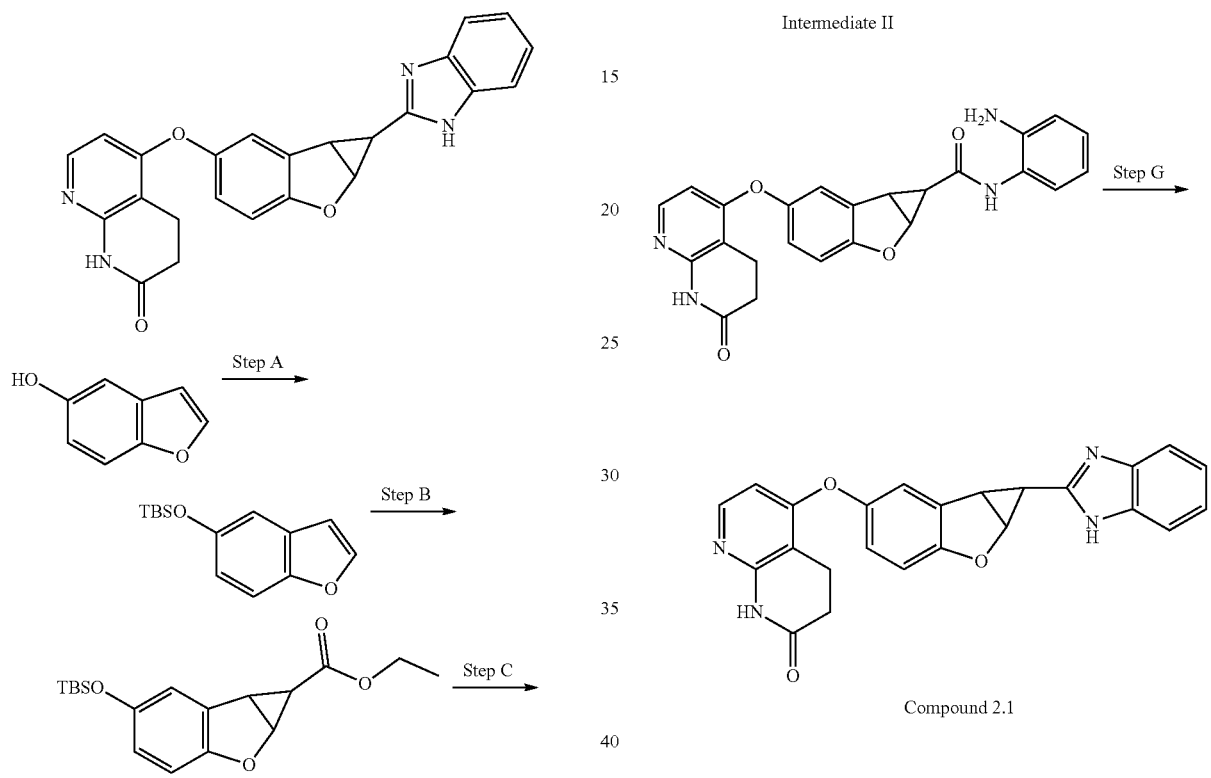

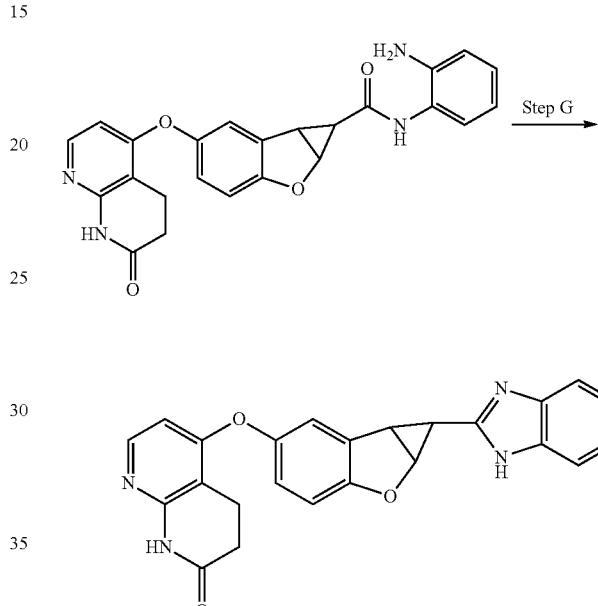

Compound 2.1

Step A:
(Benzofuran-5-yloxy)(tert-butyl)dimethylsilane

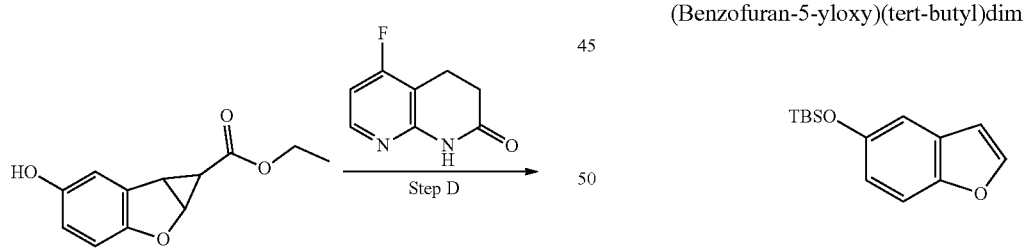

To a stirred solution of benzofuran-5-ol (5.2 g, 0.039 mol) in DMF (50 mL) was added imidazole (5.3 g, 0.078 mol) and TBSCl (6.1 g, 0.041 mol) at room temperature. The mixture was stirred at room temperature 20 hours. Then a solution of saturated NaHCO₃ (150 mL) was added into the reaction and the mixture was extracted with EtOAc (3×100 mL). The combined organic phase was washed with brine (3×100 mL) and dried over anhydrous sodium sulfate and concentrated under reduced pressure. The residue was purified by silica gel chromatography (eluted with 100% PE) to obtain the title compound (7.8 g, 81%) as colorless oil. ¹H-NMR (600 MHz, DMSO-d₆) δ 7.94 (d, J=2.1 Hz, 1H), 7.46 (d, J=8.7 Hz, 1H), 7.08 (d, J=2.5 Hz, 1H), 6.89-6.84 (m, 1H), 6.81 (dd, J=8.8, 2.5 Hz, 1H), 0.98 (s, 9H), 0.19 (s, 6H) ppm.

Step B: (±)-exo-Ethyl 5-((tert-butyldimethylsilyl)oxy)-1a,6b-dihydro-1H-cyclopropa[b]benzofuran-1-carboxylate

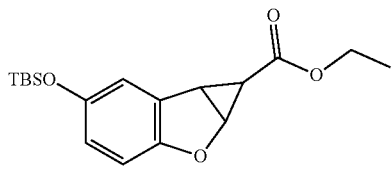 [SMILES: CCOC(=O)C1C2Oc3ccc(O[Si](C)(C)C(C)(C)C)cc3C21]

To a solution of the product from Step A (9.25 g, 0.037 mol) and Copper (I) triflate (2:1 complex with toluene, 1.9 g, 3.7 mmol) in dichloromethane (200 mL) was added ethyl diazoacetate (38.7 mL, 0.37 mol) in dichloromethane (50 ml) through a syringe pump over a period of 10 hours. Then the mixture was stirred at room temperature for another 2 hours. The reaction was filtered and the filtrate was concentrated under reduced pressure. The residue was purified by silica gel chromatography (eluted with PE=100%) to obtain the title compound. The product was used in next step without further purification.

Step C: (±)-exo-Ethyl 5-hydroxy-1a,6b-dihydro-1H-cyclopropa[b]benzofuran-1-carboxylate

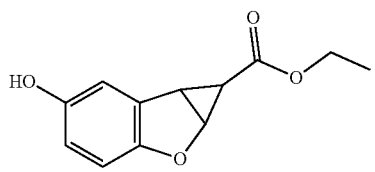 [SMILES: CCOC(=O)C1C2Oc3ccc(O)cc3C21]

To a solution of the product from Step B (10 g, 0.030 mol) in THF (25 mL) was added TBAF in THF (15 mL, 1 M, 0.015 mol) drop wise at 0° C. Then the mixture was stirred at room temperature for 1 hour. The reaction was diluted with water (30 mL) and extracted with ethyl acetate (2×50 mL). The combined organic phase was washed with brine (2×50 mL), dried over anhydrous sodium sulfate and concentrated under reduced pressure. The residue was purified by silica gel chromatography (eluted with EtOAc:PE=1:10) to obtain the title compound (3.8 g, 46% yield for two steps) as colorless oil. $^{1}$H-NMR (600 MHz, CDCl$_{3}$) δ 7.01 (s, 1H), 6.89 (d, J=2.6 Hz, 1H), 6.68 (d, J=8.6 Hz, 1H), 6.63 (dd, J=8.6, 2.6 Hz, 1H), 5.02 (dd, J=5.5, 1.1 Hz, 1H), 4.15 (q, J=7.1 Hz, 2H), 3.19 (dd, J=5.4, 3.1 Hz, 1H), 1.26 (dd, J=3.1, 1.1 Hz, 1H), 1.26-1.23 (m, 3H) ppm.

Step D: (±)-exo-Ethyl 5-((7-oxo-5,6,7,8-tetrahydro-1,8-naphthyridin-4-yl)oxy)-1a,6b-dihydro-1H-cyclopropa[b]benzofuran-1-carboxylate

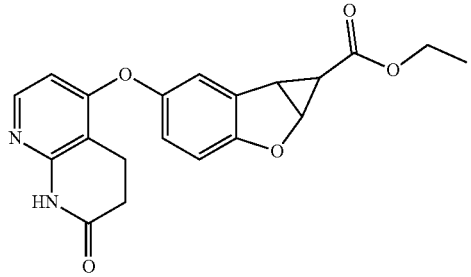 [SMILES: CCOC(=O)C1C2Oc3ccc(Oc4ccnc5c4CCC(=O)N5)cc3C21]

The mixture of the product from step C (3.8 g, 0.017 mol), 5-fluoro-3,4-dihydro-1,8-naphthyridin-2(1H)-one (2.85 g, 0.017 mol) and cesium carbonate (11.2 g, 0.034 mol) in DMF (50 mL) was stirred at 120° C. for 2 hrs. The reaction was diluted with water (20 mL) and extracted with ethyl acetate (2×30 mL). The combined organic phase was washed with brine (50 mL), dried over anhydrous sodium sulfate and concentrated under reduced pressure. The residue was purified by silica gel chromatography (eluted with EtOAc:PE=1:5~1:1) to obtain the title compound (2.8 g, 44%) as a white solid. $^{1}$H-NMR (400 MHz, CDCl$_{3}$) δ 9.99 (s, 1H), 8.06 (d, J=5.8 Hz, 1H), 7.10 (s, 1H), 6.90-6.82 (m, 2H), 6.23 (d, J=5.8 Hz, 1H), 5.10 (d, J=5.4 Hz, 1H), 4.22-4.07 (m, 2H), 3.24 (s, 1H), 3.03 (t, J=7.8 Hz, 2H), 2.67 (t, J=7.9 Hz, 2H), 1.36-1.30 (m, 1H), 1.29-1.17 (m, 3H) ppm. MS: M/e 367 (M+1)$^{+}$.

Step E: (±)-exo-5-((7-Oxo-5,6,7,8-tetrahydro-1,8-naphthyridin-4-yl)oxy)-1a,6b-dihydro-1H-cyclopropa[b]benzofuran-1-carboxylic acid (Intermediate II)

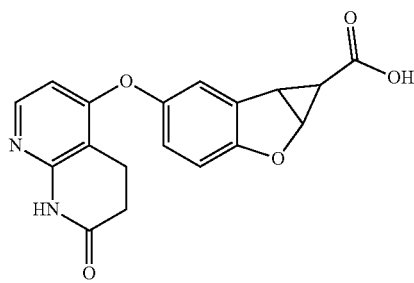 [SMILES: O=C1CCc2c(Oc3ccc4c(c3)C3C(O4)C3C(=O)O)ccnc2N1]

Sodium hydroxide aqueous solution (18 mL, 2 M, 36 mmol) was added to a stirred solution of the product from Step D (2.8 g, 7.7 mmol) in THF (54 mL) and methanol (54 mL) at room temperature. The mixture was stirred at 60° C. for 2 hours. The solvent was removed under reduced pressure and the residue was dissolved into water (20 mL). The solution was neutralized with HCl (1 mol/L) to pH=7 and white solid precipitated out of solution. The white solid was collected by filtration and dried in air to give the title compound (2.4 g, 92.7%). $^{1}$H-NMR (600 MHz, DMSO-d$_{6}$) δ 12.74 (s, 1H), 10.46 (s, 1H), 7.96 (d, J=5.4 Hz, 1H), 7.33 (d, J=2.4 Hz, 1H), 7.00 (d, J=8.6 Hz, 1H), 6.97 (d, J=2.4 Hz, 1H), 6.26 (d, J=5.4 Hz, 1H), 5.24-5.21 (m, 1H), 3.32-3.27

(m, 1H), 2.94 (t, J=7.8 Hz, 2H), 2.55 (t, J=7.8 Hz, 2H), 1.23-1.21 (m, 1H) ppm. MS: M/e 339 (M+1)+.

Step F: (±)-exo-N-(2-aminophenyl)-5-((7-oxo-5,6,7,8-tetrahydro-1,8-naphthyridin-4-yl)oxy)-1a,6b-dihydro-1H-cyclopropa[b]benzofuran-1-carboxamide

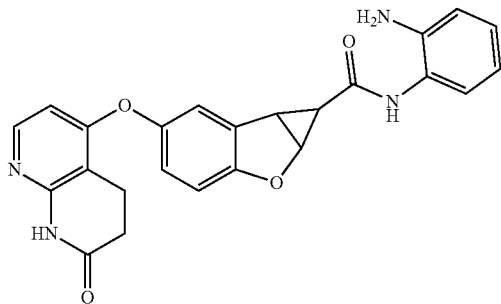 [SMILES: Nc1ccccc1NC(=O)C1C2Oc3ccc(Oc4ccnc5c4CCC(=O)N5)cc3C21]

The mixture of the product from Step E (30 mg, 0.088 mmol), benzene-1,2-diamine (9.6 mg, 0.088 mmol), DIPEA (17.2 mg, 0.130 mmol) and HATU (37 mg, 0.101 mmol) in DMF (1 mL) was stirred at room temperature overnight. The reaction was diluted with water (5 mL) and extracted with ethyl acetate (2×10 mL). The combined organic phase was washed with brine (20 mL), dried over sodium sulfate anhydrous, and concentrated under reduced pressure. The residue was used in next step directly without further purification.

Step G: (±)-exo-5-((1-(1H-benzo[d]imidazol-2-yl)-1a,6b-dihydro-1H-cyclopropa[b]benzofuran-5-yl)oxy)-3,4-dihydro-1,8-naphthyridin-2(1H)-one (Compound 2.1)

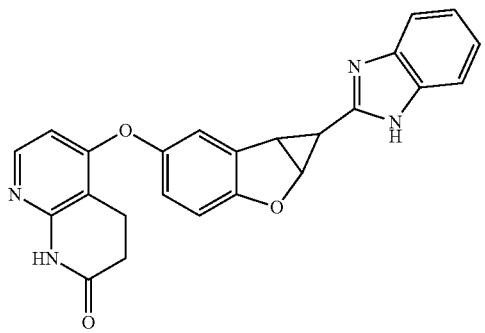

The mixture of the product from Step F (37 mg, 0.088 mmol) in acetic acid (1 mL) was stirred at 80° C. for 3 hours. Solvent was removed and a solution of NaOH (2 mL, 2 mol/L) was added to the residue. The mixture was extracted with EtOAc (2×10 mL). The combined organic phase was washed with brine (20 mL), dried over sodium sulfate anhydrous, and concentrated under reduced pressure. The residue was purified by prep-HPLC to afford the title compound (10 mg, 41%) as while solid. ¹H-NMR (600 MHz, CD₃OD) δ 7.97 (d, J=5.9 Hz, 1H), 7.51 (dd, J=6.0, 3.2 Hz, 2H), 7.31 (d, J=2.4 Hz, 1H), 7.23 (dd, J=6.0, 3.2 Hz, 2H), 7.03 (d, J=8.7 Hz, 1H), 7.00 (dd, J=8.7, 2.4 Hz, 1H), 6.36 (d, J=5.9 Hz, 1H), 5.35 (dd, J=5.5, 1.3 Hz, 1H), 3.52 (dd, J=5.4, 3.4 Hz, 1H), 3.09 (t, J=7.8 Hz, 2H), 2.69 (t, J=7.5 Hz, 2H), 1.91 (dd, J=3.3, 1.3 Hz, 1H) ppm. MS: M/e 411 (M+1)+.

Stereoselective synthesis of (1S,1aS,6bR)-ethyl 5-hydroxy-1a,6b-dihydro-1H-cyclopropa[b]benzofuran-1-carboxylate (Intermediate III)

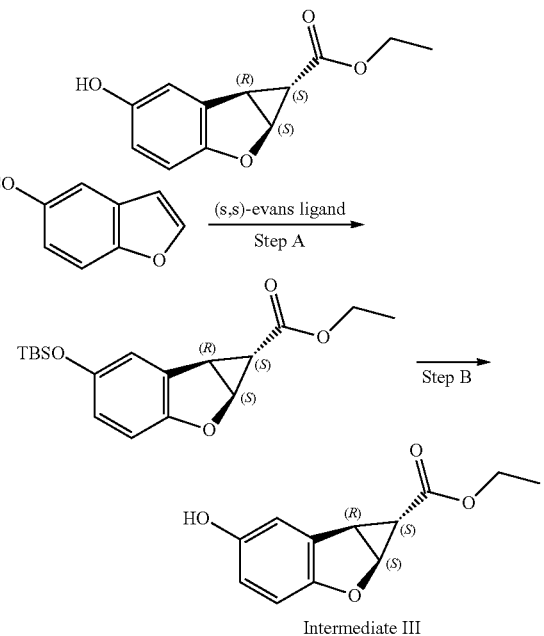

Step A: (1S,1aS,6bR)-Ethyl-5-((tert-butyldimethylsilyl)oxy)-1a,6b-dihydro-1H-cyclopropa[b]benzofuran-1-carboxylate Copper (I) inflate (2:1 complex with toluene, 250 mg, 2.4%) and (S,S)-(+)-2,2-isopropylidenebis(4-tert-butyl)-2-oxazoline (205 mg, 3.4%) were stirred in dichloromethane (15 mL) at ambient temperature under N₂ atmosphere for 1 hour. A solution of (benzofuran-5-yloxy)(tert-butyl)dimethylsilane (5.0 g, 20.2 mmol) in dichloromethane (85 mL) was added, followed by a slow addition of ethyl diazoethanoate (40 mL, 380 mmol) during a period of 10 hours using a syringe pump. The mixture was concentrated and purified by column chromatography to afford crude compound (7.3 g) which was used for the next step without any further purification.

Step B: (1S,1aS,6bR)-Ethyl 5-hydroxy-1a,6b-dihydro-1H-cyclopropa[b]benzofuran-1-carboxylate (Intermediate III)

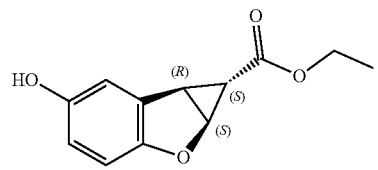

Tetra-n-butylammonium fluoride (TBAF, 1M in THF, 4 mmol) was added dropwise to a solution of the product of Step A (7.3 g, crude) in THF (100 mL) at 0° C. The reaction was stirred at RT for 30 min. The mixture was concentrated and purified by column chromatography to afford the title compound as a solid (2.52 g, 57% for 2 steps, 72% ee).

Compound 2.2: (±)-exo-5-((1-(6-(trifluoromethyl)-1H-benzo[d]imidazol-2-yl)-1a,6b-dihydro-1H-cyclopropa[b]benzofuran-5-yl)oxy)-3,4-dihydro-1,8-naphthyridin-2(1H)-one

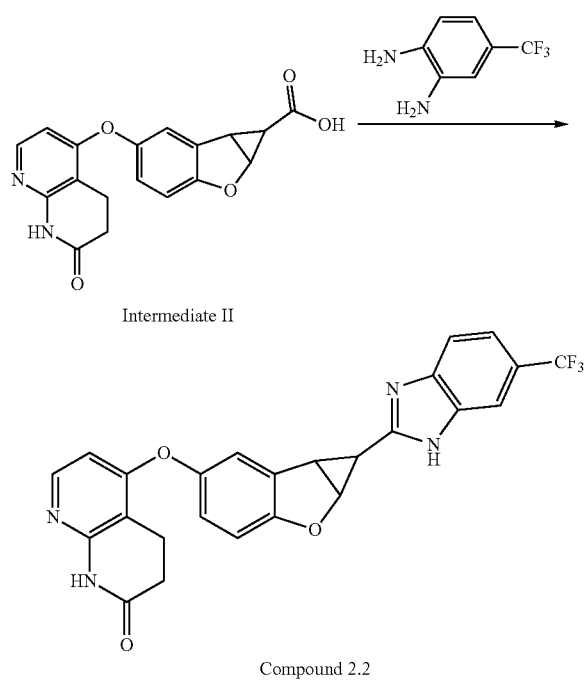

Intermediate II

Compound 2.2

The mixture of Intermediate II (1 g, 2.96 mmol), 4-(trifluoromethyl)benzene-1,2-diamine (0.52 g, 2.96 mmol), DIPEA (1.15 g, 8.88 mmol) and HATU (1.69 g, 4.44 mmol) in DMF (5 mL) was stirred at room temperature overnight. The reaction was diluted with water (10 mL) and extracted with ethyl acetate (2×30 mL). The combined organic phase was washed with brine (20 mL), dried over sodium sulfate anhydrous, and concentrated under reduced pressure.

The residue was dissolved in acetic acid (10 mL). The mixture was stirred at 80° C. for 3 hrs. Solvent was removed and a solution of NaOH (20 mL, 2 mol/L) was added to the residue. The mixture was extracted with EtOAc (2×30 mL). The combined organic phase was washed with brine (20 mL), dried over sodium sulfate anhydrous, and concentrated under reduced pressure. The residue was purified by prep-HPLC to afford the title compound (330 mg, 23.6%) as white solid. $^1$H-NMR (600 MHz, DMSO-$d_6$) δ 12.84 (s, 1H), 10.47 (s, 1H), 7.98 (d, J=5.8 Hz, 1H), 7.86 (d, J=1.2 Hz, 1H), 7.69 (m, 1H), 7.48 (t, J=6.2 Hz, 1H), 7.38 (d, J=2.6 Hz, 1H), 7.08 (d, J=8.7 Hz, 1H), 7.02 (dd, J=8.7, 2.6 Hz, 1H), 6.29 (d, J=5.8 Hz, 1H), 5.43 (dd, J=5.4, 1.2 Hz, 1H), 3.55 (dd, J=5.3, 3.3 Hz, 1H), 2.95 (t, J=7.7 Hz, 2H), 2.55 (t, J=7.7 Hz, 2H), 1.97 (d, J=1.3 Hz, 1H) ppm. MS: M/e 479 (M+1)$^+$.

Compound 2.2 was separated into two enantiomeric stereoisomers (Compound 2.2a, earlier peak, and Compound 2.2b, later peak) by chiral prep-HPLC. The chiral separation conditions are shown below:

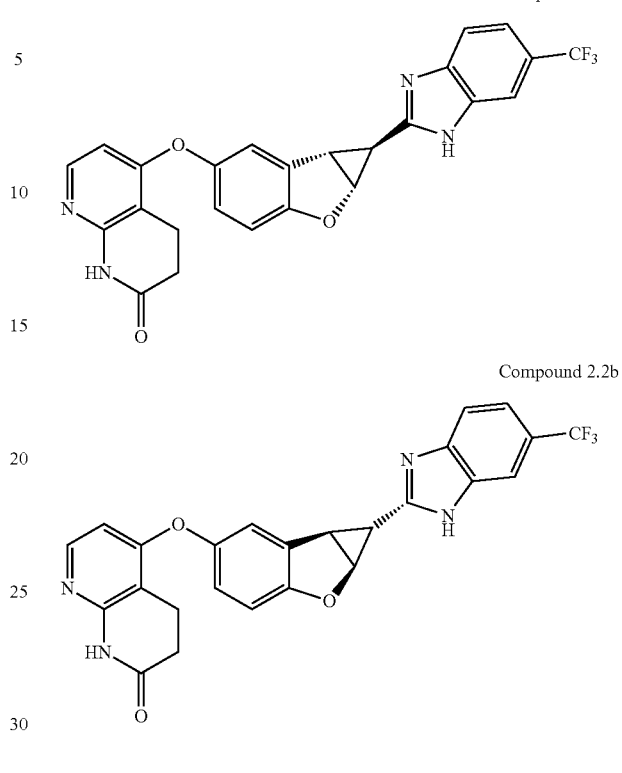

Compound 2.2a

Compound 2.2b

| Column | CHIRALCEL OD-H |
|---|---|
| Column size | 2 cm × 25 cm |
| Injection | 5 ml |
| Mobile phase | CO$_2$/E75AC N25 = 75/25 |
| Flow rate | 50 ml/min |
| Wave length | UV 254 nm |
| Temperature | 35° C. |
| Sample solution | 1.5 mg/ml in mobile phase |
| Prep-SFC equipment | DAICEL-SFC |

Compound 2.2b: 5-(((1R,1aS,6bR)-1-(6-(trifluoromethyl)-1H-benzo[d]imidazol-2-yl)-1a,6b-dihydro-1H-cyclopropa[b]benzofuran-5-yl)oxy)-3,4-dihydro-1,8-naphthyridin-2(1H)-one

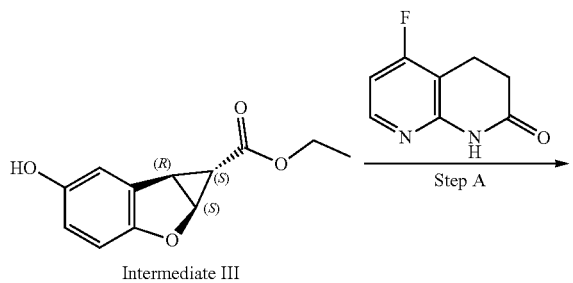

Intermediate III

53

-continued

54

Step B: (1S,1aS,6bR)-5-((7-oxo-5,6,7,8-tetrahydro-1,8-naphthyridin-4-yl)oxy)-1a,6b-dihydro-1H-cyclopropa[b]benzofuran-1-carboxylic acid

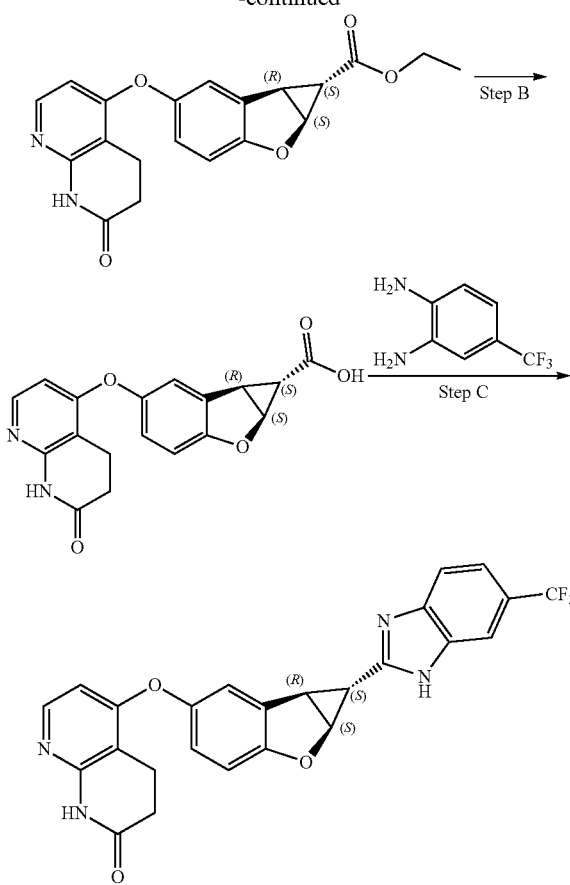

To a stirred solution of ester product of Step A (360 mg, 0.98 mmol) in THF (3 mL) and methanol (3 mL) was added sodium hydroxide aqueous solution (1 mL, 2 M, 2 mmol) at room temperature. The mixture was stirred at 60° C. for 2 hrs. The solvent was removed under reduced pressure and the residue was dissolved into water (5 mL). The solution was neutralized with HCl (2 mol/L) to pH=7 and white solid precipitated out of solution. The white solid was collected by filtration and dried in air to give the title compound (230 mg, 69.3%).

Step C: 5-(((1R,1aS,6bR)-1-(6-(trifluoromethyl)-1H-benzo[d]imidazol-2-yl)-1a,6b-dihydro-1H-cyclopropa[b]benzofuran-5-yl)oxy)-3,4-dihydro-1,8-naphthyridin-2(1H)-one Step A: (1S,1aS,6bR)-ethyl 5-((7-oxo-5,6,7,8-tetrahydro-1,8-naphthyridin-4-yl)oxy)-1a,6b-dihydro-1H-cyclopropa[b]benzofuran-1-carboxylate

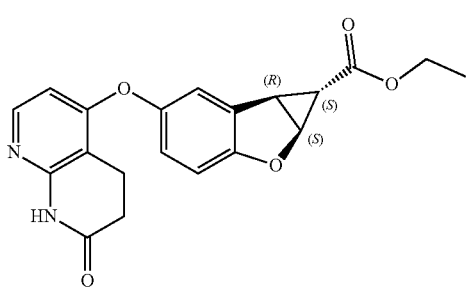

The mixture of Intermediate III (400 mg, 1.8 mmol), 5-fluoro-3,4-dihydro-1,8-naphthyridin-2(1H)-one (250 mg, 1.5 mmol) and cesium carbonate (801 mg, 2.3 mol) in DMF (20 mL) was stirred at 120° C. for 2 hrs. The reaction was diluted with water (10 mL) and extracted with ethyl acetate (2×10 mL). The combined organic phase was washed with brine (20 mL), dried over anhydrous sodium sulfate and concentrated under reduced pressure. The residue was purified by silica gel chromatography (eluted with EtOAc:PE=3:1) to obtain the title compound (360 mg, 54.6%) as a white solid.

The mixture of the product of Step B (50 mg, 0.15 mmol), 4-(trifluoromethyl)benzene-1,2-diamine (26 mg, 0.15 mmol), DIPEA (0.1 mL) and HATU (84 mg, 0.22 mmol) in DMF (1 mL) was stirred at room temperature overnight. The reaction was diluted with water (5 mL) and extracted with ethyl acetate (2×10 mL). The combined organic phase was washed with brine (10 mL), dried over sodium sulfate anhydrous, filtered and concentrated under reduced pressure. The residue was dissolved in acetic acid (1 mL). The mixture was stirred at 80° C. for 3 hours. Solvent was removed and a solution of NaOH (2 mL, 2 mol/L) was added to the residue. The mixture was extracted with EtOAc (2×5 mL). The combined organic phase was washed with brine (10 mL), dried over sodium sulfate anhydrous, and concentrated under reduced pressure. The residue was purified by prep-HPLC to afford the title compound (10 mg, 14.1% yield; 69.6% ee) as a white solid.

Compound 2.3: (±)-exo-5-((1-(5,6-dichloro-1H-benzo[d]imidazol-2-yl)-1a,6b-dihydro-1H-cyclopropa[b]benzofuran-5-yl)oxy)-3,4-dihydro-1,8-naphthyridin-2(1H)-one

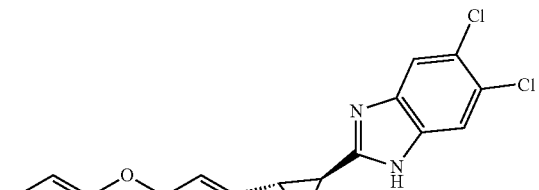

Compound 2.3b

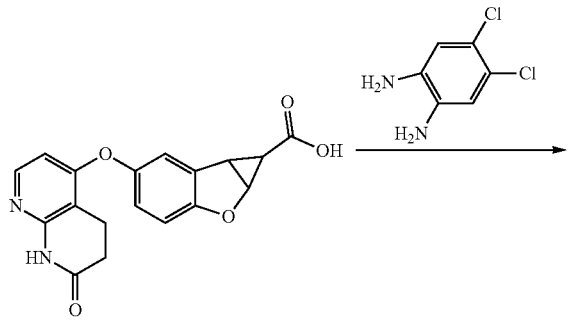

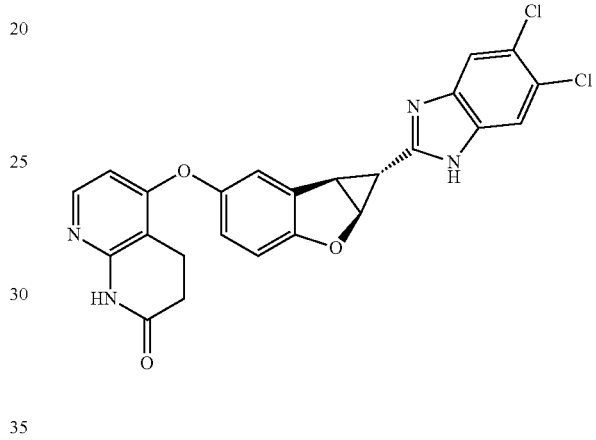

Compound 2.3a

Compound 2.3

| Column | CHIRALPAK IA |
|---|---|
| Column size | 3 cm × 25 cm |
| Injection | 20 ml |
| Mobile phase | DCM/MeOH = 95/5 |
| Flow rate | 20 ml/min |
| Wave length | UV 254 nm |
| Temperature | 35° C. |
| Sample solution | 0.1 mg/ml in mobile phase |
| Prep-SFC equipment | YMC-100 |

The mixture of Intermediate II (600 mg, 1.8 mmol), 4,5-dichlorobenzene-1,2-diamine (312 mg, 1.8 mmol), DIPEA (0.69 g, 5.4 mmol) and HATU (1.01 g, 2.7 mmol) in DMF (10 mL) was stirred under nitrogen atmosphere at room temperature overnight. The reaction was diluted with water (10 mL) and extracted with ethyl acetate (2×30 mL). The combined organic phase was washed with brine (20 mL), dried over sodium sulfate anhydrous, and concentrated under reduced pressure.

The residue was dissolved in acetic acid (10 mL). The mixture was stirred at 80° C. for 3 hrs. Solvent was removed and a solution of NaOH (10 mL, 2 mol/L) was added to the residue. The mixture was extracted with EtOAc (2×30 mL). The combined organic phase was washed with brine (20 mL), dried over sodium sulfate anhydrous, and concentrated under reduced pressure. The residue was purified by prep-HPLC to afford the title compound (320 mg, 37.6%) as white solid. $^1$H-NMR (600 MHz, DMSO-$d_6$) δ 10.44 (s, 1H), 7.93 (d, J=5.8 Hz, 1H), 7.74 (s, 2H), 7.32 (d, J=2.6 Hz, 1H), 7.03 (d, J=8.7 Hz, 1H), 6.97 (dd, J=8.6, 2.5 Hz, 1H), 6.24 (d, J=5.8 Hz, 1H), 5.39-5.36 (m, 1H), 3.52-3.46 (m, 1H), 2.90 (t, J=7.7 Hz, 2H), 2.50 (t, J=7.7 Hz, 2H), 1.91-1.87 (m, 1H) ppm. MS: M/e 479 (M+1)$^+$.

Compound 2.3 was separated into two enantiomeric stereoisomers (Compound 2.3a, earlier peak, and Compound 2.3b, later peak) by chiral prep-HPLC. The chiral separation conditions are shown below:

Compound 2.4: (±)-exo-5-((1-(5-fluoro-6-methyl-1H-benzo[d]imidazol-2-yl)-1a,6b-dihydro-1H-cyclopropa[b]benzofuran-5-yl)oxy)-3,4-dihydro-1,8-naphthyridin-2(1H)-one

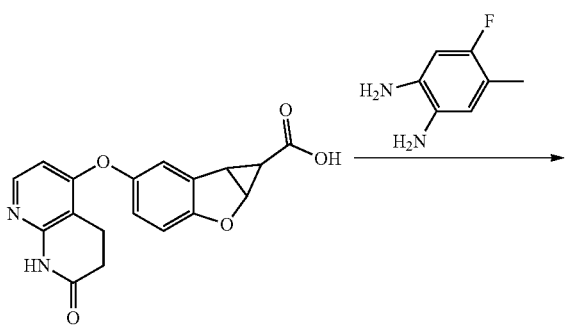

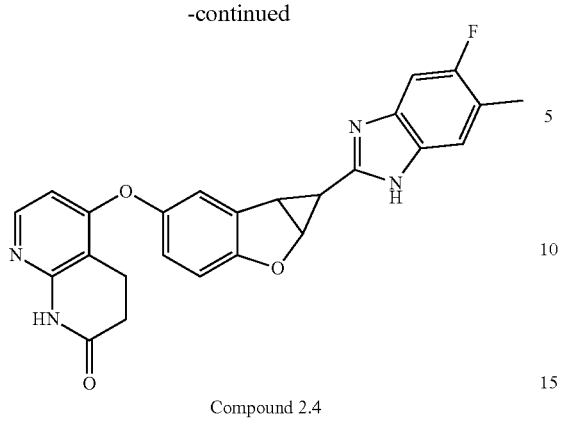

Compound 2.4

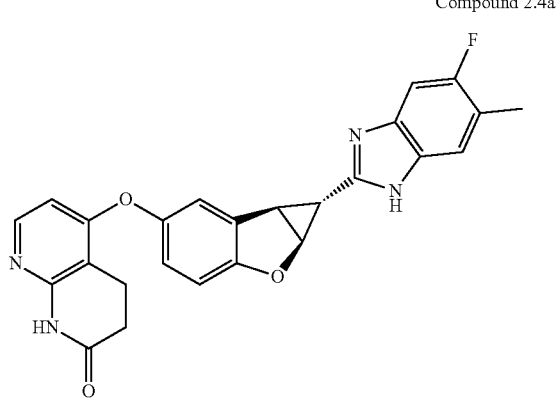

Compound 2.4a

To a solution of Intermediate II (338 mg, 1.0 mmol), 4-fluoro-5-methylbenzene-1,2-diamine (169 mg, 1.2 mmol), and triethylamine (300 mg, 3.0 mmol) in DMF (7 mL) was added HATU (420 mg, 1.1 mmol) at room temperature. The mixture was stirred at room temperature for 16 hrs. The reaction was diluted with water (30 mL) and the white solid was precipitated. The mixture was filtered and the solid was dried enough under reduced pressure.

The solid was dissolved in acetic acid (7 mL) and the mixture was stirred at 85° C. for 8 hrs. Solvent was removed. The residue was diluted with DCM (20 mL) and the organic phase was washed with a solution of NaOH (2 mol/L, 5 mL). The water phase was extracted with another 50 mL of DCM. The combined organic phase was washed with brine (2×20 mL), dried over sodium sulfate anhydrous and concentrated under reduced pressure. The residue was purified by silica gel chromatography (eluted with DCM: MeOH=50:1~20:1) to give the title compound (230 mg, 52%) as a brown solid. $^1$H-NMR (600 MHz, CD$_3$OD) δ 7.94 (d, J=6.0 Hz, 1H), 7.53 (d, J=6.2 Hz, 1H), 7.38 (d, J=9.0 Hz, 1H), 7.34 (d, J=2.4 Hz, 1H), 7.08 (d, J=8.7 Hz, 1H), 7.05 (dd, J=8.8, 2.4 Hz, 1H), 6.35 (d, J=6.0 Hz, 1H), 5.55 (dd, J=5.5, 1.3 Hz, 1H), 3.78 (dd, J=5.5, 3.4 Hz, 1H), 3.06 (t, J=7.8 Hz, 2H), 2.65 (t, J=7.8 Hz, 2H), 2.40 (d, J=2.0 Hz, 3H), 2.09 (dd, J=3.4, 1.3 Hz, 1H) ppm. MS: M/e 443 (M+1)$^+$.

Compound 2.4 was separated into two enantiomeric stereoisomers (Compound 2.4a, earlier peak, and Compound 2.4b, later peak) by chiral prep-HPLC. The chiral separation conditions are shown below:

| Column | CHIRALPAKIA |
|---|---|
| Column size | 2 cm × 25 cm |
| Injection | 5 ml |
| Mobile phase | DCM/MeOH = 95/5 |
| Flow rate | 10 ml/min |
| Wave length | UV 254 nm |
| Temperature | 35° C. |
| Sample solution | 1 mg/ml in mobile phase |
| Prep-SFC equipment | YMC-100 |

Compound 2.5: (±)-exo-5-((1-(5-chloro-6-(trifluoromethyl)-1H-benzo[d]imidazol-2-yl)-1a,6b-dihydro-1H-cyclopropa[b]benzofuran-5-yl)oxy)-3,4-dihydro-1,8-naphthyridin-2(1H)-one

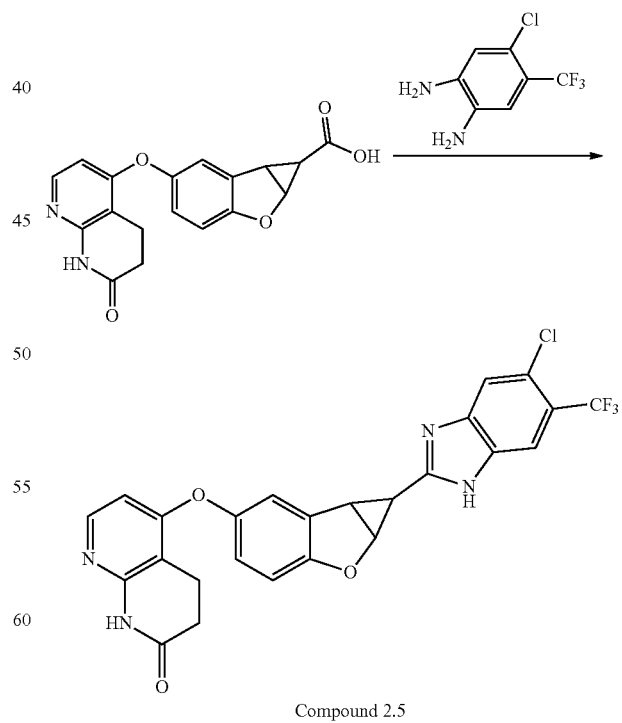

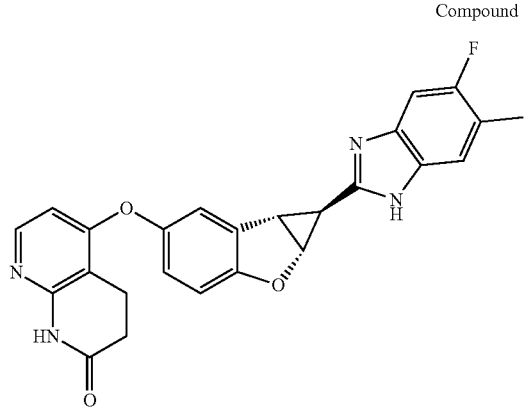

Compound 2.4b

Compound 2.5

To a solution of Intermediate II (300 mg, 0.887 mmol) and triethylamine (500 mg, 5 mmol) in DMF (5 mL) was added HATU (370 mg, 0.97 mmol) at 0° C. After the mixture was stirred for 15 min, 4-chloro-5-(trifluoromethyl)benzene-1,2-diamine (228 mg, 1.09 mmol) in DMF (1 mL) was added to the reaction. The mixture was allowed to warm to room temperature and stirred for 20 hrs. The reaction was diluted with water (50 mL) and the white solid was precipitated. The mixture was filtered and the solid was dried enough under reduced pressure.

The solid was dissolved in acetic acid (5 mL) and the mixture was stirred at 85° C. for 5 hrs. Solvent was removed. The residue was purified by silica gel chromatography (eluted with DCM: MeOH=50:1~20:1) to give the title compound (205 mg, 45%) as a light yellow solid. $^1$H-NMR (400 MHz, DMSO-$d_6$) δ 10.48 (s, 1H), 7.96 (d, J=4.1 Hz, 2H), 7.82 (s, 1H), 7.37 (d, J=2.6 Hz, 1H), 7.07 (d, J=8.7 Hz, 1H), 7.01 (dd, J=8.7; 2.6 Hz, 1H), 6.26 (d, J=5.8 Hz, 1H), 5.42 (d, J=5.3 Hz, 1H), 3.57-3.51 (m, 1H), 2.93 (t, J=7.7 Hz, 2H), 2.58-2.50 (m, 2H), 1.98 (d, J=2.1 Hz, 1H) ppm. MS: M/e 513 (M+1)$^+$.

Compound 2.5 was separated into two enantiomeric stereoisomers (Compound 2.5a, earlier peak, and Compound 2.5b, later peak) by chiral prep-HPLC. The chiral separation conditions are shown below:

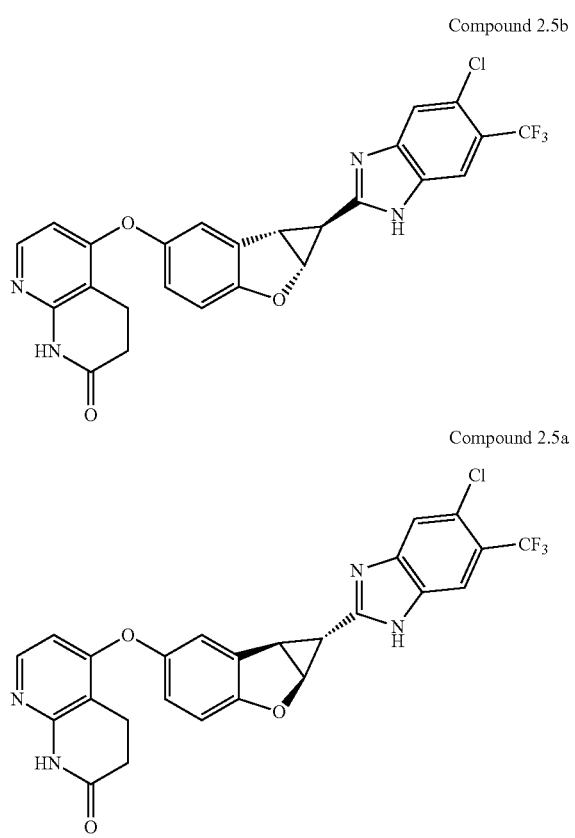

Compound 2.5b

Compound 2.5a

| Column | CHIRALCEL OJH |
| --- | --- |
| Column size | 2 cm × 25 cm |
| Injection | 1 ml |
| Mobile phase | CO$_2$/MeOH = 75/25 |
| Flow rate | 40 ml/min |
| Wave length | UV 230 nm |
| Temperature | 35° C. |

| Column | CHIRALCEL OJH |
| --- | --- |
| Sample solution | 1 mg/ml in mobile phase |
| Prep-SFC equipment | DAICEL-SFC |

Compounds 2.6-2.25 were prepared according to the procedures described for Compound 2.1 by using the corresponding benzofuran and diamine as starting materials under appropriate conditions that could be recognized by one skilled in the art.

Compound 2.6

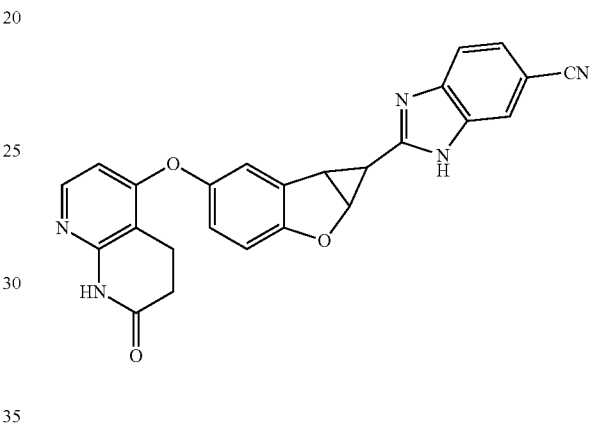

$^1$H-NMR (600 MHz, DMSO-$d_6$) δ 12.97 (s, 1H), 10.45 (s, 1H), 8.02 (d, J=24.7 Hz, 1H), 7.96 (d, J=5.8 Hz, 1H), 7.65 (dd, J=27.5, 8.3 Hz, 1H), 7.57-7.51 (m, 1H), 7.36 (d, J=2.6 Hz, 1H), 7.07 (d, J=8.7 Hz, 1H), 7.01 (dd, J=8.7, 2.5 Hz, 1H), 6.27 (d, J=5.8 Hz, 1H), 5.45-5.40 (m, 1H), 3.57-3.53 (m, 1H), 2.93 (t, J=7.7 Hz, 2H), 2.54 (t, J=7.7 Hz, 2H), 1.97-1.93 (m, 1H) ppm. MS: M/e 436 (M+1)$^+$.

Compound 2.7

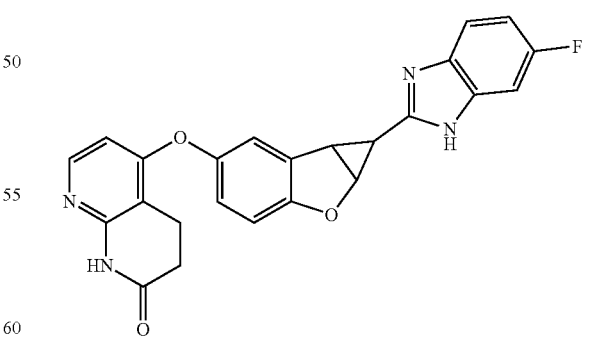

$^1$H-NMR (600 MHz, CD$_3$OD) δ 7.94 (d, J=5.4 Hz, 1H), 7.64 (d, J=6.6 Hz, 1H), 7.42 (s, 1H), 7.34 (s, 1H), 7.26 (s, 1H), 7.06 (d, J=6.6 Hz, 2H), 6.35 (d, J=4.8 Hz, 1H), 5.53 (d, J=4.8 Hz, 1H), 3,76 (s, 1H), 3.09-3.02 (m, 2H), 2.68-2.63 (m, 2H), 2.08 (s, 1H) ppm. MS: M/e 429 (M+1)$^+$.

Compound 2.8

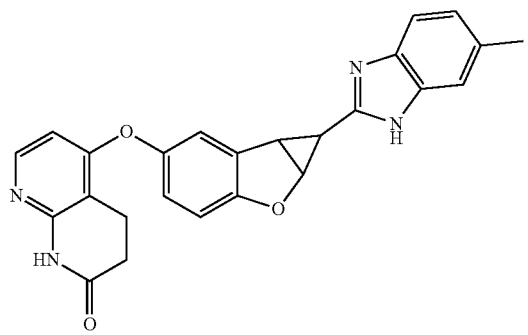 [SMILES: Cc1ccc2nc(C3C4Oc5ccc(Oc6ccnc7c6CCC(=O)N7)cc5C43)[nH]c2c1]

¹H-NMR (600 MHz, CD₃OD) δ 7.99 (d, J=6.0 Hz, 1H), 7.61 (d, J=8.4 Hz, 1H), 7.53 (s, 1H), 7.45-7.38 (m, 2H), 7.15-7.08 (m, 2H), 6.39 (d, J=6.0 Hz, 1H), 5.63 (d, J=5.4 Hz, 1H), 3.87-3.85 (m, 1H), 3.10 (t, J=7.8 Hz, 2H), 2.70 (t, J=7.8 Hz, 2H), 2.55 (s, 3H), 2.19-2.15 (m, 1H) ppm. MS: M/e 425 (M+1)⁺.

Compound 2.9

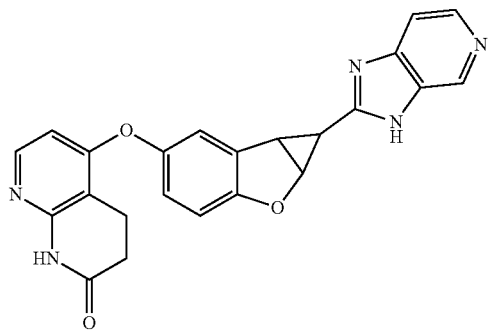 [SMILES: O=C1CCc2c(Oc3ccc4c(c3)C3C(O4)C3c3nc4ccncc4[nH]3)ccnc2N1]

¹H-NMR (600 MHz, CD₃OD) δ 9.50 (s, 1H), 8.63 (s, 1H), 8.20 (s, 1H), 7.99 (s, 1H), 7.37 (d, J=1.8 Hz, 1H), 7.24 (d, J=6.6 Hz, 1H), 7.06 (dd, J=8.5, 2.3 Hz, 1H), 7.01 (d, J=8.7 Hz, 1H), 6.39 (d, J=6.0 Hz, 1H), 5.21-5.05 (m, 1H), 3.91 (dd, J=18.4, 8.9 Hz, 1H), 3.61-3.53 (m, 1H), 3.09 (t, J=7.8 Hz, 2H), 2.70 (t, J=7.8 Hz, 2H) ppm. MS; M/e 412 (M+1)⁺.

Compound 2.10

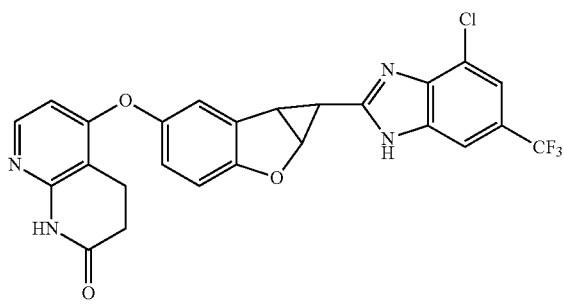 [SMILES: O=C1CCc2c(Oc3ccc4c(c3)C3C(O4)C3c3nc4c(Cl)cc(C(F)(F)F)cc4[nH]3)ccnc2N1]

¹H-NMR (600 MHz, CD₃OD) δ 8.03 (d, J=6.3 Hz, 1H), 7.78 (s, 1H), 7.56 (d, J=1.0 Hz, 1H), 7.38 (d, J=2.3 Hz, 1H), 7.10-6.99 (m, 2H), 6.51 (d, J=6.4 Hz, 1H), 5.47 (dd, J=5.4, 1.3 Hz, 1H), 3.69-3.65 (m, 1H), 3.15 (t, J=7.8 Hz, 2H), 2.79-2.70 (m, 2H), 2.01-1.93 (m, 1H) ppm. MS: M/e 513 (M+1)⁺.

Compound 2.11

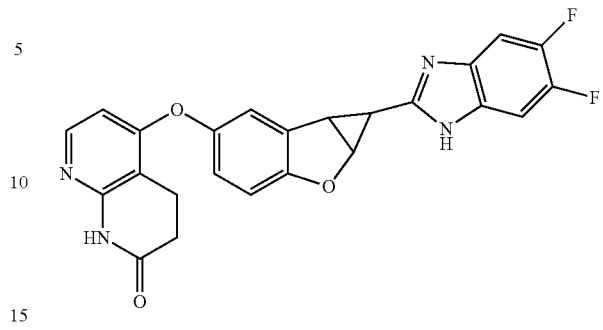

¹H-NMR (600 MHz, CD₃OD) δ 8.00 (d, J=6.1 Hz, 1H), 7.58 (t, J=8.4 Hz, 2H), 7.37 (d, J=2.3 Hz, 1H), 7.13-7.04 (m, 2H), 6.43 (d, J=6.1 Hz, 1H), 5.51 (dd, J=5.5, 1.2 Hz, 1H), 3.72 (dd, J=5.4, 3.4 Hz, 1H), 3.12 (t, J=7.8 Hz, 2H), 2.75-2.69 (m, 2H), 2.06 (dd, J=3.4, 1.2 Hz, 1H) ppm. MS: M/e 447 (M+1)⁺.

Compound 2.12

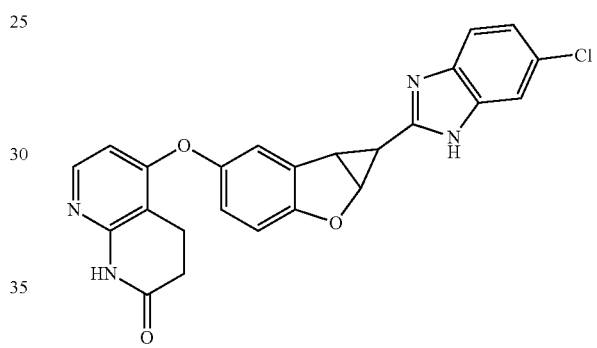

¹H-NMR (600 MHz, CD₃OD) δ 8.00 (d, J=6.1 Hz, 1H), 7.75-7.63 (m, 2H), 7.49 (dd, J=8.7, 1.9 Hz, 1H), 7.39 (d, J=2.3 Hz, 1H), 7.14-7.07 (m, 2H), 6.42 (d, J=6.0 Hz, 1H), 5.57 (dd, J=5.5, 1.3 Hz, 1H), 3.80 (dd, J=5.4, 3.4 Hz, 1H), 3.11 (t, J=7.8 Hz, 2H), 2.73-2.67 (m, 2H), 2.11 (dd, J=3.4, 1.3 Hz, 1H) ppm. MS: M/e 445 (M+1)⁺.

Compound 2.13

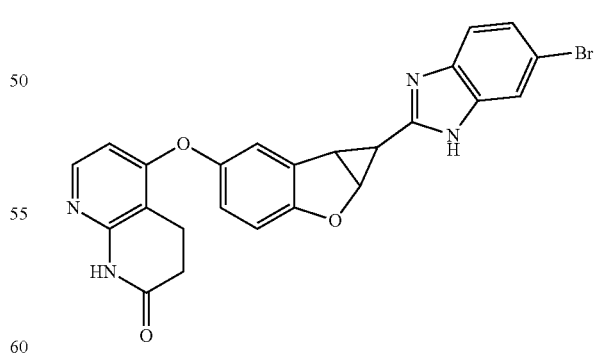

¹H-NMR (600 MHz, CD₃OD) δ 7.99 (d, J=6.0 Hz, 1H), 7.83 (s, 1H), 7.58 (s, 2H), 7.38 (d, J=2.4 Hz, 1H), 7.14-7.04 (m, 2H), 6.40 (d, J=6.0 Hz, 1H), 5.54 (dd, J=5.5, 1.3 Hz, 1H), 3.76 (dd, J=5.4, 3.4 Hz, 1H), 3.11 (t, J=7.8 Hz, 2H), 2.73-2.67 (m, 2H), 2.08 (dd, J=3.4, 1.3 Hz, 1H) ppm. MS: M/e 489 (M+1)⁺.

Compound 2.14

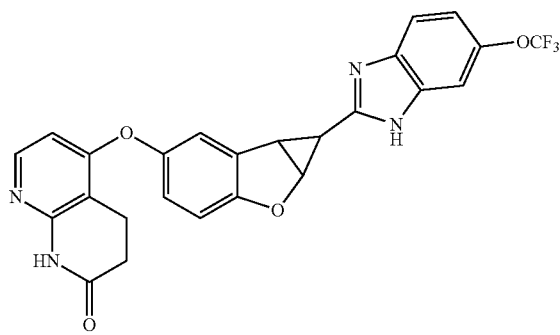 [SMILES: O=C1CCc2c(Oc3ccc4c(c3)C3C(O4)C3c3nc4ccc(OC(F)(F)F)cc4[nH]3)ccnc2N1]

$^1$H-NMR (600 MHz, DMSO-d$_6$) δ 10.51 (s, 1H), 7.99 (d, J=5.8 Hz, 1H), 7.64 (d, J=8.7 Hz, 1H), 7.58 (s, 1H), 7.39 (d, J=2.6 Hz, 1H), 7.23 (d, J=8.6 Hz, 1H), 7.10 (d, J=8.7 Hz, 1H), 7.04 (dd, J=8.7, 2.6 Hz, 1H), 6.30 (d, J=5.8 Hz, 1H), 5.48 (d, J=5.3 Hz, 1H), 3.61 (s, 1H), 2.95 (t, J=7.7 Hz, 2H), 2.56 (t, J=7.7 Hz, 2H), 2.01 (s, 1H) ppm. MS: M/e 495 (M+1)$^+$.

Compound 2.15

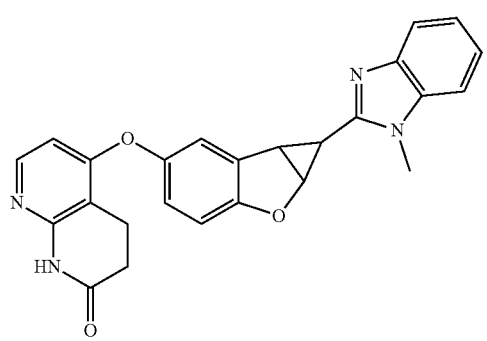 [SMILES: Cn1c(C2C3Oc4ccc(Oc5ccnc6c5CCC(=O)N6)cc4C32)nc2ccccc21]

$^1$H-NMR (600 MHz, CD$_3$OD) δ 8.00 (d, J=6.0 Hz, 1H), 7.88-7.85 (m, 1H), 7.77-7.73 (m, 1H), 7.66-7.60 (m, 2H), 7.42 (d, J=2.4 Hz, 1H), 7.18-7.09 (m, 2H), 6.43 (d, J=6.0 Hz, 1H), 5.64 (dd, J=5.5, 1.4 Hz, 1H), 4.12 (d, J=5.6 Hz, 3H), 3.90 (dd, J=5.5, 3.5 Hz, 1H), 3.12 (t, J=7.8 Hz, 2H), 2.71 (t, J=7.8 Hz, 2H), 2.46 (dd, J=3.5, 1.5 Hz, 1H) ppm. MS: M/e 425 (M+1)$^+$.

Compound 2.16

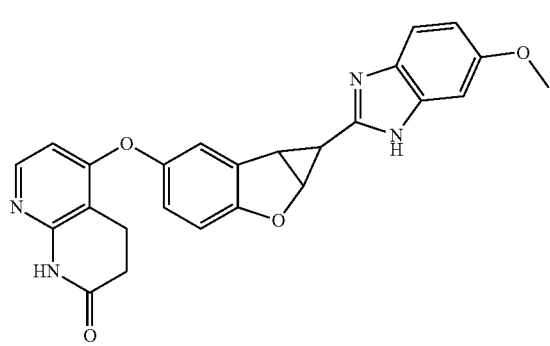 [SMILES: COc1ccc2nc(C3C4Oc5ccc(Oc6ccnc7c6CCC(=O)N7)cc5C43)[nH]c2c1]

$^1$H-NMR (600 MHz, DMSO-d$_6$) δ 10.49 (s, 1H), 7.99 (d, J=5.8 Hz, 1H), 7.61 (d, J=8.9 Hz, 1H), 7.40 (d, J=2.6 Hz, 1H), 7.18 (d, J=2.1 Hz, 1H), 7.14 (d, J=8.7 Hz, 1H), 7.09-7.05 (m, 2H), 6.30 (d, J=5.8 Hz, 1H), 5.67 (d, J=5.5 Hz, 1H), 3.85 (s, 3H), 3.84-3.79 (m, 1H), 2.95 (t, J=7.7 Hz, 2H), 2.56 (t, J=7.7 Hz, 2H), 2.21-2.08 (m, 1H) ppm. MS: M/e 441 (M+1)$^+$.

Compound 2.17

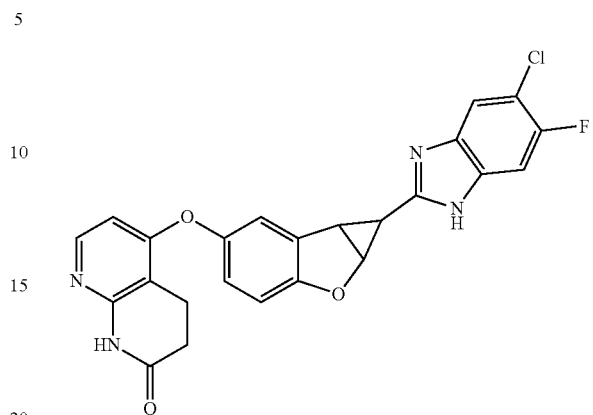

$^1$H-NMR (600 MHz, DMSO-d$_6$) δ 10.48 (s, 1H), 7.98 (d, J=5.8 Hz, 1H), 7.71 (d, J=6.7 Hz, 1H), 7.56 (d, J=9.7 Hz, 1H), 7.36 (d, J=2.5 Hz, 1H), 7.06 (d, J=8.7 Hz, 1H), 7.01 (dd, J=8.7, 2.6 Hz, 1H), 6.28 (d, J=5.8 Hz, 1H), 5.40 (dd, J=5.3, 1.0 Hz, 1H), 3.54-3.50 (m, 1H), 2.95 (t, J=7.7 Hz, 2H), 2.55 (t, J=7.7 Hz, 2H), 1.97-1.89 (m, 1H) ppm. MS: M/e 463 (M+1)$^+$.

Compound 2.18

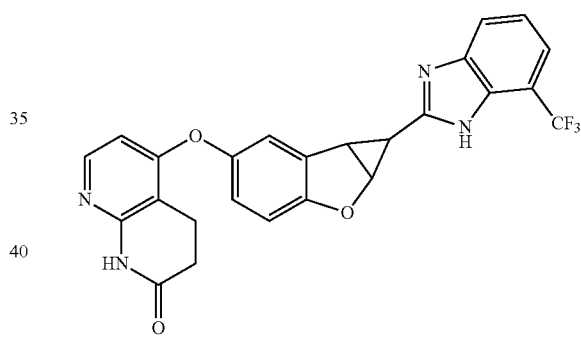

$^1$H-NMR (600 MHz, CD$_3$OD) δ 8.02 (d, J=6.2 Hz, 1H), 7.87 (d, J=8.2 Hz, 1H), 7.66 (d, J=7.6 Hz, 1H), 7.50 (t, J=7.9 Hz, 1H), 7.38 (d, J=2.3 Hz, 1H), 7.15-7.03 (m, 2H), 6.46 (d, J=6.2 Hz, 1H), 5.53 (dd, J=5.5, 1.3 Hz, 1H), 3.75-3.71 (m, 1H), 3.14 (t, J=7.8 Hz, 2H), 2.73 (t, J=7.8 Hz, 2H), 2.08 (dd, J=3.4, 1.3 Hz, 1H) ppm. M/e 479 (M+1)$^+$.

Compound 2.19

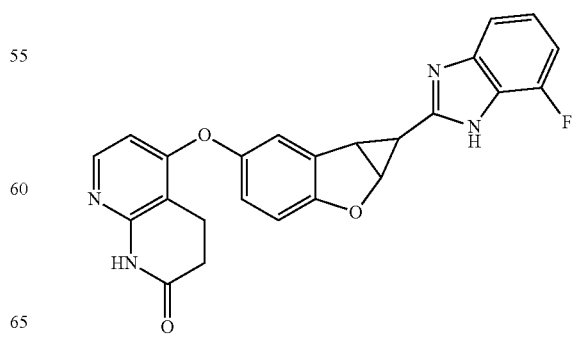

¹H-NMR (400 MHz, CD₃OD) δ 7.96 (d, J=6.2 Hz, 1H), 7.41 (d, J=8.2 Hz, 1H), 7.38-7.35 (m, 1H), 7.35-7.33 (m, 1H), 7.14 (dd, J=10.1, 8.3 Hz, 1H), 7.06 (d, J=8.5 Hz, 1H), 7.03 (dd, J=8.7, 2.3 Hz, 1H), 6.38 (d, J=6.1 Hz, 1H), 5.50 (dd, J=5.5, 1.3 Hz, 1H), 3.72 (dd, J=5.5, 3.4 Hz, 1H), 3.07 (t, J=7.7 Hz, 2H), 2.67 (t, J=7.7 Hz, 2H), 2.01 (dd, J=3.4, 1.4 Hz, 1H) ppm. MS: M/e 429 (M+1)⁺.

Compound 2.20

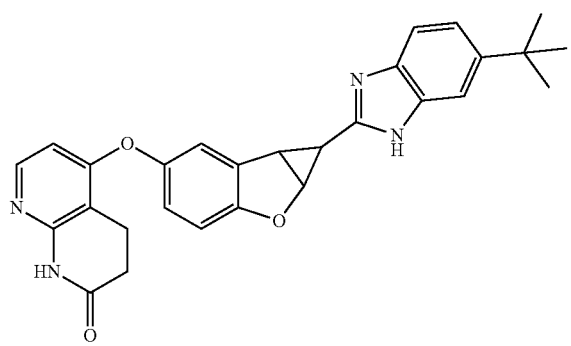 [SMILES: CC(C)(C)c1ccc2nc(C3C4Oc5ccc(Oc6ccnc7c6CCC(=O)N7)cc5C43)[nH]c2c1]

¹H-NMR (400 MHz, CD₃OD) δ 7.94 (d, J=5.8 Hz, 1H), 7.49 (s, 1H), 7.40 (d, J=8.6 Hz, 1H), 7.31 (dd, J=8.6, 1.7 Hz, 1H), 7.28 (d, J=2.2 Hz, 1H), 7.00 (d, J=8.6 Hz, 1H), 6.96 (dd, J=8.7, 2.3 Hz, 1H), 6.33 (d, J=5.9 Hz, 1H), 5.32-5.29 (m, 1H), 3.51-3.43 (m, 1H), 3.07 (t, J=7.8 Hz, 2H), 2.66 (t, J=7.8 Hz, 2H), 1.84-1.87 (m, 1H), 1.37 (s, 9H) ppm. MS: M/e 467 (M+1)⁺.

Compound 2.21

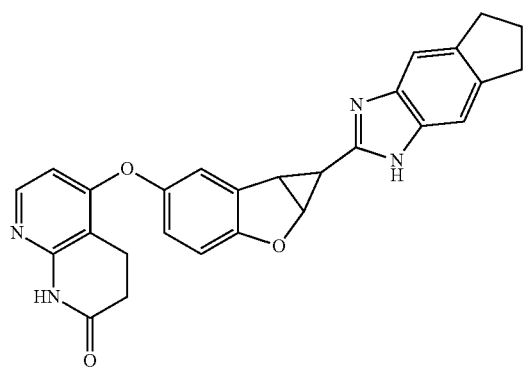 [SMILES: O=C1CCc2c(Oc3ccc4c(c3)C3C(O4)C3c3nc4cc5c(cc4[nH]3)CCC5)ccnc2N1]

¹H-NMR (400 MHz, DMSO-d₆) δ 12.18 (s,1H), 10.46 (s,1H), 7.96 (d, J=5.6 Hz, 1H), 7.35 (d, J=2.4 Hz, 1H), 7.27 (s, 2H), 7.04 (d, J=8.8 Hz, 1H), 6.98 (dd, J=2.4, 8.4 Hz, 1H), 6.27 (d, J=5.6 Hz, 1H), 5.33 (dd, J=1.2, 5.6 Hz, 1H), 3.43 (dd, J=3.2, 5.2 Hz, 1H), 2.95-2.88 (m, 6H), 2.54 (t, J=6.4 Hz, 2H), 2.07-2.00 (m, 2H), 1.83 (dd, J=0.8, 3.2 Hz, 1H) ppm. MS: M/e 451 (M+1)⁺.

Compound 2.22

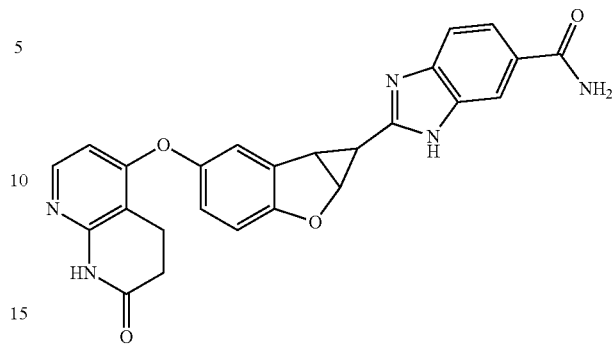

¹H-NMR (600 MHz, DMSO-d₆) δ 12.66-12.59 (m, 1H), 10.45 (s, 1H), 8.10-7.95 (m, 2H), 7.94-7.89 (m, 1H), 7.75-7.70 (m, 1H), 7.55-7.45 (m, 1H), 7.36 (d, J=2.4 Hz, 1H), 7.25-7.19 (m, 1H), 7.06 (dd, J=1.8, 9.0 Hz, 1H), 7.00 (d, J=8.4 Hz, 1H), 6.27 (dd, J=1.2, 6.0 Hz, 1H), 5.42-5.39 (m, 1H), 3.53-3.51 (m, 1H), 2.94 (t, J=7.2 Hz, 2H), 2.54 (t, J=7.2 Hz, 2H), 1.90 (dd, J=1.2, 3.0 Hz, 1H). MS: M/e 454 (M+1)⁺.

Compound 2.23

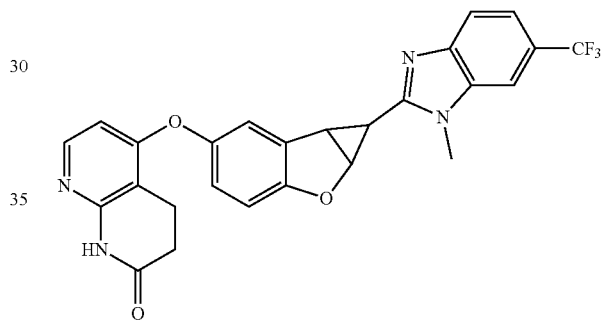

¹H-NMR (400 MHz, CD₃OD) δ 7.93 (d, J=5.5 Hz, 1H), 7.83 (s, 1H), 7.68 (d, J=8.5 Hz, 1H), 7.50 (d, J=8.4 Hz, 1H), 7.30 (d, J=2.4 Hz, 1H), 7.04-6.95 (m, 2H), 6.34 (d, J=5.9 Hz, 1H), 5.35 (dd, J=5.4, 1.3 Hz, 1H), 3.91 (s, 3H), 3.59-3.56 (m, 1H), 3.06 (t, J=7.8 Hz, 2H), 2.68-2.61 (m, 2H), 2.10 (dd, J=3.3, 1.3 Hz, 1H) ppm. MS: M/e 493 (M+1)⁺.

Compound 2.24

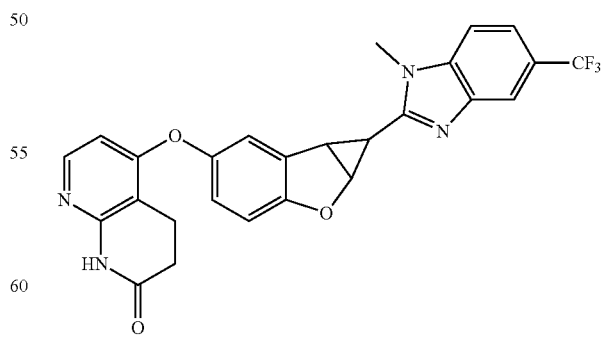

¹H-NMR (600 MHz, DMSO-d₆) δ 10.46 (s, 1H), 7.97 (d, J=6.0 Hz, 1H), 7.88 (s, 1H), 7.73 (d, J=9.0 Hz, 1H), 7.54 (d, J=8.4 Hz, 1H), 7.38 (d, J=2.4 Hz, 1H), 7.07 (d, J=8.4 Hz, 1H), 7.01 (dd, J=2.4, 8.4 Hz, 1H), 6.29 (d, J=6.0 Hz, 1H), 5.37 (dd, J=1.2, 5.4 Hz, 1H), 3.90 (s, 3H), 3.58-3.54 (m, 1H), 2.94 (t, J=7.2 Hz, 2H), 2.54 (t, J=7.2 Hz, 2H), 2.26 (dd, J=1.2, 3.0 Hz, 1H) ppm. MS: M/e 493 (M+1)+.

Compound 2.25

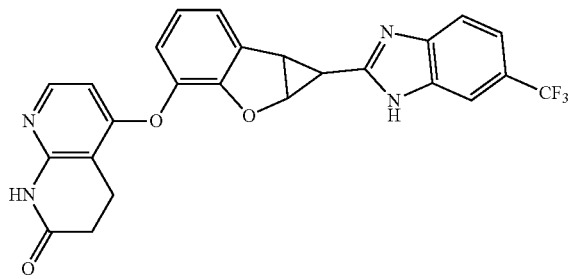 [SMILES: O=C1CCc2c(Oc3cccc4c3OC3C(c5nc6ccc(C(F)(F)F)cc6[nH]5)C43)ccnc2N1]

¹H-NMR (400 MHz, DMSO-d₆) δ 12.87 (br.s, 1H), 10.51 (s, 1H), 7.96 (d, J=6.0 Hz, 1H), 7.84 (s, 1H), 7.67 (d, J=8.4 Hz, 1H), 7.50-7.45 (m, 2H), 7.11-7.04 (m, 2H), 6.24 (d, J=5.6 Hz, 1H), 5.42 (dd, J=1.2, 5.2 Hz, 1H), 3.62 (dd, J=2.8, 4.8 Hz, 1H), 2.96 (t, J=8.0 Hz, 2H), 2.55 (t, J=8.0 Hz, 2H), 2.02 (d, J=1.6, 3.2 Hz, 1H) ppm. MS: M/e 479 (M+1)+.

Compound 2.26: (±)-exo-5-((1-(7-chloro-1H-benzo[d]imidazol-2-yl)-1a,6b-dihydro-1H-cyclopropa[b]benzofuran-5-yl)oxy)-3,4-dihydro-1,8-naphthyridin-2(1H)-one

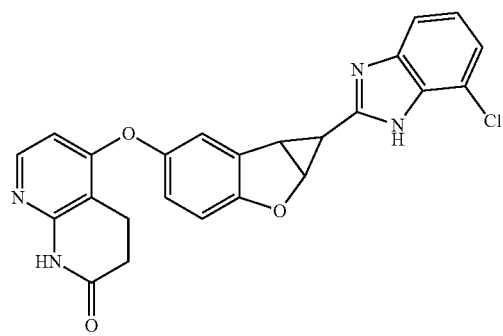

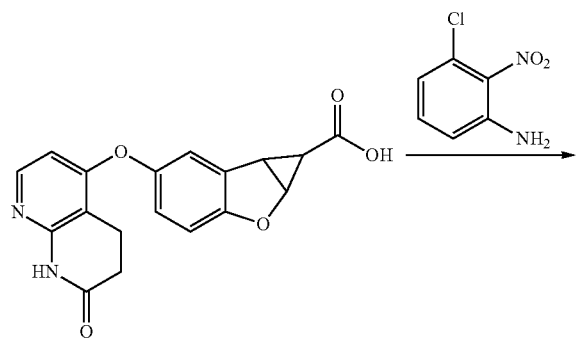

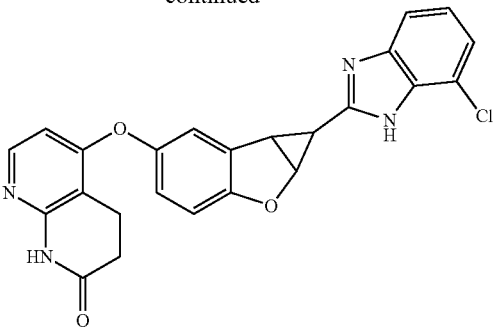

To a solution of Intermediate II (30 mg, 0.09 mmol) and 3-chloro-2-nitrobenzenamine (15.3 mg, 0.09 mmol) in pyridine (1 mL) was added phosphoryl trichloride (2 drops) at 0° C. Then the mixture was stirred at room temperature for 30 minutes. The reaction was diluted with water (10 mL) and extracted with ethyl acetate (2×10 mL). The combined organic phase was washed with brine (10 mL), dried over anhydrous sodium sulfate and concentrated under reduced pressure. The residue was dissolved into acetic acid (2 mL) and iron powder (15 mg, 0.27 mmol) was added into the reaction. The mixture was stirred at 70° C. for 2 hrs. The reaction was diluted was methanol (20 ml) and filtered through a celite pad. The filtrate was concentrate under reduced pressure and the residue was purified by prep-HPLC to give the title compound (6 mg, 15%), as a white solid. ¹H-NMR (600 MHz, CD₃OD) δ 7.97 (d, J=5.6 Hz, 1H), 7.56 (d, J=8.0 Hz, 1H), 7.44 (d, J=7.8 Hz, 1H), 7.38 (t, J=8.0 Hz, 1H), 7.35 (d, J=2.3 Hz, 1H), 7.07 (d, J=8.7 Hz, 1H), 7.05 (dd, J=8.7, 2.3 Hz, 1H), 6.40 (d, J=6.1 Hz, 1H), 5.55 (dd J=5.5, 0.9 Hz, 1H), 3.78 (dd, J=5.4, 3.4 Hz, 1H), 3.08 (t, J=7.8 Hz, 2H), 2.68 (t, J=7.8 Hz, 2H), 2.05 (d, J=2.8 Hz, 1H) ppm. MS: M/e 445 (M+1)+.

Compound 2.27: (±)-exo-5-((1-(6-hydroxy-1H-benzo[d]imidazol-2-yl)-1a,6b-dihydro-1H-cyclopropa[b]benzofuran-5-yl)oxy)-3,4-dihydro-1,8-naphthyridin-2(1H)-one

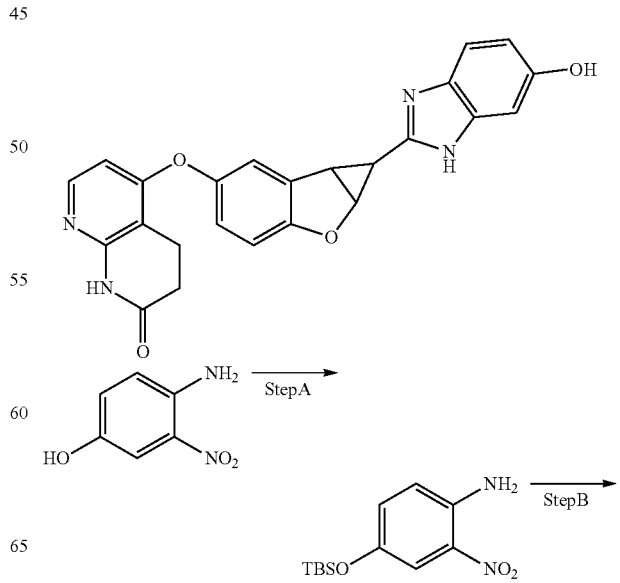

-continued

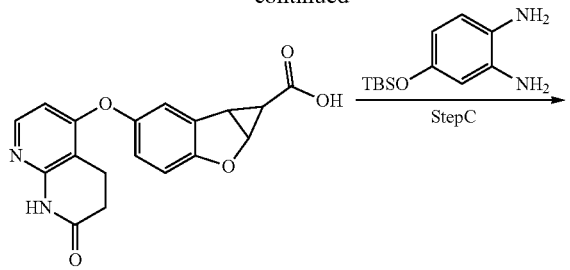

Step C

Step B: 4-((tert-butyldimethylsilyl)oxy)benzene-1,2-diamine

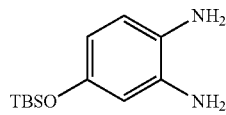

The mixture of 4-(tert-butyldimethylsilyloxy)-2-nitrobenzenamine (0.5 g, 1.9 mmol), Fe powder (1.1 g, 19 mmol) and acetic acid (1.0 mL, 18 mmol) in EtOH (10 mL) was stirred at reflux for 4 hrs. The mixture was filtered through celite pad and the filtrate was concentrated. Then the residue was diluted with ethyl acetate (100 mL), washed with a solution of saturated $NaHCO_3$ (3×30 mL) and brine (30 mL) and dried over anhydrous sodium sulfate and concentrated. The residue was purified by flash silica gel chromatography (eluted with PE:EtOAc 2:1) to obtain the title compound (0.34 g, 77%) as gray liquid. 1HNMR (600 MHz, DMSO-$d_6$) δ 6.31 (d, J=8.2 Hz, 1H), 6.06 (d, J=2.7 Hz, 1H), 5.84 (dd, J=8.2, 2.6 Hz, 1H), 0.88 (s, 9H), 0.07 (s, 6H).

Step C: (±)-exo-5-((1-(6-(((tert-butyldimethylsilyl)oxy)-1H-benzo[d]imidazol-2-yl)-1a,6b-dihydro-1H-cyclopropa[b]benzofuran-5-yl)oxy)-3,4-dihydro-1,8-naphthyridin-2(1H)-one

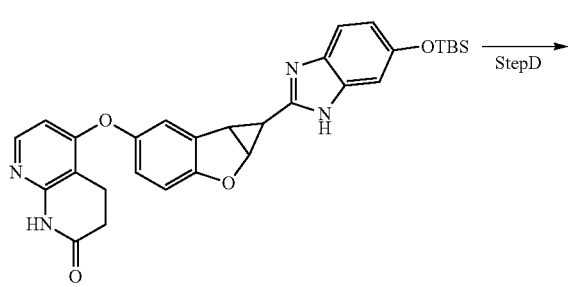

Step D

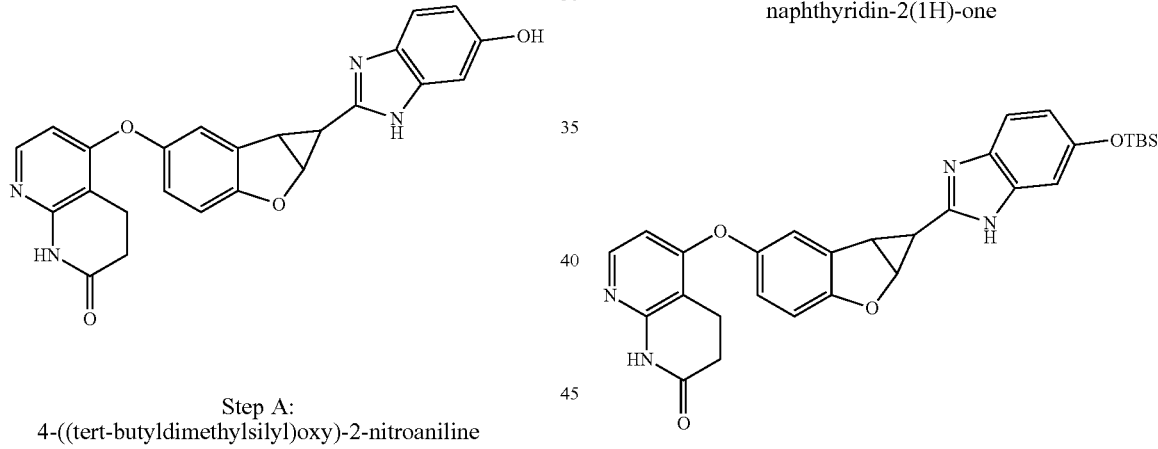

Step A: 4-((tert-butyldimethylsilyl)oxy)-2-nitroaniline

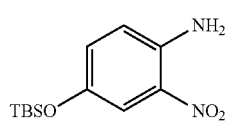

To a solution of 4-amino-3-nitrophenol (1.0 g, 6.5 mmol) and TBSCl (1.32 g, 8.8 mmol) in DMF (10 mL) was added imidazole (0.88 g, 13.0 mmol) at room temperature. The mixture was stirred at room temperature overnight. The mixture was diluted with ethyl acetate (300 mL), and washed with brine (100 mL) and dried over anhydrous sodium sulfate and concentrated. The residue was purified by silica gel chromatography (eluted with PE: EtOAc 2:1) to obtain the title compound (1.85 g, 100%) as gray solid. 1HNMR (600 MHz, $CDCl_3$) δ 7.54 (d, J=2.7 Hz, 1H), 6.96 (dd, J=8.9, 2.7 Hz, 1H), 6.70 (d, J=8.9 Hz, 1H), 0.96 (s, 9H), 0.18 (s, 6H).

The mixture of Intermediate II (30 mg, 0.09 mmol), 4-(tert-butyldimethylsilyloxy) benzene-1,2-diamine (9.6 mg, 0.089 mmol), DIPEA (0.5 mL) and HATU (37 mg, 0.101 mmol) in DMF (2 mL) was stirred at room temperature overnight. The reaction was diluted with ethyl acetate (20 mL), washed with brine, dried over sodium sulfate anhydrous and concentrated under reduced pressure. The residue was used in next step directly without further purification.

The mixture of above product in acetic acid (2 mL) was stirred at 80° C. for 3 hrs. Solvent was removed and the residue was diluted with water and adjusted to pH 7-8 by 2N NaOH. The mixture was extracted with DCM (2×10 mL). The combined organic phase was washed with brine (10 mL), dried over sodium sulfate anhydrous and concentrated under reduced pressure. The residue was purified by prep-HPLC to give the title compound as a white solid (20 mg, 40%).

Step D: (±)-exo-5-((1-(6-hydroxy-1H-benzo[d]imidazol-2-yl)-1a,6b-dihydro-1H-cyclopropa[b]benzofuran-5-yl)oxy)-3,4-dihydro-1,8-naphthyridin-2(1H)-one (Compound 2.27)

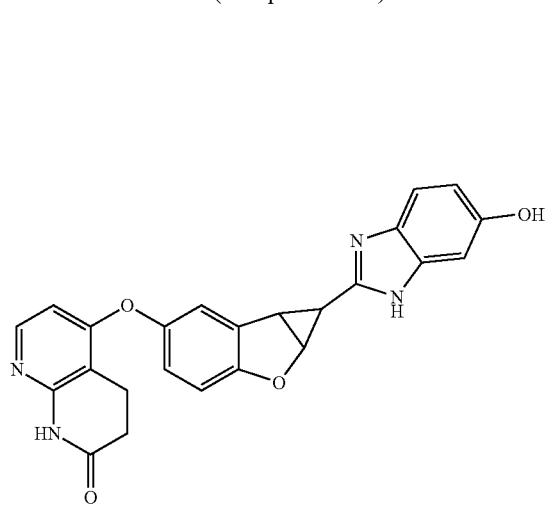

To a solution of the above product (30 mg, 0.037 mmol) in THF (2 mL) was added TBAF in THF (0.01 mL, 1 M, 0.01 mmol) drop wise at 0° C. Then the mixture was stirred at room temperature for 30 minutes. The reaction was diluted with water (10 mL) and extracted with ethyl acetate (20 mL×2). The combined organic phase was washed with brine (10 mL), dried over anhydrous sodium sulfate and concentrated under reduced pressure. The residue was purified by prep-HPLC to afford the title compound (10 mg, 63%) as a white solid. $^1$H-NMR (400 MHz, CD$_3$OD) δ 7.92 (d, J=5.9 Hz, 1H), 7.27 (d, J=6.2 Hz, 1H), 7.26 (s, 1H), 6.97 (d, J=8.6 Hz, 1H), 6.94 (dd, J=8.7, 2.3 Hz, 1H), 6.84 (d, J=2.1 Hz, 1H), 6.70 (dd, J=8.6, 2.3 Hz, 1H), 6.31 (d, J=5.9 Hz, 1H), 5.26 (dd, J=5.5, 1.4 Hz, 1H), 3.41 (dd, J=5.5, 3.4 Hz, 1H), 3.05 (t, J=7.7 Hz, 3H), 2.64 (t, J=7.7 Hz, 3H), 1.80 (dd, J=3.4, 1.4 Hz, 1H) ppm. MS: M/e 427 (M+1)$^+$.

Compound 2.28: (±)-exo-5-((1-(6-phenyl-1H-benzo[d]imidazol-2-yl)-1a,6b-dihydro-1H-cyclopropa[b]benzofuran-5-yl)oxy)-3,4-dihydro-1,8-naphthyridin-2(1H)-one

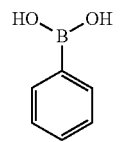

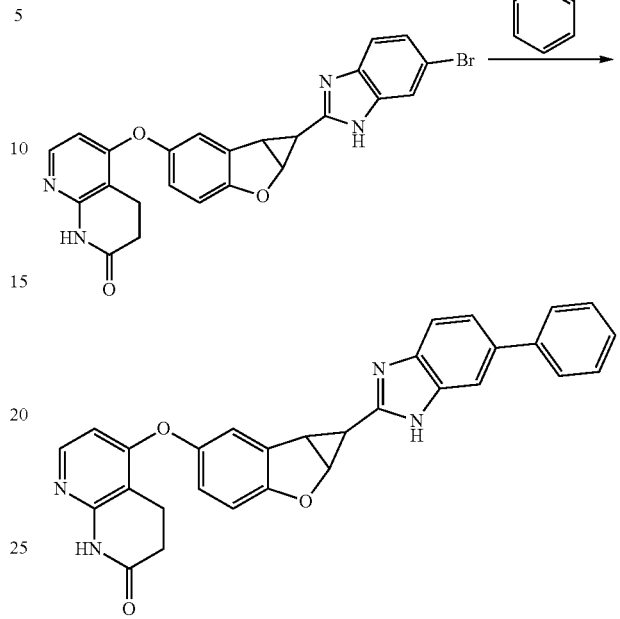

The mixture of 5-((1-(6-bromo-1H-benzo[d]imidazol-2-yl)-1a,6b-dihydro-1H-cyclopropa[b]benzofuran-5-yl)oxy)-3,4-dihydro-1,8-naphthyridin-2(1H)-one (22 mg, 0.045 mmol), phenylboronic acid (16.5 mg, 0.135 mmol), Pd(PPh3)4 (20 mg, 0.017 mmol) and K$_2$CO$_3$ (21 mg, 0.15 mmol) in a mixed solution of dioxane and water (2 mL, 4/1) was stirred at reflux under N$_2$ for 5 hrs. The mixture was diluted with brine (2 mL) and extracted with ethyl acetate (2 mL×3). The combined organics was washed with brine (2 mL×3), dried over Na$_2$SO$_4$ and concentrated. The residue was purified by prep-HPLC to give the title compound (12 mg, 55%) as a white solid. $^1$H-NMR (600 MHz, CD$_3$OD) δ 8.00 (d, J=5.9 Hz, 1H), 7.90 (s, 1H), 7.84 (dd, J=8.5, 1.5 Hz, 1H), 7.79 (d, J=8.6 Hz, 1H), 7.73-7.68 (m, 2H), 7.52 (t, J=7.7 Hz, 2H), 7.46-7.40 (m, 2H), 7.17-7.10 (m, 2H), 6.40 (d, J=6.0 Hz, 1H), 5.67 (dd, J=5.5, 1.2 Hz, 1H), 3.93-3.88 (m, 1H), 3.11 (t, J=7.8 Hz, 2H), 2.72-2.68 (m, 2H), 2.23-2.18 (m, 1H) ppm. MS: M/e 487 (M+1)$^+$.

Compound 2.29: (±)-exo-5-((1-(3-phenyl-1,2,4-oxadiazol-5-yl)-1a,6b-dihydro-1H-cyclopropa[b]benzofuran-5-yl)oxy)-3,4-dihydro-1,8-naphthyridin-2(1H)-one

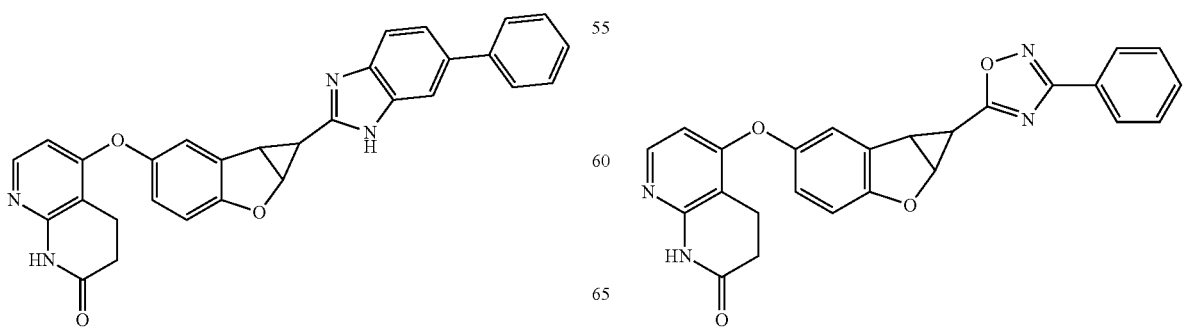

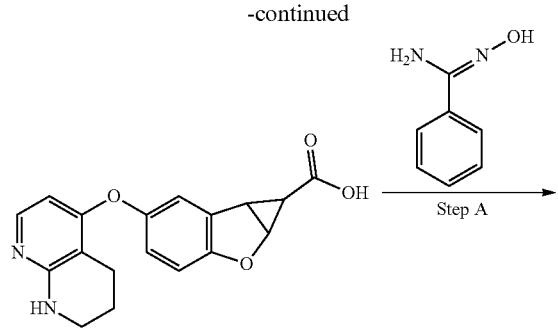

Intermediatre II

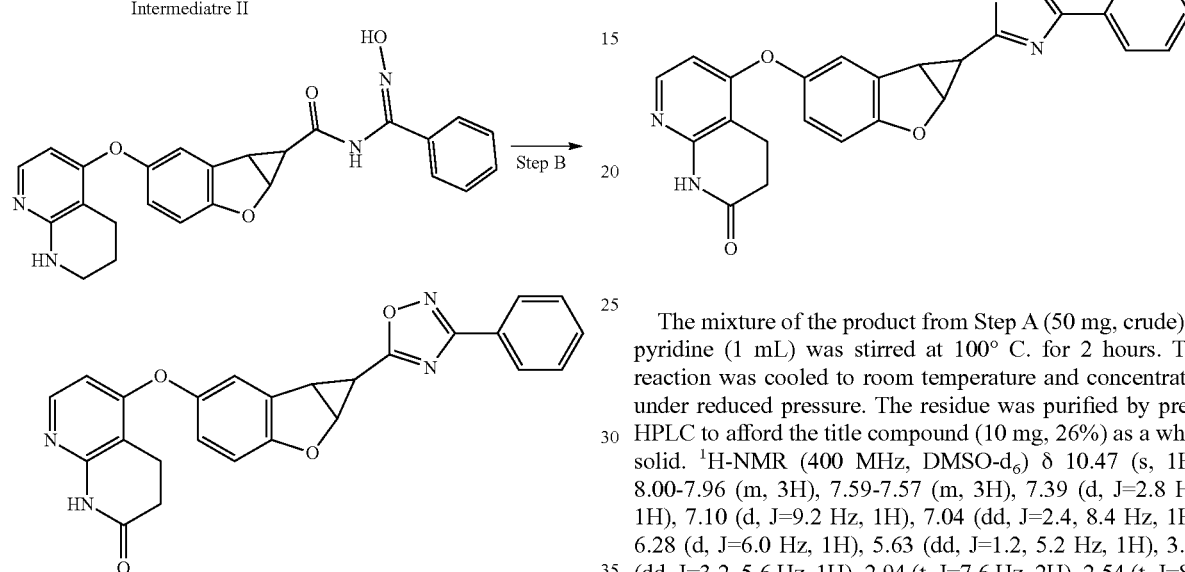

Step A: (±)-exo-N-((hydroxyimino)(phenyl)methyl)-5-((7-oxo-5,6,7,8-tetrahydro-1,8-naphthyridin-4-yl)oxy)-1a,6b-dihydro-1H-cyclopropa[b]benzofuran-1-carboxamide The mixture of Intermediate II (30 mg, 0.088 mmol), N-hydroxybenzimidamide (12 mg, 0.088 mol), HATU (37 mg, 0.1 mmol), and DIEPA (17 mg, 0.13 mmol) in DMF (1 mL) was stirred at room temperature overnight. The reaction was diluted with water (10 mL) and extracted with ethyl acetate (2×15 mL). The combined organic phase was washed with brine (2×5 mL), dried over anhydrous sodium sulfate, filtered and concentrated under reduced pressure. The residue (50 mg) was used directly in the next step without further purification.

Step B: (±)-exo-5-((1-(3-phenyl-1,2,4-oxadiazol-5-yl)-1a,6b-dihydro-1H-cyclopropa[b]benzofuran-5-yl)oxy)-3,4-dihydro-1,8-naphthyridin-2(1H)-one (Compound 2.29)

The mixture of the product from Step A (50 mg, crude) in pyridine (1 mL) was stirred at 100° C. for 2 hours. The reaction was cooled to room temperature and concentrated under reduced pressure. The residue was purified by prep-HPLC to afford the title compound (10 mg, 26%) as a white solid. $^1$H-NMR (400 MHz, DMSO-d$_6$) δ 10.47 (s, 1H), 8.00-7.96 (m, 3H), 7.59-7.57 (m, 3H), 7.39 (d, J=2.8 Hz, 1H), 7.10 (d, J=9.2 Hz, 1H), 7.04 (dd, J=2.4, 8.4 Hz, 1H), 6.28 (d, J=6.0 Hz, 1H), 5.63 (dd, J=1.2, 5.2 Hz, 1H), 3.74 (dd, J=3.2, 5.6 Hz, 1H), 2.94 (t, J=7.6 Hz, 2H), 2.54 (t, J=8.4 Hz, 2H), 2.36 (dd, J=1.2, 3.2 Hz, 1H) ppm. MS: M/e 439 (M+1)$^+$.

Compound 2.30: (±)-exo-5-((1-(4-phenyl-1H-imidazol-2-yl)-1a,6b-dihydro-1H-cyclopropa[b]benzofuran-5-yl)oxy)-3,4-dihydro-1,8-naphthyridin-2(1H)-one

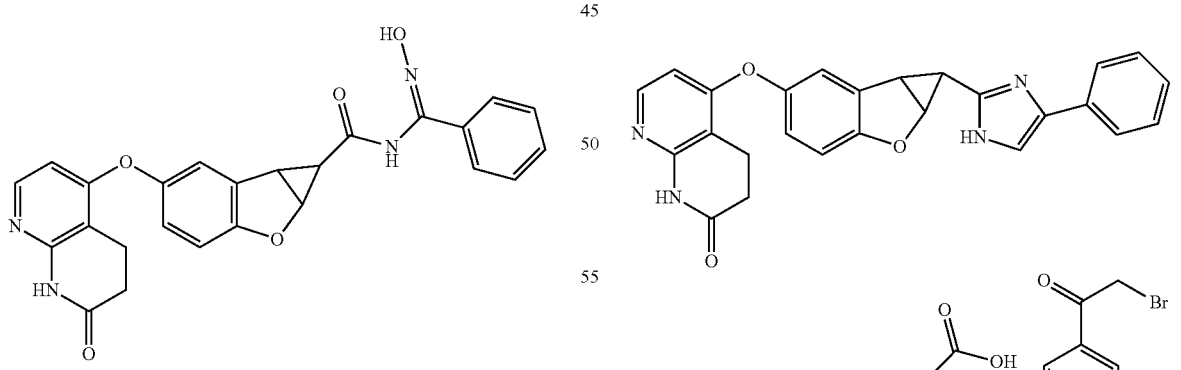

-continued

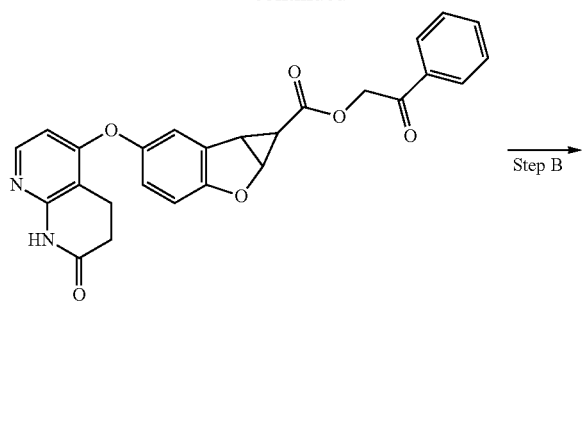

Step A: (±)-exo-2-oxo-2-phenylethyl 5-((7-oxo-5,6,7,8-tetrahydro-1,8-naphthyridin-4-yl)oxy)-1a,6b-dihydro-1H-cyclopropa[b]benzofuran-1-carboxylate

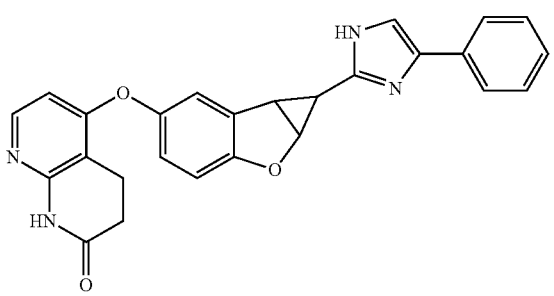

The mixture of Intermediate II (30 mg, 0.088 mmol), 2-bromo-1-phenylethanone (35 mg, 0.176 mol) and K₂CO₃ (36 mg, 0.264 mmol) in DMF (1 mL) was stirred at rt for 0.5 hour. The reaction was diluted with water (10 mL) and extracted with ethyl acetate (2×15 mL). The combined organic phases were washed with brine (10 mL), dried over anhydrous sodium sulfate and concentrated under reduced pressure. The residue (50 mg) was used in the next step directly without further purification.

Step B: (±)-exo-5-((1-(4-phenyl-1H-imidazol-2-yl)-1a,6b-dihydro-1H-cyclopropa[b]benzofuran-5-yl)oxy)-3,4-dihydro-1,8-naphthyridin-2(1H)-one (Compound 2.30)

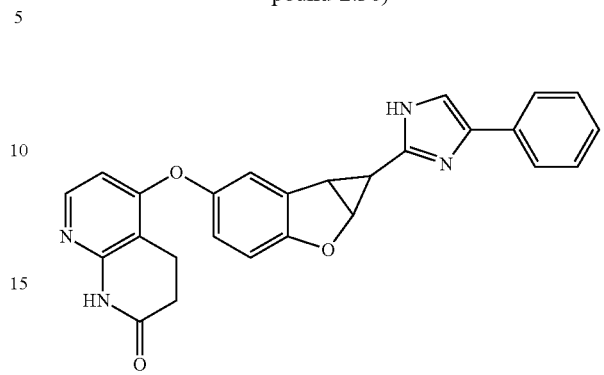

The mixture of the product from Step A (50 mg, crude) and NH4OAc in AcOH (1 mL) was stirred at 120° C. for 10 hours. The reaction was cooled to rt and the mixture was diluted with saturated NaHCO₃ solution (30 mL) and extracted with ethyl acetate (2×15 mL). The combined organic phase was washed with brine (10 mL), dried over anhydrous sodium sulfate, and concentrated under reduced pressure. The residue was purified by prep-HPLC to afford the title compound (7 mg, 18%) as a while solid. ¹H-NMR (400 MHz, DMSO-d₆) δ 12.08 (s, 1H), 10.46 (s, 1H), 7.96 (d, J=6.0 Hz, 1H), 7.73-7.70 (m, 2H), 7.56-7.55 (m, 1H), 7.36-7.30 (m, 3H), 7.20-7.17 (m, 1H), 7.01 (d, J=8.4 Hz, 1H), 6.95 (dd, J=2.4, 8.8 Hz, 1H), 6.26 (d, J=6.0 Hz, 1H), 5.26 (dd, J=1.6, 5.6 Hz, 1H), 3.31 (s, 1H), 2.94 (t, J=7.2 Hz, 2H), 2.54 (t, J=6.4 Hz, 2H), 1.75 (dd, J=1.2, 3.2 Hz, 1H) ppm. MS: M/e 437 (M+1)⁺.

Compound 2.31

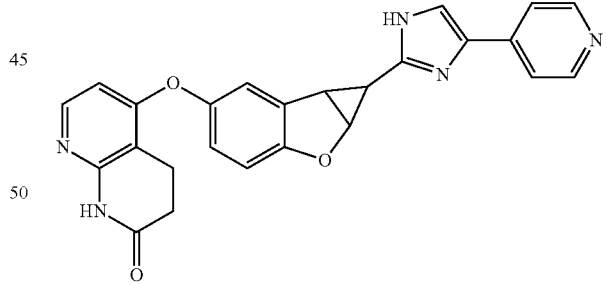

Compound 2.31 was prepared according to the procedures described for compound 2.30 by using 2-bromo-1-(pyridin-4-yl)ethanone.

¹H-NMR (400 MHz, CD₃OD) δ 8.54-8.45 (m, 2H), 7.95 (d, J=6.0 Hz, 1H), 7.78-7.73 (m, 2H), 7.70 (s, 1H), 7.27 (d, J=2.4 Hz, 1H), 6.99-9.64 (m, 2H), 6.33 (d, J=6.0 Hz, 1H), 5.27 (dd, J=1.6, 5.6 Hz, 1H), 3.38 (dd, J=3.6, 5.6 Hz, 1H), 3.08 (t, J=7.6 Hz, 2H), 2.69-2.65 (m, 2H), 1.81 (dd, J=1.6, 3.6 Hz, 1H) ppm. MS: M/e 438 (M+1)⁺.

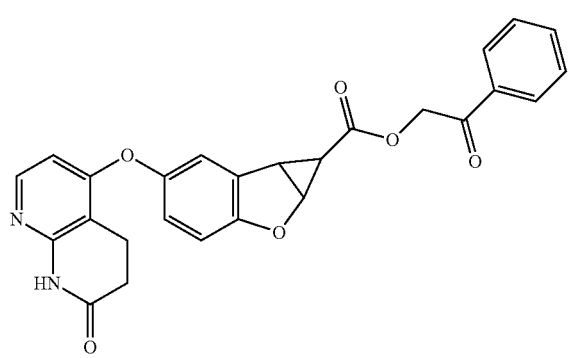 [SMILES: O=C1CCc2c(Oc3ccc4c(c3)C3C(O4)C3C(=O)OCC(=O)c3ccccc3)ccnc2N1]

Compound 2.32

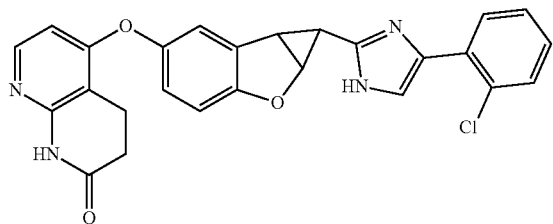 [SMILES: O=C1CCc2c(Oc3ccc4c(c3)C3C(O4)C3c3nc(-c4ccccc4Cl)c[nH]3)ccnc2N1]

Compound 2.32 was prepared according to the procedures described for compound 2.30 by using 2-bromo-1-(2-chlorophenyl)ethanone.

$^1$H-NMR (400 MHz, DMSO-d$_6$) δ 12.25 (br.s, 1H), 10.43 (s, 1H), 8.22-8.21 (m, 1H), 8.10-8.00 (m, 1H), 7.94-7.93 (m, 1H), 7.71-7.60 (m, 1H), 7.43-7.42 (m, 1H), 7.34-7.30 (m, 1H), 7.25-7.15 (m, 1H), 6.99-9.92 (m, 2H), 6.23 (d, J=4.4 Hz, 1H), 5.25 (s, 1H), 3.38-3.30 (m, 1H), 3.08-2.89 (m, 2H), 2.69-2.55 (m, 2H), 1.76 (s, 1H) ppm. MS: M/e 471 (M+1)$^+$.

Compound 2.33: (±)-exo-5-((1-(4-(trifluoromethyl)-1H-imidazol-2-yl)-1a,6b-dihydro-1H-cyclopropa[b]benzofuran-5-yl)oxy)-3,4-dihydro-1,8-naphthyridin-2(1H)-one

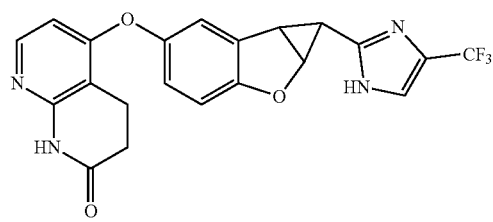

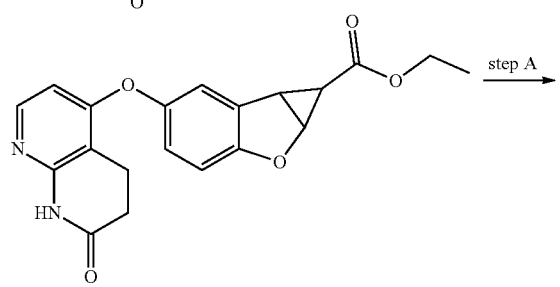
step A

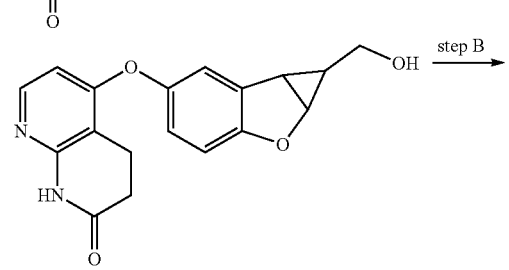
step B

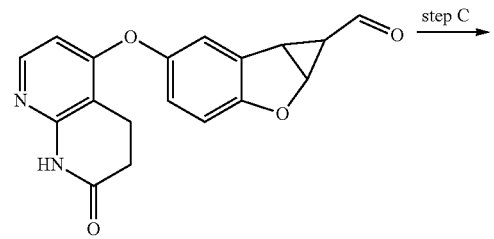
step C

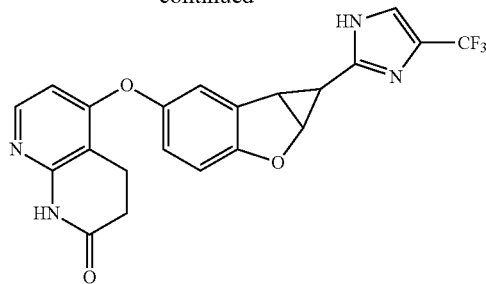

Step A: (±)-exo-5-((1-(hydroxymethyl)-1a,6b-dihydro-1H-cyclopropa[b]benzofuran-5-yl)oxy)-3,4-dihydro-1,8-naphthyridin-2(1H)-one

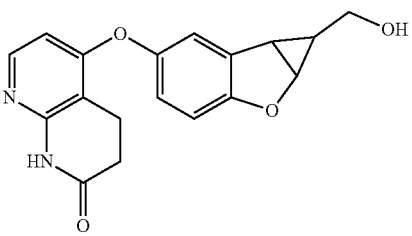 [SMILES: O=C1CCc2c(Oc3ccc4c(c3)C3C(CO)C3O4)ccnc2N1]

To a mixture of ethyl 5-((7-oxo-5,6,7,8-tetrahydro-1,8-naphthyridin-4-yl)oxy)-1a,6b-dihydro-1H-cyclopropa[b]benzofuran-1-carboxylate (Intermediate II, 217 mg, 0.59 mmol) in THF (10 mL) was added LiAlH4 (27 mg, 0.71 mmol). The reaction was stirred at rt for 0.25 hour. Water (10 mL) was added dropwise and the mixture was extracted with ethyl acetate (2×15 mL). The combined organic layers were washed with brine (10 mL), dried over anhydrous sodium sulfate and concentrated under reduced pressure. The residue (190 mg) was used into next step directly without further purification.

Step B: (±)-exo-5-((7-oxo-5,6,7,8-tetrahydro-1,8-naphthyridin-4-yl)oxy)-1a,6b-dihydro-1H-cyclopropa[b]benzofuran-1-carbaldehyde

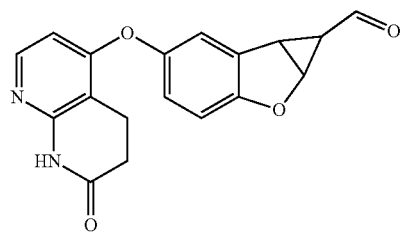 [SMILES: O=CC1C2Oc3ccc(Oc4ccnc5c4CCC(=O)N5)cc3C12]

The mixture of the product of Step A (190 mg, crude) and PCC (255 mg, 1.2 mmol) in DCM (5 mL) was stirred at rt overnight. The mixture was diluted with saturated water (30 mL) and extracted with DCM (2×15 mL). The combined organic phase was washed with brine (10 mL), dried over anhydrous sodium sulfate, and concentrated under reduced pressure. The residue was purified by prep-TLC (DCM/MeOH=15/1) to afford the title compound (35 mg, 17% for two steps) as a white solid.

Step C: (±)-exo-5-((1-(4-(trifluoromethyl)-1H-imidazol-2-yl)-1a,6b-dihydro-1H-cyclopropa[b]benzofuran-5-yl)oxy)-3,4-dihydro-1,8-naphthyridin-2(1H)-one (Compound 2.33)

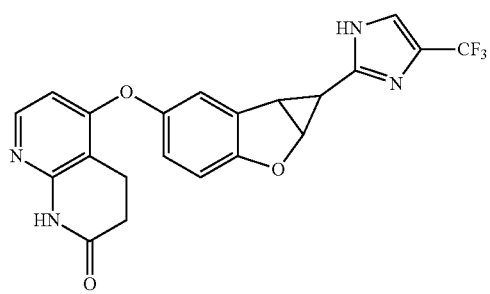 [SMILES: O=C1CCc2c(Oc3ccc4c(c3)C3C(O4)C3c3nc(C(F)(F)F)c[nH]3)ccnc2N1]

3,3-Dibromo-1,1,1-trifluoropropan-2-one (30 mg, 0.11 mmol) and NaOAc (8 mg, 0.11 mmol) were dissolved in water (1 mL) and heated to 100° C. for one hour. The mixture was added to a solution of the product of Step B (35 mg, 0.1 mmol) and ammonium hydroxide (0.5 mL) in methanol (3 mL). The resulting mixture was stirred at rt for 40 min and then heated to reflux for one hour. After cooling, the mixture was concentrated under reduced pressure. The residue was purified by prep-HPLC to afford the title compound (8 mg, 19%) as a while solid. $^1$H-NMR (400 MHz, DMSO-$d_6$) δ 12.60 (s,1H), 10.43 (s,1H), 7.92 (d, J=6.0 Hz, 1H), 7.68 (s, 1H), 7.29 (d, J=2.4 Hz, 1H), 6.98 (d, J=8.4 Hz, 1H), 6.93 (dd, J=2.4, 8.4 Hz, 1H), 6.22 (d, J=5.2 Hz, 1H), 5.21 (dd, J=1.2, 5.6 Hz, 1H), 3.31-3.28 (m, 1H), 2.90 (t, J=7.6 Hz, 2H), 2.51 (t, J=6.0 Hz, 2H), 1.74 (dd, J=1.6, 3.2 Hz, 1H) ppm MS: M/e 429 (M+1)$^+$.

Compound 2.34: (±)-exo-5-((1-( 1-(2-hydroxyethyl)-5-(trifluoromethyl)-1H-benzo[d]imidazol-2-yl)-1a,6b-dihydro-1H-cyclopropa[b]benzofuran-5-yl)oxy)-3,4-dihydro-1,8-naphthyridin-2(1H)-one

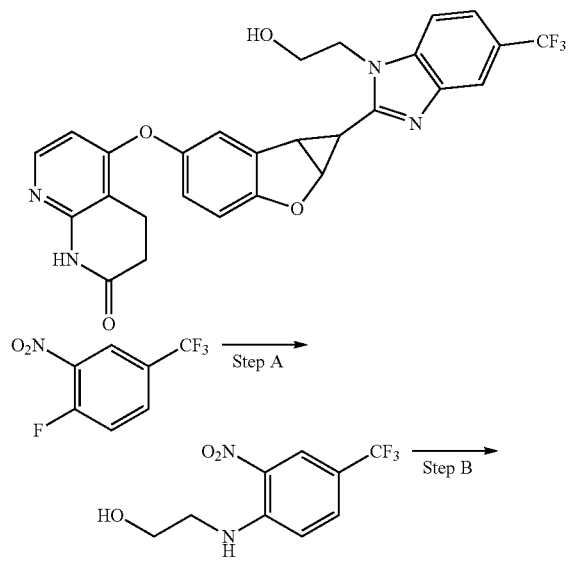

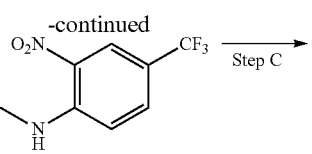

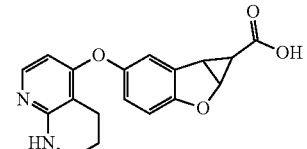

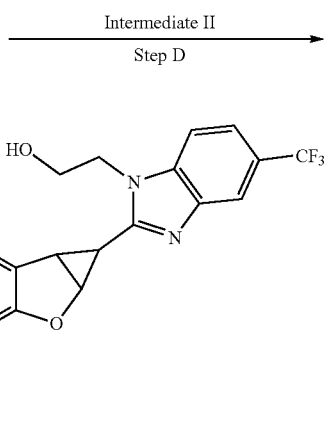

Step A: 2-((2-nitro-4-(trifluoromethyl)phenyl)amino)ethanol

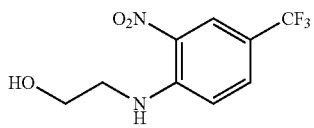 [SMILES: O=[N+]([O-])c1cc(C(F)(F)F)ccc1NCCO]

To a solution of 2-aminoethanol (1.76 g, 28.8 mmol) in THF (10 mL) was added 1-fluoro-2-nitro-4-(trifluoromethyl)benzene (2.0 g, 9.6 mmol) at 0 oC. The solution was allowed to warm to RT and stirred at RT for 2 h. Solvent was removed under reduced pressure, and the residue was diluted with EtOAc (100 mL)washed with brine (30 mL×3), dried over anhydrous sodium sulfate, filtered and concentrated to give the title compound (2.4 g, 100%), which was used in the next step without further purification. $^1$H NMR (600 MHz, CDCl$_3$) δ 8.59-8.44 (m, 2H), 7.65 (dd, J=9.0, 2.2 Hz, 1H), 7.03 (d, J=9.0 Hz, 1H), 4.03-3.99 (m, 2H), 3.60-3.56 (m, 2H).

Step B: N-(2-((tert-butyldimethylsilyl)oxy)ethyl)-2-nitro-4-(trifluoromethyl)aniline

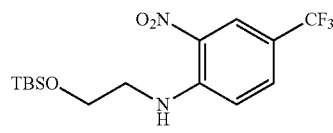

To a solution of the product of Step A (2.4 g, 9.6 mmol) and TBSCl (1.73 g, 11.5 mmol) in DMF (15 mL) was added imidazole (1.3 g, 19.2 mmol) at room temperature. The mixture was stirred at room temperature overnight. The mixture was diluted with ethyl acetate (100 mL), and washed with brine (30 mL×3) and dried over anhydrous sodium sulfate and concentrated. The residue was purified by silica gel chromatography (eluted with PE) to obtain the title compound (3.5 g, 100%) as yellow solid. $^1$H NMR (600 MHz, CDCl$_3$) δ 8.56 (s, 1H), 8.50 (d, J=1.2 Hz, 1H), 7.63 (dd, J=9.0, 2.2 Hz, 1H), 7.00 (d, J=9.0 Hz, 1H), 4.02-3.87 (m, 2H), 3.52-3.48 (m, 2H), 0.94 (s, 9H), 0.13 (s, 6H).

Step C: N1-(2-(((tert-butyldimethylsilyl)oxy)ethyl)-4-(trifluoromethyl)benzene-1,2-diamine

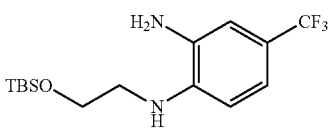 [SMILES: CC(C)(C)[Si](C)(C)OCCNc1ccc(C(F)(F)F)cc1N]

A mixture of the product of Step B (3.5 g, 9.6 mmol) and Pd/C (0.3 g) in MeOH (20 mL) was stirred at RT for 4 hrs under H$_2$ atmosphere. The mixture was filtered through celite pad and the filtrate was concentrated. Then the residue was diluted with ethyl acetate (100 mL), washed with brine (30 mL×3) and dried over anhydrous sodium sulfate and concentrated to obtain the title compound (3.1 g, 90%) as violetsolid. $^1$H NMR (600 MHz, CDCl$_3$) δ 7.10 (dd, J=8.2, 1.0 Hz, 1H), 6.95 (d, J=1.8 Hz, 1H), 6.67 (d, J=8.2 Hz, 1H), 3.92 (t, J=5.3 Hz, 2H), 3.27 (t, J=5.3 Hz, 2H), 0.95 (s, 9H), 0.12 (s, 6H).

Step D: (±)-exo-5-((1-(1-(2-hydroxyethyl)-5-(trifluoromethyl)-1H-benzo[d]imidazol-2-yl)-1a,6b-dihydro-1H-cyclopropa[b]benzofuran-5-yl)oxy)-3,4-dihydro-1,8-naphthyridin-2(1H)-one (Compound 2.34)

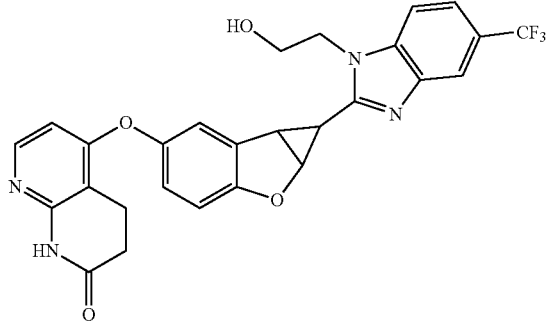 [SMILES: O=C1CCc2c(Oc3ccc4c(c3)C3C(O4)C3c3nc4cc(C(F)(F)F)ccc4n3CCO)ccnc2N1]

The mixture of Intermediate II (300 mg, 0.9 mmol), the product of Step C (440 mg, 1.45 mmol), DIPEA (1 mL), and HATU (551 mg, 1.45 mmol) in DMF (5 mL) was stirred at room temperature overnight. The reaction was diluted with ethyl acetate (20 mL), washed with brine, dried over sodium sulfate anhydrous and concentrated under reduced pressure. The residue was used in next step directly without further purification.

The mixture of the crude product in acetic acid (5 mL) was stirred at 80° C. for 8 hrs. Solvent was removed and the residue was diluted with water. The pH value of the resulting mixture was adjusted to 7-8 using 2N NaOH. The mixture was extracted with DCM (2×10 mL). The combined organic phase was washed with brine (10 mL), dried over sodium sulfate anhydrous and concentrated under reduced pressure. The residue was purified by flash silica gel chromatography (eluted with PE: EtOAc 1:3) to afford the crude product which was then further purified by prep-HPLC to give the title compound as a white solid (61 mg, 13%). $^1$H-NMR (400 MHz, DMSO-d$_6$) δ 10.45 (s, 1H), 7.94 (d, J=5.8 Hz, 1H), 7.86 (s, 1H), 7.72 (d, J=8.4 Hz, 1H), 7.51-7.47 (m, 1H), 7.33 (d, J=2.5 Hz, 1H), 7.04 (d, J=8.7 Hz, 1H), 6.97 (dd, J=8.7, 2.6 Hz, 1H), 6.26 (d, J=5.8 Hz, 1H), 5.34 (dd, J=5.3, 1.2 Hz, 1H), 4.43-4.37 (m, 2H), 3.68 (t, J=5.3 Hz, 2H), 3.53 (dd, J=5.2, 3.3 Hz, 1H), 2.91 (t, J=7.7 Hz, 2H), 2.51 (t, J=7.7 Hz, 2H), 2.23 (dd, J=3.2, 1.2 Hz, 1H).

Compound 2.35: (±)-exo-5-((3-methyl-1-(6-(trifluoromethyl)-1H-benzo[d]imidazol-2-yl)-1a,6b-dihydro-1H-cyclopropa[b]benzofuran-5-yl)oxy)-3,4-dihydro-1,8-naphthyridin-2(1H)-one

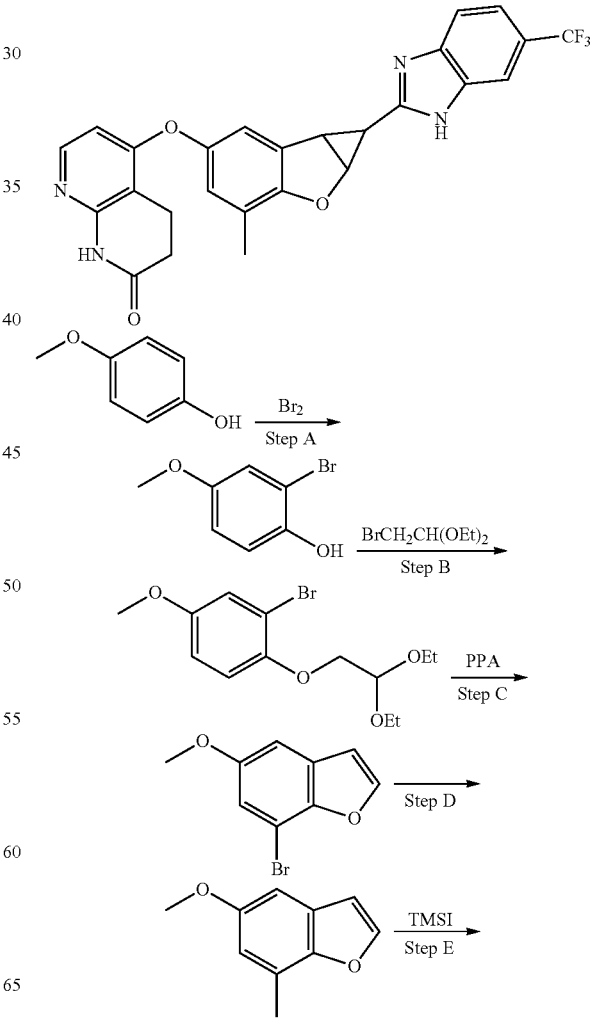

83
-continued

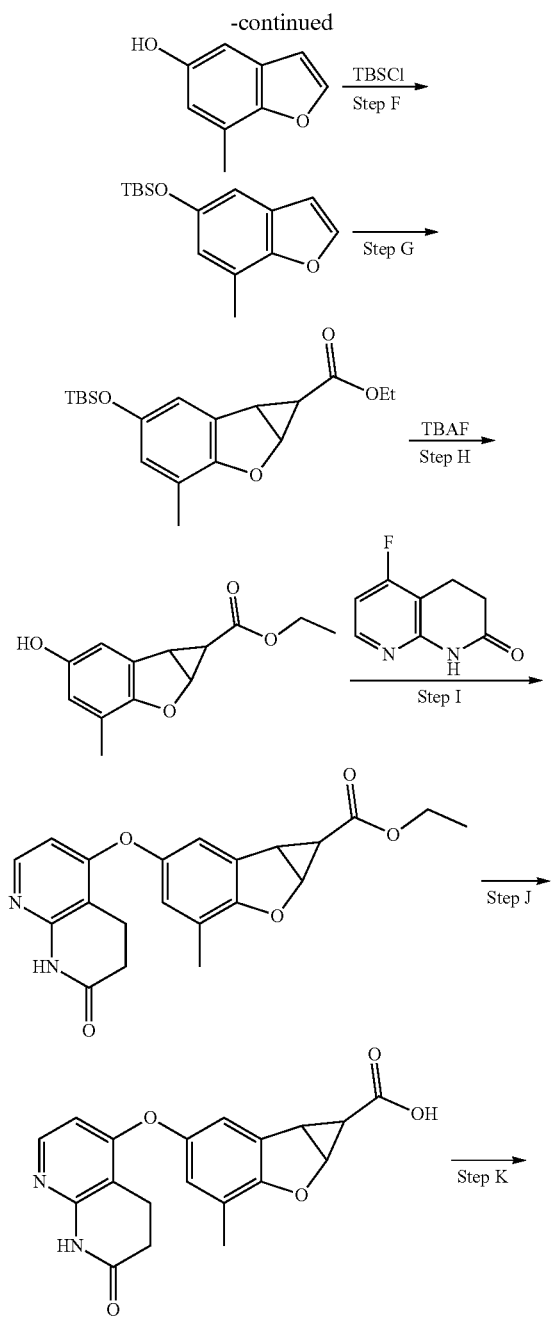

84

Step A: 2-bromo-4-methoxyphenol

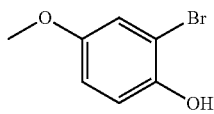

To a solution of 4-methoxyphenol (10 g, 81 mmol) in CHCl3 (50 mL) was added BR² (4 mL, 78 mmol) at 0° C. The mixture was stirred at 0° C. for 1 h, then allowed to warm to room temperature, the mixture was stirred at room temperature for 1 h. The resulting mixture was diluted with dichloromethane (500 mL) and washed with saturated NaHSO3 (3×100 mL) and brine (200 mL), dried over anhydrous sodium sulfate, filtered and concentrated to afford the title compound (16.6 g, 100%) as an off-white solid which was used in the next step.

Step B:
2-bromo-1-(2,2-diethoxyethoxy)-4-methoxybenzene

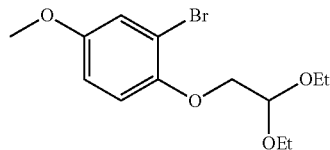 [SMILES: CCOC(COc1ccc(OC)cc1Br)OCC]

A mixture of the product from Step A (1.01 g, 5 mmol), 2-bromo-1,1-diethoxyethane (1.05 g, 5.25 mmol) and Cs₂CO₃ (2.04 g, 6 mmol) in DMF (10 mL) was stirred at 120° C. for 2 hrs. The reaction was cooled to room temperature. The mixture was diluted with EtOAc (200 mL) and washed with brine (50 mL), dried over anhydrous sodium sulfate and concentrated. The residue was purified by column chromatography (eluted with PE:EtOAc=6:1) to the title compound (2.7 g, 85%) as an oil. ¹H-NMR (600 MHz, CDCl₃) δ 7.12 (d, J=3.0 Hz, 1H), 6.89 (d, J=9.0 Hz, 1H), 6.81 (dd, J=9.0, 3.0 Hz, 1H), 4.87 (t, J=5.2 Hz, 1H), 4.02 (d, J=5.2 Hz, 2H), 3.84-3.78 (m, 2H), 3.77 (s, 3H), 3.73-3.67 (m, 2H), 1.27 (t, J=7.1 Hz, 6H) ppm.

Step C: 7-bromo-5-methoxybenzofuran

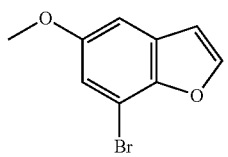

To a mixture of the product from step B (2.7 g, 8.5 mmol) in toluene (10 mL) was added PPA (1.0 mL). The reaction was heated at 70° C. for 1 hr. The reaction was cooled to room temperature. The mixture was diluted with EtOAc (200 mL) and the water phase was adjusted to pH 7-8 by NaOH (2 mol/L). The organic phase was washed with brine (50 mL), dried over anhydrous sodium sulfate and concentrated under reduced pressure. The residue was purified by silica column chromatography (eluted with PE) to afford the

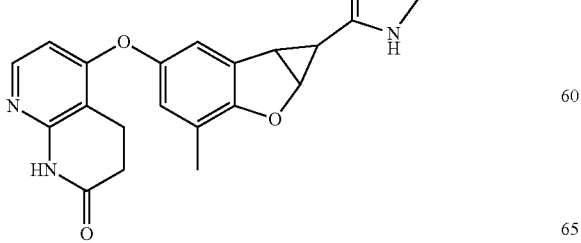

title compound (0.27 g, 16%) as an oil. $^1$H-NMR (600 MHz, CDCl$_3$) δ 7.68 (d, J=2.1 Hz, 1H), 7.13 (d, J=2.2 Hz, 1H), 7.04 (d, J=2.3 Hz, 1H), 6.79 (d, J=2.1 Hz, 1H), 3.86 (s, 3H) ppm.

Step D: 5-methoxy-7-methylbenzofuran

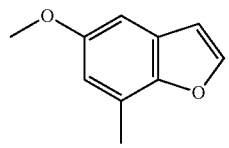

A mixture of the product from Step C (3.6 g, 16 mmol); methylboronic acid (1.4 g, 24 mmol), Pd(dppf)$_2$Cl$_2$ (0.65 g, 0.8 mmol) and CS$_2$CO$_3$ (13.0 g, 40 mmol) in 1,4-dioxane (50 mL) and H2O (10 mL) was refluxed for 3 hrs under N$_2$ atmosphere. The reaction was cooled to room temperature and filtered through a celite pad. The filtrate was diluted with EtOAc (200 mL) and washed with brine (50 mL), dried over anhydrous sodium sulfate, and concentrated under reduced pressure. The residue was purified by silica column, chromatography (eluted with PE), to afford the title compound (1.0 g, 38%) as an oil. $^1$H-NMR (600 MHz, CDCl$_3$) δ 7.63 (d, J=1.6 Hz, 1H), 6.92 (d, J=2.1 Hz, 1H), 6.76 (s, 1H), 6.73 (d, J=1.8 Hz, 1H), 3.86 (s, 3H), 2.53 (s, 3H) ppm.

Step E: 7-methylbenzofuran-5-ol

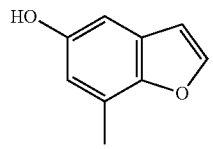

To a mixture of the product from Step D (850 mg, 5.2 mmol) and K$_2$CO$_3$ in acetonitrile (10 mL) was added TMSI (1.1 mL). The mixture was refluxed for 2 hrs. The reaction was cooled to room temperature. The mixture was diluted with EtOAc (100 mL) and washed with brine (30 mL), dried over anhydrous sodium sulfate and concentrated under reduced pressure. The residue was purified by silica gel column chromatography (eluted with PE:EtOAc=5:1) to afford the title compound (200 mg, 25%) as an oil.

Step F: tert-butyldimethyl((7-methylbenzofuran-5-yl)oxy)silane

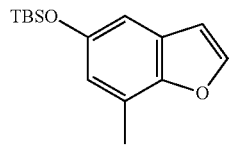 [SMILES: Cc1cc(O[Si](C)(C)C(C)(C)C)cc2ccoc12]

A solution of the product from Step E (200 mg, 1.4 mmol), TBSCl (225 mg, 1.5 mmol) and imidazole (190 mg, 2.8 mmol) in DMF (5 mL) was stirred at room temperature for 1 hr. The mixture was diluted with EtOAc (100 mL) and washed with brine (30 mL), dried over anhydrous sodium sulfate and concentrated under reduced pressure. The residue was purified by silica gel column chromatography (eluted with PE) to afford the title compound as an oil (260 mg, 71%).

Step G: (±)-exo-ethyl5-((tert-butyldimethylsilyl)oxy)-3-methyl-1a,6b-dihydro-1H-cyclopropa[b]benzofuran-1-carboxylate

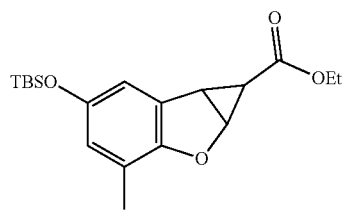 [SMILES: CCOC(=O)C1C2Oc3c(C)cc(O[Si](C)(C)C(C)(C)C)cc3C21]

To a solution of the product from Step F (260 mg, 1 mmol) and copper (I) triflate (2:1 complex with toluene, 1 mg, 0.03 mmol) in dichloromethane (2 mL) was added ethyl diazoacetate (1.0 mL, 10 mol) in dichloromethane (10 mL) through a syringe pump over a period of 10 hrs. Solvent was removed under reduced pressure, and the residue was purified by silica gel chromatography (eluted with PE) to obtain the title compound (200 mg, crude), which was used in next step without further purification.

Step H: (±)-exo-ethyl5-hydroxy-3-methyl-1a,6b-dihydro-1H-cyclopropa[b]benzofuran-1-carboxylate

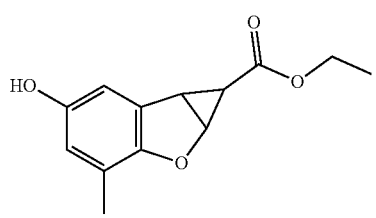 [SMILES: CCOC(=O)C1C2Oc3c(C)cc(O)cc3C21]

To a solution of the product from Step G (200 mg, 0.6 mmol) in THF (5 mL) was added TBAF in THF (0.15 mL, 1 M, 0.15 mmol) dropwise at 0° C. Then the mixture was stirred at room temperature for 10 minutes. The reaction was concentrated and purified by silica gel chromatography (eluted with EtOAc:PE=1:10) to obtain the title compound (100 mg, 43% yield for two steps) as colorless oil, which was used directly in next step.

Step I: (±)-exo-ethyl 3-methyl-5-((7-oxo-5,6,7,8-tetrahydro-1,8-naphthyridin-4-yl)oxy)-1a,6b-dihydro-1H-cyclopropa[b]benzofuran-1-carboxylate

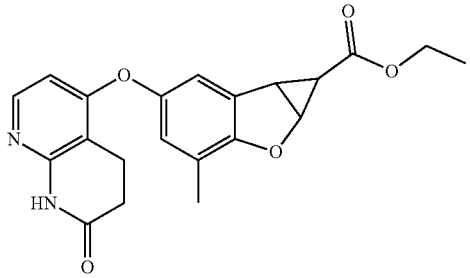

The mixture of the product from step H (90 mg, 0.38 mmol), 5-fluoro-3,4-dihydro-1,8-naphthyridin-2(1H)-one (64 mg, 0.38 mmol) and cesium carbonate (188 mg, 0.58 mmol) in DMF (5 mL) was stirred at 120° C. for 2 hrs. The reaction was diluted with water (10 mL) and extracted with ethyl acetate (2×20 mL). The combined organic phase was washed with brine (20 mL), dried over sodium sulfate anhydrous and concentrated under reduced pressure. The residue was used in next step without further purification.

Step J: (±)-exo-3-methyl-5-((7-oxo-5,6,7,8-tetrahydro-1,8-naphthyridin-4-yl)oxy)-1a,6b-dihydro-1H-cyclopropa[b]benzofuran-1-carboxylic acid

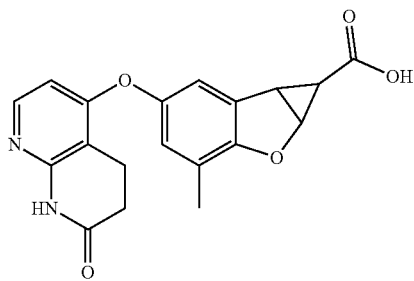 [SMILES: Cc1cc(Oc2ccnc3c2CCC(=O)N3)cc2c1OC1C(C(=O)O)C21]

Sodium hydroxide solution (3 mL, 2 M) was added to a stirred solution of ester product from Step I (60 mg, 3.8 mmol) in methanol (9 mL) at room temperature. The mixture was stirred at room temperature overnight. Solvent was removed under reduced pressure and the residue was dissolved into water (10 mL). The solution was neutralized with HCl (2 mol/L) to pH=7 and extracted with EA (2×10 mL). The combined organic phase was washed with brine (10 mL), dried over sodium sulfate anhydrous and concentrated under reduced pressure. The residue was used into next step without further purification. $^1$H-NMR (600 MHz, DMSO-$d_6$) δ 12.57 (s, 1H), 10.45 (s, 1H), 7.97-7.95 (m, 1H), 7.15 (d, J=2.5 Hz, 1H), 6.85 (d, J=2.0 Hz, 1H), 6.27 (d, J=5.8 Hz, 1H), 5.25 (dd, J=5.3, 1.0 Hz, 1H), 3.32-3.30 (m, 1H), 2.93 (t, J=7.7 Hz, 2H), 2.54 (t, J=7.7 Hz, 2H), 2.17 (s, 3H), 1.21 (dd, J=3.0, 1.0 Hz, 1H).

Step K: (±)-exo-5-((3-methyl-1-(6-(trifluoromethyl)-1H-benzo[d]imidazol-2-yl)-1a,6b-dihydro-1H-cyclopropa[b]benzofuran-5-yl)oxy)-3,4-dihydro-1,8-naphthyridin-2(1H)-one (Compound 2.35)

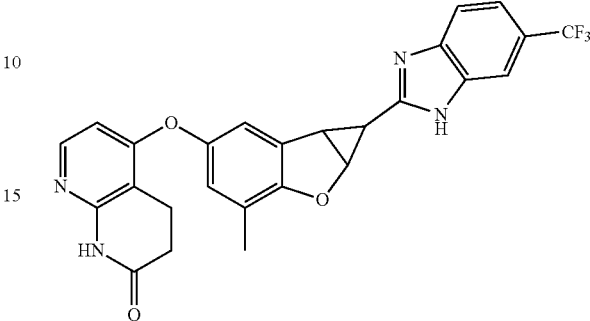

The mixture of the product from Step J (45 mg, 0.13 mmol), 4-(trifluoromethyl)benzene-1,2-diamine (25 mg, 0.14 mmol), DIPEA (0.5 ml) and HATU (61 mg, 0.16 mmol) in DMF (2 mL) was stirred at room temperature for 2 hrs. Water (2 mL) was added and the solid that precipitated out was collected and washed with water (2 mL) to afford intermediate amide product.

A solution of the intermediate amide product in acetic acid (2 mL) was stirred at 80° C. for 2 hrs. Solvent was removed and an aqueous solution of NaOH (2 mL, 2 mol/L) was added to the residue. The mixture was extracted with EtOAc (2×10 mL). The combined organic phase was washed with brine (20 mL), dried over sodium sulfate anhydrous and concentrated under reduced pressure. The residue was purified by prep-HPLC to afford the title compound (6 mg, 9.5%) as a white solid. $^1$H-NMR (400 MHz, CD$_3$OD) δ 7.93 (d, J=5.9 Hz, 1H), 7.78 (s, 1H), 7.62 (s, 1H), 7.49 (d, J=7.1 Hz, 1H), 7.11 (d, J=2.5 Hz, 1H), 6.84 (d, J=2.0 Hz, 1H), 6.34 (d, J=5.9 Hz, 1H), 5.36 (dd, J=5.4, 1.3 Hz, 1H), 3.53 (dd, J=5.4, 3.3 Hz, 1H), 3.06 (t, J=7.7 Hz, 2H), 2.66 (t, J=7.8 Hz, 2H), 2.26 (s, 3H), 1.88 (dd, J=3.3, 1.3 Hz, 1H) ppm.

Compound 2.36: (±)-exo-5-((4-chloro-1-(6-(trifluoromethyl)-1H-benzo[d]imidazol-2-yl)-1a,6b-dihydro-1H-cyclopropa[b]benzofuran-5-yl)oxy)-3,4-dihydro-1,8-naphthyridin-2(1H)-one

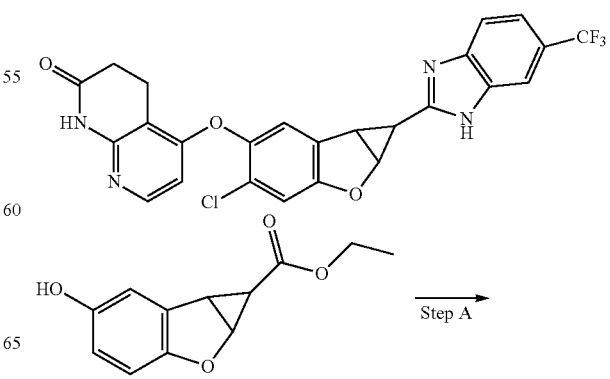

89
-continued

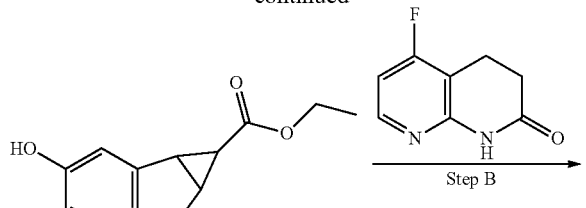

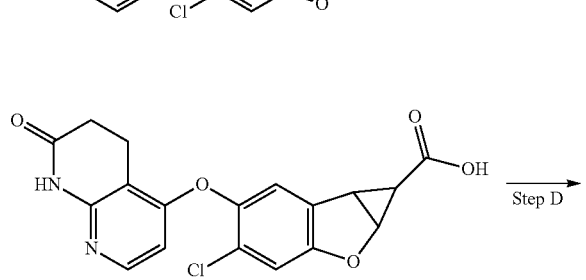

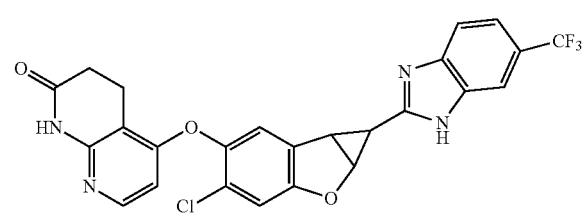

Step A: (±)-exo-ethyl 4-chloro-5-hydroxy-1a,6b-dihydro-1H-cyclopropa[b]benzofuran-1-carboxylate

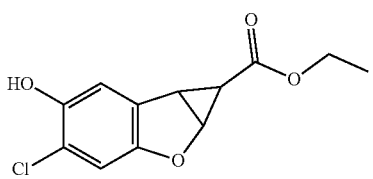 [SMILES: CCOC(=O)C1C2Oc3cc(Cl)c(O)cc3C21]

To a solution of ethyl 5-hydroxy-1a,6b-dihydro-1H-cyclopropa[b]benzofuran-1-carboxylate (the product from Step C in the synthesis of Compound 2.1, 500 mg, 2.3 mmol) in acetonitrile (10 mL) was added NCS (302 mg, 2.3 mmol) at room temperature. The mixture was stirred at room temperature overnight. The reaction was diluted with water (20 mL) and extracted with EtOAc (2×10 mL). The combined organic phase was washed with brine (20 mL), dried over anhydrous sodium sulfate and concentrated under reduced pressure. The residue was used into next step without further purification. $^1$H-NMR (600 MHz, CDCl$_3$) δ 7.06 (s, 1H), 6.86 (s, 1H), 5.81 (s, 1H), 5.18-4.89 (m, 1H), 4.23-4.15 (m, 2H), 3.22 (dd, J=5.4, 3.1 Hz, 1H), 1.31 (dd, J=3.1, 1.1 Hz, 1H), 1.28 (t, J=7.2 Hz, 3H) ppm.

90

Step B: (±)-exo-ethyl 4-chloro-5-((7-oxo-5,6,7,8-tetrahydro-1,8-naphthyridin-4-yl)oxy)-1a,6b-dihydro-1H-cyclopropa[b]benzofuran-1-carboxylate The mixture of the product from step A (577 mg, 2.3 mmol), 5-fluoro-3,4-dihydro-1,8-naphthyridin-2(1H)-one (377 mg, 2.3 mmol) and cesium carbonate (1.1 g, 3.4 mmol) in DMF (20 mL) was stirred at 120° C. for 2 hrs. The reaction was diluted with wafer (40 mL) and extracted with ethyl acetate (2×30 mL). The combined organic phase was washed with brine (40 mL), dried over sodium sulfate anhydrous and concentrated under reduced pressure. The residue was purified by silica gel chromatography (eluted with EtOAc:PE=1:5-1:1) to afford the title compound (320 mg, 80%) as a white solid.

Step C: (±)-exo-4-chloro-5-((7-oxo-5,6,7,8-tetrahydro-1,8-naphthyridin-4-yl)oxy)-1a,6b-dihydro-1H-cyclopropa[b]benzofuran-1-carboxylic acid

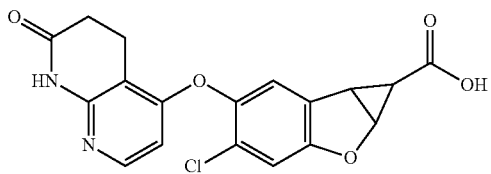 [SMILES: O=C1CCc2c(Oc3cc4c(cc3Cl)OC3C(C(=O)O)C43)ccnc2N1]

Sodium hydroxide solution (1 mL, 2 M) was added to a stirred solution of ester product from Step B (320 mg, 0.8 mmol) in methanol (3 mL) at room temperature. The mixture was stirred at room temperature for 2 hrs. Solvent was removed under reduced pressure and the residue was dissolved into water (10 mL). The solution was neutralized with HCl (1 mol/L) to pH=7 and the while solid was precipitated out of solution. The white solid was collected by filtration and dried in air to give the title compound (230 mg, 77.2%). $^1$H-NMR (600 MHz, DMSO-d$_6$) δ 12.68 (s, 1H), 10.50 (s, 1H), 7.96 (d, J=5.8 Hz, 1H), 7.53 (s, 1H), 7.30 (s, 1H), 6.18 (d, J=5.8 Hz, 1H), 5.32 (d, J=5.3 Hz, 1H), 3.34-3.31 (m, 1H), 2.98 (t, J=7.7 Hz, 2H), 2.57 (t, J=7.7 Hz, 2H), 1.38-1.33 (m, 1H) ppm.

Step D: (±)-exo-5-((4-chloro-1-(6-(trifluoromethyl)-1H-benzo[d]imidazol-2-yl)-1a,6b-dihydro-1H-cyclopropa[b]benzofuran-5-yl)oxy)-3,4-dihydro-1,8-naphthyridin-2(1H)-one (Compound 2.36)

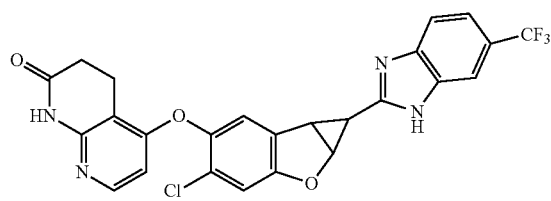 [SMILES: O=C1CCc2c(Oc3cc4c(cc3Cl)OC3C(c5nc6ccc(C(F)(F)F)cc6[nH]5)C43)ccnc2N1]

To a solution of the product from Step C (60 mg, 0.16 mmol), 4-fluoro-5-methylbenzene-1,2-diamine (22.6 mg, 0.16 mmol), and DIPEA (0.1 mL) in DMF (2 mL) was added HATU (92 mg, 0.24 mmol) at room temperature. The mixture was stirred at room temperature for 20 hrs. The reaction was diluted with EtOAc (5 mL). The mixture was washed with brine (3×5 mL), dried over anhydrous sodium sulfate and concentrated under reduced pressure.

The residue was dissolved in acetic acid (5 mL) and the mixture was stirred at 80° C. for 3 hrs. Solvent was removed and a solution of NaOH (2 mol/L, 10 mL) was added to the residue. The water phase was extracted with EtOAc (2×20 mL). The combined organic phase was washed with brine (20 mL), dried over anhydrous sodium sulfate and concentrated under reduced pressure. The residue was purified by prep-HPLC to give the title compound (20 mg, 26.0%) as a white solid. $^1$H-NMR (600 MHz, DMSO-$d_6$) δ 12.90 (s, 1H), 10.51 (s, 1H), 7.98 (d, J=5.8 Hz, 1H), 7.88 (s, 1H), 7.67 (s, 1H), 7.58 (s, 1H), 7.48 (s, 1H), 7.38 (s, 1H), 6.21 (d, J=5.8 Hz, 1H), 5.50 (d J=5.0 Hz, 1H), 3.61-3.52 (m, 1H), 2.99 (t, J=7.7 Hz, 2H), 2.57 (t, J=7.8 Hz, 2H), 2.10-2.05 (m, 1H) ppm. MS: M/e 513 (M+1)$^+$.

Compound 2.37: (±)-exo-5-((4-chloro-1-(6-fluoro-5-methyl-1H-benzo[d]imidazol-2-yl)-1a,6b-dihydro-1H-cyclopropa[b]benzofuran-5-yl)oxy)-3,4-dihydro-1,8-naphthyridin-2(1H)-one

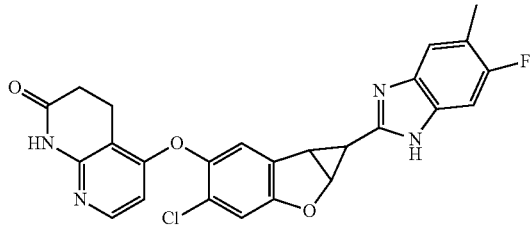 [SMILES: Cc1cc2nc(C3C4Oc5cc(Cl)c(Oc6ccnc7c6CCC(=O)N7)cc5C43)[nH]c2cc1F]

Compound 2.37 was prepared from the product of Step C in the synthesis of Compound 2.36, according to the procedures described for Compound 2.36 by using 4-fluoro-5-methylbenzene-1,2-diamine under appropriate conditions that could be recognized by one skilled in the art. $^1$H-NMR (600 MHz, DMSO-$d_6$) δ 12.43 (s, 1H), 10.50 (s, 1H), 7.97 (d, J=5.8 Hz, 1H), 7.55 (s, 1H), 7.43-7.21 (m, 3H), 6.20 (d, J=5.8 Hz, 1H), 5.43 (d, J=4.5 Hz, 1H), 3.49-3.40 (m, 1H), 2.98 (t, J=7.7 Hz, 2H), 2.57 (t, J=7.8 Hz, 2H), 2.31 (s, 3H), 1.97 (d, J=2.2 Hz, 1H) ppm. MS: M/e 477 (M+1)$^+$.

EXAMPLE 3

Synthesis of Compounds 3.1-3.8

Compound 3.1: (±)-exo-N-methyl-4-((1-(6-(trifluoromethyl)-1H-benzo[d]imidazol-2-yl)-1a,6b-dihydro-1H-cyclopropa[b]benzofuran-5-yl)oxy)picolinamide

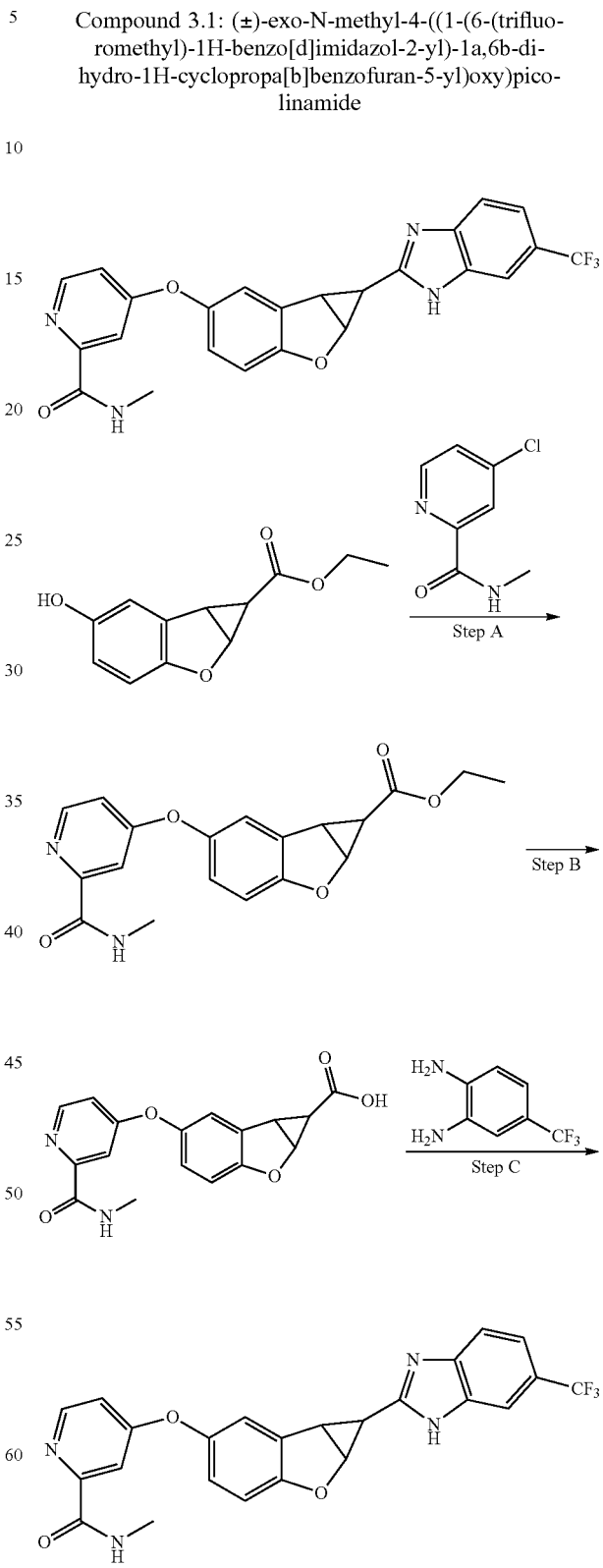

Compound 3.1

Step A: (±)-exo-Ethyl 5-((2-(methylcarbamoyl)pyridin-4-yl)oxy)-1a,6b-dihydro-1H-cyclopropa[b]benzofuran-1-carboxylate

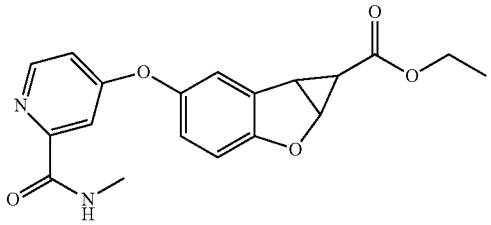 [SMILES: CCOC(=O)C1C2Oc3ccc(Oc4ccnc(C(=O)NC)c4)cc3C21]

The mixture of ethyl 5-hydroxy-1a,6b-dihydro-1H-cyclopropa[b]benzofuran-1-carboxylate (the compound from Step C in the synthesis of compound 2.1, 50 mg, 0.23 mmol), 4-chloro-N-methyl picolinamide (39 mg, 0.23 mol), and cesium carbonate (225 mg, 0.69 mmol) in DMF (4 mL) was stirred at 120° C. for 30 min. The reaction was diluted with water (10 mL) and extracted with ethyl acetate (3×30 mL). The combined organic phase was washed with brine (2×10 mL), dried over anhydrous sodium sulfate and concentrated under reduced pressure. The residue was purified by prep-TLC (EtOAc:PE=1:2) to obtain the title compound (40 mg, 50%) as a white solid, $^1$H-NMR (600 MHz, CDCl$_3$) δ 8.39 (d, J=5.4 Hz, 1H), 8.03 (s, 1H), 7.68 (d, J=1.8 Hz, 1H), 7.16 (d, J=1.8 Hz, 1H), 6.96 (dd, J=3.0, 6.0 Hz, 1H), 6.93-6.92 (m, 2H), 5.16 (dd, J=0.6, 5.4 Hz, 1H), 4.21 (dd, J=7.2, 14.4 Hz, 2H), 3.29 (dd, J=3.0, 5.4 Hz, 1H), 3.03 (d, J=4.8 Hz, 3H), 1.41 (dd, J=1.2, 3.0 Hz, 1H), 1.31 (t, J=7.2 Hz. 3H) ppm. MS: M/e 355 (M+1)$^+$.

Step B: (±)-exo-5-((2-(methylcarbamoyl)pyridin-4-yl)oxy)-1a,6b-dihydro-1H-cyclopropa[b]benzofuran-1-carboxylic acid

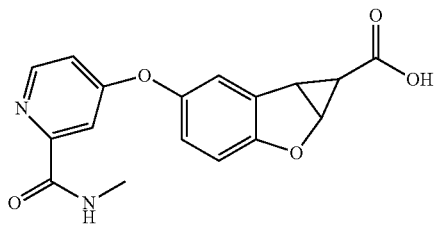 [SMILES: CNC(=O)c1cc(Oc2ccc3c(c2)C2C(O3)C2C(=O)O)ccn1]

A mixture of the product from Step A (60 mg, 0.17 mmol), sodium hydroxide aqueous solution (0.34 mL, 2 M, 0.68 mmol), THF (2 mL) and methanol (2 mL) was stirred at 60° C. for 1 h. The solution was neutralized with HCl (2 mol/L) to pH=7 and the solvent was removed. The residue was dissolved with ethyl acetate (3×30 mL), washed with water (2×10 mL), dried over anhydrous sodium sulfate, filtered and concentrated under reduced pressure to obtain the title compound (57 mg, 100%) which was used directly in the next step. MS: M/e 327(M+1)$^+$.

Step C: (±)-exo-N-methyl-4-((1-(6-(trifluoromethyl)-1H-benzo[d]imidazol-2-yl)-1a,6b-dihydro-1H-cyclopropa[b]benzofuran-5-yl)oxy)picolinamide (Compound 3.1)

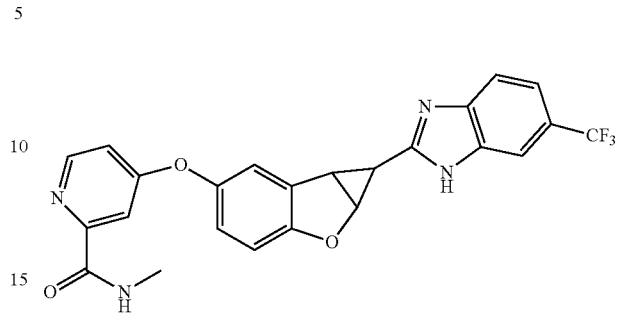

The mixture of the product from Step B (57 mg, 0.17 mmol), 4-(trifluoromethyl) benzene-1,2-diamine (34 mg, 0.19 mmol), DIPEA (0.035 mL, 0.20 mmol) and HATU (72 mg, 0.19 mmol) in DMF (3 mL) was stirred at room temperature overnight. The reaction was extracted with ethyl acetate (3×20 mL), washed with brine (2×10 mL), dried over sodium sulfate anhydrous, filtered and concentrated under reduced pressure. The residue was used in next step directly without further purification.

The crude product was dissolved in acetic acid (3 mL) and stirred at 60° C. for 6 hrs. The mixture was extracted with EtOAc (50 mL), basified with aq. NaHCO$_3$, washed with brine (2×10 mL), dried over sodium sulfate anhydrous, filtered and concentrated under reduced pressure. The residue was purified by prep-TLC (EtOAc:PE=1:2) to afford the title compound (50 mg, 63%) as a white solid. $^1$H-NMR (400 MHz, CDCl$_3$) δ 8.35 (d, J=5.6 Hz, 1H), 7.75 (s, 1H), 7.54 (d, J=8.4 Hz, 1H), 7.44-7.39 (m, 2H), 7.12 (d, J=2.4 Hz, 1H), 7.02 (dd, J=2.8, 5.6 Hz, 1H), 6.94-6.88 (m, 2H), 5.38 (dd, J=1.2, 5.2 Hz, 1H), 3.50 (dd, J=3.6, 5.6 Hz, 1H), 2.94 (s, 3H), 1.85 (dd, J=1.6, 3.6 Hz, 1H) ppm. MS: M/e 467 (M+1)$^+$.

Compound 3.2: (±)-exo-2-(5-(pyrimidin-4-yloxy)-1a,6b-dihydro-1H-cyclopropa[b]benzofuran-1-yl)-6-(trifluoromethyl)-1H-benzo[d]imidazole

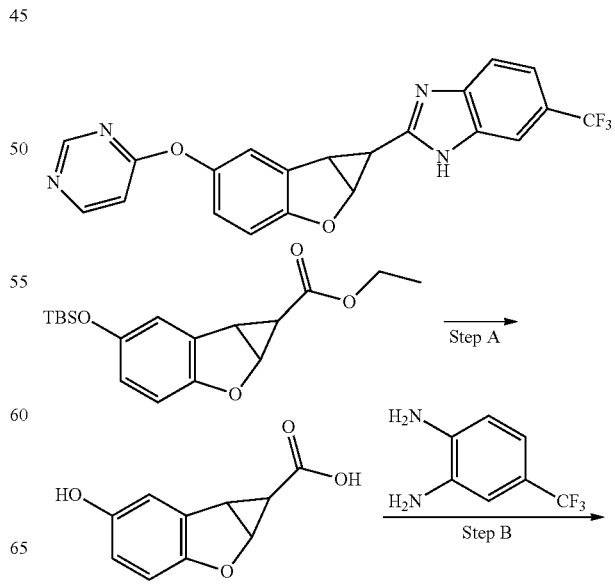

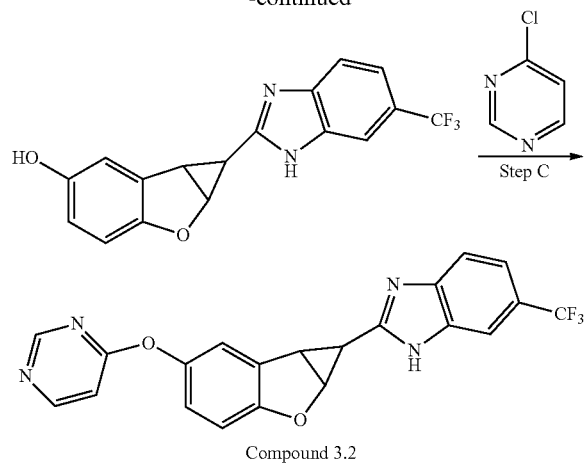

Compound 3.2

Step A: (±)-exo-5-hydroxy-1a,6b-dihydro-1H-cyclopropa[b]benzofuran-1-carboxylic acid

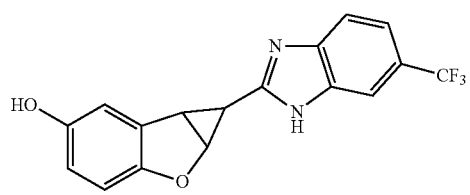 [SMILES: Oc1ccc2c(c1)C1C(O2)C1c1nc2ccc(C(F)(F)F)cc2[nH]1]

To a stirred solution of ethyl 5-((tert-butyldimethylsilyl)oxy)-1a,6b-dihydro-1H-cyclopropa[b]benzofuran-1-carboxylate (the product from Step B in the synthesis of Compound 2.1, 1.5 g, 4.5 mmol) in methanol (13.5 mL) was added sodium hydroxide aqueous solution (4.5 mL, 2 M, 9.0 mmol) at room temperature. The mixture was stirred at 60° C. for 2 h. The solvent was removed under reduced pressure and the residue was dissolved in water (30 mL). The solution was neutralized with HCl (2 mol/L) to pH=7 and white solid was precipitated out of the solution. The white solid was collected by filtration and dried in air to give the title compound (450 mg, 52%) which was used directly in the next step. $^1$H-NMR (600 MHz, DMSO-$d_6$) δ 9.03 (s, 1H), 6.90 (d, J=2.4 Hz, 1H), 6.72 (d, J=8.4 Hz, 1H), 6.55 (dd, J=3.0, 9.0 Hz, 1H), 5.08 (dd, J=1.2, 5.4 Hz, 1H), 3.22 (d, J=2.4 Hz, 1H), 1.07 (d, J=3.0 Hz, 1H) ppm. MS: M/e 193 (M+1)$^+$.

Step B: (±)-exo-1-(6-(trifluoromethyl)-1H-benzo[d]imidazol-2-yl)-1a,6b-dihydro-1H-cyclopropa[b]benzofuran-5-ol

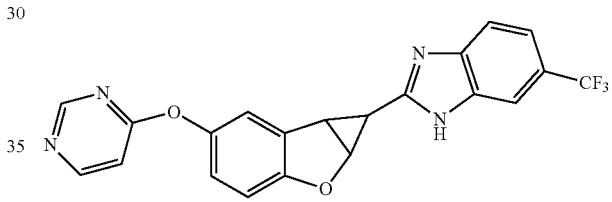

A mixture of the product from Step A (100 mg, 0.52 mmol), 4-(trifluoromethyl) benzene-1,2-diamine (101 mg, 0.57 mmol), DIPEA (0.11 mL, 0.62 mmol) and HATU (217 mg, 0.57 mmol) in DMF (5 mL) was stirred at room temperature overnight. The reaction was $CH_2Cl_2$ (3×30 mL), washed with brine (2×10 mL), dried over sodium sulfate anhydrous, filtered and concentrated under reduced pressure. The residue was used in next step directly without further purification.

The crude product was dissolved in acetic acid (3 mL) and stirred at 60° C. for 1.5 hr. The mixture was basified with aq. NaHCO$_3$, extracted with EtOAc (3×30 mL), washed with brine (2×10 mL), dried over sodium sulfate anhydrous, filtered and concentrated under reduced pressure. The residue was purified by prep-TLC (EtOAc:PE=1:2) to afford the title compound (30 mg, 17%) as a brown oil. $^1$H-NMR (400 MHz, CDCl$_3$) δ 7.79 (s, 1H), 7.63-7.61 (m, 1H), 7.49-7.48 (m, 1H), 6.94-6.93 (m, 1H), 6.76-6.74 (m, 1H), 6.65-6.63 (m, 1H), 5.22-5.21 (m, 1H), 3.43-3.42 (m, 1H), 1.79 (d, J=1.8 Hz, 1H) ppm. MS: M/e 333 (M+1)$^+$.

Step C: (±)-exo-2-(5-(pyrimidin-4-yloxy)-1a,6b-dihydro-1H-cyclopropa[b]benzofuran-1-yl)-6-(trifluoromethyl)-1H-benzo[d]imidazole (Compound 3.2)

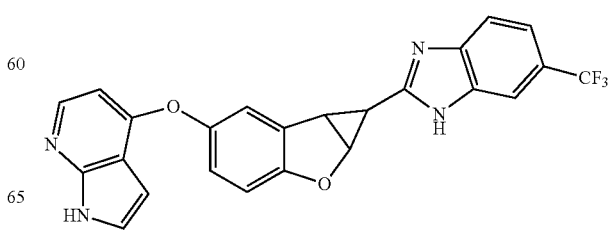

The mixture of the product from Step B (20 mg, 0.06 mmol), 4-chloropyrimidine (8 mg, 0.06 mol) and cesium carbonate (60 mg, 0.18 mmol) in DMF (2 mL) was stirred at 100° C. for 2 h. The reaction was extracted with ethyl acetate (3×30 mL). The combined organic phase was washed with brine (2×10 mL), dried over anhydrous sodium sulfate and concentrated under reduced pressure. The residue was purified by prep-TLC (EtOAc: PE=1:2) to obtain the crude compound (16 mg) as a light yellow solid and then further purified by prep-HPLC to give the desired product (5 mg, 24.6%) as a light yellow solid. $^1$H-NMR (600 MHz, CDCl$_3$) δ 8.73 (s, 1H), 8.63 (s, 1H), 7.82 (s, 1H), 7.66 (d, J=1.2 Hz, 1H), 7.52 (d, J=8.4 Hz, 1H), 7.37 (d, J=1.8 Hz, 1H), 7.08-7.02 (m, 3H), 5.38 (dd, J=1.2, 5.4 Hz, 1H), 3.57 (dd, J=3.0, 4.8 Hz, 1H), 1.94 (d, J=2.4 Hz, 1H) ppm. MS: M/e 411 (M+1)$^+$.

Compound 3.3

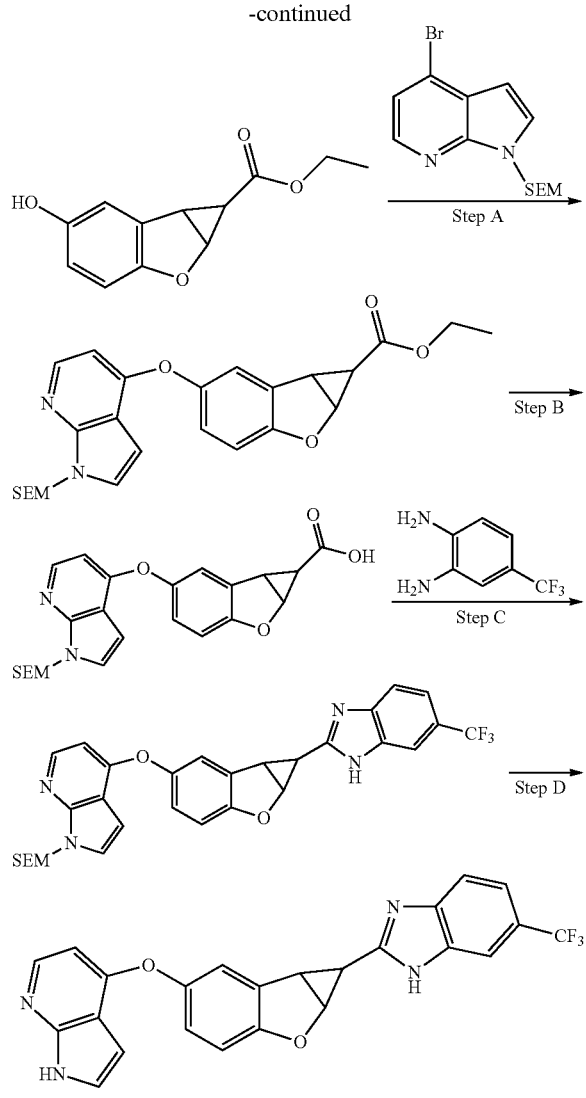

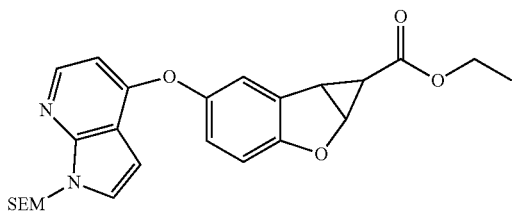 [SMILES: CCOC(=O)C1C2Oc3ccc(Oc4ccnc5c4ccn5COCC[Si](C)(C)C)cc3C21]

Compound 3.3

Step A: (±)-exo-Ethyl 5-((1-((2-(trimethylsilyl)ethoxy)methyl)-1H-pyrrolo[2,3-b]pyridin-4-yl)oxy)-1a,6b-dihydro-1H-cyclopropa[b]benzofuran-1-carboxylate

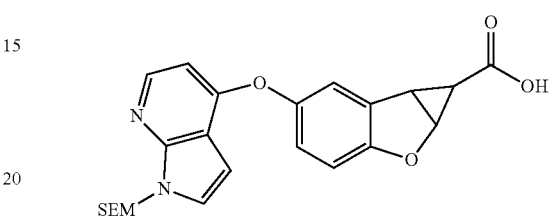

The mixture of ethyl 5-hydroxy-1a,6b-dihydro-1H-cyclopropa[b]benzofuran-1-carboxylate (the compound from Step C in the synthesis of compound 2.1, 100 mg, 0.46 mmol), 4-bromo-1-((2-(trimethylsilyl)ethoxy)methyl)-1H-pyrrolo[2,3-b]pyridine (180 mg, 0.46 mol), K$_2$CO$_3$ (158 mg, 1.15 mmol), Pd$_2$(dba)$_3$ (cat.), X-PHOS (22 mg, 0.046 mmol) in toluene (5 mL) was degassed and stirred at 130° C. for 60 min within microwave. The mixture was filtered and the filtrate was concentrated under reduced pressure. The residue was purified by prep-TLC (EtOAc:PE=1:4) to obtain the title compound (120 mg, 56%) as a yellow oil.

Step B: (±)-exo-5-((1-((2-(trimethylsilyl)ethoxy)methyl)-1H-pyrrolo[2,3-b]pyridin-4-yl)oxy)-1a,6b-dihydro-1H-cyclopropa[b]benzofuran-1-carboxylic acid

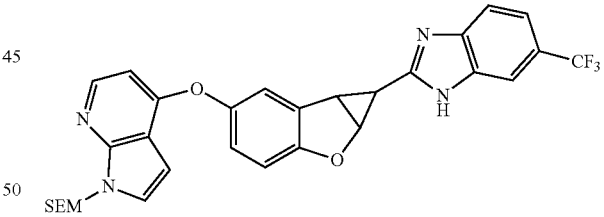

Sodium hydroxide aqueous solution (0.54 mL, 2 M, 1.08 mmol) was added to a stirred solution of the product from Step A (125 mg, 0.27 mmol) in THF (4 mL) and methanol (4 mL) at room temperature. The mixture was stirred at 60° C. for 10 min. The solvent was removed under reduced pressure and the residue was dissolved in water (5 mL). The solution was neutralized with HCl (2 mol/L) to pH=7 and extracted, with ethyl acetate (3×30 mL). The combined organic phase was washed with brine (2×10 mL), dried over anhydrous sodium sulfate, filtered and concentrated under reduced pressure to obtain the title compound (120 mg, 100%), which was used directly in the next step.

Step C: (±)-exo-6-(trifluoromethyl)-2-(5-((1-((2-(trimethylsilyl)ethoxy)methyl)-1H-pyrrolo[2,3-b]pyridin-4-yl)oxy)-1a,6b-dihydro-1H-cyclopropa[b]benzofuran-1-yl)-1H-benzo[d]imidazole To a solution of the product from Step B (120 mg, 0.28 mmol) in DMF (5 mL) was added DIPEA (0.049 mL, 0.33 mmol) and HATU (115 mg, 0.31 mmol). After stirring for 30 min, 4-(trifluoromethyl) benzene-1,2-diamine (53.4 mg, 0.31 mmol) was added at room temperature overnight. The mixture was stirred overnight. The reaction was extracted with ethyl acetate (3×20 mL), washed with brine (2×10 mL), dried over sodium sulfate anhydrous, filtered and concentrated under reduced pressure. The residue was used in next step directly without further purification.

The crude product was dissolved in acetic acid (5 mL) and the mixture was stirred at 60° C. for 6 hrs. The mixture was extracted with EtOAc (3×20 mL), basified with aq. NaHCO$_3$, washed with brine (10 mL), dried over sulfate sodium anhydrous, filtered and concentrated under reduced pressure. The residue was purified by prep-TLC (EtOAc: PE=1:2) to afford the title compound (100 mg, 63%) as a white solid. MS: M/e 579 (M+1)⁺.

Step D: (±)-exo-2-(5-((1H-pyrrolo[2,3-b]pyridin-4-yl)oxy)-1a,6b-dihydro-1H-cyclopropa[b]benzofuran-1-yl)-6-(trifluoromethyl)-1H-benzo[d]imidazole (Compound 3.3)

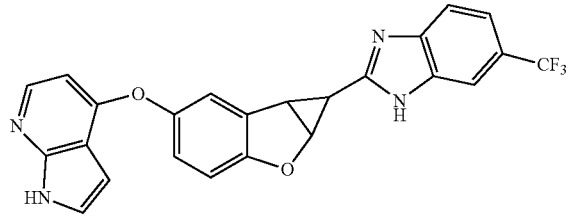 [SMILES: FC(F)(F)c1ccc2nc(C3C4Oc5ccc(Oc6ccnc7[nH]ccc67)cc5C43)[nH]c2c1]

A solution of the product from step C (43 mg, 0.074 mmol), ethane-1,2-diamine (0.5 mL) and a solution of TBAF in THF (0.3 mL, 1.0 M) in THF (10 mL) was stirred at 60° C. under N₂ atmosphere. After stirred for 10 hours, more TBAF in THF (0.5 mL, 1.0 M) was added and stirred another 10 hours. The reaction mixture was treated with EtOAc (10 mL) and washed with brine, dried over Na₂SO₄, concentrated and purified by prep-TLC (EtOAc:PE=1:2) to give the title product (20 mg, 60.3%) as a white solid. ¹H-NMR (600 MHz, CD₃OD) δ 8.04 (d, J=5.4 Hz, 1H), 7.81 (s, 1H), 7.64 (s, 1H), 7.50 (dd, J=1.2, 7.8 Hz, 1H), 7.36 (d, J=2.4 Hz, 1H), 7.27 (d, J=3.0 Hz, 1H), 7.07-7.03 (m, 2H), 6.44 (d, J=5.4 Hz, 1H), 6.35 (d, J=3.0 Hz, 1H), 5.39 (dd, J=1.2, 5.4 Hz, 1H), 3.56 (dd, J=3.0, 5.4 Hz, 1H), 1.95 (dd, J=1.2, 3.0 Hz, 1H) ppm. MS: M/e 449 (M+1)⁺.

Compound 3.4: (±)-exo-6-(trifluoromethyl)-2-(5-((2-(4-(trifluoromethyl)-1H-imidazol-2-yl)pyridin-4-yl)oxy)-1a,6b-dihydro-1H-cyclopropa[b]benzofuran-1-yl)-1H-benzo[d]imidazole

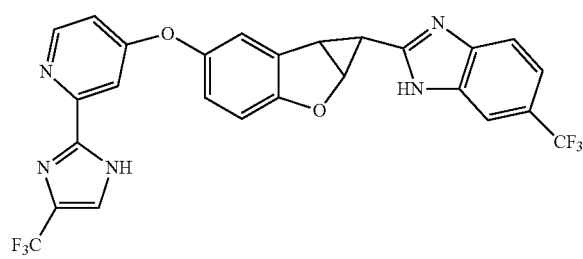

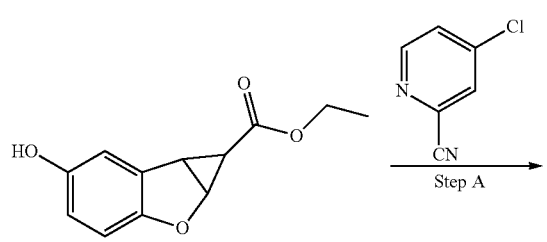

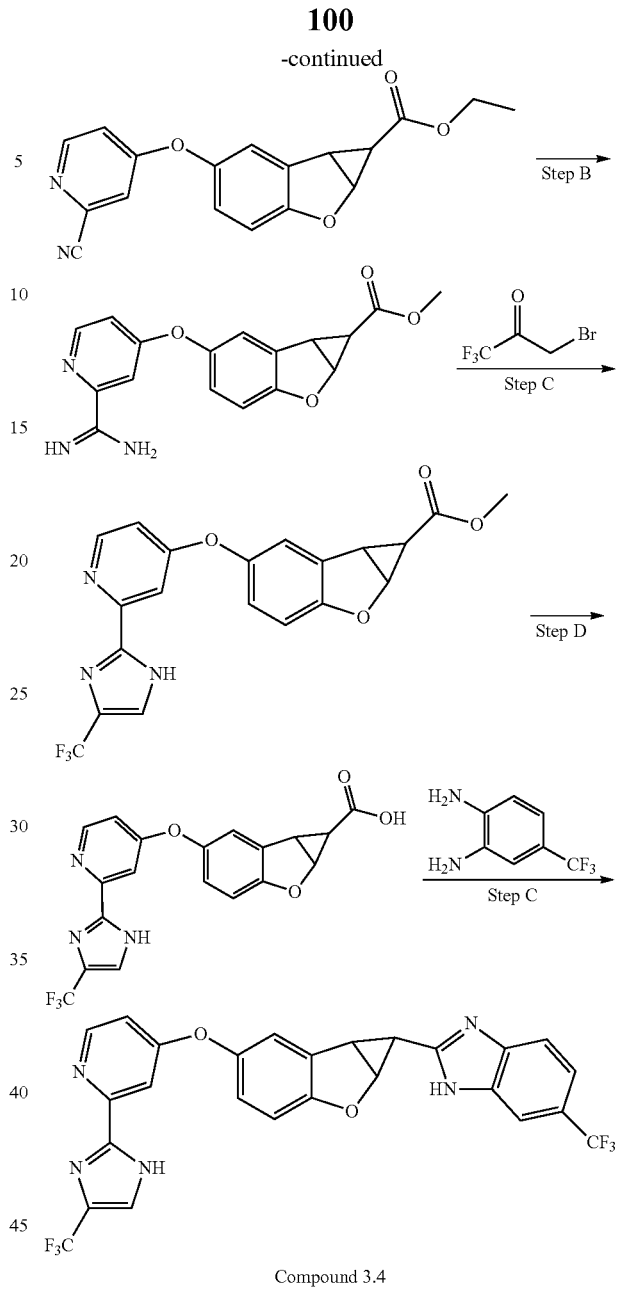

Compound 3.4

Step A: (±)-exo-Ethyl 5-((2-cyanopyridin-4-yl)oxy)-1a,6b-dihydro-1H-cyclopropa[b]benzofuran-1-carboxylate

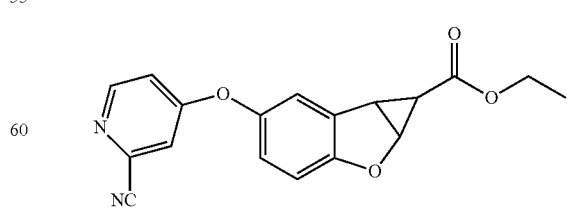

The mixture of ethyl 5-hydroxy-1a,6b-dihydro-1H-cyclopropa[b] benzofuran-1-carboxylate (the compound from Step C in the synthesis of compound 2.1, 100 mg, 0.46 mmol), 4-chloropicolinonitrile (64 mg, 0.46 mol) and cesium carbonate (450 mg, 1.3 mmol) in DMF (6 mL) was stirred at 100° C. for 120 min. The reaction was extracted with ethyl acetate (3×30 mL). The combined organic phases were washed with brine (2×10 mL), dried over anhydrous sodium sulfate and concentrated under reduced pressure. The residue was purified by prep-TLC (EtOAc:PE=1:3) to obtain the title compound (100 mg, 67.5%) as a white solid. $^1$H-NMR (600 MHz, CDCl$_3$) δ 8.51 (d, J=5.4 Hz, 1H), 7.16 (d, J=2.4 Hz, 1H), 7.12 (d, J=2.4 Hz, 1H), 6.98 (dd, J=3.0, 6.0 Hz, 1H), 6.93 (d, J=9.0 Hz, 1H), 6.88 (dd, J=2.4, 8.4 Hz, 1H), 5.14 (d, J=5.4 Hz, 1H), 4.18 (dd, J=7.2, 11.8 Hz, 2H), 3.27 (dd, J=3.0, 5.4 Hz, 1H), 1.37 (d, J=3.0 Hz, 1H), 1.28 (t, J=7.2 Hz, 3H) ppm. MS: M/e 323 (M+1)$^+$.

Step B: (±)-exo-Methyl 5-((2-carbamimidoylpyridin-4-yl)oxy)-1a,6b-dihydro-1H-cyclopropa[b]benzofuran-1-carboxylate

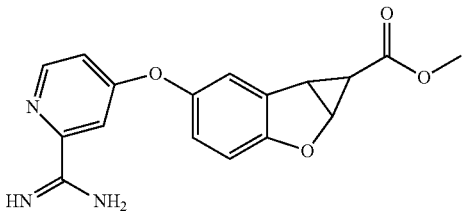 [SMILES: COC(=O)C1C2Oc3ccc(Oc4ccnc(C(=N)N)c4)cc3C21]

To a solution of the product from Step A (45 mg, 0.14 mmol) in methanol (3 mL) was added NaOMe (15 mg, 0.28 mmol) at room temperature. The mixture was stirred at room temperature for 3 h. Then NH$_4$Cl (12 mg, 0.21 mmol) was added at room temperature and the mixture was stirred for 1 h and then at 60° C. for 1.5 h. The solvent was removed and the residue was used directly in the next step without further purification.

Step C: (±)-exo-methyl 5-((2-(4-(trifluoromethyl)-1H-imidazol-2-yl)pyridin-4-yl)oxy)-1a,6b-dihydro-1H-cyclopropa[b]benzofuran-1-carboxylate

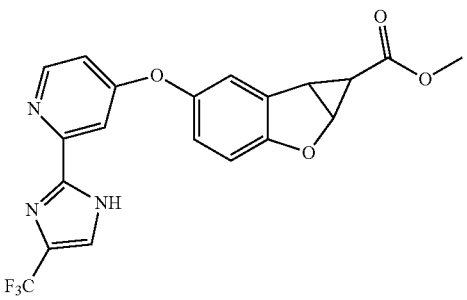 [SMILES: COC(=O)C1C2Oc3ccc(Oc4ccnc(-c5nc(C(F)(F)F)c[nH]5)c4)cc3C21]

To a solution of the crude product from Step B in CH$_3$CN (3 mL) was added K$_2$CO$_3$ (78 mg, 0.56 mmol) and 3-bromo-1,1,1-trifluoropropan-2-one (32 mg, 0.17 mmol) at room temperature. The mixture was stirred at 60° C. for 2h. The solvent was removed under reduced pressure and the residue was dissolved in ethyl acetate (100 mL). The organic phase was washed with brine (2×10 mL), dried over anhydrous sodium sulfate, filtered and concentrated under reduced pressure. The residue was purified by prep-TLC (EtOAc:PE=1:2) to obtain the title compound (10 mg, 17%) as a yellow solid. $^1$H-NMR (600 MHz, CDCl$_3$) δ 8.35 (d, J=5.4 Hz, 1H), 7.71 (d, J=3.0 Hz, 1H), 7.44 (s, 1H), 7.14 (s, 1H), 6.91 (s, 2H), 6.83 (dd, J=3.0, 6.6 Hz, 1H), 5.14 (d, J=5.4 Hz, 1H), 3.72 (s, 3H), 3.27 (dd, J=3.0, 5.4 Hz, 1H), 1.40 (d, J=2.4 Hz, 1H) ppm. MS: M/e 418 (M+1)$^+$.

Step D: (±)-exo-5-((2-(4-(trifluoromethyl)-1H-imidazol-2-yl)pyridin-4-yl)oxy)-1a,6b-dihydro-1H-cyclopropa[b]benzofuran-1-carboxylic acid

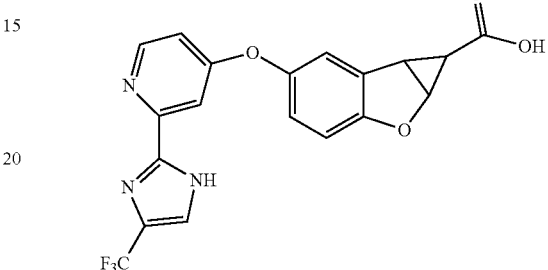

Sodium hydroxide aqueous solution (0.28 mL, 2 M, 0.56 mmol) was added to a stirred solution of the product from Step C (60 mg, 0.14 mmol) in THF (1 mL) and methanol (1 mL) at room temperature. The mixture was stirred at 50° C. for 1 h. The solvent was removed under reduced pressure and the residue was dissolved in CH$_2$Cl$_2$ (20 mL) and water (5 mL). The solution was neutralized with HCl (2 mol/L) to pH=7 and extracted with CH$_2$Cl$_2$ (3×30 mL), dried over anhydrous sodium sulfate, filtered and concentrated under reduced pressure to obtain the title compound (40 mg, 72%) as a yellow solid which was used directly in the next step. MS: M/e 404(M+1)$^+$.

Step E: (±)-exo-6-(trifluoromethyl)-2-(5-((2-(4-(trifluoromethyl)-1H-imidazol-2-yl)pyridin-4-yl)oxy)-1a,6b-dihydro-1H-cyclopropa[b]benzofuran-1-yl)-1H-benzo[d]imidazole (Compound 3.4)

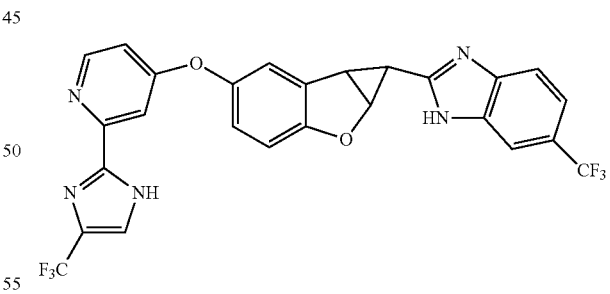

To a solution of the product from Step D (40 mg, 0.1 mmol), 4-(trifluoromethyl) benzene-1,2-diamine (19 mg, 0.11 mmol), DIPEA (0.02 mL, 0.12 mmol) in DMF (2 mL) was added HATU (42 mg, 0.11 mmol). The mixture was stirred at room temperature for 8 h. The reaction was extracted with ethyl acetate (3×30 mL), washed with brine (2×10 mL), dried over sodium sulfate anhydrous, filtered and concentrated under reduced pressure. The residue was used in next step directly without further purification.

The crude product was dissolved in acetic acid (2 mL) and stirred at 60° C. for 2 hrs. The solvent was removed and the residue was purified by prep-HPLC to afford the title compound (5.1 mg, 10%) as a white solid. $^1$H-NMR (400 MHz, CDCl$_3$) δ 8.55-8.43 (m, 1H), 7.77 (s, 1H), 7.63-7.60 (m, 2H), 7.56-7.55 (m, 1H), 7.48-7.46 (m, 1H), 7.33 (s, 1H), 7.03-6.96 (m, 3H), 5.37-5.36 (m, 1H), 3.55-3.53 (m, 1H), 1.94-1.92 (m, 1H) ppm. MS: M/e 544 (M+1)$^+$.

Compound 3.5: (±)-exo-6-((1-(6-(trifluoromethyl)-1H-benzo[d]imidazol-2-yl)-1a,6b-dihydro-1H-cyclopropa[b]benzofuran-5-yl)oxy)-9H-purine

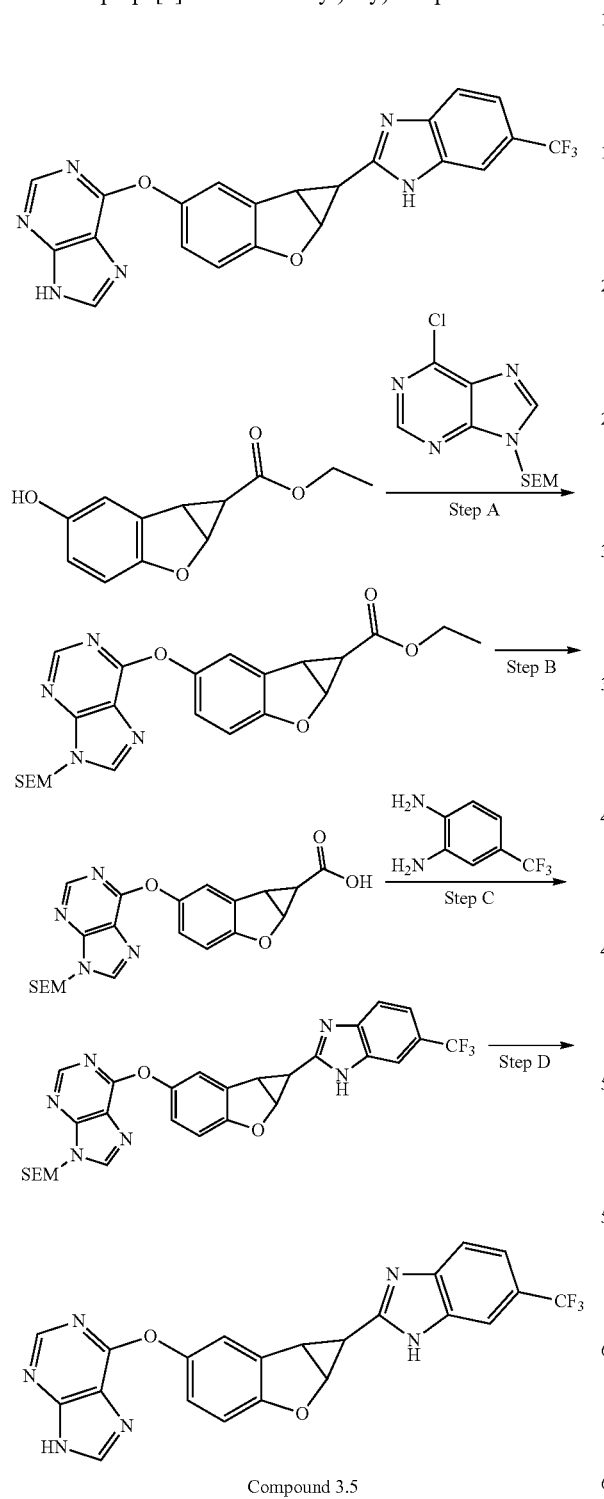

Compound 3.5

Step A: (±)-exo-Ethyl 5-((9-((2-(trimethylsilyl)ethoxy)methyl)-9H-purin-6-yl)oxy)-1a,6b-dihydro-1H-cyclopropa[b]benzofuran-1-carboxylate

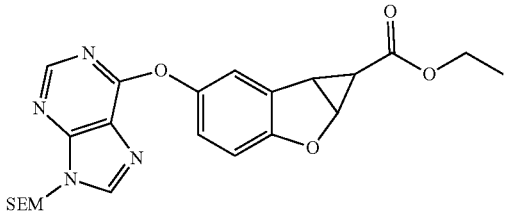 [SMILES: CCOC(=O)C1C2Oc3ccc(Oc4ncnc5c4ncn5COCC[Si](C)(C)C)cc3C21]

The mixture of ethyl 5-hydroxy-1a,6b-dihydro-1H-cyclopropa[b]benzofuran-1-carboxylate (the compound from Step C in the synthesis of compound 2.1, 61 mg, 0.28 mmol), 6-chloro-9-((2-(trimethylsilyl)ethoxy)methyl)-9H-purine (80 mg, 0.28 mol), K$_2$CO$_3$ (96.6 mg, 0.70 mmol), Pd$_2$(dba)$_3$ (cat.), X-PhOS (13.3 mg, 0.028 mmol) in toluene (5 mL) was degassed and stirred at 130° C. for 2.5 h within a microwave. The mixture was filtered and the filtrate was concentrated under reduced pressure. The residue was purified by prep-TLC (EtOAc:PE=1:2) to obtain the title compound (73 mg, 56%) as a colorless oil. MS: M/e 469 (M+1)$^+$.

Step B: (±)-exo-5-((9-((2-(trimethylsilyl)ethoxy)methyl)-9H-purin-6-yl)oxy)-1a,6b-dihydro-1H-cyclopropa[b]benzofuran-1-carboxylic acid

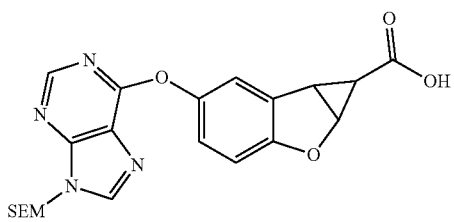 [SMILES: C[Si](C)(C)CCOCn1cnc2c(Oc3ccc4c(c3)C3C(O4)C3C(=O)O)ncnc21]

A stirred solution of the product from Step A (65 mg, 0.14 mmol), sodium hydroxide aqueous solution (0.28 mL, 2 M, 0.56 mmol) and THF (4 mL) was refluxed for 6 h. The solvent was removed under reduced pressure and the residue was neutralized with HCl (2 mol/L) to pH=4-5 and extracted with ethyl acetate (3×30 mL). The combined organic phases were washed with brine (2×10 mL), dried over anhydrous sodium sulfate, filtered and concentrated under reduced pressure to obtain the title compound (62 mg, 100%), which was used directly in the next step.

Step C: (±)-exo-6-((1-(6-(trifluoromethyl)-1H-benzo[d]imidazol-2-yl)-1a,6b-dihydro-1H-cyclopropa[b]benzofuran-5-yl)oxy)-9-((2-(trimethylsilyl)ethoxy)methyl)-9H-purine

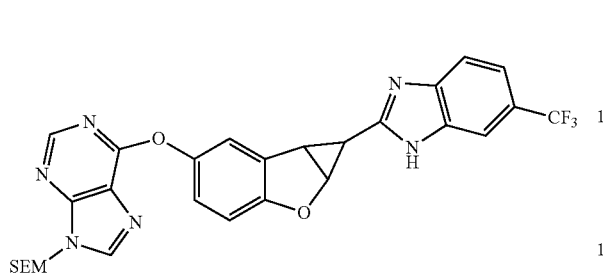

To a solution of the product from Step B (62 mg, 0.14 mmol) in DMF (5 mL) was added DIPEA (21.7 mg, 0.188 mmol) and HATU (58.5 mg, 0.154 mmol). After stirring for 0.5 h, (trifluoromethyl) benzene-1,2-diamine (27.1 mg, 0.15 mmol) was added and the mixture was stirred at room temperature overnight. Water was added and the mixture was extracted with ethyl acetate (3×20 mL). The combined organic phases were washed with brine (2×10 mL), dried over sodium sulfate anhydrous, filtered and concentrated under reduced pressure. The residue was used in next step directly without further purification.

The crude product was dissolved in acetic acid (5 mL) and stirred at 60° C. for 5 hrs. The mixture was extracted with EtOAc (3×20 mL). The combined organic phases were washed with aq. Na2CO3 and brine (10 mL), dried over sodium sulfate anhydrous, filtered and concentrated under reduced pressure. The residue was purified by prep-TLC (EtOAc) to afford the title compound (50 mg, 61.4%) as a white solid. MS: M/e 581 (M+1)$^+$.

Step D: (±)-exo-6-((1-(6-(trifluoromethyl)-1H-benzo[d]imidazol-2-yl)-1a,6b-dihydro-1H-cyclopropa[b]benzofuran-5-yl)oxy)-9H-purine (Compound 3.5)

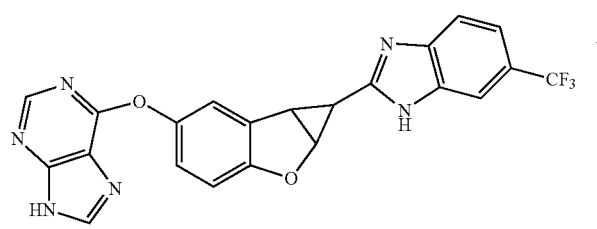

To a solution of the product from Step C (50 mg, 0.086 mmol), ethane-1,2-diamine (0.5 mL) in THF (10 mL) was added a solution of TBAF in THF (0.3 mL, 1.0 M) under N$_2$ atmosphere. The mixture was stirred at 60° C. for 5 h. The reaction mixture was treated with EtOAc (20 mL) and washed with brine, dried over Na$_2$SO$_4$, filtered and concentrated. The residue was purified by prep-TLC (CH$_2$Cl$_2$: MeOH=10:1) to give the title product (10 mg, 26%) as a white solid. $^1$H-NMR (600 MHz, CD$_3$OD) δ 8.46 (s, 2H), 7.83 (br.s, 1H), 7.67 (br.s, 1H), 7.54 (d, J=8.5 Hz, 1H), 7.50 (d, J=2.4 Hz, 1H), 7.17 (dd, J=2.4, 9.0 Hz, 1H), 7.07 (d, J=8.4 Hz, 1H), 5.43 (dd, J=1.2, 3.0 Hz, 1H), 3.62 (dd, J=3.0, 5.4 Hz, 1H), 2.01 (dd, J=1.2, 3.0 Hz, 1H) ppm. MS: M/e 451 (M+1)$^+$.

Compound 3.6: (±)-exo-2-(5-(pyridin-4-yloxy)-1a,6b-dihydro-1H-cyclopropa[b]benzofuran-1-yl)-6-(trifluoromethyl)-1H-benzo[d]imidazole

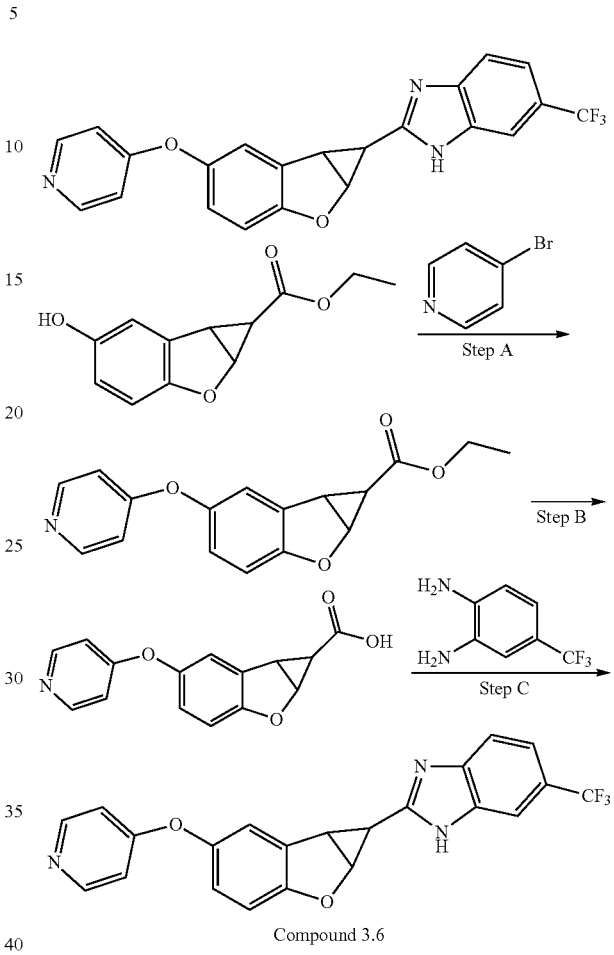

Compound 3.6

Step A: (±)-exo-Ethyl 5-(pyridin-4-yloxy)-1a,6b-dihydro-1H-cyclopropa[b]benzofuran-1-carboxylate

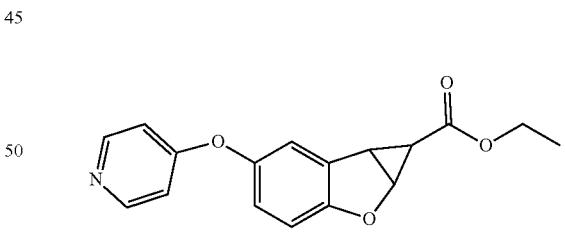

The mixture of ethyl 5-hydroxy-1a,6b-dihydro-1H-cyclopropa[b]benzofuran-1-carboxylate (the compound from Step C in the synthesis of compound 2.1, 150 mg, 0.69 mmol), 4-bromopyridine hydrochloride (134 mg, 0.69 mol), cesium carbonate (681 mg, 2.07 mmol) and Cu powder (cat.) in DMF (5 mL) was stirred at 150° C. for 30 min within microwave. The reaction was filtered and the filtrate was diluted with water (20 mL) and extracted with ethyl acetate (5×10 mL). The combined organic phases were washed with brine (2×10 mL), dried over anhydrous sodium sulfate and concentrated under reduced pressure. The residue was purified by prep-TLC (EtOAc:PE=1:2) to obtain the title compound (20 mg, 10%) as colorless oil. MS: M/e 298 (M+1)$^+$.

Step B: (±)-exo-5-(pyridin-4-yloxy)-1a,6b-dihydro-1H-cyclopropa[b]benzofuran-1-carboxylic acid

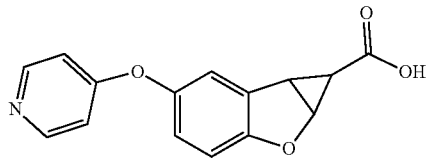 [SMILES: O=C(O)C1C2Oc3ccc(Oc4ccncc4)cc3C21]

A mixture of the product from Step A (20 mg, 0.077 mmol) and sodium hydroxide aqueous solution (0.15 mL, 2 M, 0.30 mmol) in THF (4 mL) was stirred at 60° C. for 5 h. The solvent was removed under reduced pressure and the mixture was neutralized with HCl (2 mol/L) to pH=7 and concentrated under reduced pressure to obtain the title crude compound which was used directly in the next step.

Step C: (±)-exo-2-(5-(pyridin-4-yloxy)-1a,6b-dihydro-1H-cyclopropa[b]benzofuran-1-yl)-6-(trifluoromethyl)-1H-benzo[d]imidazole (Compound 3.6)

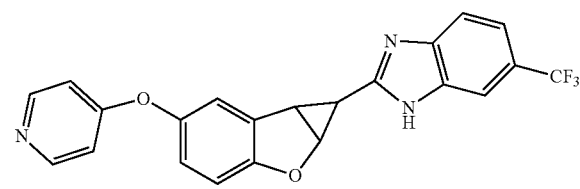 [SMILES: FC(F)(F)c1ccc2nc(C3C4Oc5ccc(Oc6ccncc6)cc5C43)[nH]c2c1]

To a solution of the product from Step B (0.077 mmol) in DMF (3 mL) was added DIPEA (20 mg, 0.155 mmol) and HATU (32.4 mg, 0.0853 mmol). After for 30 min, 4-(trifluoromethyl) benzene-1,2-diamine (15 mg, 0.0853 mmol) was added and the mixture was stirred at room temperature overnight. Water was added and the mixture was extracted with ethyl acetate (3×20 mL). The combined organic phases were washed with brine (2×10 mL), dried over sodium sulfate anhydrous, filtered and concentrated under reduced pressure. The residue was used in next step directly without further purification.

The crude product was dissolved in acetic acid (4 mL) and the mixture was stirred at 60° C. for 6 hrs. The mixture was extracted with EtOAc (3×20 mL). The combined organic phases were washed with aq. Na2CO3 and brine, dried over sodium sulfate anhydrous, filtered and concentrated under reduced pressure. The residue was purified by prep-HPLC to afford the title compound (10 mg, 31.6%, three steps) as a white solid. $^1$H-NMR (400 MHz, CD$_3$OD) δ 8.39 (br.s, 2H), 7.77 (s, 1H), 7.62 (d, J=8.4 Hz, 1H), 7.47 (dd, J=1.2, 8.8 Hz, 1H), 7.31 (d, J=2.4 Hz, 1H), 7.03-6.91 (m, 4H), 5.35 (dd, J=1.2, 5.6 Hz, 1H), 3.53 (dd, J=3.6, 5.6 Hz, 1H), 1.90 (dd, J=1.6, 3.6 Hz, 1H) ppm. MS: M/e 410 (M+1)$^+$.

Compound 3.7: (±)-exo-5-((1-(6-(trifluoromethyl)-1H-benzo[d]imidazol-2-yl)-1a,6b-dihydro-H-cyclopropa[b]benzofuran-5-yl)oxy)-1H-pyrido[2,3-d][1,3]oxazin-2(4H)-one

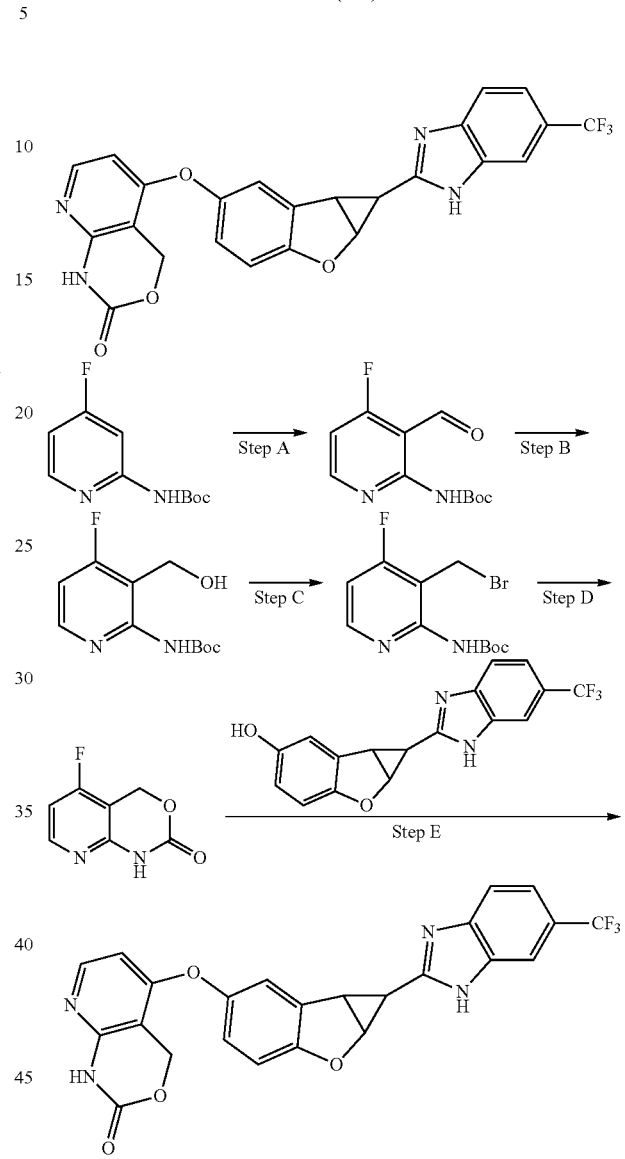

Step A: tert-butyl (4-fluoro-3-formylpyridin-2-yl)carbamate

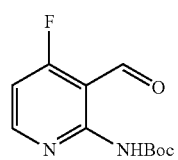

To a stirred solution of tert-butyl 4-fluoropyridin-2-ylcarbamate (1 g, 4.72 mmol) in THF (20 mL) was added dropwise n-BuLi (4.7 mL, 11.8 mmol) at −78° C. After stirring for 0.5 h, a solution of DMF (2 mL) in THF (2 mL) was added dropwise at −78° C. TLC indicated the reaction was completed. The reaction was quenched with 1N HCl at −78° C. to pH=4. Then water (20 mL) was added and extracted with ethyl acetate (3×20 mL). The combined organic phase was washed with brine, dried over anhydrous sodium sulfate and concentrated under reduced pressure. The residue was purified by column chromatography (EtOAc:PE=1:2) to give the title compound (0.65 g, 57%) as a white solid. $^1$H-NMR (600 MHz, DMSO-$d_6$) δ 10.35 (s, 1H), 9.99 (s, 1H), 8.58-8.56 (m, 1H), 7.23-7.21 (m, 1H), 1.46 (s, 9H) ppm.

Step B: tert-butyl 4-fluoro-3-(hydroxymethyl)pyridin-2-ylcarbamate

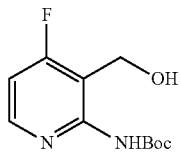 [SMILES: CC(C)(C)OC(=O)Nc1nccc(F)c1CO]

To a solution of the product of step A (480 mg, 2 mmol) in MeOH (3 mL) was added NaBH4 (76 mg, 2 mmol) at 0° C. The reaction was stirred at 0° C. for 30 min. The reaction was quenched with saturated NH$_4$Cl (1 mL) and water (5 mL), extracted with ethyl acetate (2×15 mL). The combined organic phase was dried over anhydrous sodium sulfate, filtered and concentrated under reduced pressure to obtain the title compound (460 mg, 95%) as a white solid which was used directly in the next step. $^1$H-NMR (600 MHz, DMSO-$d_6$) δ 9.20 (s, 1H), 8.31-8.28 (m, 1H), 7.11-7.09 (m, 1H), 5.26 (t, J=6.0 Hz, 1H), 4.48 (d, J=6.0 Hz, 2H), 1.45 (s, 9H) ppm. MS: M/e 243 (M+1)$^+$.

Step C: tert-butyl 3-(bromomethyl)-4-fluoropyridin-2-ylcarbamate

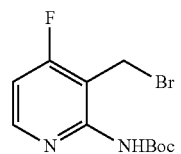 [SMILES: CC(C)(C)OC(=O)Nc1nccc(F)c1CBr]

CBr$_4$ (531 mg, 1.6 mmol) was added to a solution of the product of Step B (242 mg, 1 mmol) in THF (3 mL). Then a solution of triphenylphosphine in THF (1 mL) was added dropwise and the mixture was stirred at room temperature for 3 hours. The mixture, was loaded onto a silica gel column. Elution with (EtOAc:PE=1:3) to afford the title compound (160 mg, 52%) as a while solid. $^1$H-NMR (400 MHz, CDCl$_3$) δ 8.38-8.35 (m, 1H), 7.09 (s, 1H), 6.90-6.86 (m, 1H), 4.61 (s, 2H), 1.54 (s, 9H) ppm MS: M/e 305(M+1)$^+$.

Step D: 5-fluoro-1H-pyrido[2,3-d][1,3]oxazin-2(4H)-one

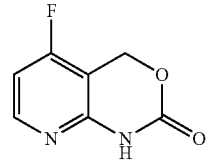 [SMILES: O=C1Nc2nccc(F)c2CO1]

The solution of the product of Step C (120 mg, 0.4 mmol) in DMSO (1 mL) was stirred at 60° C. for 4 hours under N$_2$. Then water (10 mL) was added and extracted with ethyl acetate (3×15 mL). The combined organic phase was washed with brine, dried over anhydrous sodium sulfate and concentrated under reduced pressure. The residue was purified by prep-TLC (EtOAc:PE=1:1) to give the title compound (20 mg, 30%) as a solid. $^1$H-NMR (600 MHz, DMSO-$d_6$) δ 10.95 (s, 1H), 8.21-8.18 (m, 1H), 6.97-6.94 (m, 1H), 5.37 (s, 2H) ppm. MS: M/e 169 (M+1)$^+$.

Step E: (±)-exo-5-((1-(6-(trifluoromethyl)-1H-benzo[d]imidazol-2-yl)-1a,6b-dihydro-1H-cyclopropa[b]benzofuran-5-yl)oxy)-1H-pyrido[2,3-d][1,3]oxazin-2(4H)-one

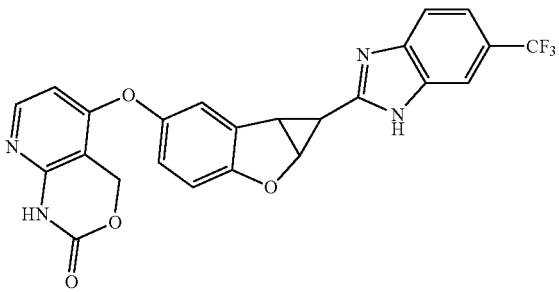 [SMILES: O=C1Nc2nccc(Oc3ccc4c(c3)C3C(O4)C3c3nc4ccc(C(F)(F)F)cc4[nH]3)c2CO1]

The mixture of the product of Step B of Compound 3.2 (16 mg, 0.1 mmol), the product of Step D (33 mg, 0.1 mmol) and Cs$_2$CO$_3$ (98 mg, 0.3 mmol) in DMF (2 mL) was stirred at 110° C. for 3 hour. The mixture was cooled to rt, water (10 mL) was added and extracted with ethyl acetate (3×15 mL). The combined organic phase was washed with brine, dried over anhydrous sodium sulfate and concentrated under reduced pressure. The residue was purified by prep-HPLC to give the title compound (7 mg, 15%) as a white solid. $^1$H-NMR (400 MHz, DMSO-$d_6$) δ 12.85 (s, 1H), 10.73 (s, 1H), 8.03 (d, J=6.0 Hz, 1H), 7.85 (s, 1H), 7.67 (d, J=8.4 Hz, 1H), 7.46 (d, J=8.0 Hz, 1H), 7.41 (d, J=2.4 Hz, 1H), 7.10-7.06 (m, 2H), 6.30 (d, J=6.0 Hz, 1H), 5.44-5.42 (m, 3H), 3.55 (dd, J=3.6, 5.2 Hz, 1H), 1.97 (d, J=2.8 Hz, 1H) ppm. MS: M/e 481(M+1)$^+$.

Compound 3.8: (±)-exo-6-chloro-5-((1-(6-(trifluoromethyl)-1H-benzo[d]imidazol-2-yl)-1a,6b-dihydro-1H-cyclopropa[b]benzofuran-5-yl)oxy)-3,4-dihydro-1,8-naphthyridin-2(1H)-one

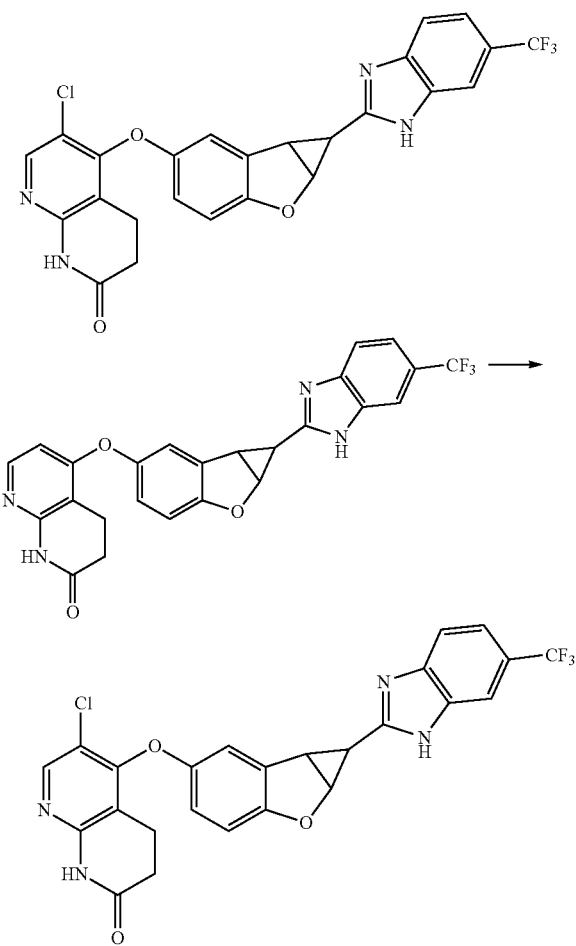

To a stirred solution of Compound 2.2 (70 mg, 0.15 mmol) in AcOH (2 mL) was added NCS (19 mg, 0.15 mmol) at ambient temperature and the mixture was heated at 60° C. for 3 hrs. The mixture was concentrated under reduced pressure and the residue was added 2 mL of 2 N aqueous NaOH, extracted with EtOAc (2 mL×3). The combined extracts were washed with brine (2 mL×3), dried over anhydrous sodium sulfate and concentrated under reduced pressure. The residue was purified by prep-TLC to give the title compound (9 mg, 12%) as a white solid. $^1$H-NMR (600 MHz, DMSO-$d_6$) δ 12.85 (s, 1H), 10.76 (s, 1H), 8.29 (s, 1H), 7.83 (s, 1H), 7.66 (d, J=8.4 Hz, 1H), 7.45 (d, J=8.3 Hz, 1H), 7.14 (d, J=2.8 Hz, 1H), 6.95 (d, J=8.8 Hz, 1H), 6.77 (dd, J=8.8, 2.8 Hz, 1H), 5.36 (dd, J=5.4, 1.2 Hz, 1H), 3.48 (dd, J=5.3, 3.3 Hz, 1H), 2.74 (t, J=7.8 Hz, 2H), 2.48 (t, J=7.8 Hz, 2H), 1.91 (s, 1H) ppm. MS: M/e 513 (M+1)$^+$.

Raf IC$_{50}$ Assay Protocol

Compounds disclosed herein were tested against B-Raf (V600E) (PV3849, from Invitrogen) or C-Raf (Y340D/Y341D) (PV3805, from Invitrogen) in a time-resolved fluorescence energy transfer assay. The assay was carried out in reactions (10 μL) containing 0.0625 nM B-Raf or 0.5 nM C-Raf, 25 mM Tris pH 7.4, 10 mM MgCl$_2$, 0.5 mM EGTA, 0.5 mM Na$_3$BO$_4$, 5 mM beta-glycerophosphate, 0.01%Triton X-100, 2.5 mM DTT, 0.1% BSA, 0.1 mM ATP, 13.7 nM GST-tagged MEK1 (Full-length protein with K97R mutation, recombinant protein purified from bacterial expression system) and 0-5 μM compounds disclosed herein (final concentration of 1% DMSO). The enzyme was incubated with the compounds at room temperature for 60 minutes and the reactions were initiated by the addition of ATP and GST-MEK1. After incubating at room temperature for 60 minutes, an equal volume of stop buffer containing 25 mM Tris pH 7.4, 400 mM KF, 50 mM EDTA, 0.01% BSA, 0.01% Triton X-100, 1 test of Eu3+ Cryptate-conjugated rabbit polyclonal antibody anti-Phospho MEK1/2 (Ser217/221) and 1 test of d2-conjugated mouse monoclonal antibody anti-glutathione S-transferase was added to stop the reactions. Plates were sealed and incubated at room temperature for 2 hours, and then the TR-FRET signals were read on BMG PHERAstar FS instrument. The IC$_{50}$ for each compound was calculated by non linear regression by Graphpad Prism software.

Compounds 1.1-1.3, 2.1-2.37 and 3.1-3.8 inhibited B-Raf (V600E)/C-Raf with IC$_{50}$ values ranging from 0.1 nM to 10 μM.

TABLE 1

| | IC$_{50}$s | |
|---|---|---|
| Compound No. | B-Raf (V600E) IC$_{50}$ (nM) | C-Raf IC$_{50}$ (nM) |
| 1.1 | 11 | 1.4 |
| 1.2 | 72 | 12 |
| 1.3 | 88 | 5.5 |
| 2.1 | 3.1 | 0.3 |
| 2.2 | 7.2 | 1.4 |
| 2.2a | 6.7 | 1.2 |
| 2.2b | 53 | 8.8 |
| 2.3 | 32 | 4.9 |
| 2.3a | 11 | 3 |
| 2.3b | 32 | 4 |
| 2.4 | 2.4 | <0.56 |
| 2.4a | 3.4 | 0.54 |
| 2.4b | 21 | 2.5 |
| 2.5 | 19 | 5 |
| 2.5a | 126 | 21 |
| 2.5b | 11 | 2.5 |
| 2.6 | 22 | 4.5 |
| 2.7 | 10 | 2.1 |
| 2.8 | 3.7 | 0.71 |
| 2.9 | 42 | 4.5 |
| 2.10 | 80 | 25 |
| 2.11 | 5.9 | 3.3 |
| 2.12 | 12 | 4.1 |
| 2.13 | 7.2 | 1.7 |
| 2.14 | 28 | 9.7 |
| 2.15 | 12 | 3.6 |
| 2.16 | 15 | 3.8 |
| 2.17 | 5.4 | 5.9 |
| 2.18 | 89 | 6.2 |
| 2.19 | 11 | 1.6 |
| 2.20 | 33 | 4.4 |
| 2.21 | 1.2 | 0.4 |
| 2.22 | 4 | 1 |
| 2.23 | 204 | 35 |
| 2.24 | 47 | 4.3 |
| 2.25 | 849 | 36 |
| 2.26 | 16 | <0.25 |
| 2.27 | 2.5 | <0.25 |
| 2.28 | 232 | 81 |
| 2.29 | 3.2 | <0.25 |
| 2.30 | 0.72 | <0.25 |
| 2.31 | 3.7 | 0.35 |
| 2.32 | 3.3 | 0.9 |
| 2.33 | 6.0 | 0.6 |
| 2.34 | 30 | 4.2 |
| 2.35 | 61 | 12 |

TABLE 1-continued

| | IC$_{50}$s | |
|---|---|---|
| Compound No. | B-Raf (V600E) IC$_{50}$ (nM) | C-Raf IC$_{50}$ (nM) |
| 2.36 | 117 | 32 |
| 2.37 | 173 | 23 |
| 3.1 | 56 | 6.5 |
| 3.2 | 569 | 223 |
| 3.3 | 522 | 104 |
| 3.4 | 291 | 56 |
| 3.5 | 56 | 20 |
| 3.6 | 518 | 86 |
| 3.7 | 26 | 3.2 |
| 3.8 | >1000 | 432 |
| Intermediate I | >5000 | >5000 |
| Intermediate II | >5000 | 2915 |

What is claimed is:

1. A method of treating cancer comprising administering to a subject in need thereof, an effective amount of a compound selected from compounds of Formula I:

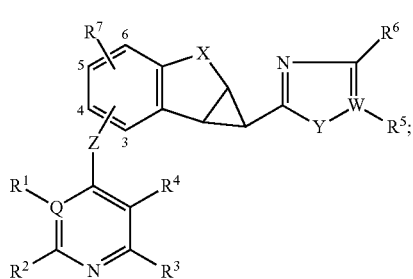

or a stereoisomer or a pharmaceutically acceptable salt thereof,
wherein:
Q is C or N;
W is C or N;
X is CH$_2$ or O;
Y is NR$^{12}$, O, or S;
Z is O;
R$^1$ and R$^2$ are hydrogen, provided that R$^1$ is absent when Q is N;
R$^3$ and R$^4$, which may be the same or different, are each selected from hydrogen, —CONR$^{13}$R$^{14}$, or heteroaryl optionally substituted with at least one substituent R$^{16}$; or R$^3$ and R$^4$ together with the ring to which they are attached, form a fused ring selected from heterocyclyl or heteroaryl rings optionally substituted with at least one substituent R$^{16}$;
R$^5$ and R$^6$, which may be the same or different, are each selected from hydrogen, alkyl, aryl, or heteroaryl, wherein the alkyl, heteroaryl, and aryl, are optionally substituted with at least one substituent R$^{16}$, or R$^5$ and R$^6$ together with the ring to which they are attached, form a fused ring which is a heteroaryl ring optionally substituted with at least one substituent R$^{16}$; provided that R$^5$ is absent when W is N;
R$^7$ is hydrogen, halogen, or alkyl;
R$^{12}$ is hydrogen or alkyl;
R$^{13}$ and R$^{14}$, which may be the same or different, are each selected from H, haloalkyl, alkyl, alkenyl, alkynyl, cycloalkyl, heterocyclyl, aryl, or heteroaryl; and
R$^{16}$ is halogen, haloalkyl, alkyl, —CN, haloalkyloxy, alkyloxy, hydroxyl or phenyl;

wherein the cancer is selected from melanoma, colorectal cancer, or thyroid cancer and wherein the cancer has a B-Raf V600E mutation.

2. The method of claim 1, wherein the compound has the structure of Formula (V):

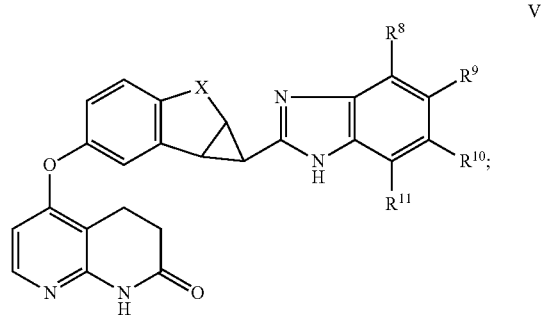

or a stereoisomer or a pharmaceutically acceptable salt thereof,
wherein:
X is CH$_2$ or O;
R$^8$, R$^9$, R$^{10}$ and R$^{11}$, which may be the same or different, are each selected from hydrogen, halogen, alkyl, haloalkyl, hydroxyl, haloalkyloxy, alkyloxy, phenyl, or —CN.

3. The method of claim 2, wherein X is O.

4. The method of claim 2, wherein R$^8$, R$^9$, R$^{10}$ and R$^{11}$, which may be the same or different, are each selected from hydrogen, halogen, C1-C4 alkyl, C1-C4 haloalkyl, —CN, —OCH$_3$, —OCF$_3$, —OH, or phenyl.

5. The method of claim 2, wherein R$^8$, R$^9$, R$^{10}$ and R$^{11}$, which may be the same or different, are each selected from hydrogen or —CF$_3$.

6. The method of claim 2, wherein R$^{10}$ is —CF$_3$.

7. The method of claim 2, wherein R$^8$, R$^9$, and R$^{11}$ are each hydrogen.

8. A method of treating cancer comprising administering to a subject in need thereof, an effective amount of a compound selected from the group consisting of:

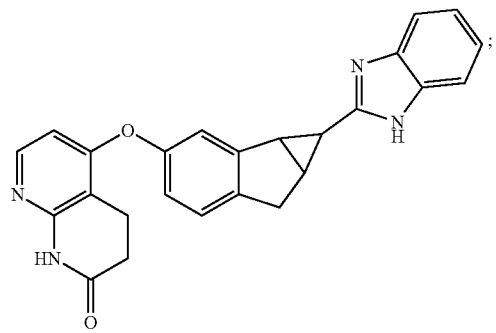

-continued
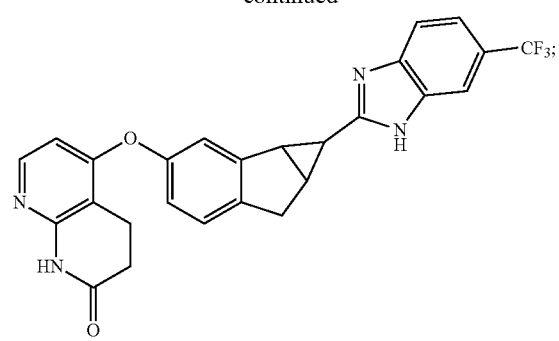
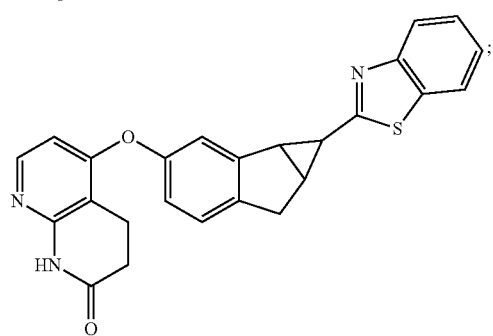
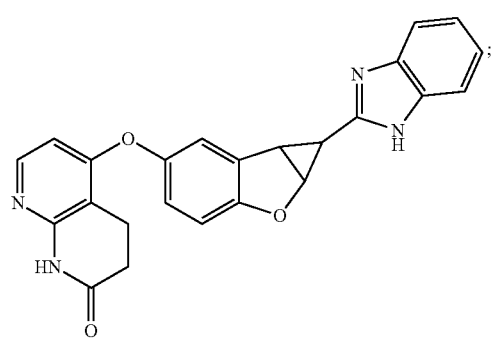
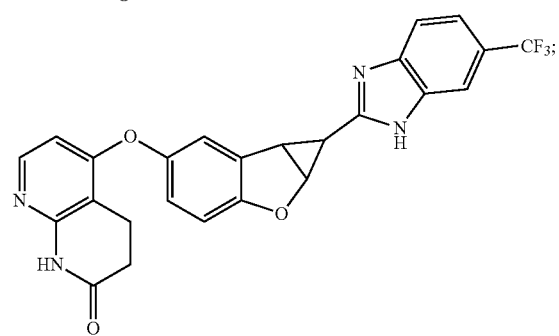
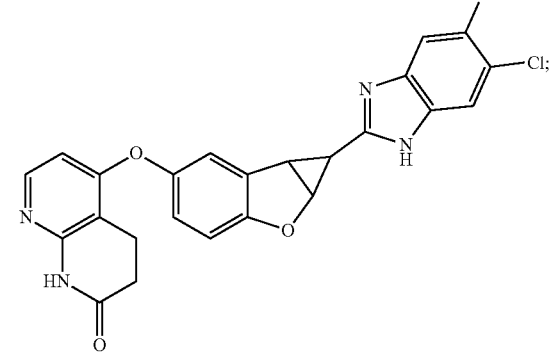
-continued
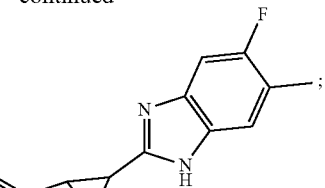
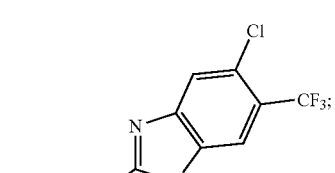
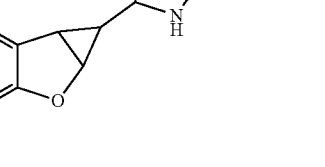
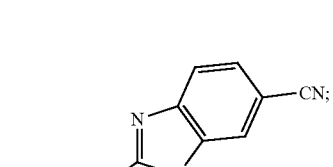
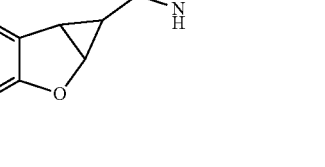

117
-continued
118
-continued
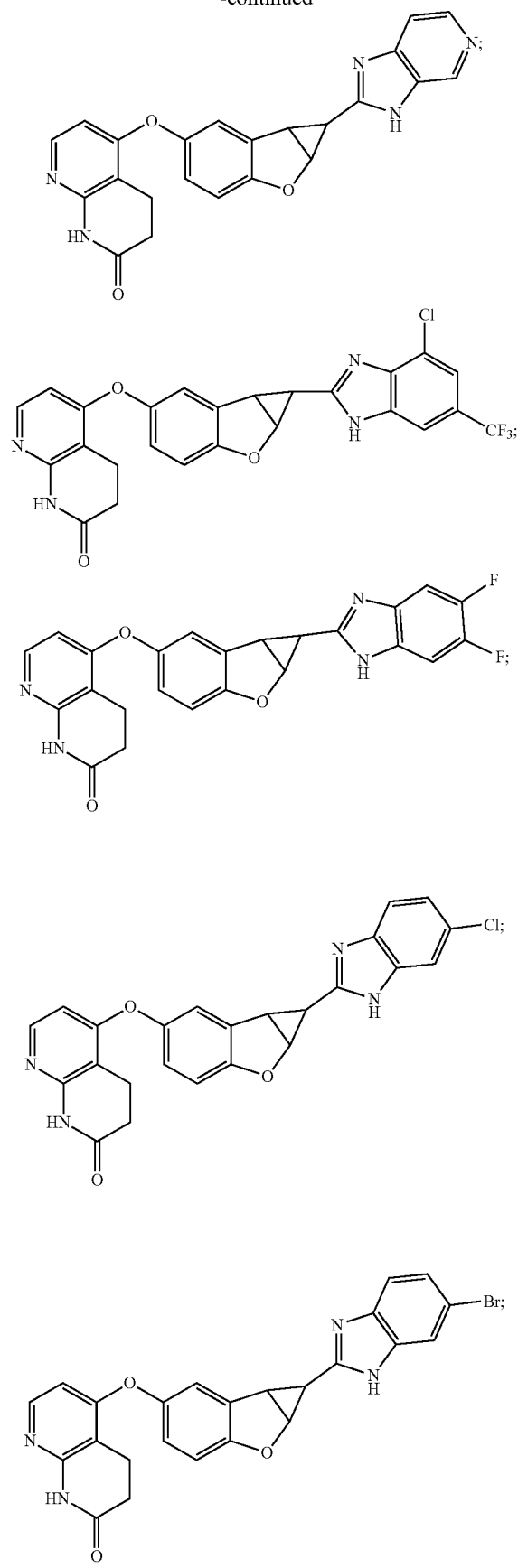
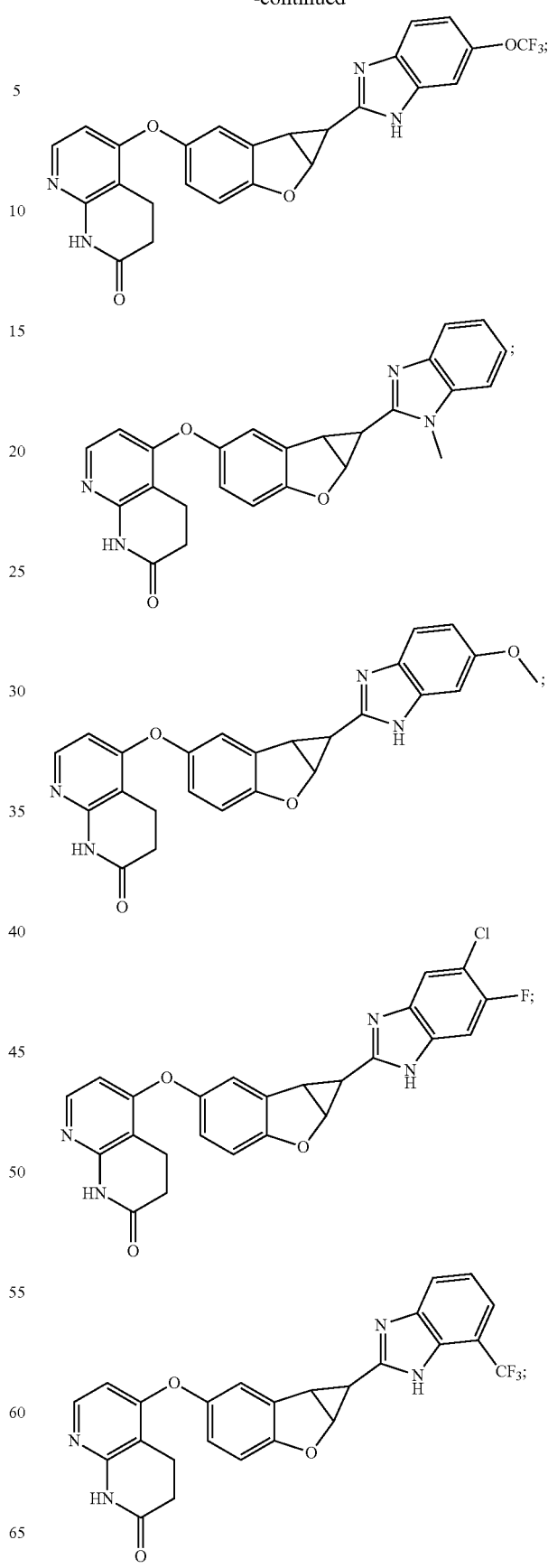

119
-continued
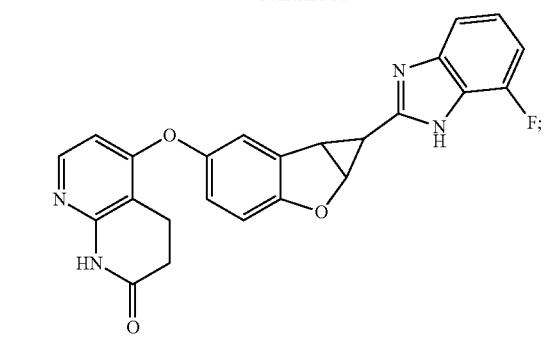
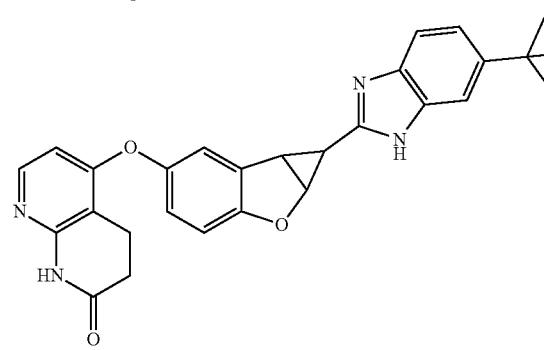
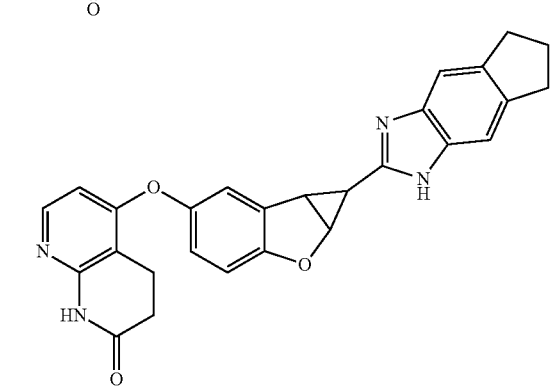
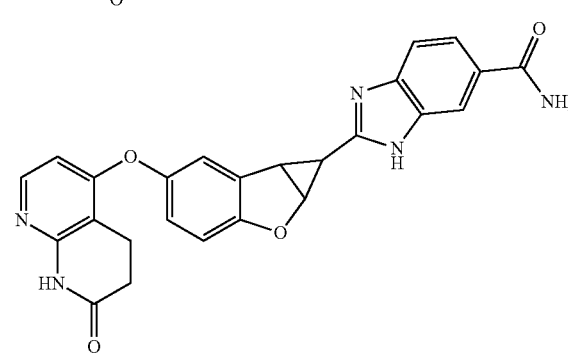
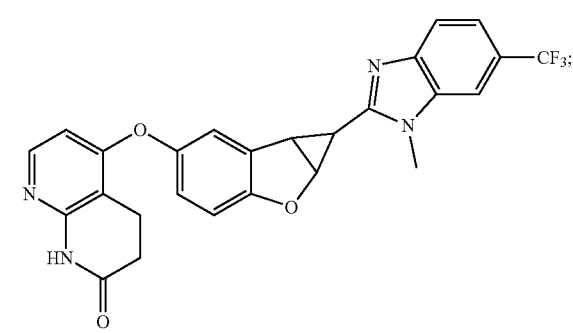
120
-continued
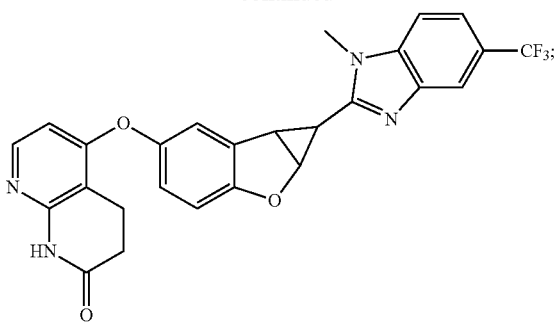
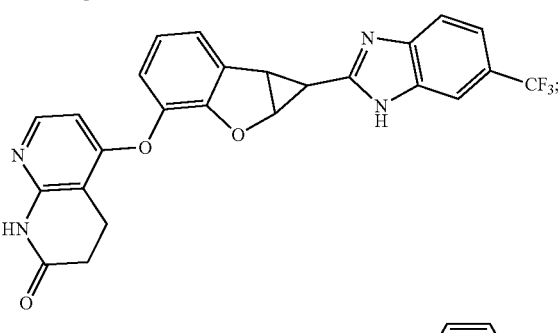
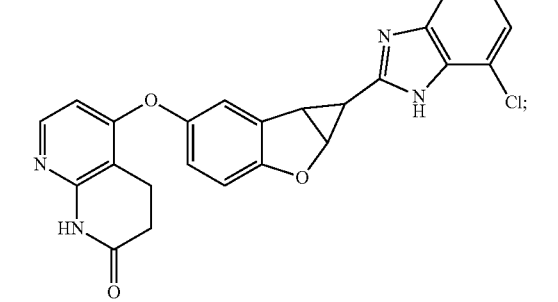
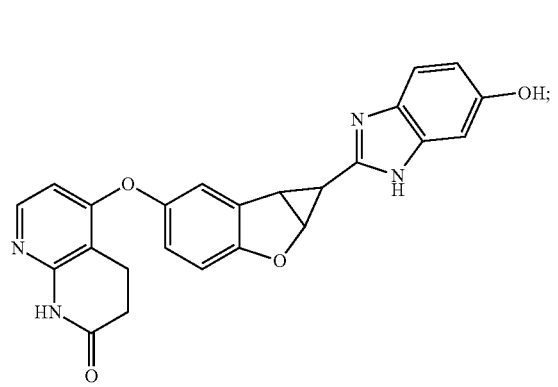
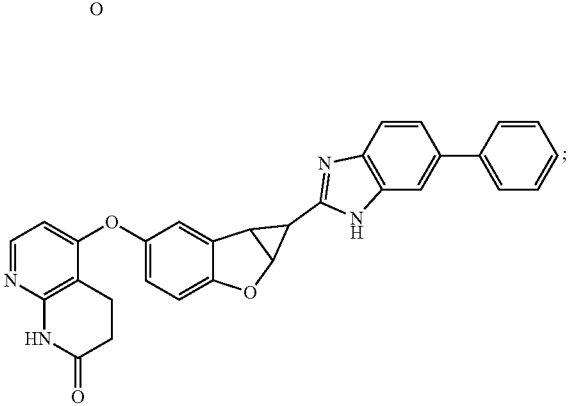

121
-continued
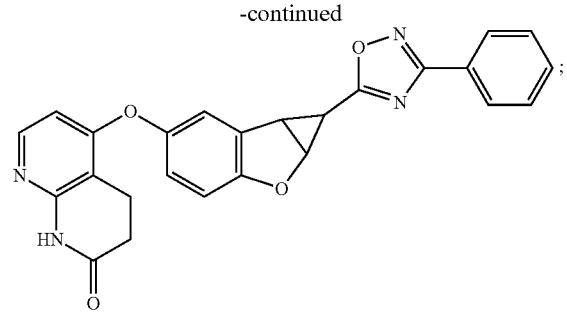
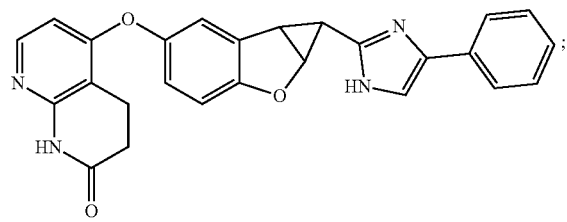
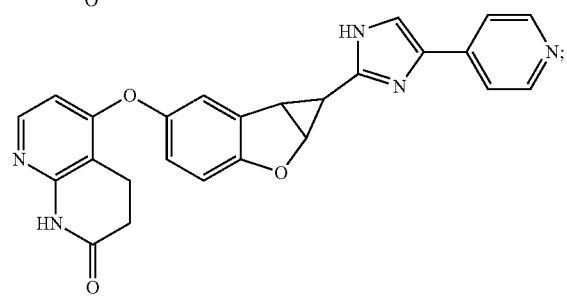
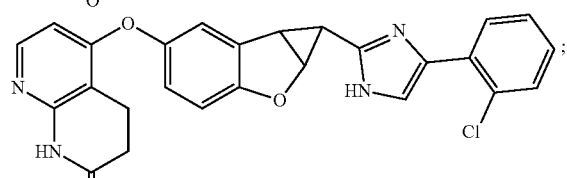
122
-continued
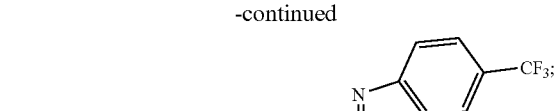
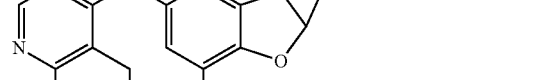
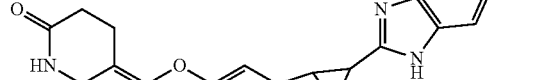
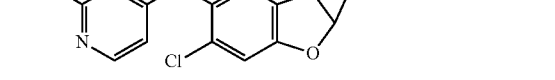
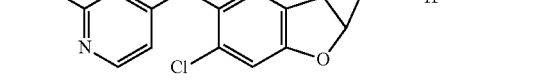
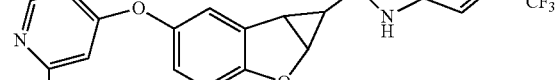
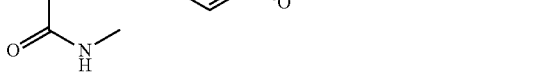

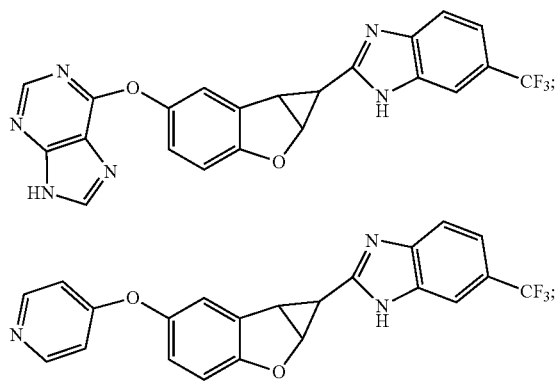
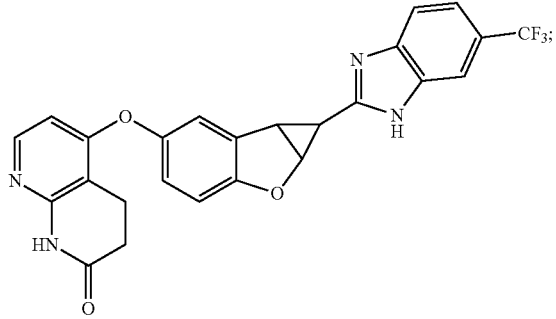
or a stereoisomer or a pharmaceutically acceptable salt thereof;
wherein the cancer is selected from melanoma, colorectal cancer, or thyroid cancer and wherein the cancer has a B-Raf V600E mutation.
9. The method of claim 8, wherein the compound is selected from the group consisting of:
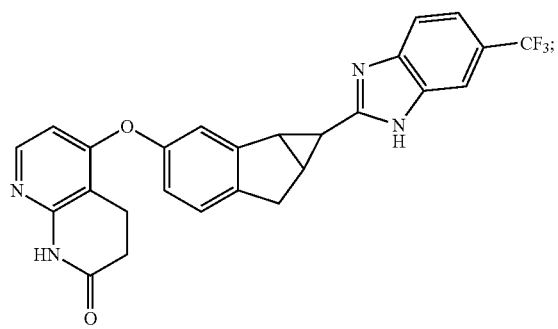
or a stereoisomer or a pharmaceutically acceptable salt thereof.

10. The method of claim 8, wherein the compound is selected from the group consisting of:
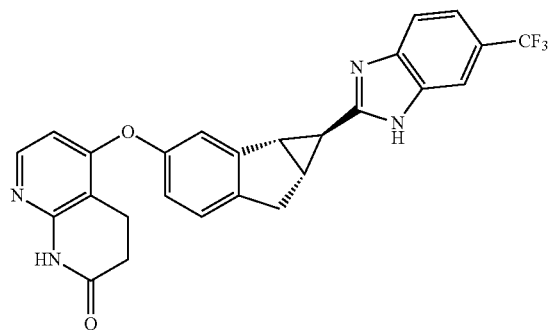
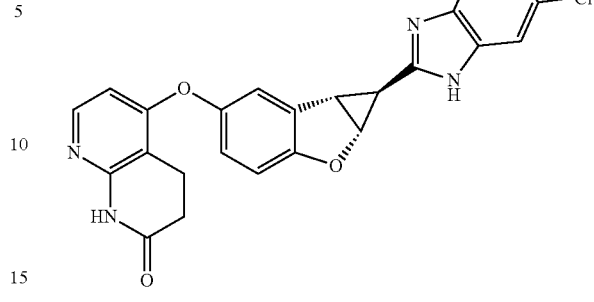
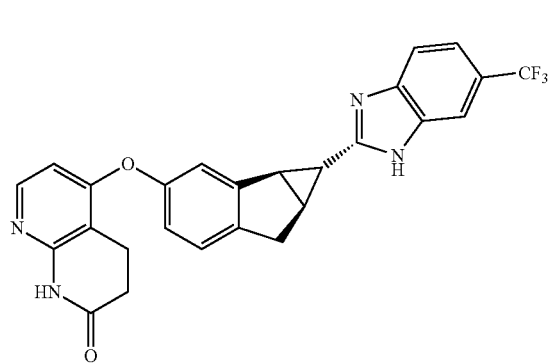
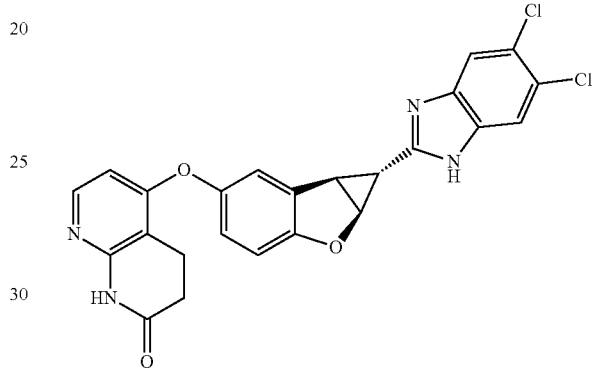
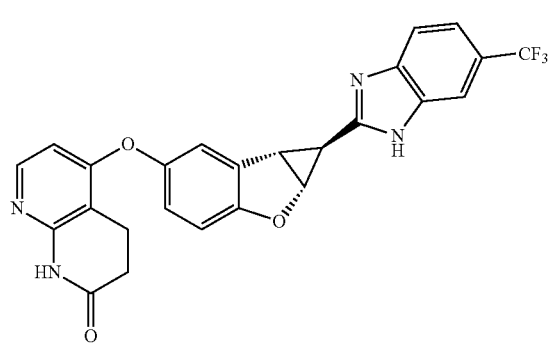
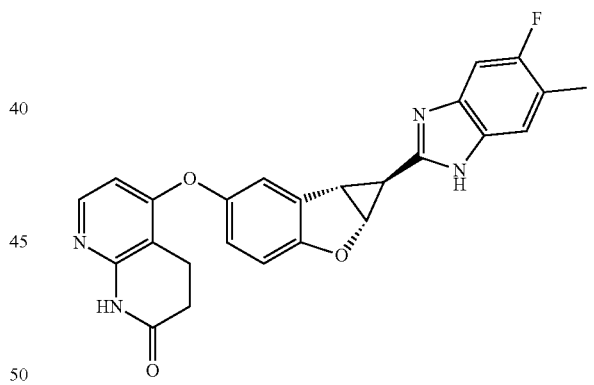
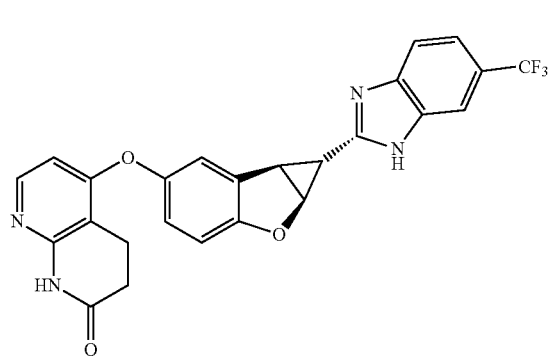
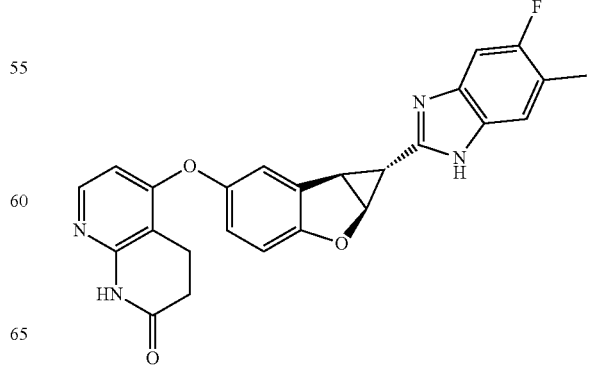

-continued

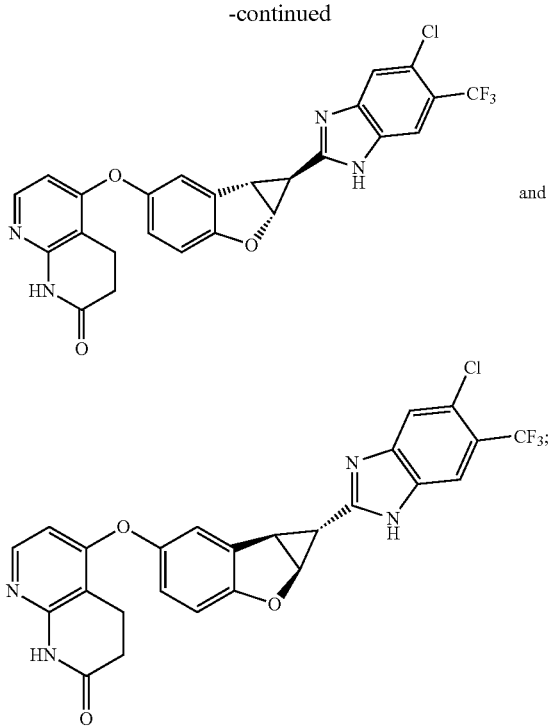

or a stereoisomer or a pharmaceutically acceptable salt thereof.

11. The method of claim 8, wherein the compound is

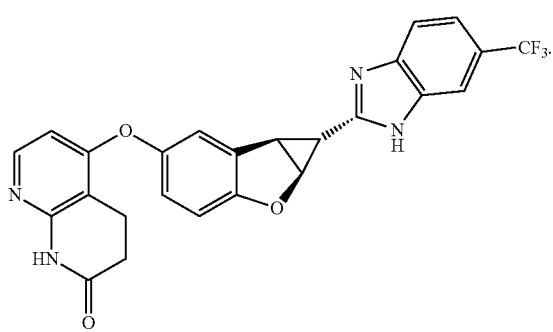

12. A method of inhibiting B-Raf kinase in a subject in need thereof, comprising administering to the subject, an effective amount of a compound selected from compounds of Formula I:

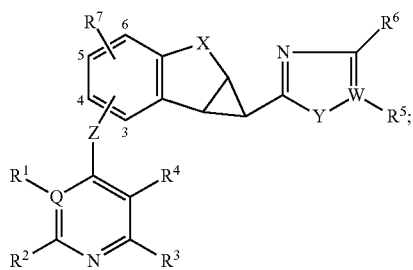

or a stereoisomer or a pharmaceutically acceptable salt thereof, wherein:

Q is C or N;

W is C or N;

X is $CH_2$ or O;

Y is $NR^{12}$, O, or S;

Z is O;

$R^1$ and $R^2$ are hydrogen, provided that $R^1$ is absent when Q is N;

$R^3$ and $R^4$, which may be the same or different, are each selected from hydrogen, —$CONR^{13}R^{14}$, or heteroaryl optionally substituted with at least one substituent $R^{16}$; or $R^3$ and $R^4$ together with the ring to which they are attached, form a fused ring selected from heterocyclyl or heteroaryl rings optionally substituted with at least one substituent $R^{16}$;

$R^5$ and $R^6$, which may be the same or different, are each selected from hydrogen, alkyl, aryl, or heteroaryl, wherein the alkyl, heteroaryl, and aryl, are optionally substituted with at least one substituent $R^{16}$, or $R^5$ and $R^6$ together with the ring to which they are attached, form a fused ring which is a heteroaryl ring optionally substituted with at least one substituent $R^{16}$; provided that $R^5$ is absent when W is N;

$R^7$ is hydrogen, halogen, or alkyl;

$R^{12}$ is hydrogen or alkyl;

$R^{13}$ and $R^{14}$, which may be the same or different, are each selected from H, haloalkyl, alkyl, alkenyl, alkynyl, cycloalkyl, heterocyclyl, aryl, or heteroaryl; and $R^{16}$ is halogen, haloalkyl, alkyl, —CN, haloalkyloxy, alkyloxy, hydroxyl or phenyl.

13. The method of claim 12, wherein the compound has the structure of Formula (V):

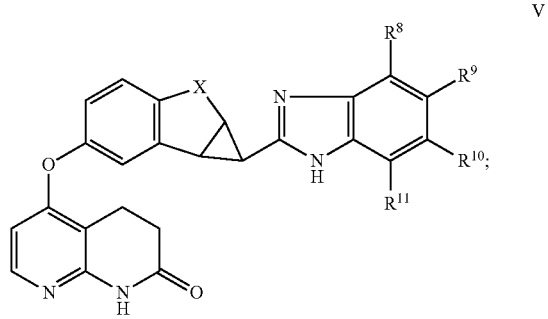

or a stereoisomer or a pharmaceutically acceptable salt thereof, wherein:

X is $CH_2$ or O;

$R^8$, $R^9$, $R^{10}$ and $R^{11}$, which may be the same or different, are each selected from hydrogen, halogen, alkyl, haloalkyl, hydroxyl, haloalkyloxy, alkyloxy, phenyl, or —CN.

14. The method of claim 12, wherein the compound is selected from the group consisting of:
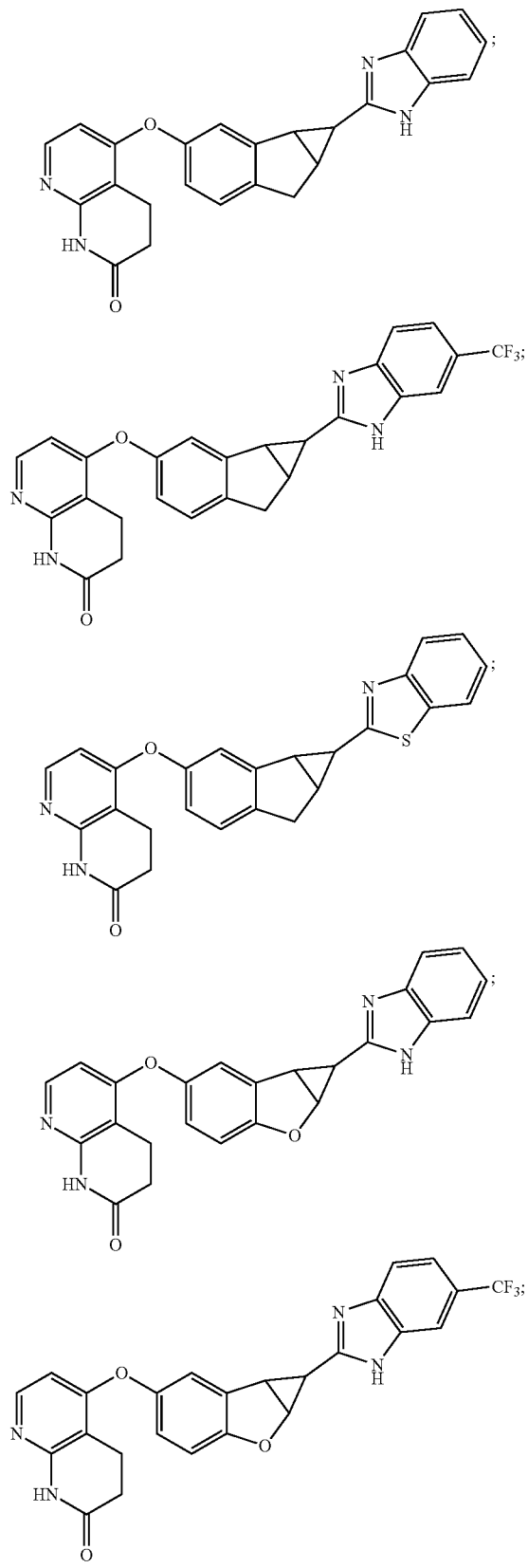 [SMILES: O=C1CCc2c(Oc3ccc4c(c3)C3C(C4)C3c3nc4ccccc4[nH]3)ccnc2N1 ; O=C1CCc2c(Oc3ccc4c(c3)C3C(C4)C3c3nc4ccc(C(F)(F)F)cc4[nH]3)ccnc2N1 ; O=C1CCc2c(Oc3ccc4c(c3)C3C(C4)C3c3nc4ccccc4s3)ccnc2N1 ; O=C1CCc2c(Oc3ccc4c(c3)C3C(O4)C3c3nc4ccccc4[nH]3)ccnc2N1 ; O=C1CCc2c(Oc3ccc4c(c3)C3C(O4)C3c3nc4ccc(C(F)(F)F)cc4[nH]3)ccnc2N1]
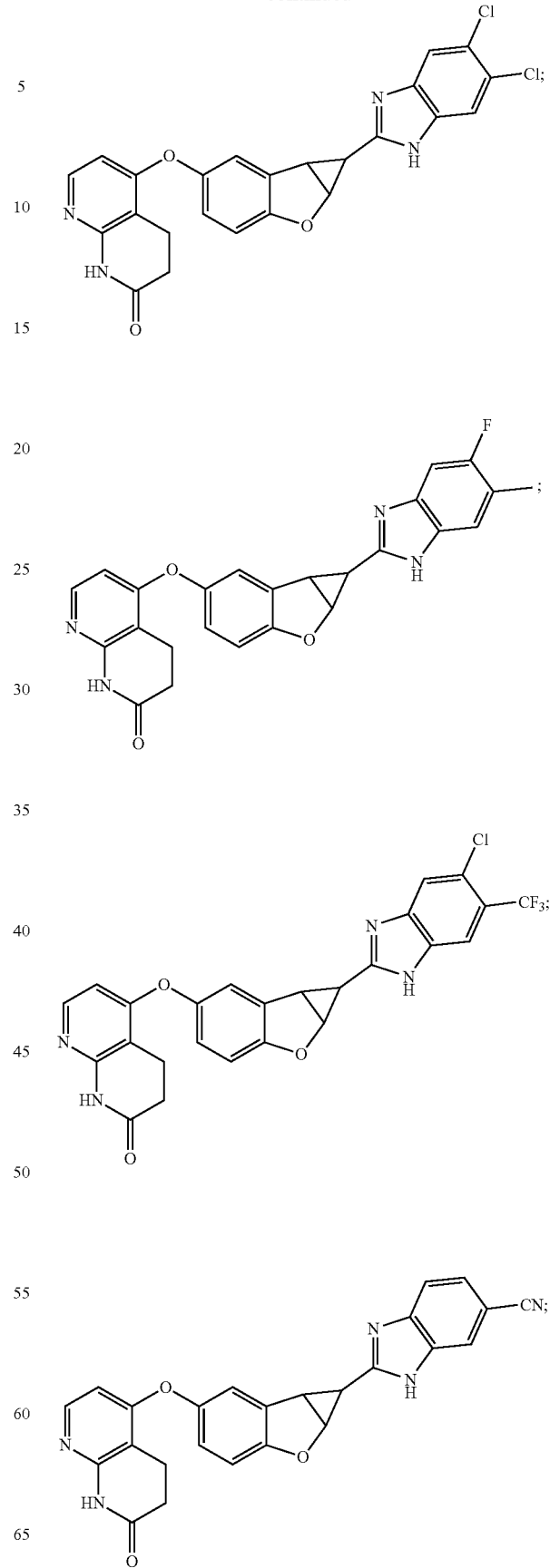

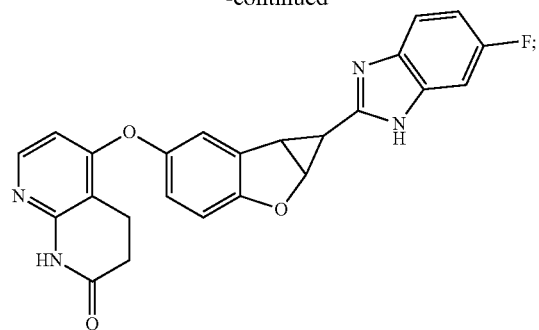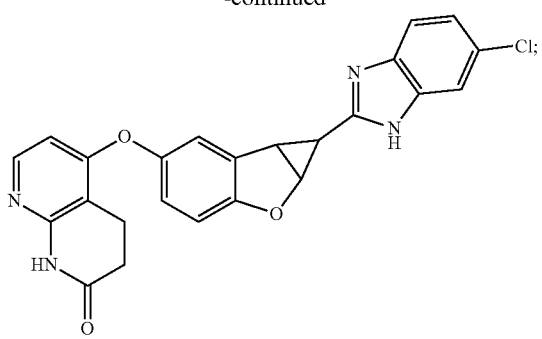

-continued
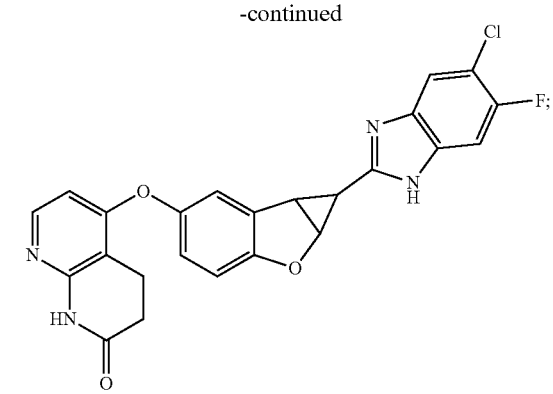
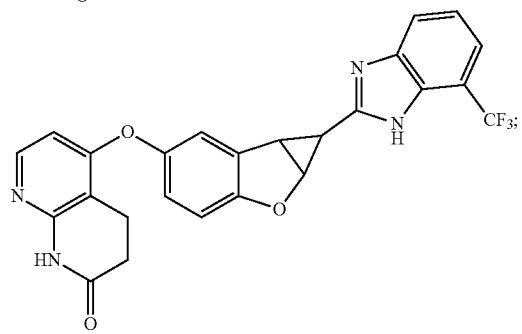
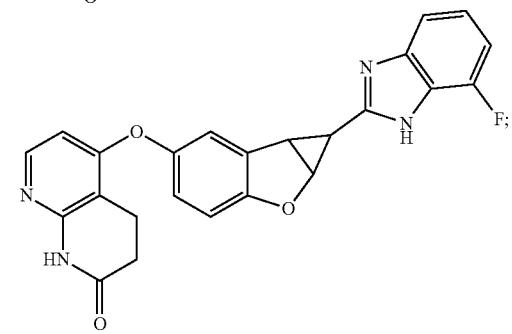
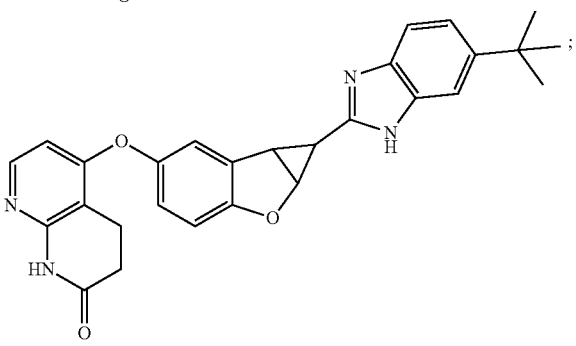
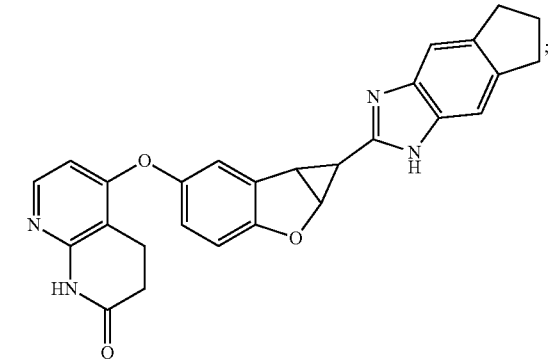
-continued
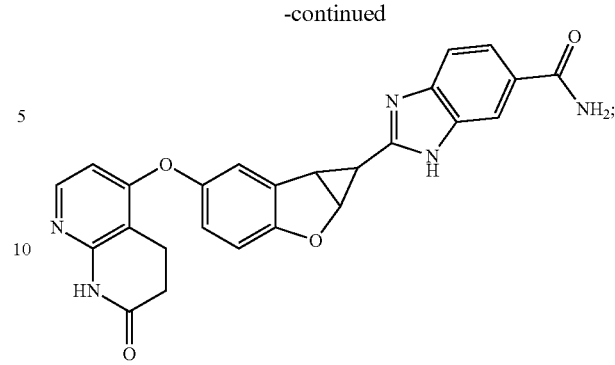
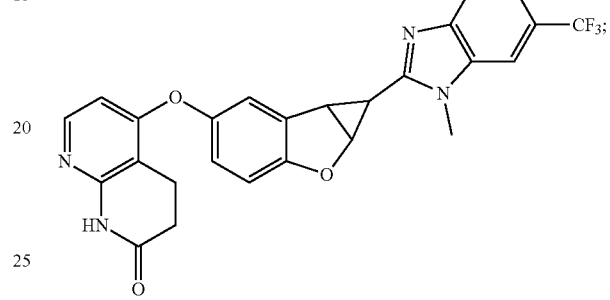
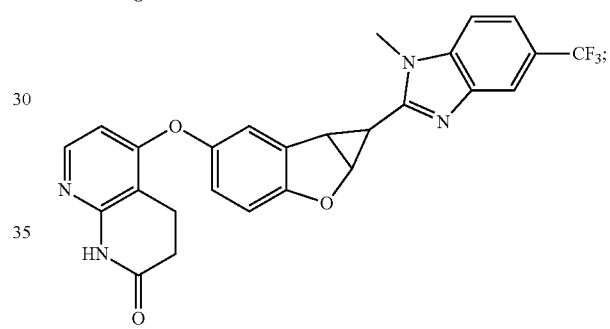
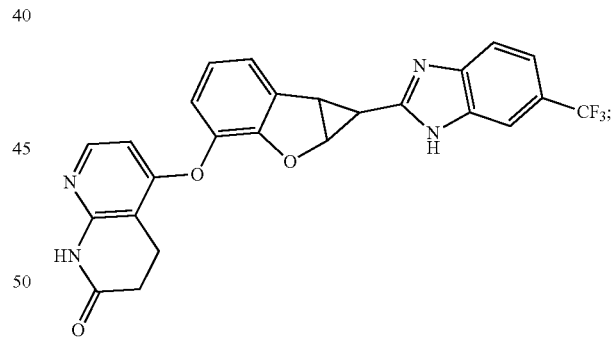
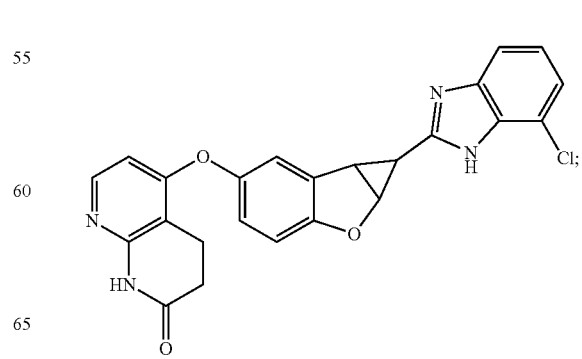

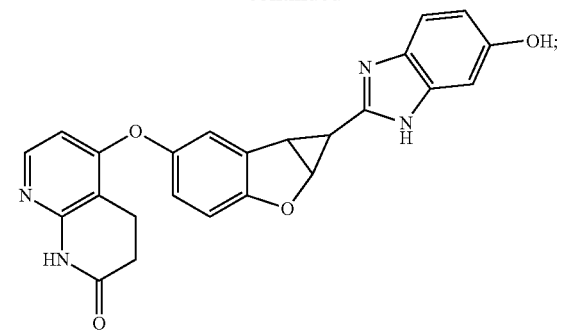
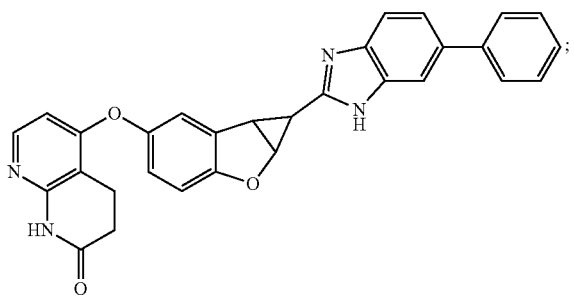
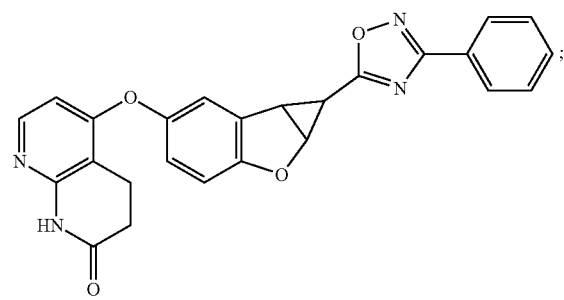
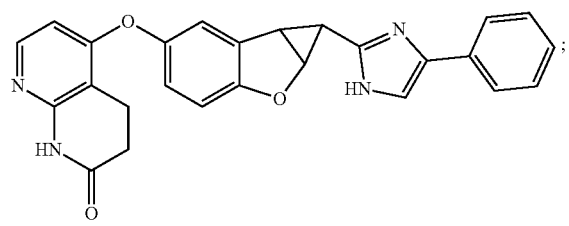
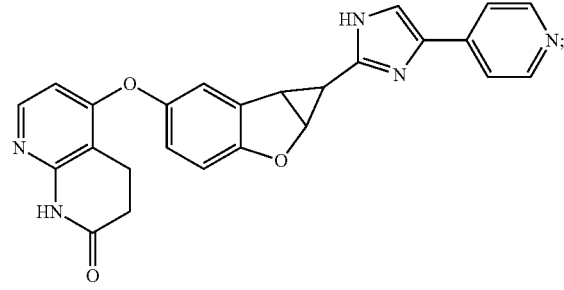
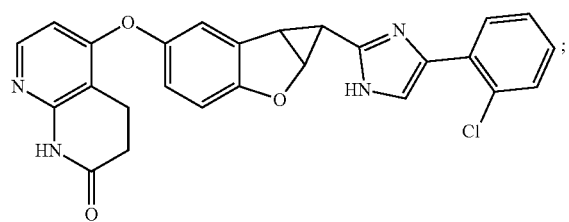
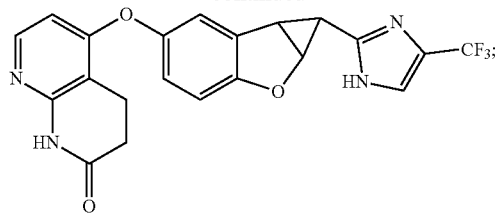
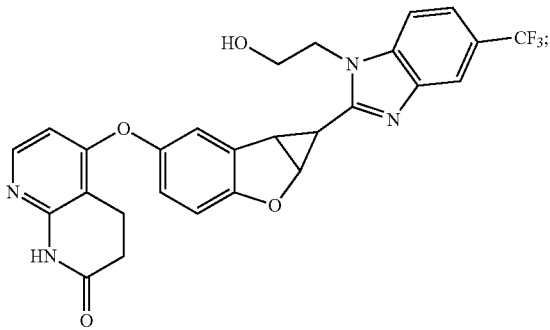
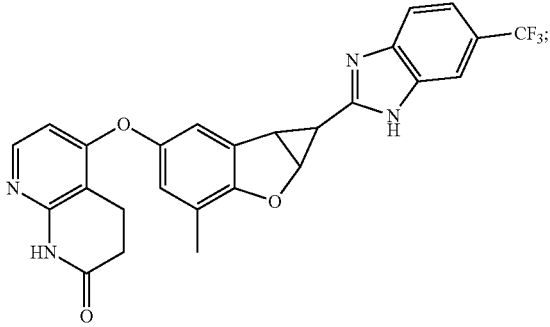
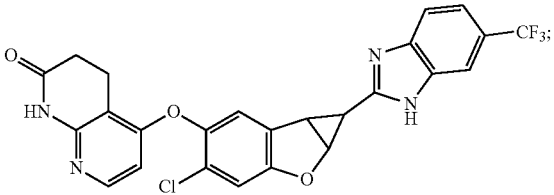
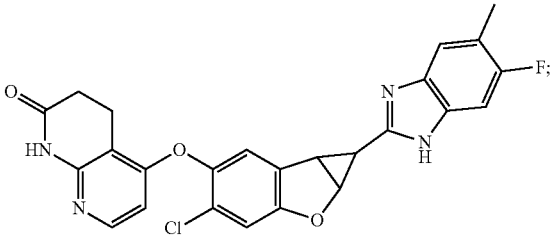
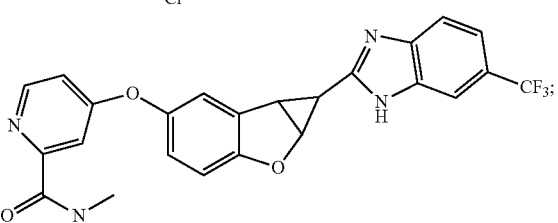
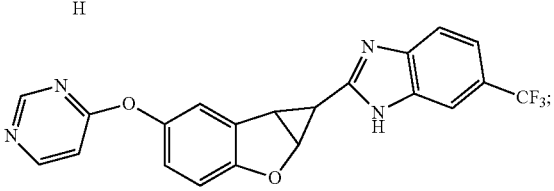

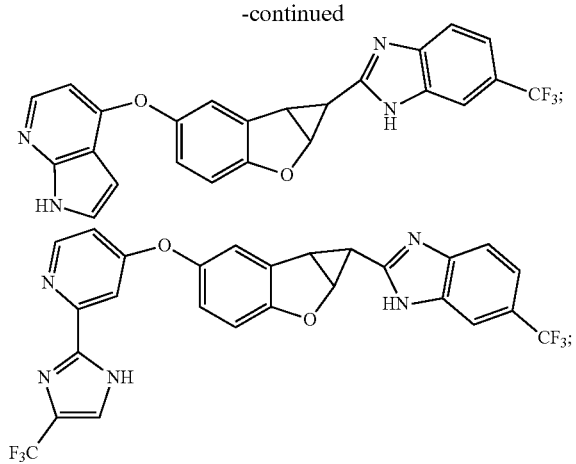
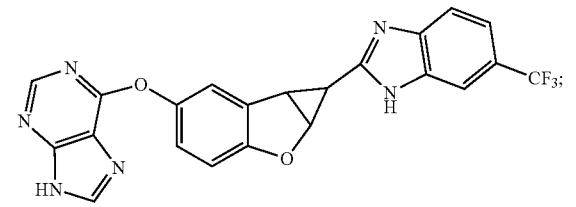
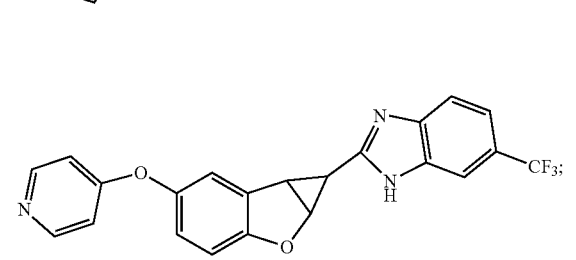
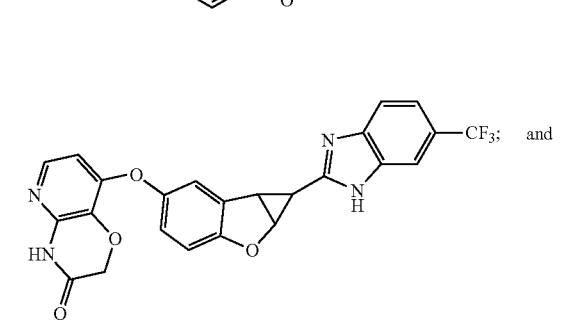
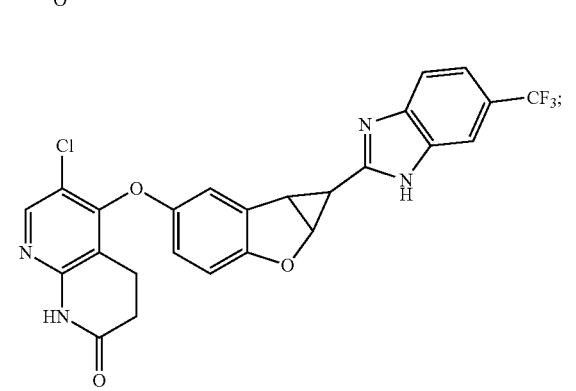
or a stereoisomer or a pharmaceutically acceptable salt thereof.
15. The method of claim 12, wherein the compound is selected from the group consisting of:
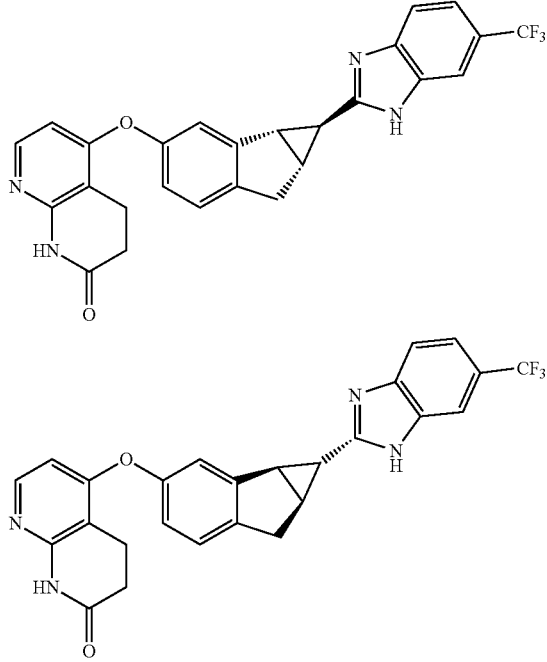
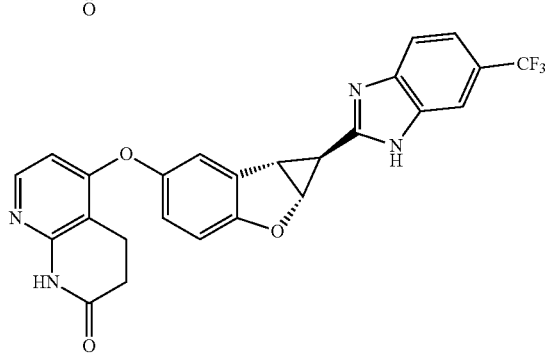
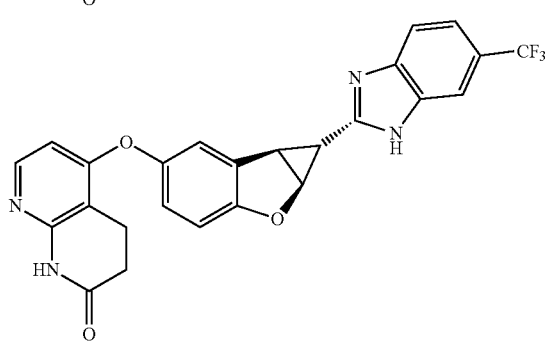
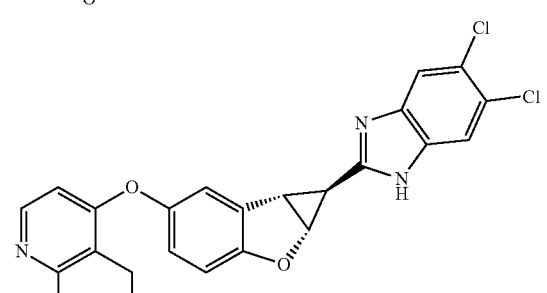

-continued
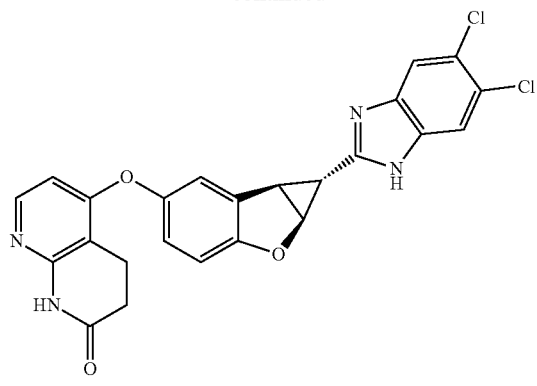
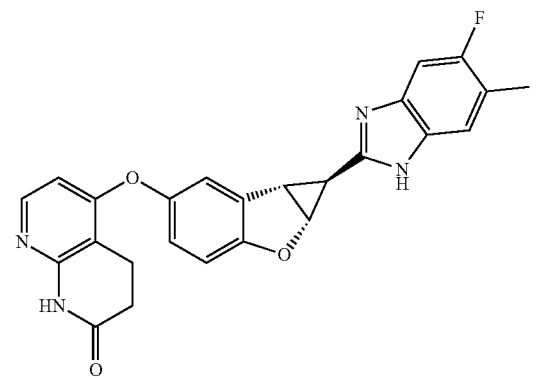
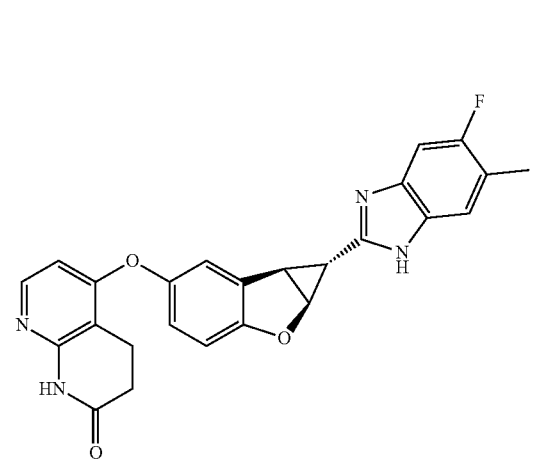
-continued
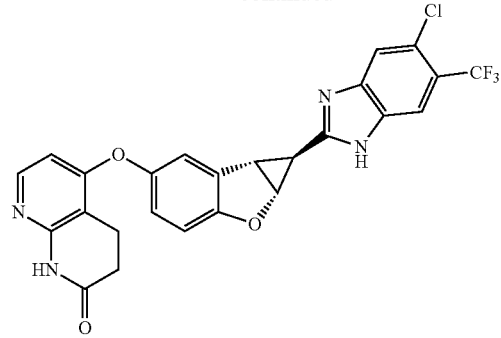
and
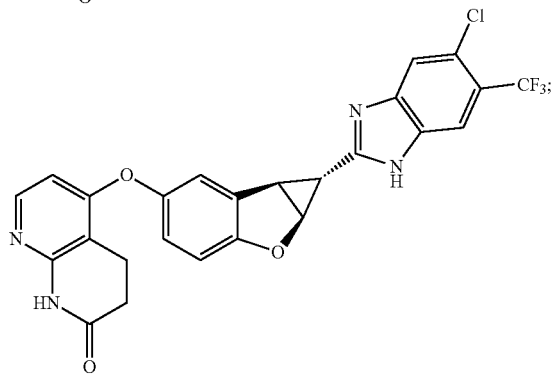
or a pharmaceutically acceptable salt thereof.
16. The method of claim 12, wherein the compound is
* * * * *